US012453283B2

(12) United States Patent
Jung et al.

(10) Patent No.: US 12,453,283 B2
(45) Date of Patent: Oct. 21, 2025

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Sang Duk Suh, Daejeon (KR); Seulchan Park, Daejeon (KR); Sunghyun Hwang, Daejeon (KR); Boonjae Jang, Daejeon (KR); Jungha Lee, Daejeon (KR); Su Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 960 days.

(21) Appl. No.: 17/046,647

(22) PCT Filed: Jul. 29, 2019

(86) PCT No.: PCT/KR2019/009417
§ 371 (c)(1),
(2) Date: Oct. 9, 2020

(87) PCT Pub. No.: WO2020/022860
PCT Pub. Date: Jan. 30, 2020

(65) Prior Publication Data

US 2021/0184131 A1 Jun. 17, 2021

(30) Foreign Application Priority Data

Jul. 27, 2018 (KR) ........................ 10-2018-0088202
Jul. 26, 2019 (KR) ........................ 10-2019-0091211

(51) Int. Cl.
*H10K 85/60* (2023.01)
*C07D 405/14* (2006.01)
(Continued)

(52) U.S. Cl.
CPC ......... *H10K 85/654* (2023.02); *C07D 405/14* (2013.01); *C07D 409/14* (2013.01);
(Continued)

(58) Field of Classification Search
CPC .............. C07B 2200/05; C07D 405/14; C07D 409/14; C09K 11/06; C09K 2211/1018;
(Continued)

(56) References Cited

U.S. PATENT DOCUMENTS 10,505,121 B2 12/2019 Song et al.
2002/0076576 A1* 6/2002 Li .......................... H10K 85/00 428/917
(Continued)

FOREIGN PATENT DOCUMENTS

EP 3 034 506 A1 6/2016
JP 2001240854 A 9/2001
(Continued)

OTHER PUBLICATIONS

Tsuji et al., Chem. Commun., 2014, 50, 14870 (Year: 2014).*
(Continued)

*Primary Examiner* — Elizabeth M. Dahlburg
(74) *Attorney, Agent, or Firm* — Bryan Cave Leighton Paisner LLP

(57) ABSTRACT

Provided is a novel compound of Chemical Formula 1:

(Continued)

wherein: $X_1$ to $X_3$ are each independently CH or N, provided that at least two of $X_1$ to $X_3$ are N, $Y_1$ and $Y_2$ are each independently O or S, L is a single bond; a substituted or unsubstituted $C_{6-60}$ arylene; a substituted or unsubstituted $C_{2-60}$ heteroarylene containing one or more selected from the group consisting of N, O, and S, $Ar_1$ is a $C_{6-60}$ aryl substituted with at least one deuterium, and the other substituent are as defined in the specification; and an organic light emitting device including the same. The compound of Chemical Formula 1 can be used as a material of an organic material layer of an organic light emitting device, and can improve efficiency, achieve a low driving voltage, and/or improve lifetime characteristics in the organic light emitting device.

9 Claims, 1 Drawing Sheet

(51) Int. Cl.

| | |
|---|---|
| ***C07D 409/14*** | (2006.01) |
| ***C09K 11/06*** | (2006.01) |
| *H10K 50/11* | (2023.01) |
| *H10K 101/10* | (2023.01) |

(52) U.S. Cl.

CPC .......... *C09K 11/06* (2013.01); *H10K 85/6572* (2023.02); *H10K 85/6574* (2023.02); *H10K 85/6576* (2023.02); *C07B 2200/05* (2013.01); *C09K 2211/1018* (2013.01); *H10K 50/11* (2023.02); *H10K 2101/10* (2023.02)

(58) Field of Classification Search

CPC ...... H10K 50/00; H10K 50/11; H10K 85/654; H10K 85/657; H10K 85/6572; H10K 85/6574; H10K 85/6576; H10K 2101/10; H01L 51/50; H01L 51/0067; H01L 51/0071; H01L 51/0072; H01L 51/0073; H01L 51/0074; H01L 51/5016

See application file for complete search history.

(56) References Cited

U.S. PATENT DOCUMENTS

| | | | | |
|---|---|---|---|---|
| 2004/0251816 | A1 | 12/2004 | Leo et al. | |
| 2014/0332793 | A1 | 11/2014 | Park et al. | |
| 2017/0062736 | A1 | 3/2017 | Parham et al. | |
| 2017/0207399 | A1 † | 7/2017 | Parham | |
| 2019/0058131 | A1 | 2/2019 | Cho et al. | |
| 2019/0276599 | A1 | 9/2019 | Dai et al. | |
| 2020/0119286 | A1 † | 4/2020 | Liaptsis | |
| 2020/0123133 | A1 * | 4/2020 | No ..................... | H10K 85/6576 |
| 2020/0168804 | A1 * | 5/2020 | Song .................. | H10K 85/6572 |

FOREIGN PATENT DOCUMENTS

| | | | | |
|---|---|---|---|---|
| JP | 6319228 | B2 | 5/2018 | |
| KR | 10-2000-0051826 | A | 8/2000 | |
| KR | 10-2012-0129733 | A | 11/2012 | |
| KR | 10-2015-0129282 | A | 11/2015 | |
| KR | 10-2017-0057797 | A | 5/2017 | |
| KR | 10-2018-0010144 | A | 1/2018 | |
| KR | 10-1857632 | A | 5/2018 | |
| KR | 1020180045798 | A † | 5/2018 | |
| KR | 10-2018-0060991 | A | 6/2018 | |
| KR | 10-2018-0061077 | A | 6/2018 | |
| KR | 10-2018-0062208 | A | 6/2018 | |
| KR | 10-2018-0071621 | A | 6/2018 | |
| WO | 03/012890 | A2 | 2/2003 | |
| WO | 2015165563 | A1 | 11/2015 | |
| WO | 2017078494 | A1 | 5/2017 | |
| WO | 2018117618 | A1 | 6/2018 | |
| WO | WO-2019143108 | A1 * | 7/2019 | ........... C07D 209/82 |

OTHER PUBLICATIONS

WO 2019143108 A1 machine translation (Year: 2019).*

Tsuji et al., The hydrogen/deuterium isotope effect of the host material on the lifetime of organic light-emitting diodes, pp. 14870-14872, Sep. 15, 2014, Chem. Commun.†

* cited by examiner

† cited by third party

[FIG. 1]
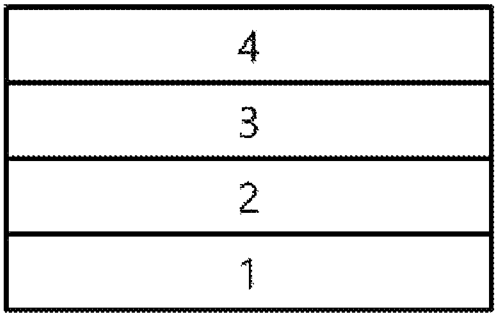
[FIG. 2]
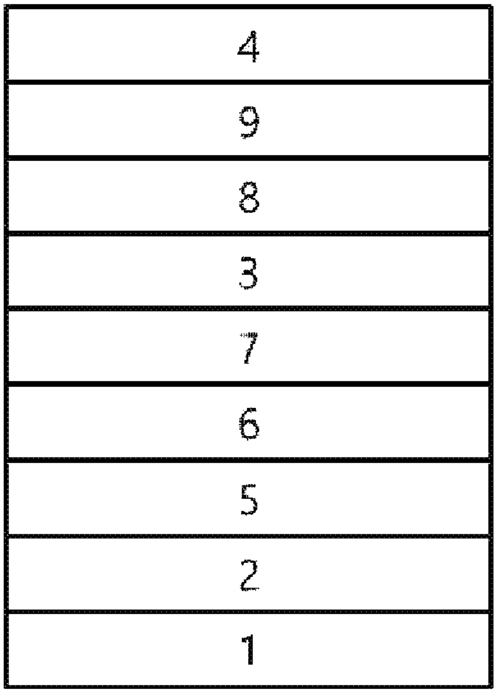

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/009417 filed on Jul. 29, 2019, which claims the benefit of the filing dates of Korean Patent Application No. 10-2018-0088202 filed with Korean Intellectual Property Office on Jul. 27, 2018, and Korean Patent Application No. 10-2019-0091211 filed with Korean Intellectual Property Office on Jul. 26, 2019, the entire contents of which are incorporated herein by reference.

TECHNICAL FIELD

The present invention relates to a novel compound and to an organic light emitting device including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, an excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE (Patent Literature 1) Korean Patent Laid-open Publication No. 10-2000-0051826

Technical Problem

It is an object of the present invention to provide a novel organic light emitting material and an organic light emitting device including the same.

Technical Solution

In one aspect of the invention, a compound of the following Chemical Formula 1 is provided:

Chemical Formula 1

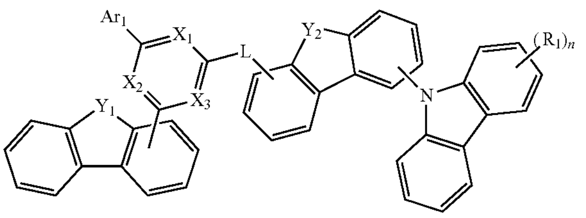

wherein, in Chemical Formula 1, $X_1$ to $X_3$ are each independently CH or N, provided that at least two of $X_1$ to $X_3$ are N, $Y_1$ and $Y_2$ are each independently O or S, L is a single bond; a substituted or unsubstituted $C_{6-60}$ arylene; or a substituted or unsubstituted $C_{2-60}$ heteroarylene containing one or more selected from the group consisting of N, O, and S, $Ar_1$ is a $C_{6-60}$ aryl substituted with at least one deuterium, each $R_1$ is independently hydrogen; deuterium; a halogen; cyano; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heteroaryl containing any one or more heteroatoms selected from the group consisting of N, O, and S, or two adjacent groups of $R_1$ are linked together to form a $C_{6-60}$ aromatic ring or a $C_{2-60}$ heteroaromatic ring containing one or more heteroatoms selected from the group consisting of N, O, and S, and n is an integer of 0 to 4.

In another aspect of the invention, an organic light emitting device is provided, including: a first electrode; a second electrode provided to face the first electrode; and one or more organic material layers provided between the first electrode and the second electrode, wherein one or more layers of the organic material layers includes the compound of Chemical Formula 1.

Advantageous Effects

The compound of Chemical Formula 1 described above can be used as a material of an organic material layer of an organic light emitting device, and may improve efficiency, achieve a low driving voltage, and/or improve lifetime characteristics in the organic light emitting device. In particular, the compound of Chemical Formula 1 described above can be used as a material for hole injection, hole transport, hole injection and transport, light emitting, electron transport, or electron injection.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION

Hereinafter, the present invention will be described in more detail to help understanding of the present invention.

In one embodiment of the invention, the compound of Chemical Formula 1 is provided.

As used herein, the notation ╪ or ┆ means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group containing at least one of N, O, and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group, and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulae, but is not limited thereto.

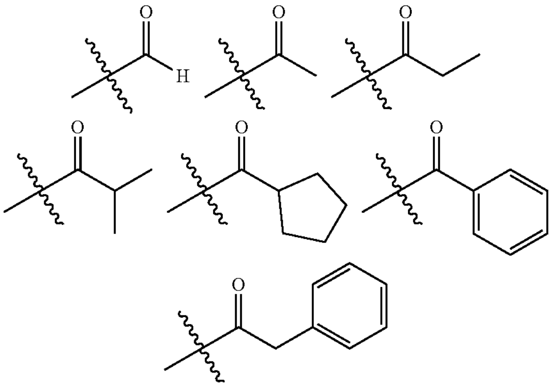

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

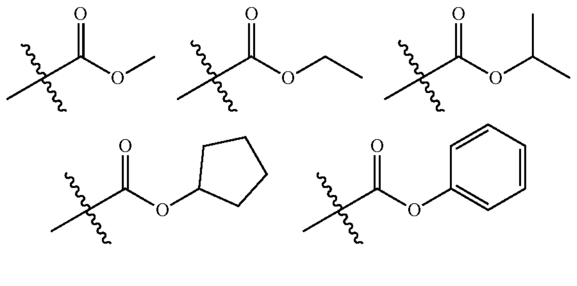

-continued

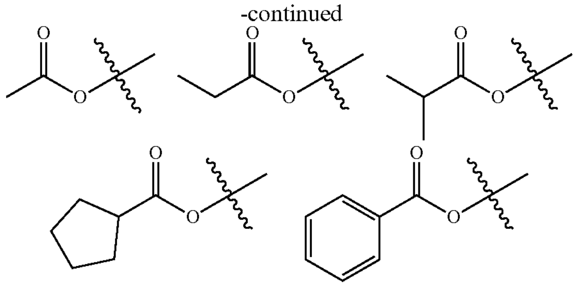

In the present specification, the number of carbon atoms of an imide group is not particularly limited, but is preferably 1 to 25. Specifically, the imide group may be a compound having the following structural formulae, but is not limited thereto.

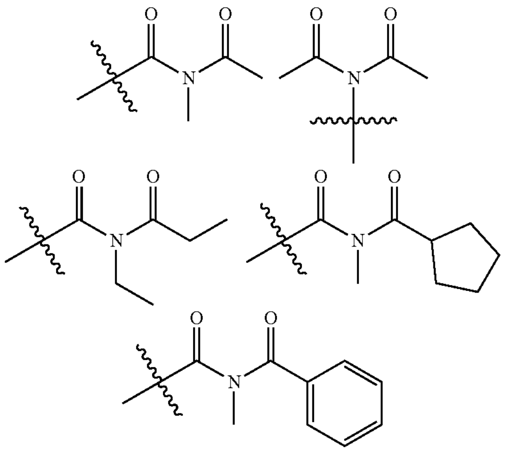

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituent groups may be bonded to each other to form a spiro structure. In the case where the fluorenyl group is substituted,

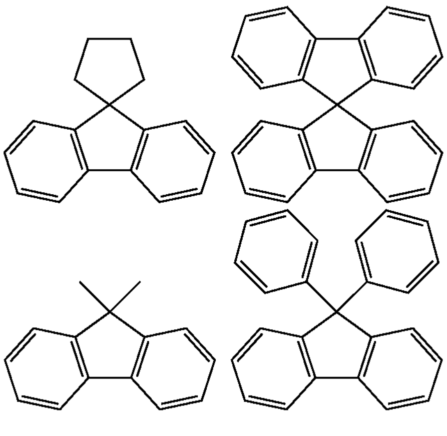

-continued

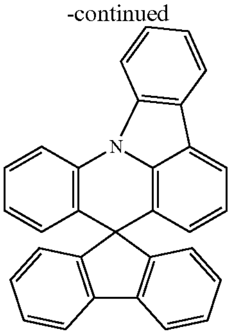

and the like can be formed. However, the structure is not limited thereto.

In the present specification, a heterocyclic group is one including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Preferably, Chemical Formula 1 may be any one of the following Chemical Formula 2 to Chemical Formula 5:

Chemical Formula 2

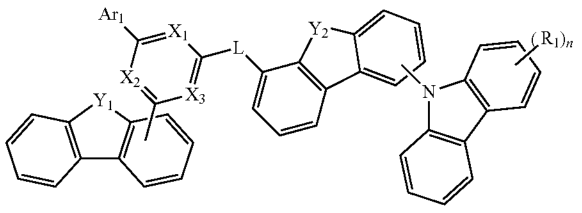

Chemical Formula 3

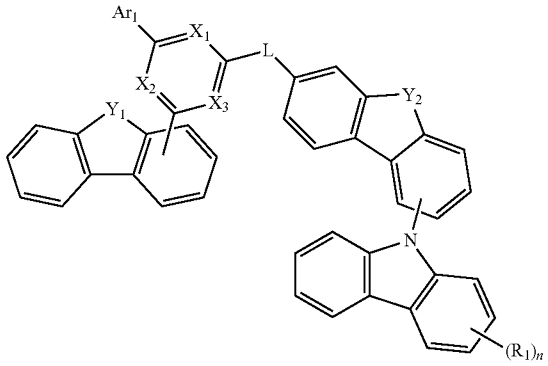

Chemical Formula 4

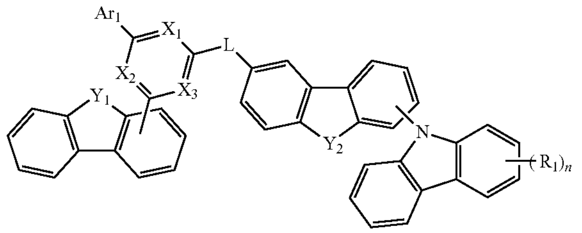

Chemical Formula 5

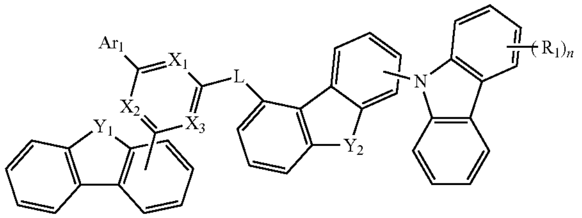

wherein, in Chemical Formulas 2 to 5, $X_1$ to $X_3$, $Y_1$, $Y_2$, L, $Ar_1$, $R_1$, and n are the same as those defined in Chemical Formula 1.

More preferably, Chemical Formula 1 may be any one of the following Chemical Formula 2-1 to Chemical Formula 5-4:

Chemical Formula 2-1

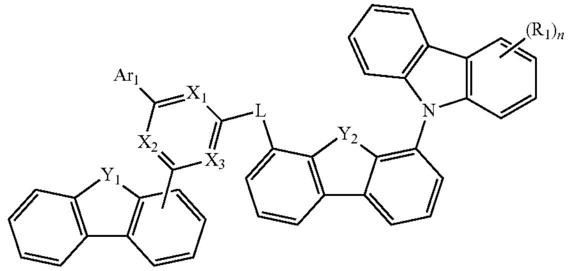

Chemical Formula 2-2

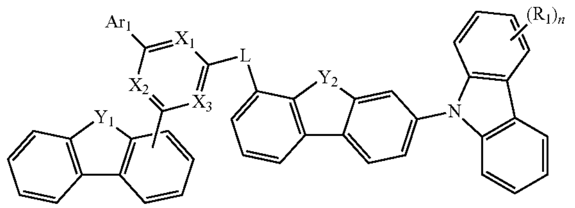

Chemical Formula 2-3

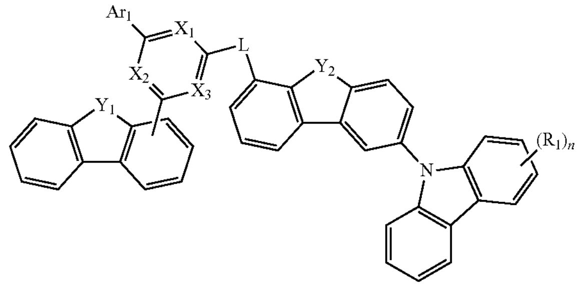

Chemical Formula 2-4

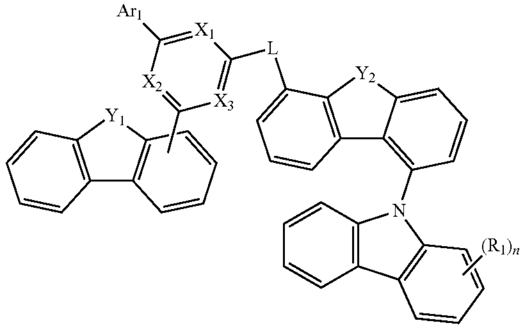

Chemcial Formula 3-1

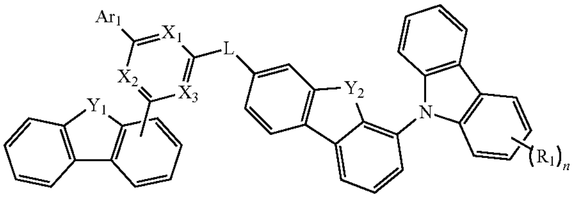

-continued
Chemical Formula 3-2
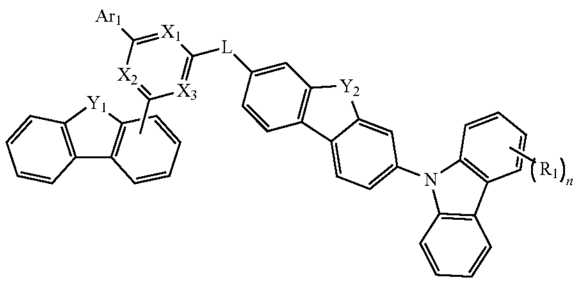
Chemical Formula 3-3
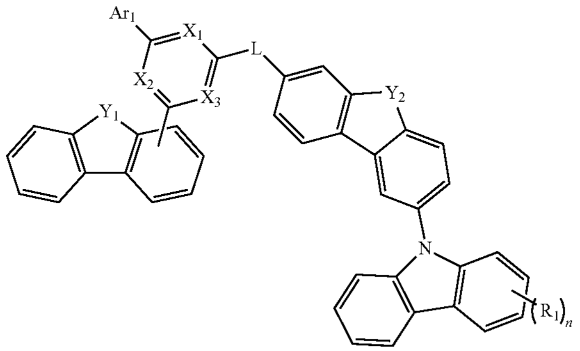
Chemical Formula 3-4
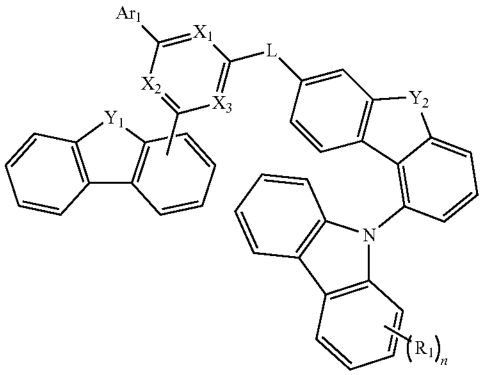
Chemical Formula 4-1
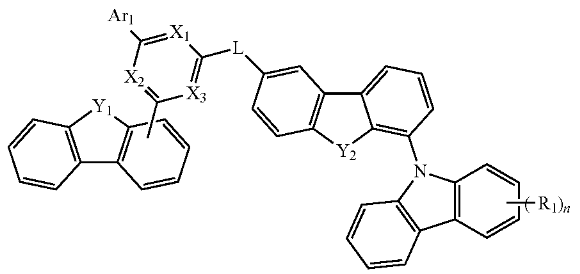
Chemical Formula 4-2
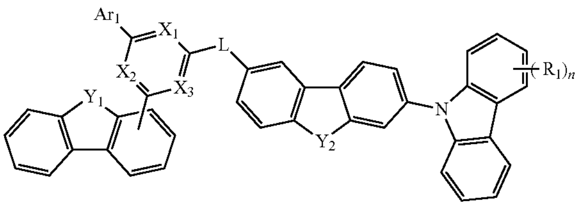
-continued
Chemical Formula 4-3
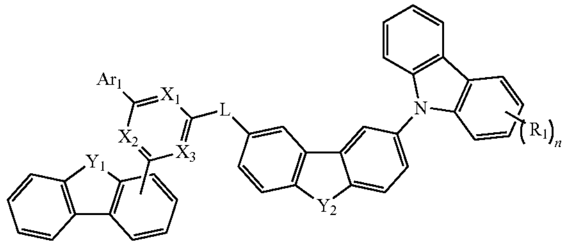
Chemical Formula 4-4
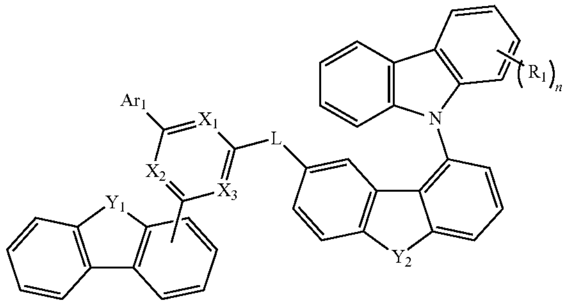
Chemical Formula 5-1
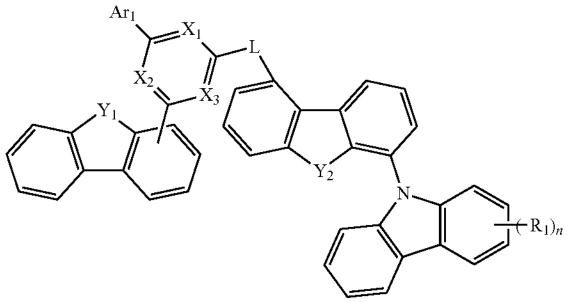
Chemical Formula 5-2
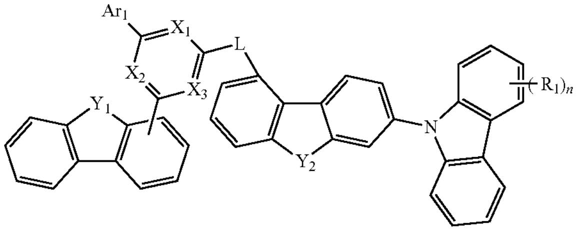
Chemical Formula 5-3
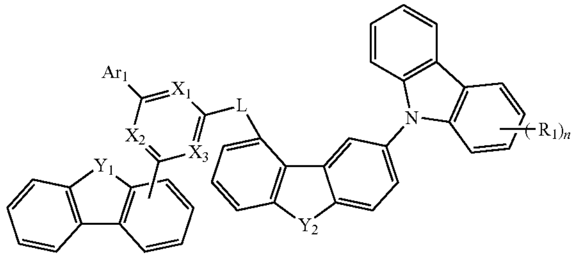

-continued

Chemical Formula 5-4

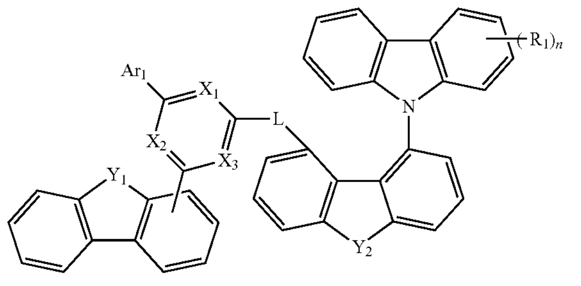

wherein, in Chemical Formulas 2-1 to 5-4, $X_1$ to $X_3$, $Y_1$, $Y_2$, L, $Ar_1$, $R_1$, and n are the same as those defined in Chemical Formula 1.

Preferably, $X_1$ to $X_3$ may all be N.

Preferably, L may be a single bond; a substituted or unsubstituted $C_{6-20}$ arylene; or a substituted or unsubstituted $C_{6-20}$ heteroarylene containing any one or more selected from the group consisting of N, O, and S.

More preferably, L may be a single bond, phenylene, biphenylene, naphthylene, carbazolylene, dibenzofuranylene, or dibenzothiophenylene.

Most preferably, L may be a single bond.

$Ar_1$ is a $C_{6-20}$ aryl substituted with at least one deuterium.

More preferably, $Ar_1$ may be phenyl substituted with five deuteriums.

Preferably, each $R_1$ may independently be hydrogen; deuterium; a halogen; cyano; nitro; amino; a substituted or unsubstituted $C_{1-10}$ alkyl; a substituted or unsubstituted $C_{3-20}$ cycloalkyl; a substituted or unsubstituted $C_{2-10}$ alkenyl; a substituted or unsubstituted $C_{6-20}$ aryl; or a substituted or unsubstituted $C_{6-20}$ heteroaryl containing any one or more heteroatoms selected from the group consisting of N, O, and S, or two adjacent groups of $R_1$ may be linked together to form a $C_{6-20}$ aromatic ring or a $C_{2-20}$ heteroaromatic ring containing one or more heteroatoms selected from the group consisting of N, O, and S.

More preferably, each $R_1$ may independently be hydrogen or phenyl, or two adjacent groups of $R_1$ may be linked together to form one ring selected from the group consisting of the following.

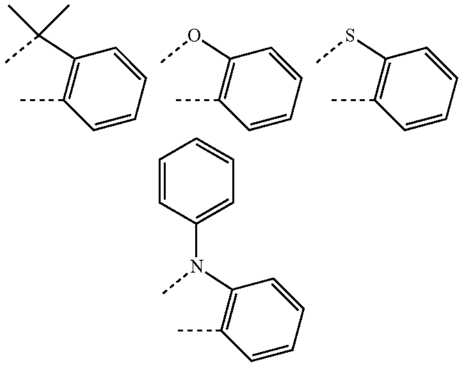

Most preferably, each $R_1$ may independently be hydrogen or phenyl, or two adjacent groups of $R_1$ may be linked together to form

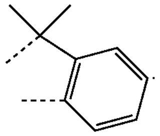

Preferably, n is an integer of 0 to 2.

Preferably, Chemical Formula 1 may be either one of the following Chemical Formula 1-1 or Chemical Formula 1-2:

[Chemical Formula 1-1]

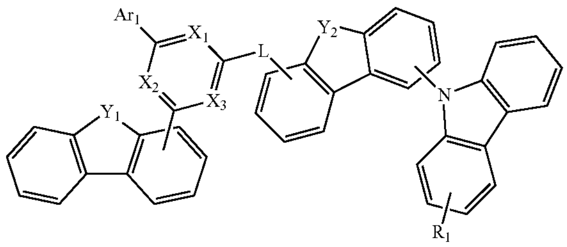

[Chemical Formula 1-2]

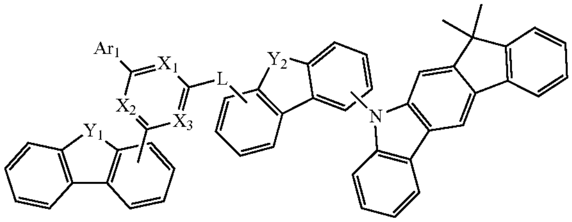

wherein, in Chemical Formula 1-1 and 1-2, $X_1$ to $X_3$, $Y_1$, $Y_2$, L, $Ar_1$, and $R_1$ are the same as those defined in Chemical Formula 1.

Representative examples of the compound of Chemical Formula 1 are as follows.

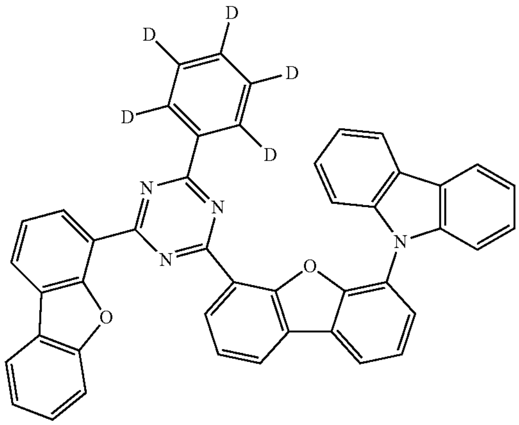

-continued
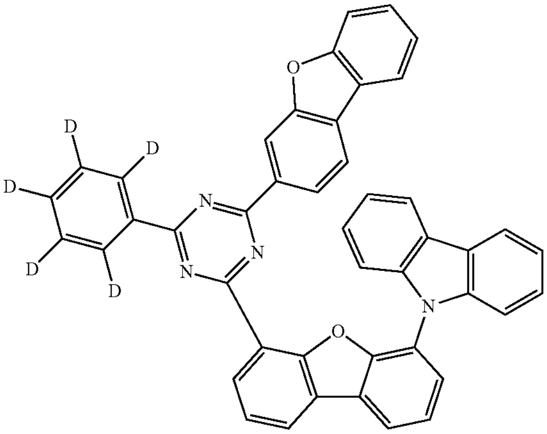
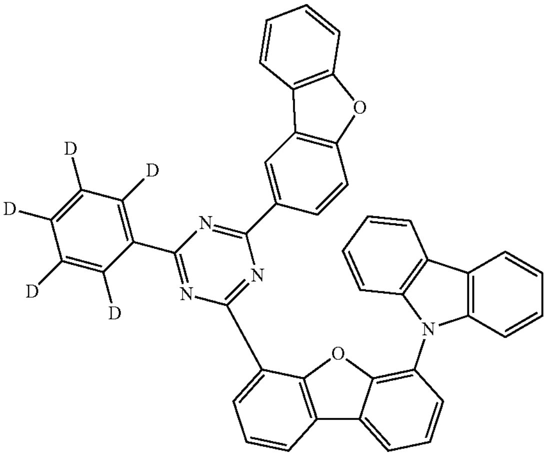
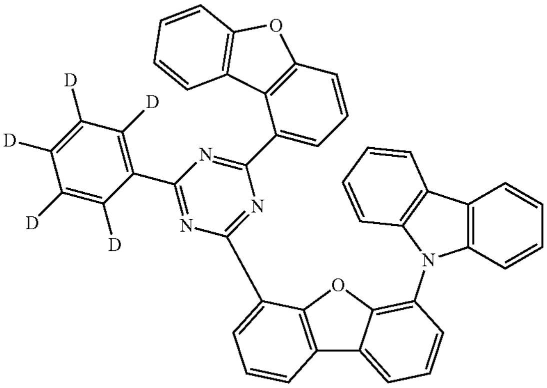
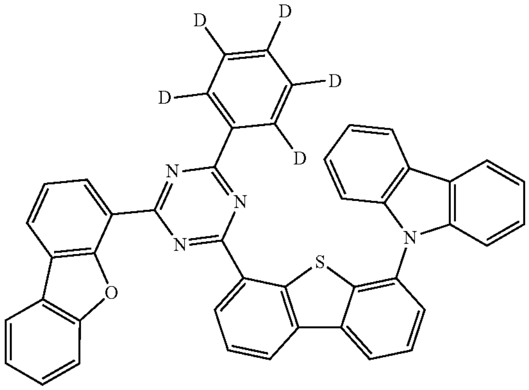
-continued
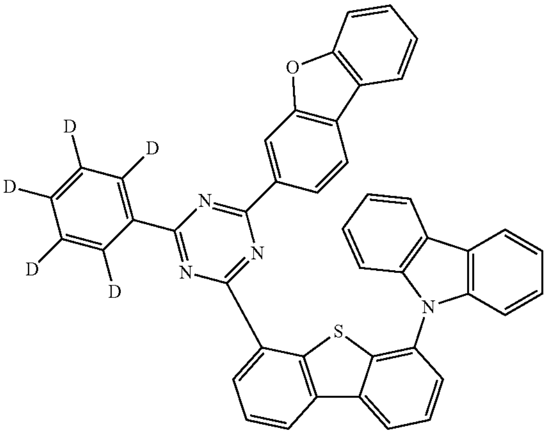
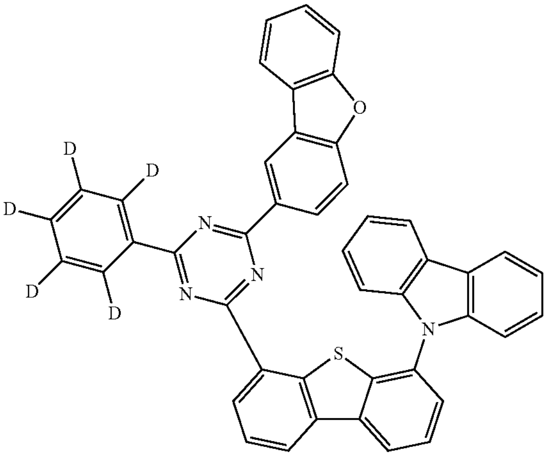
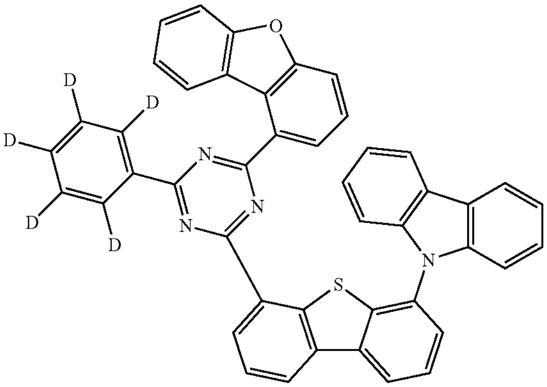
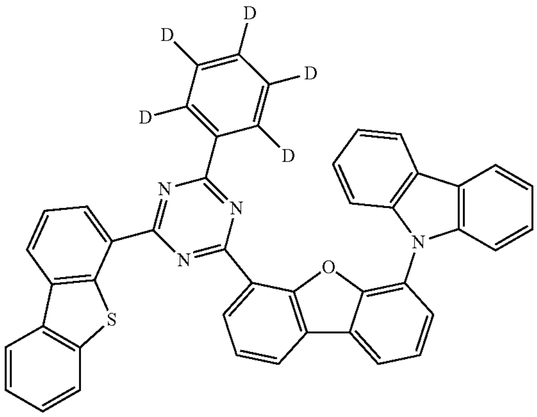

-continued
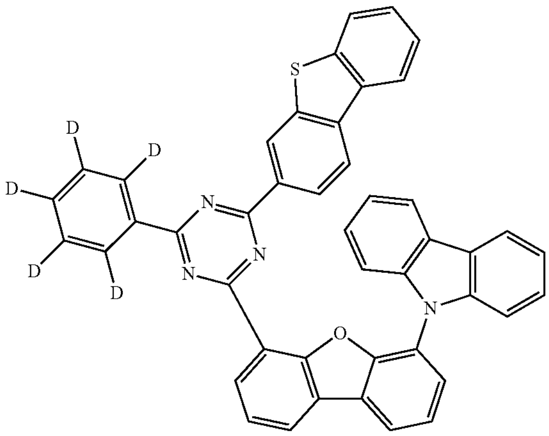
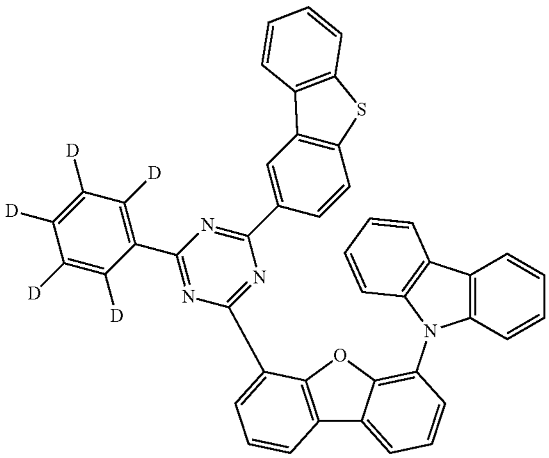
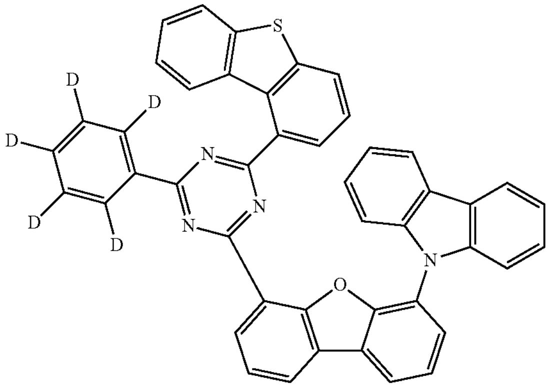
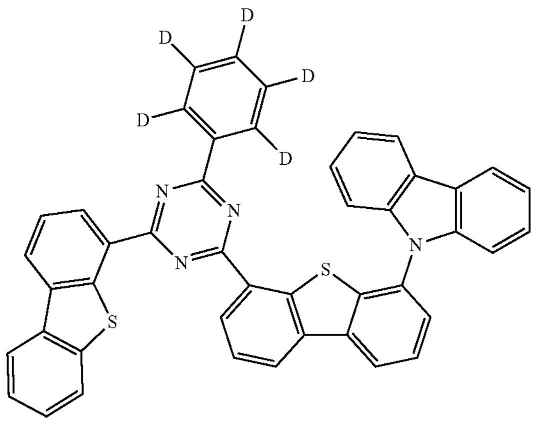
-continued
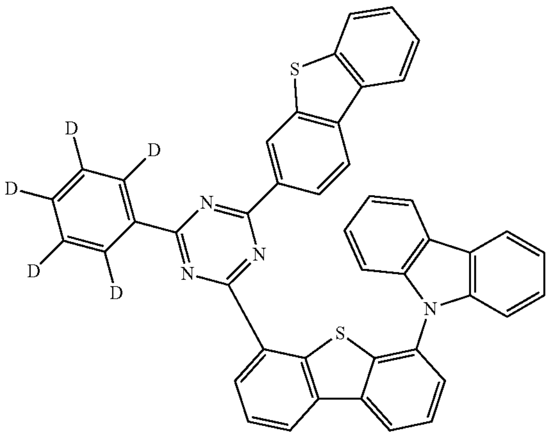
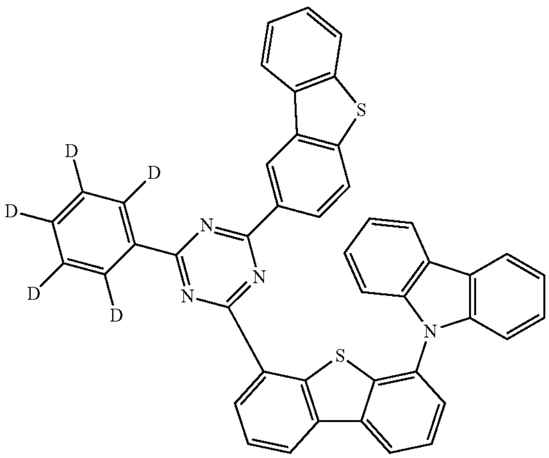
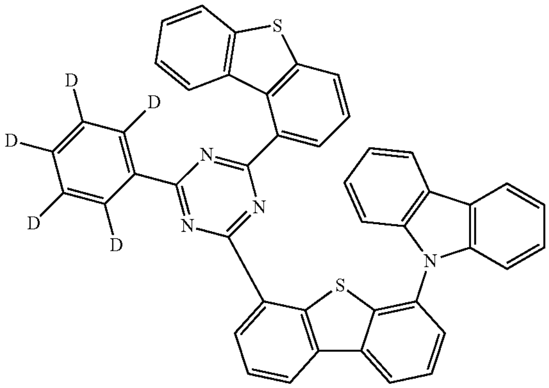
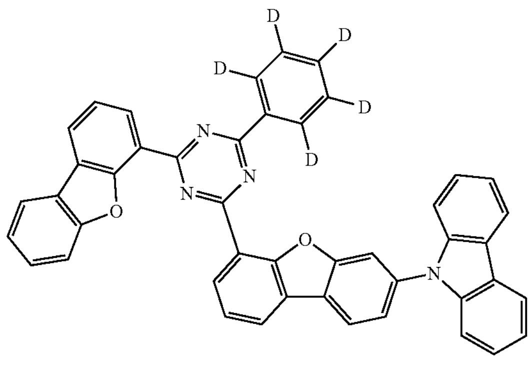

-continued
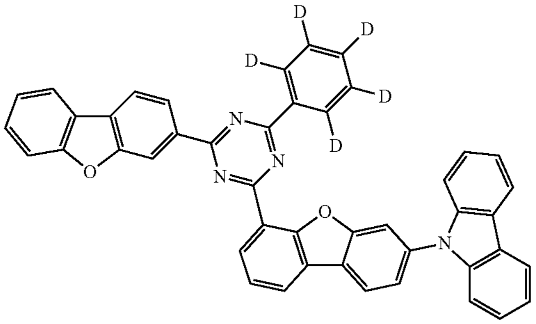
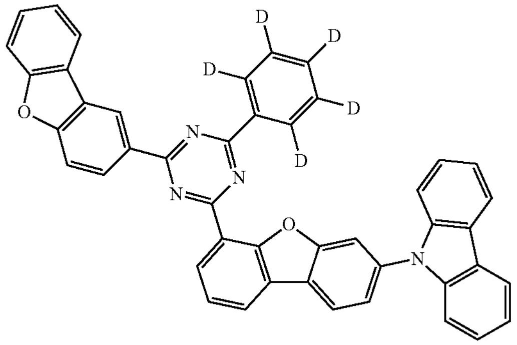
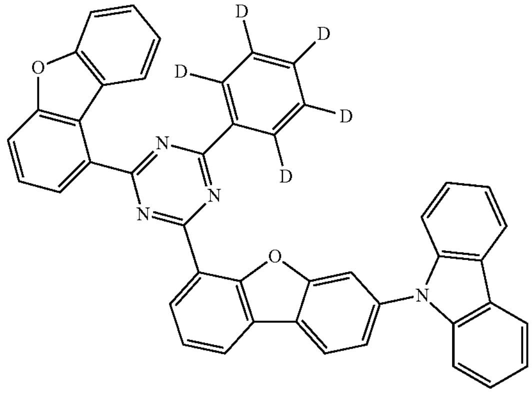
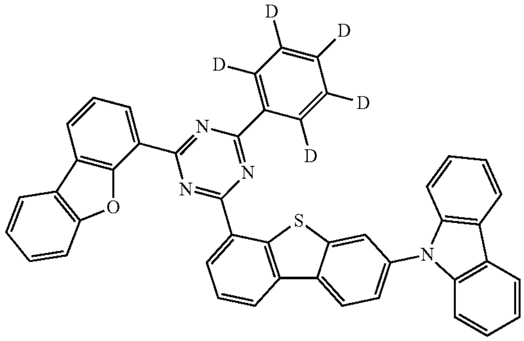
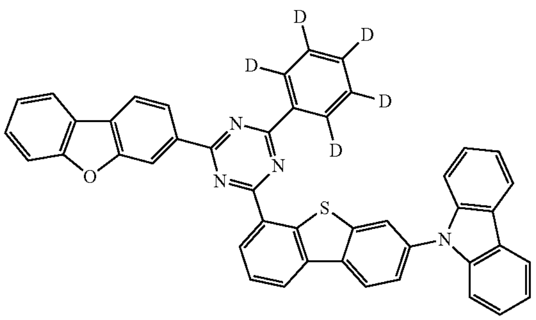
-continued
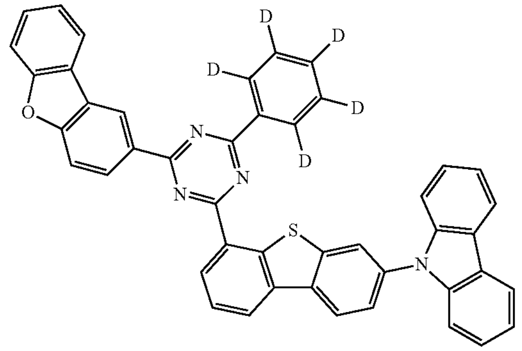
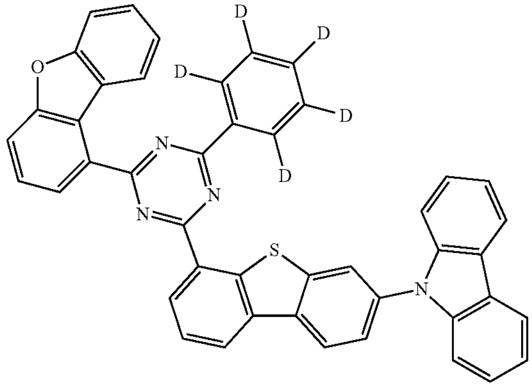
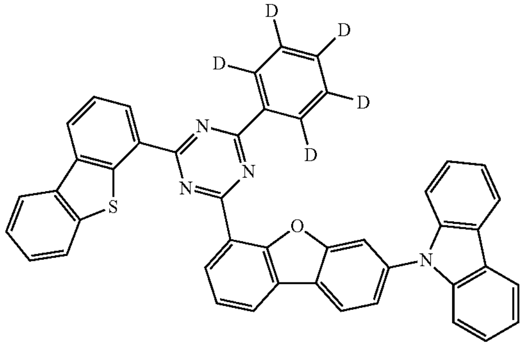
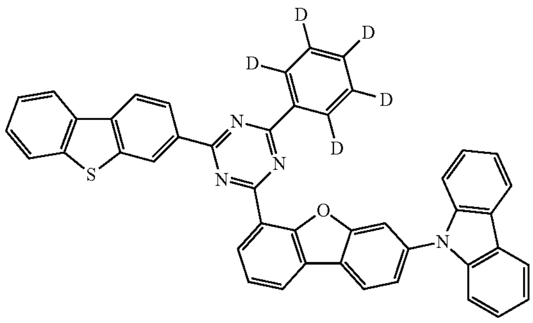

-continued
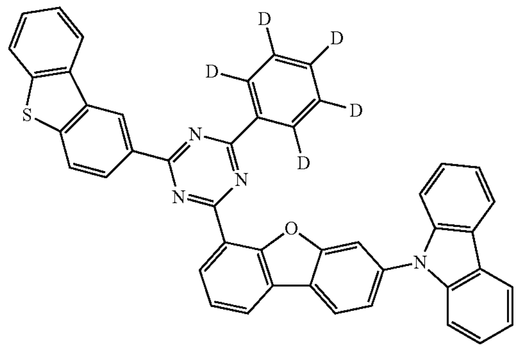
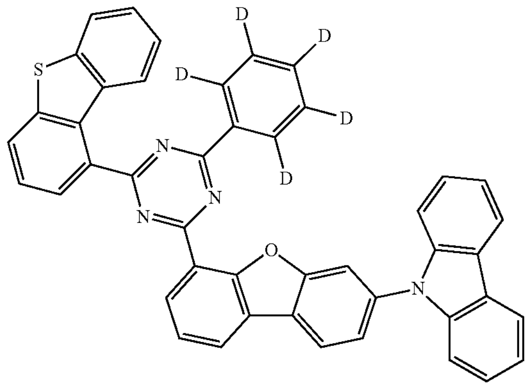
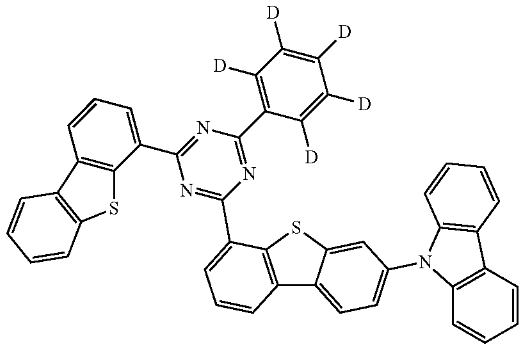
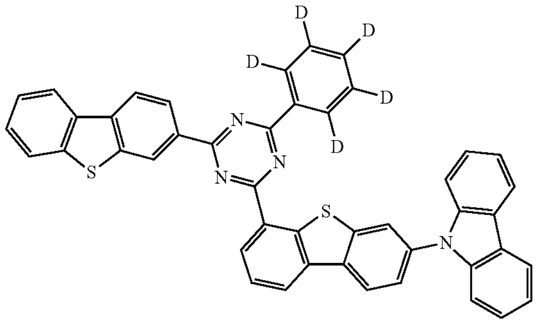
-continued
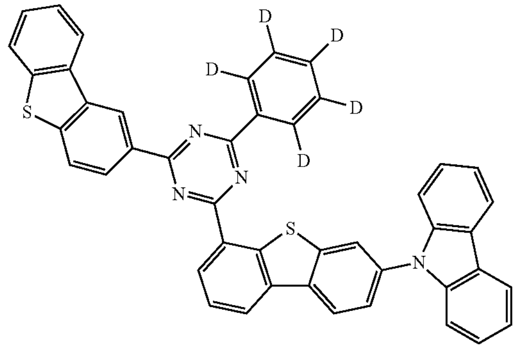
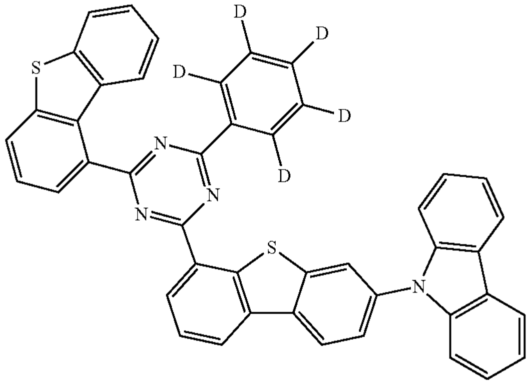
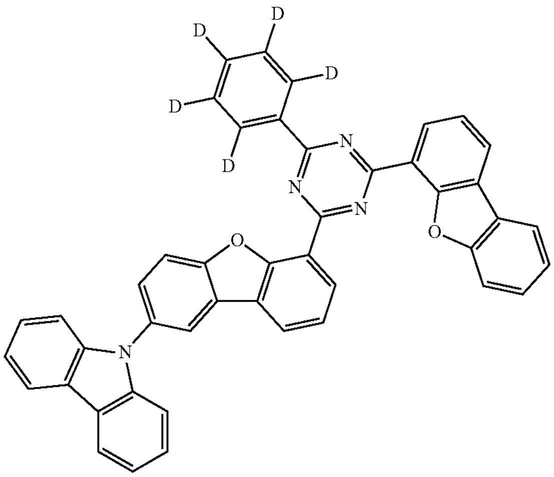
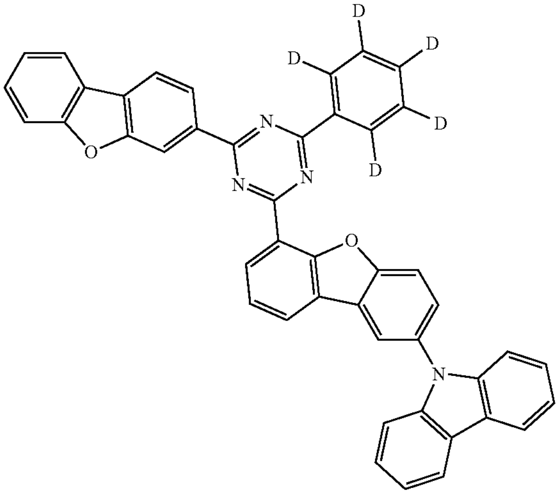

-continued
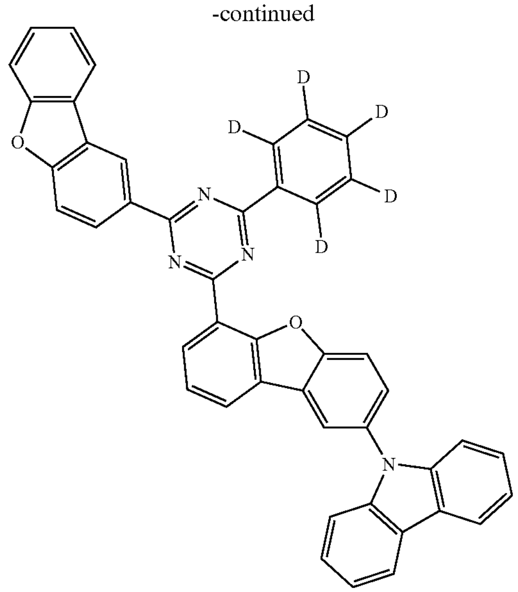
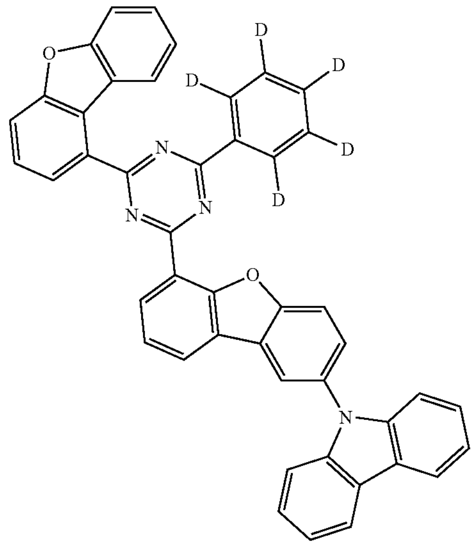
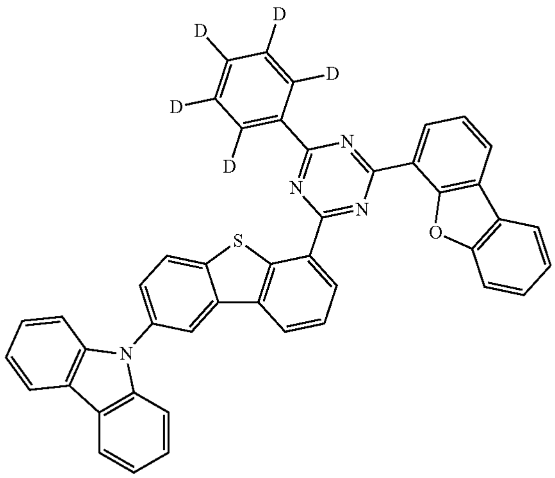
-continued
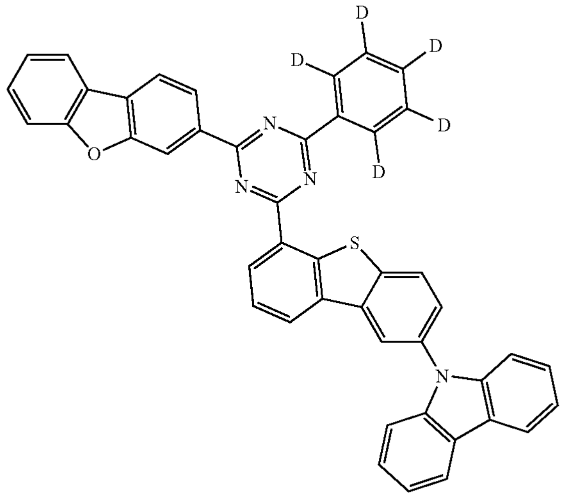
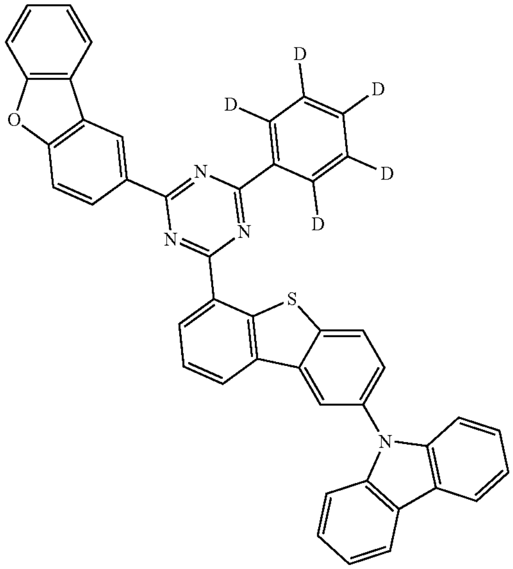
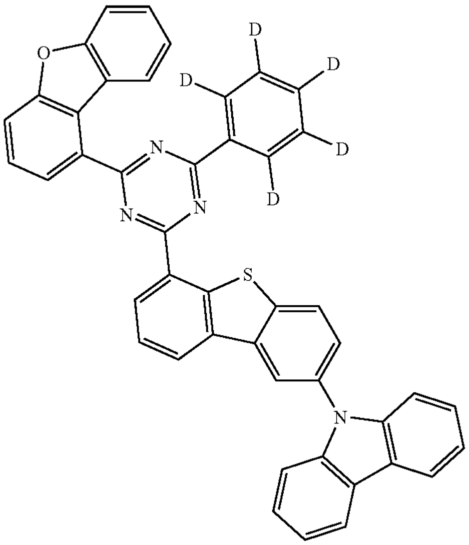

-continued
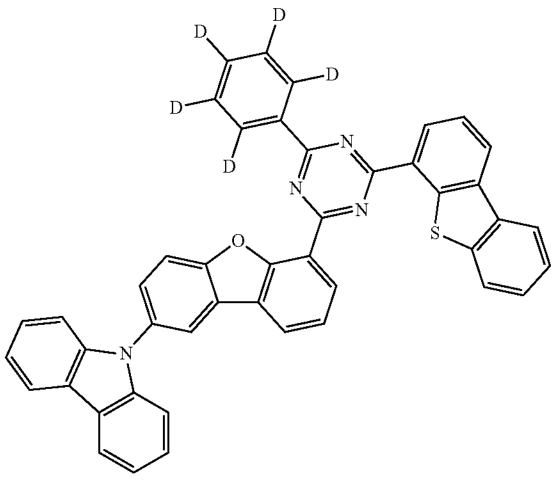
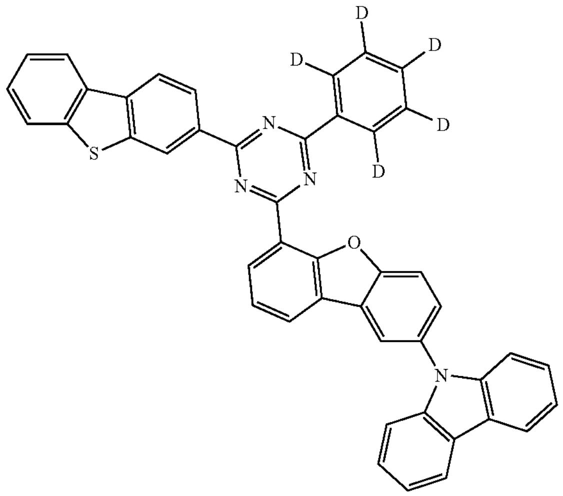
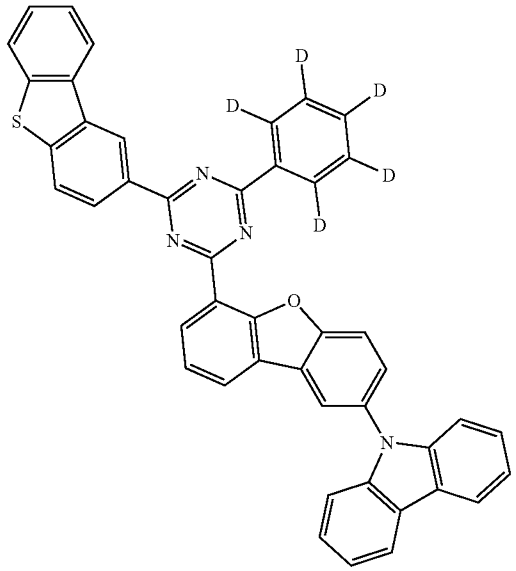
-continued
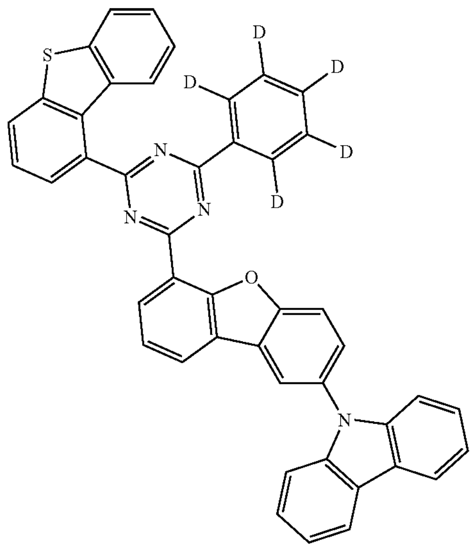
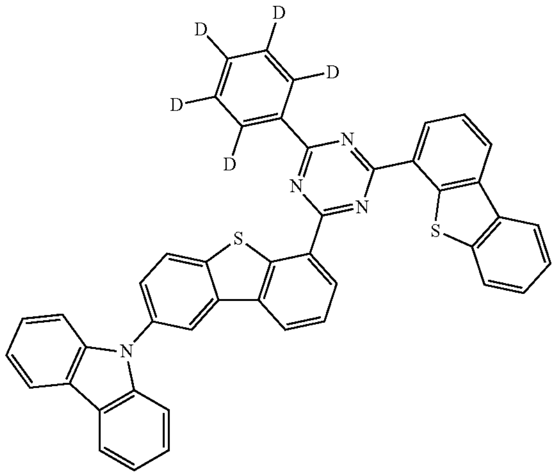
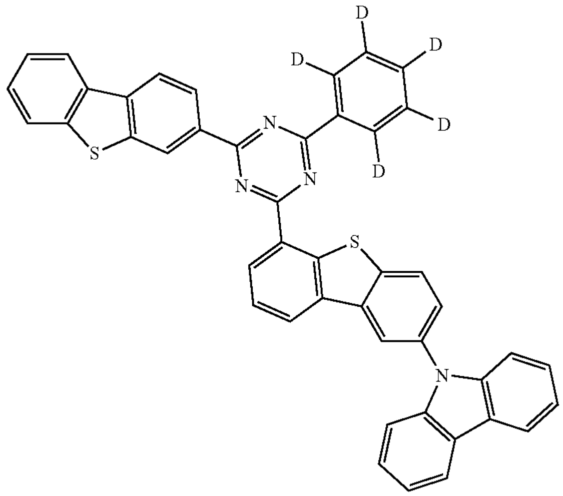

-continued
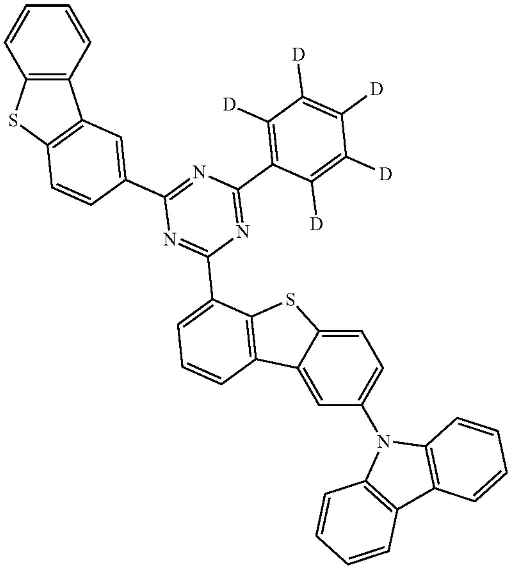
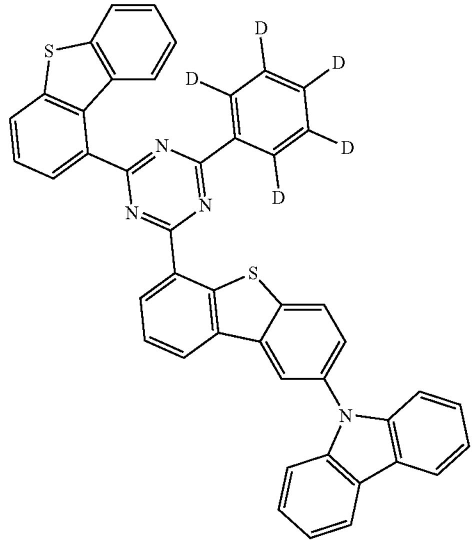
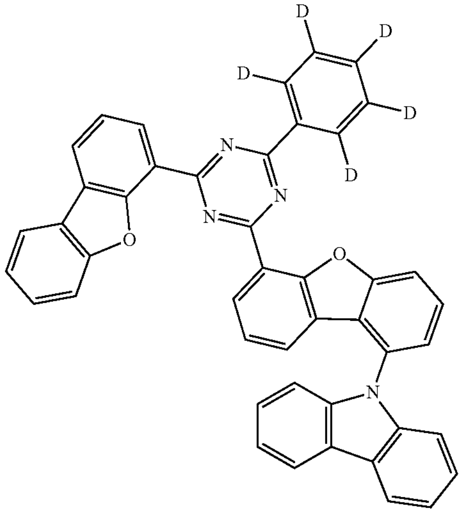
-continued
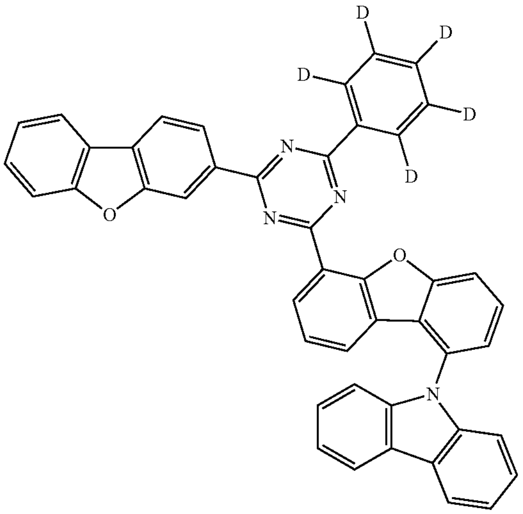
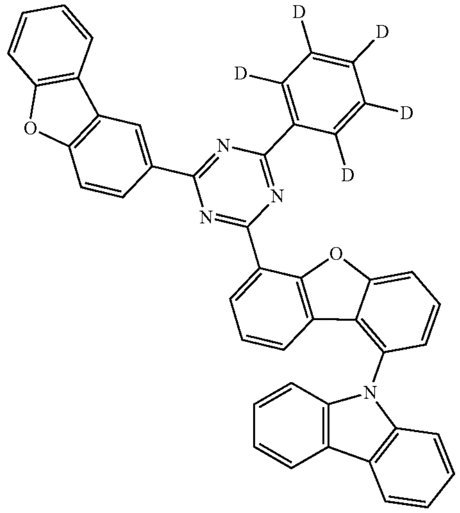
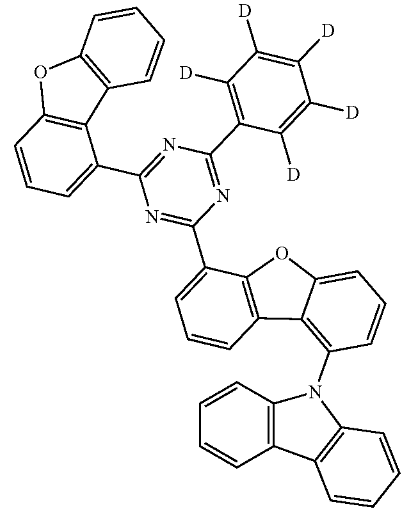

-continued
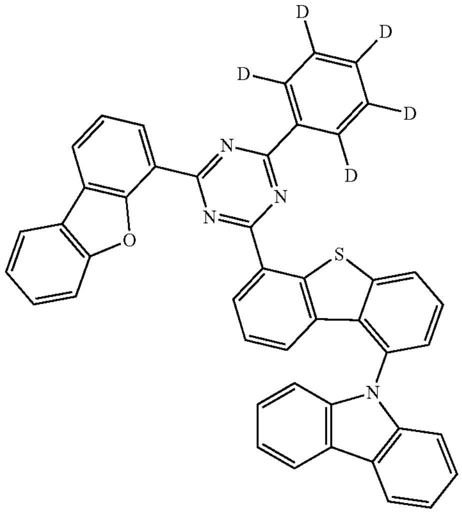
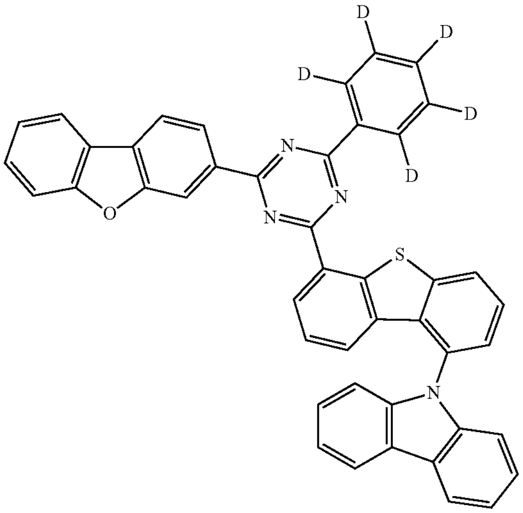
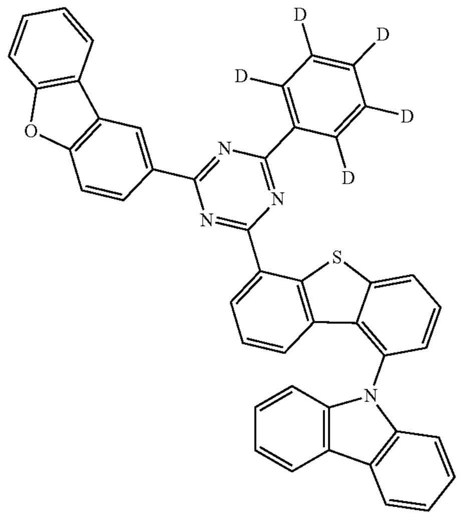
-continued
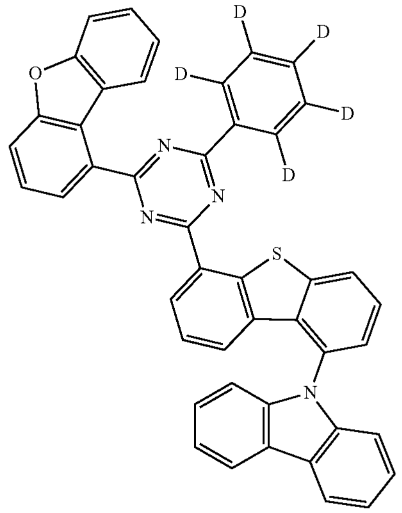
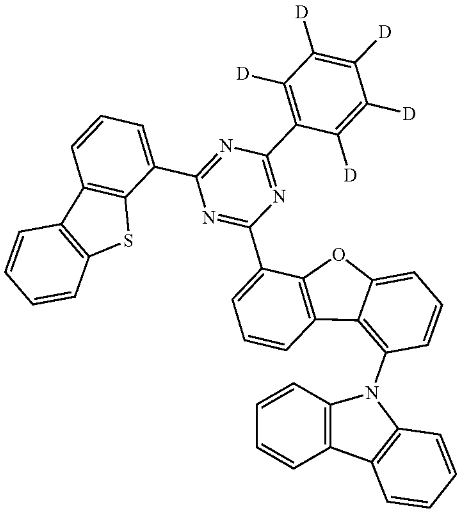
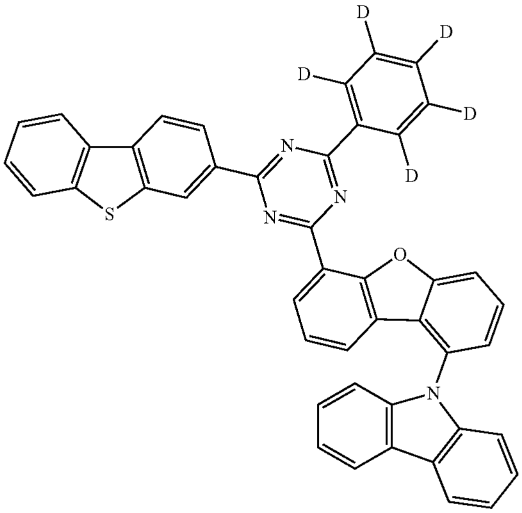

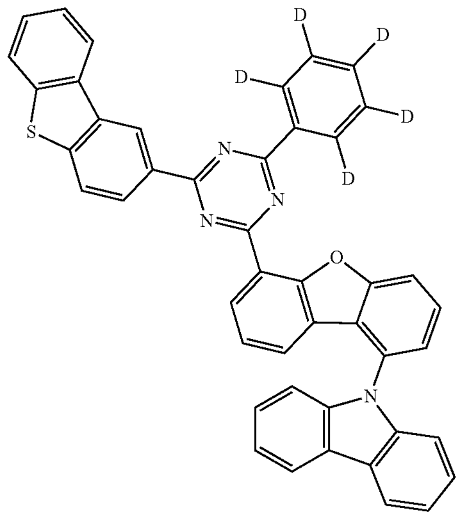
-continued
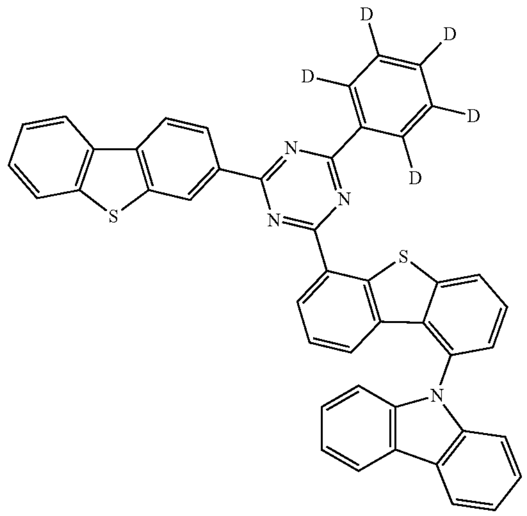
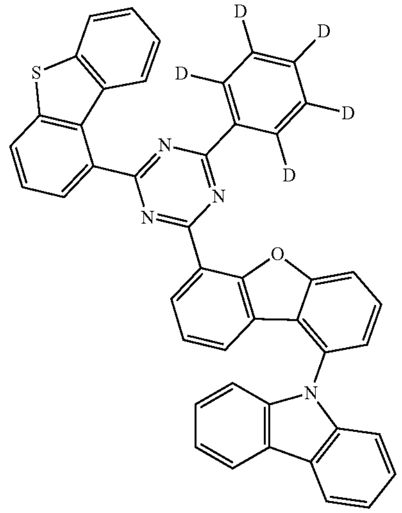
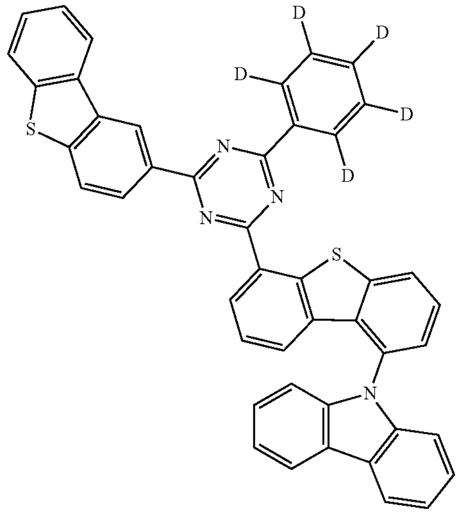
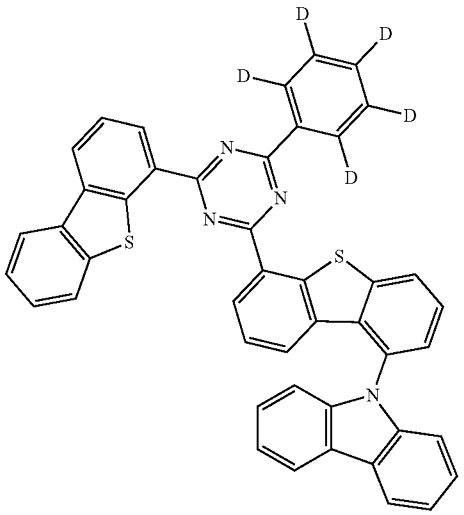
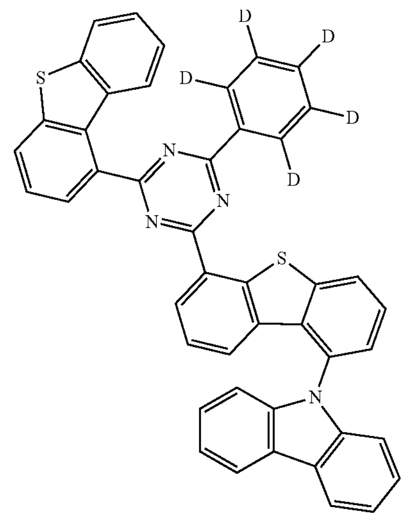

-continued
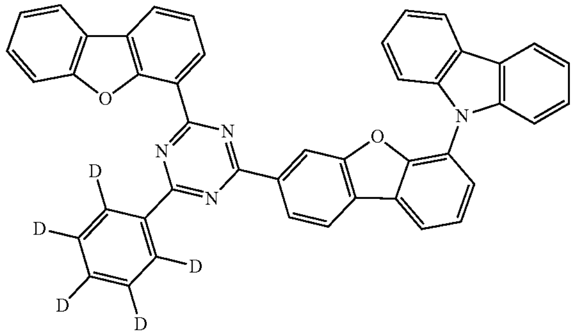
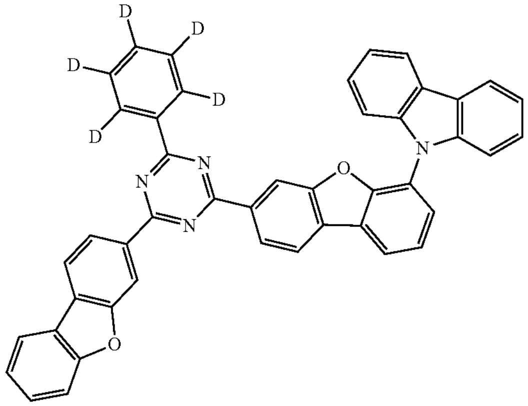
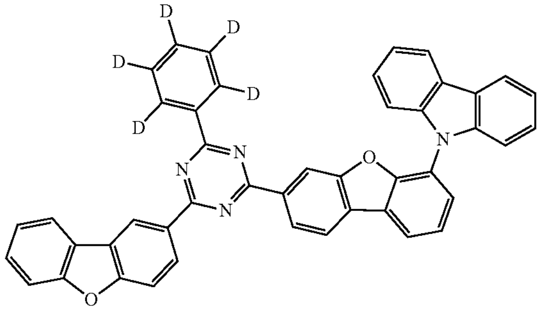
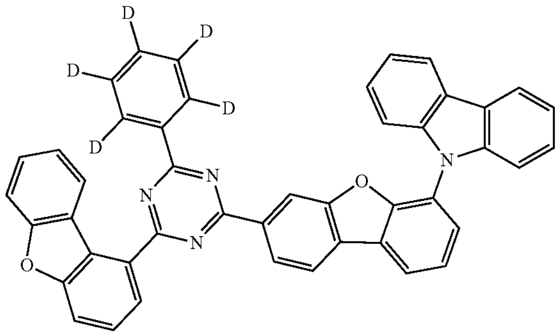
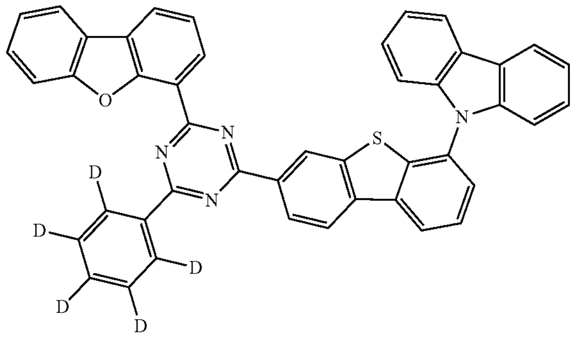
-continued
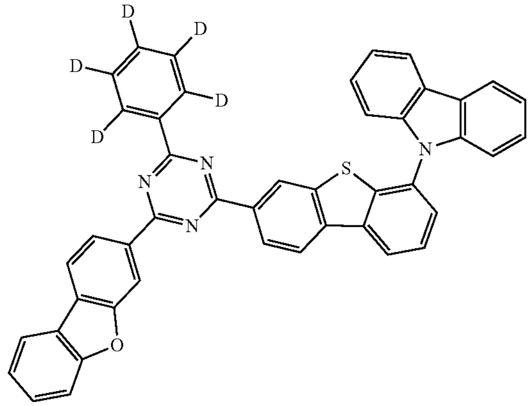
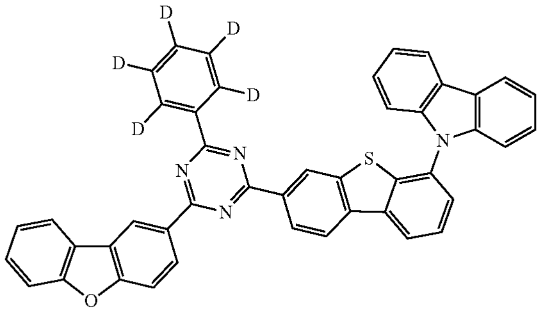
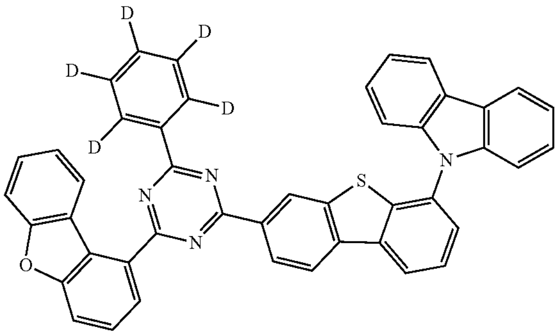
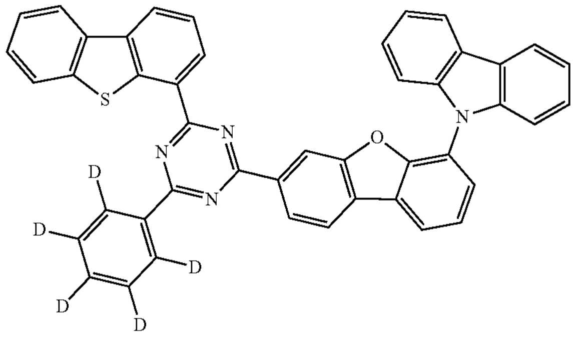

-continued
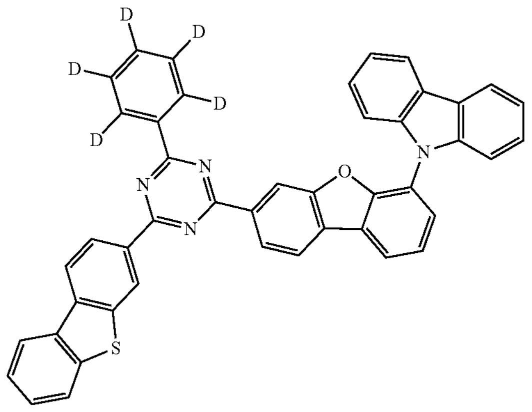
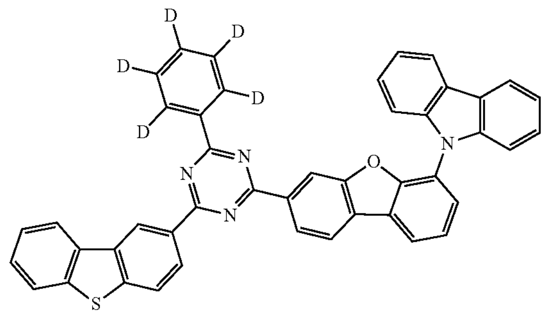
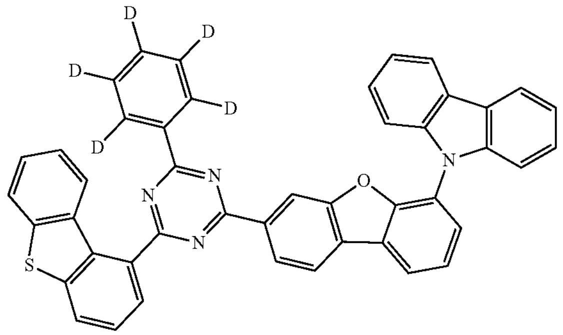
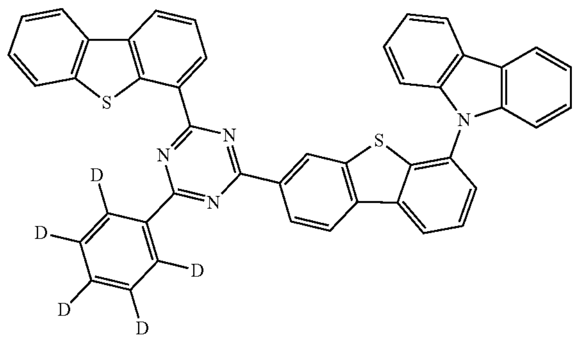
-continued
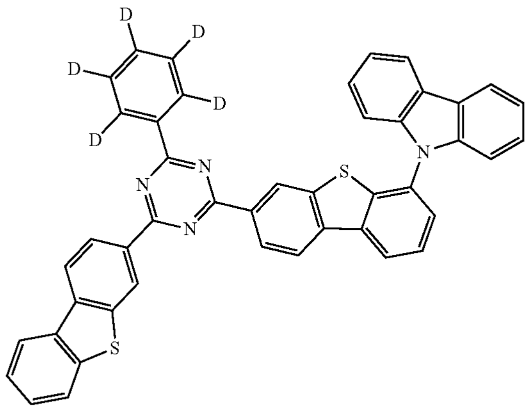
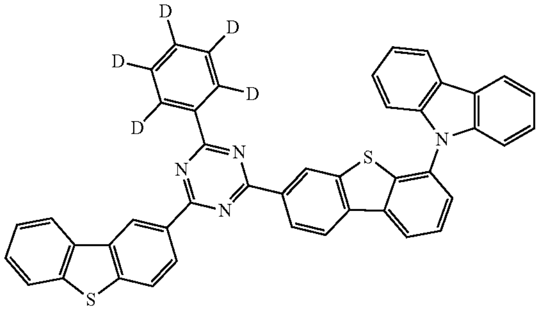
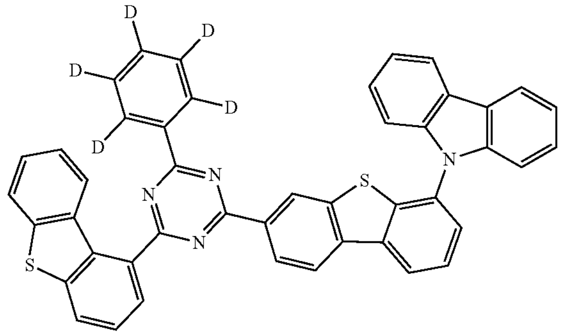
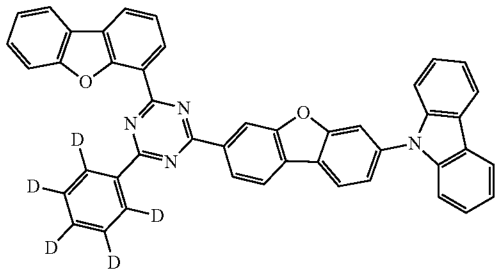
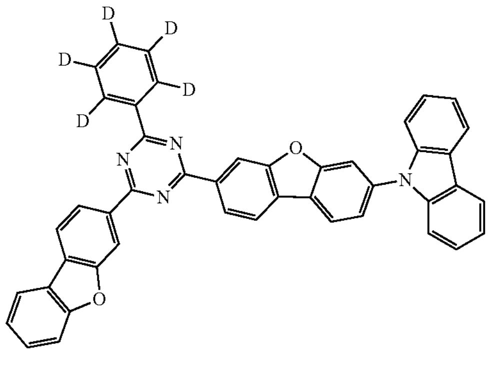

-continued
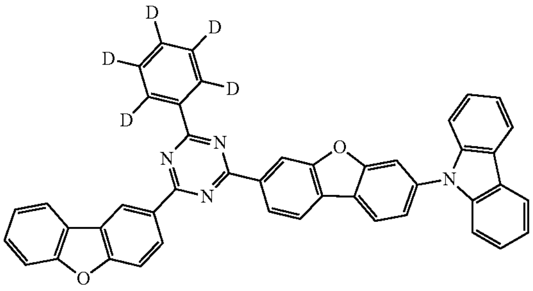
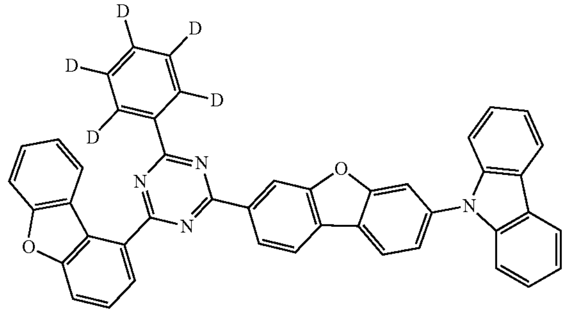
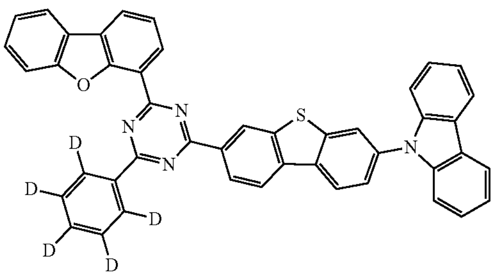
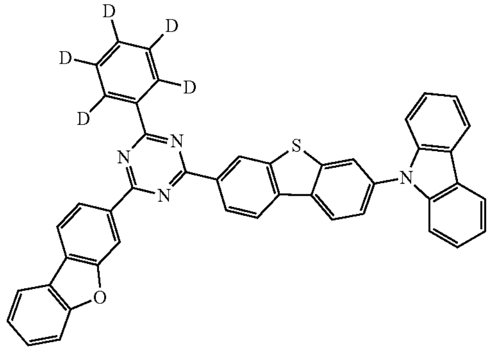
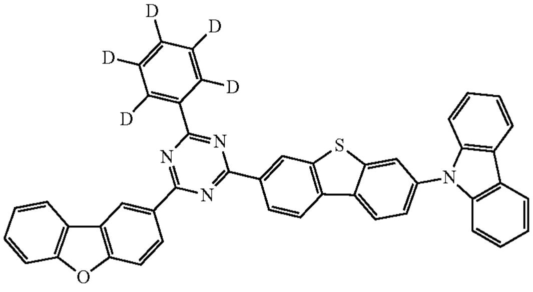
-continued
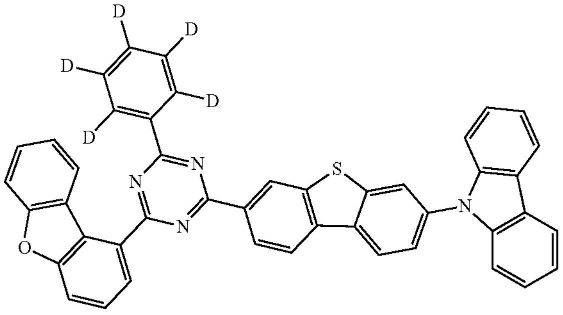
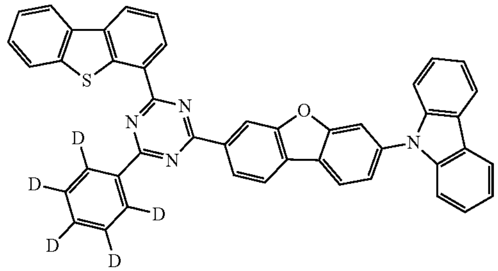
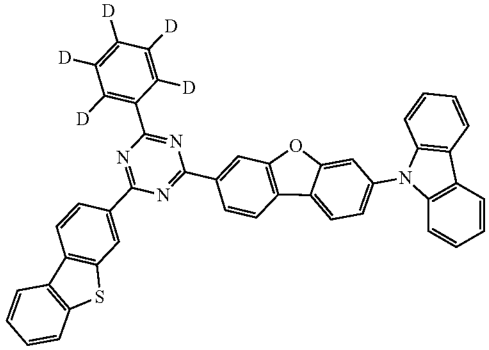
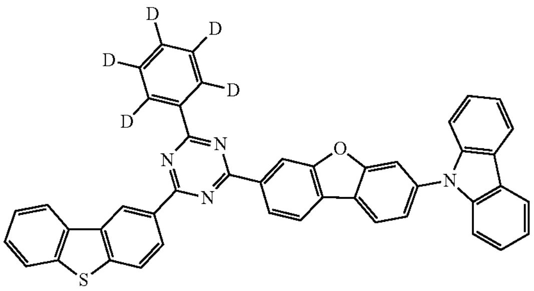
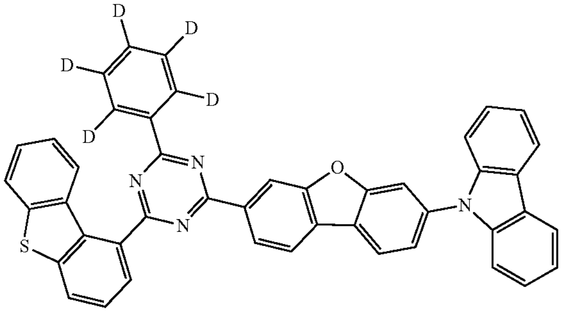

-continued
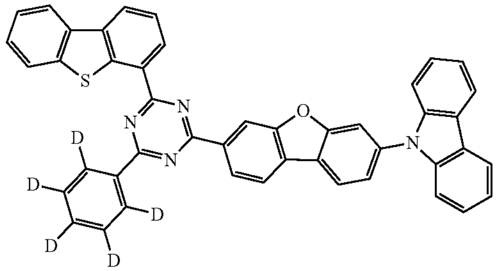
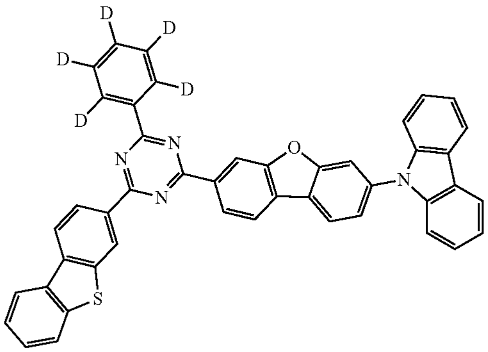
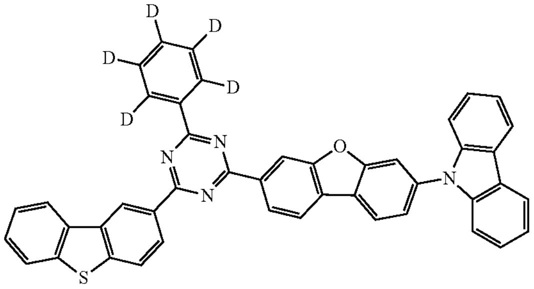
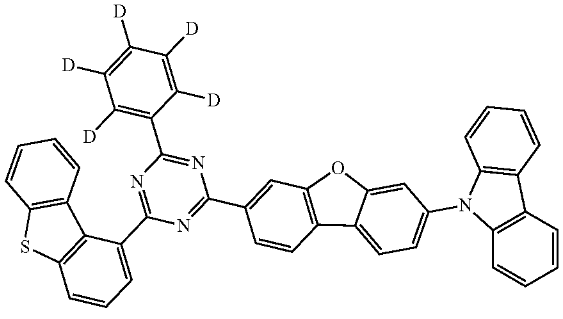
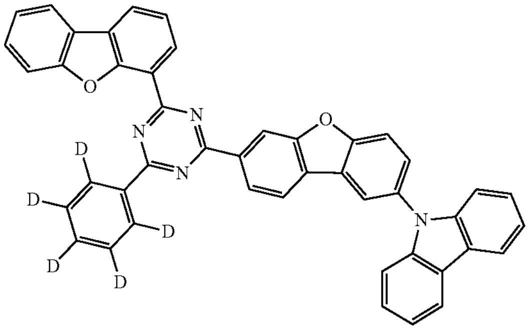
-continued
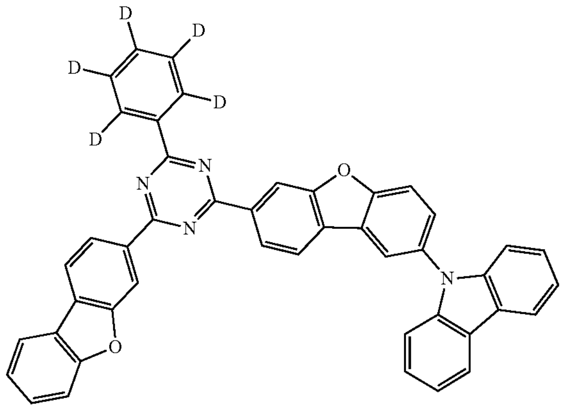
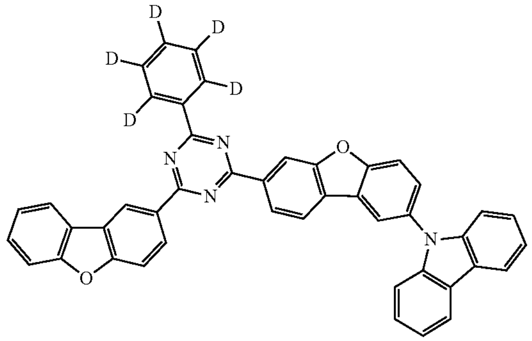
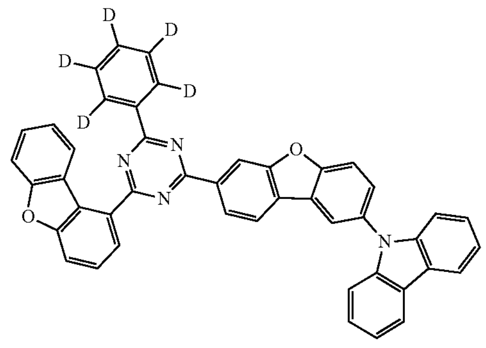
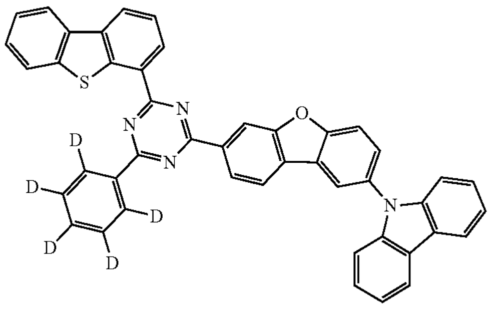

-continued
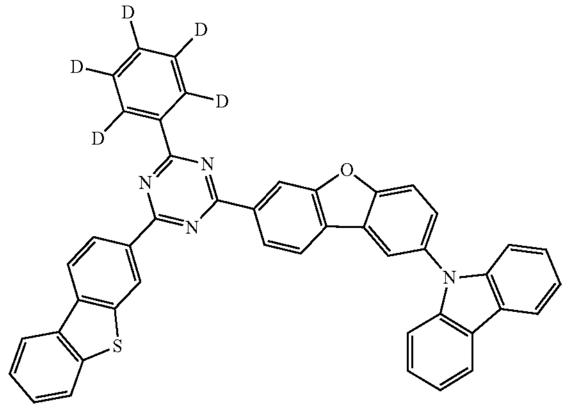
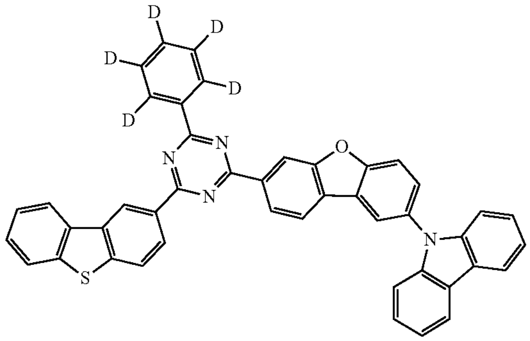
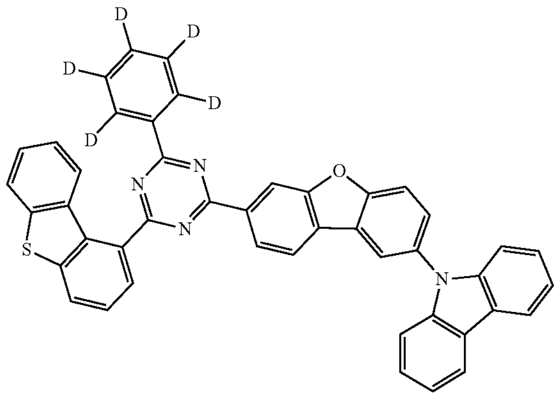
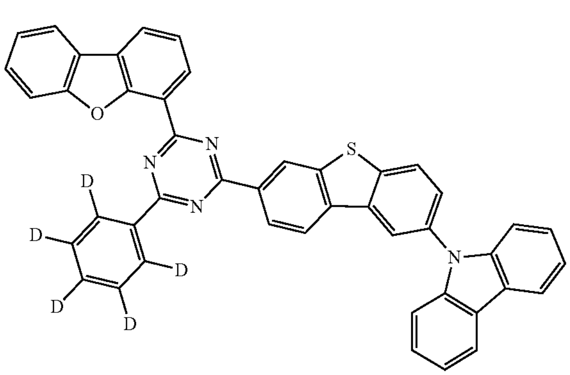
-continued
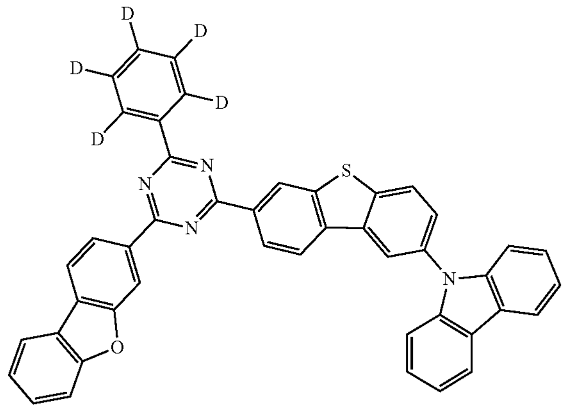
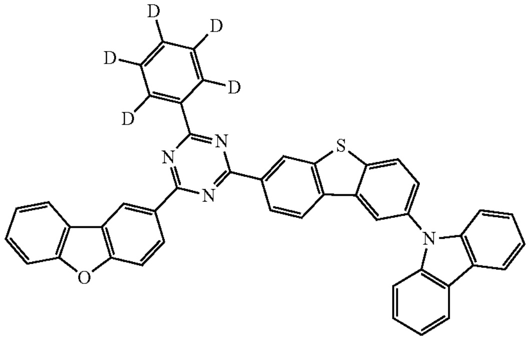
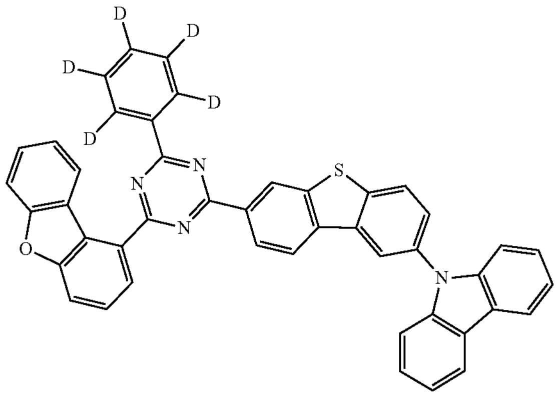
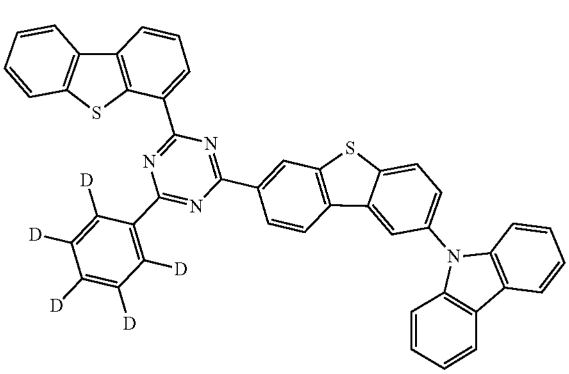

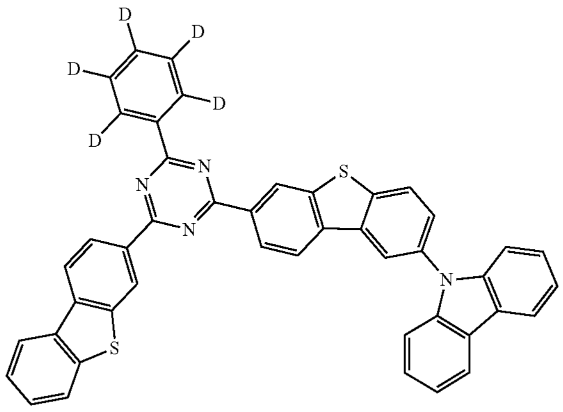
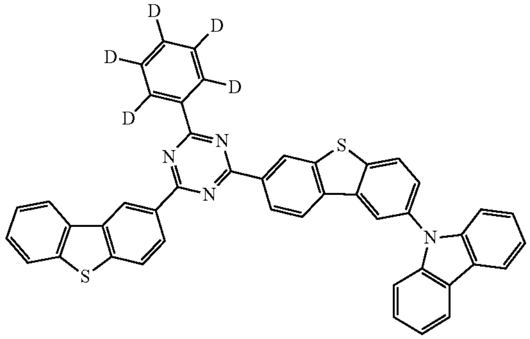
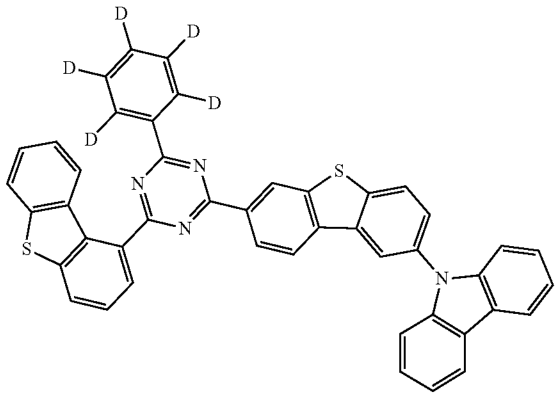
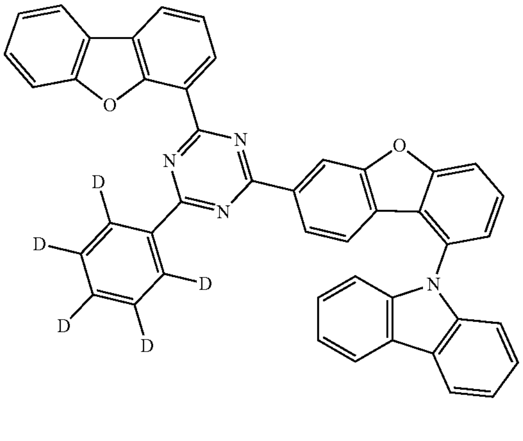
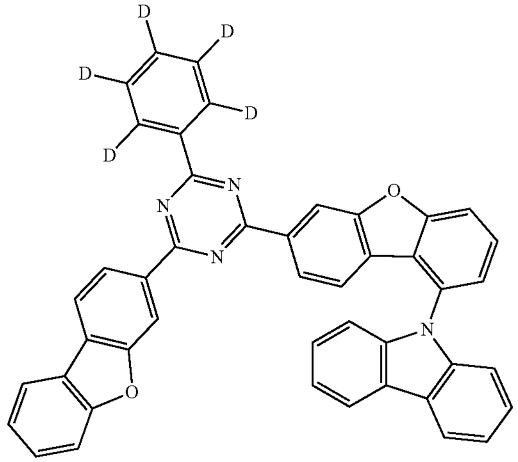
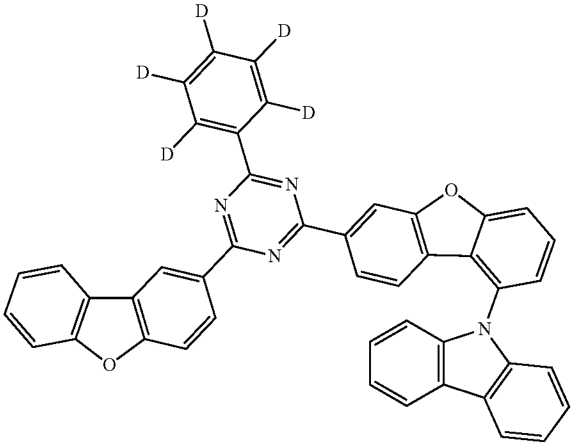
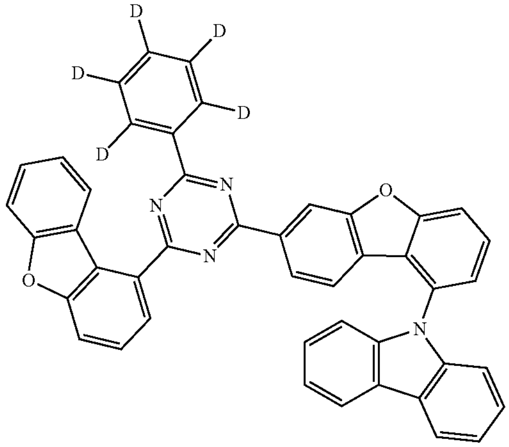

-continued
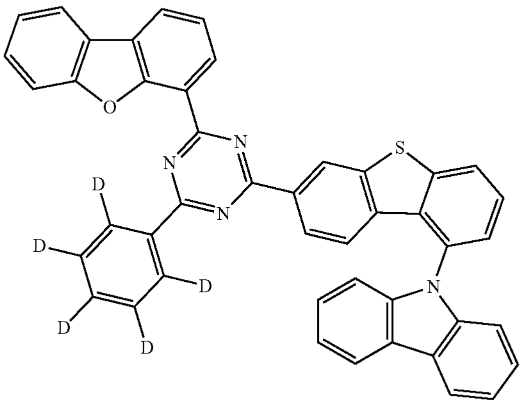
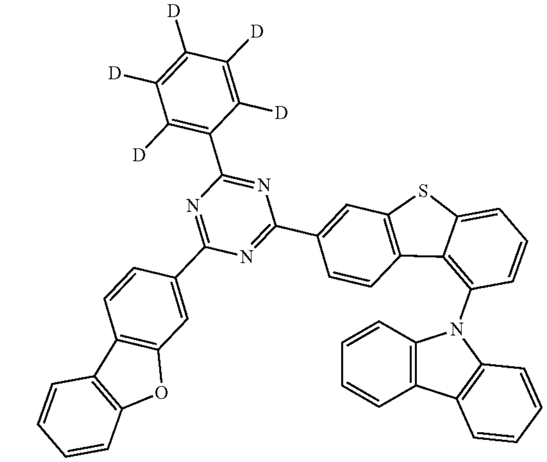
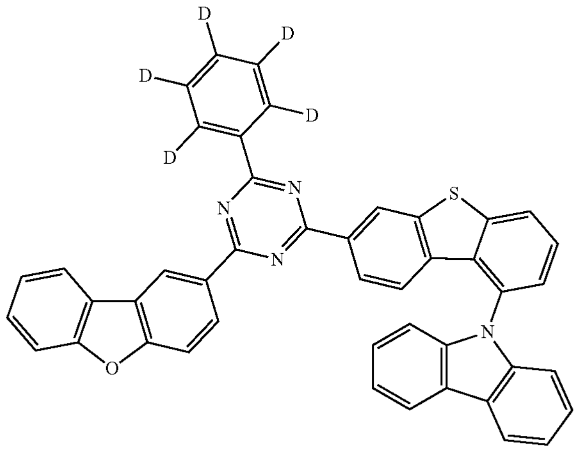
-continued
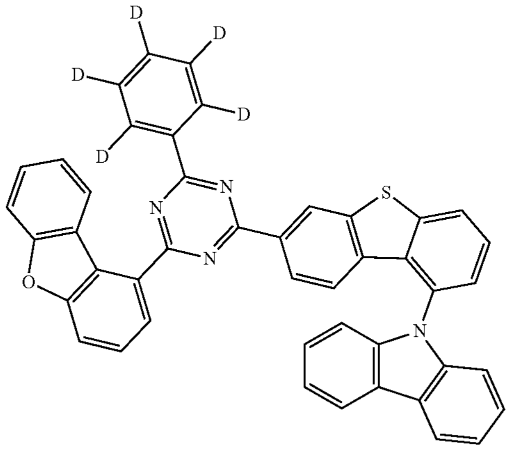
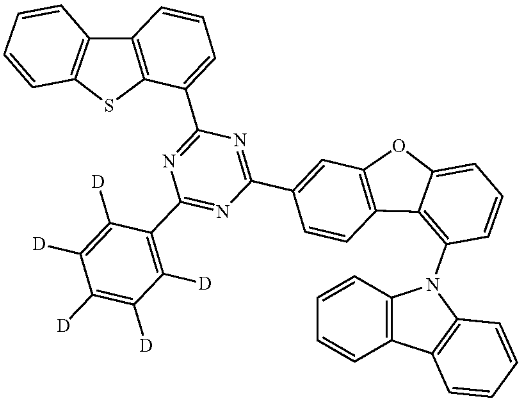
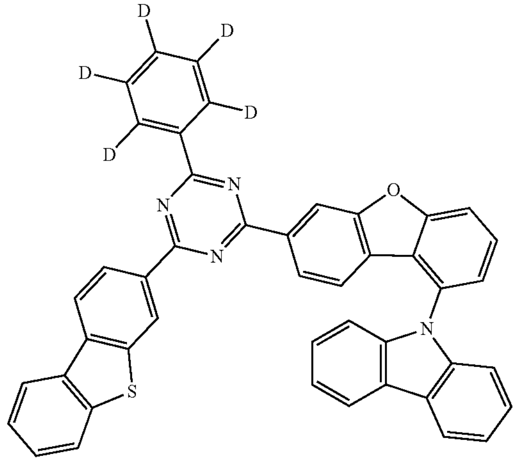

-continued
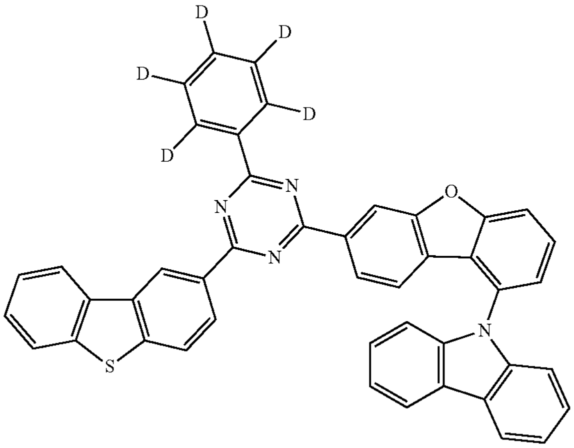
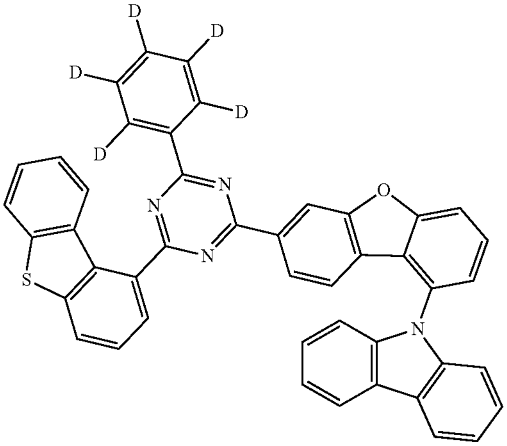
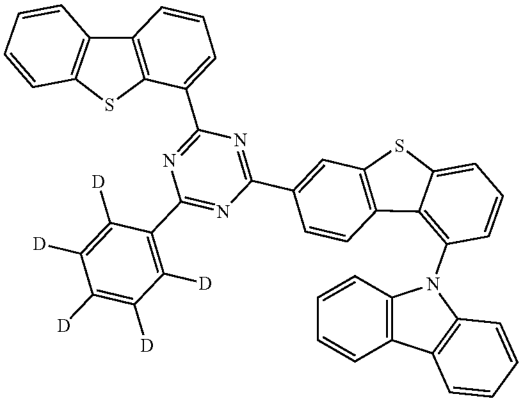 [SMILES: [2H]c1c([2H])c([2H])c(-c2nc(-c3ccc4c(c3)oc3cccc(-n5c6ccccc6c6ccccc65)c34)nc(-c3cccc4c3oc3ccccc34)n2)c([2H])c1[2H]]
-continued
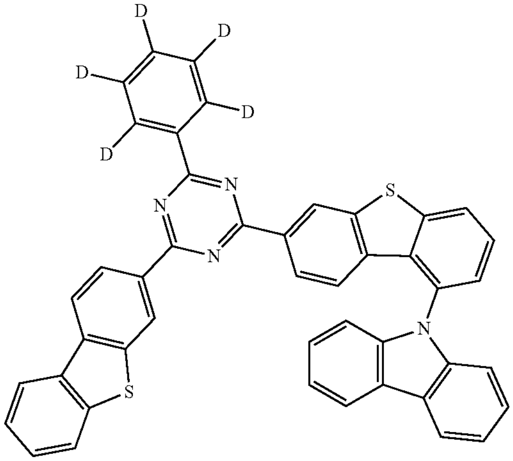
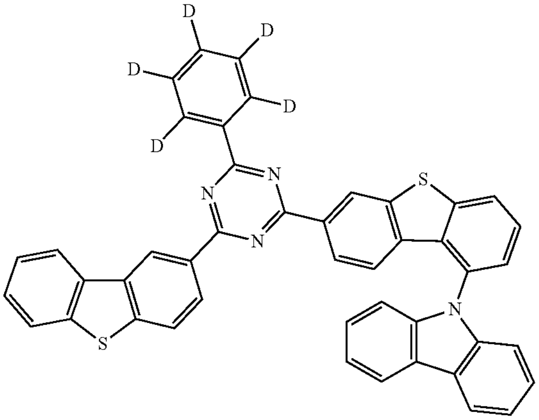
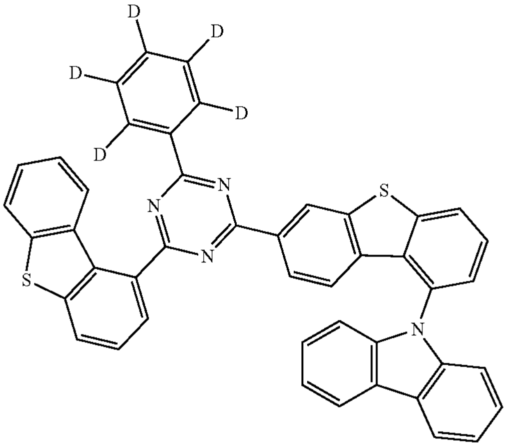

-continued
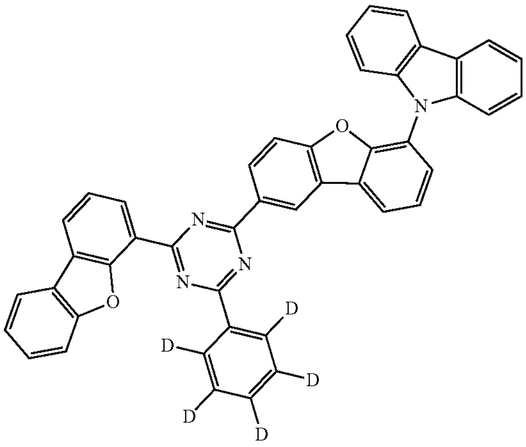
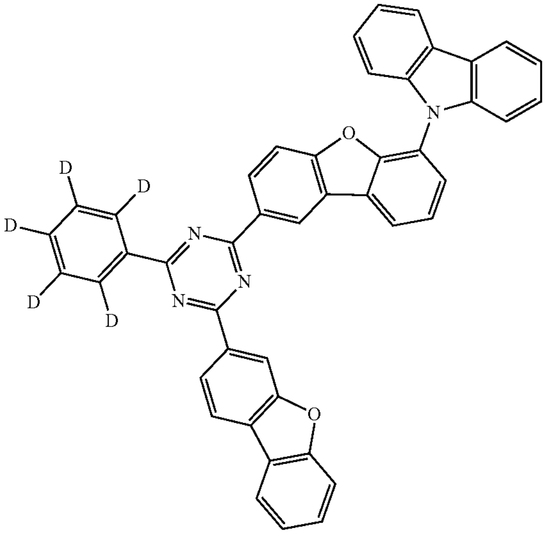
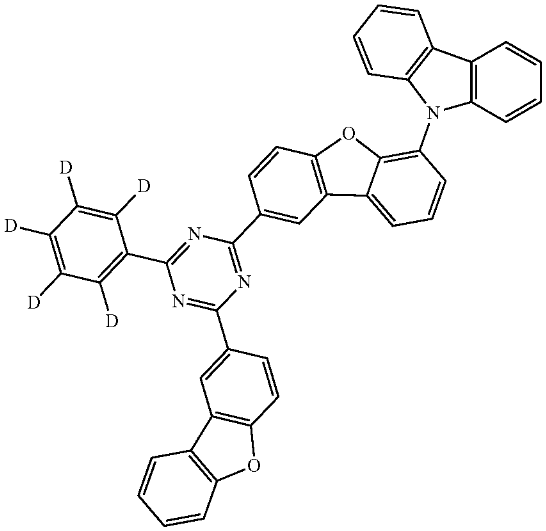
-continued
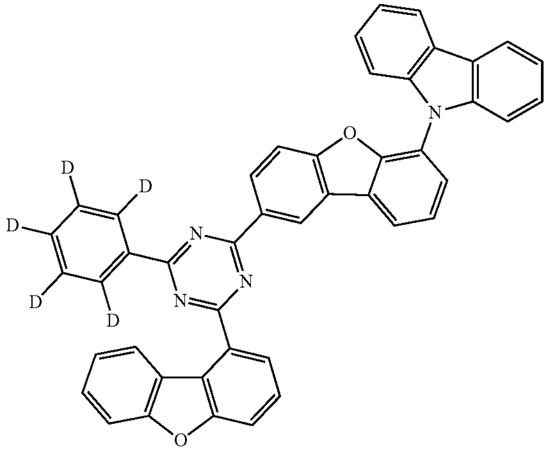
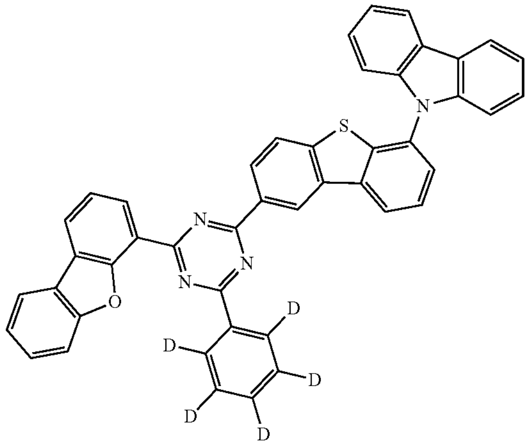
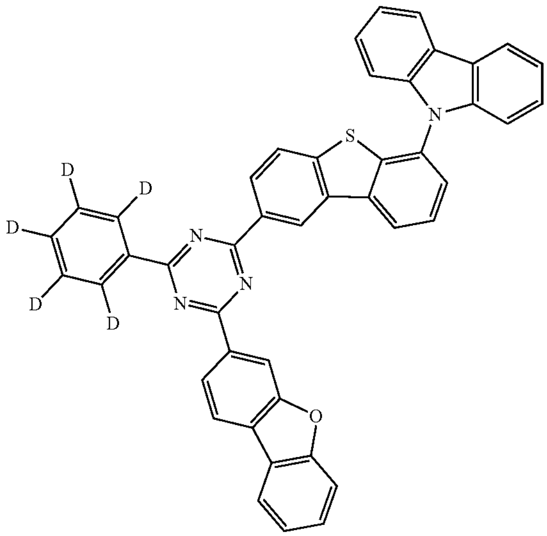

-continued
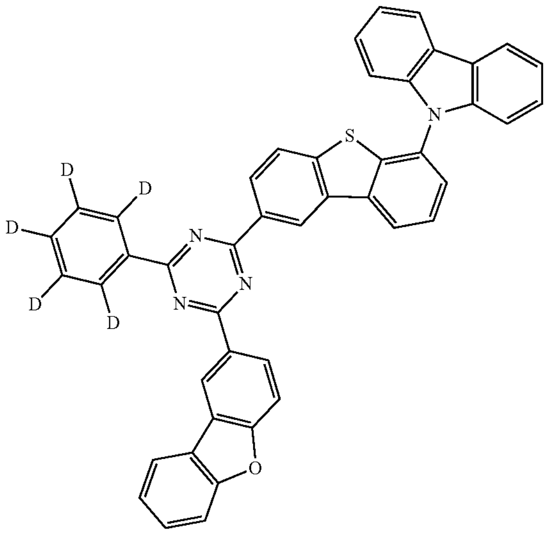
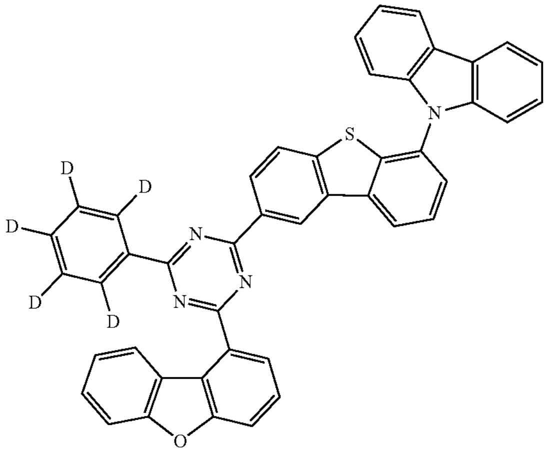
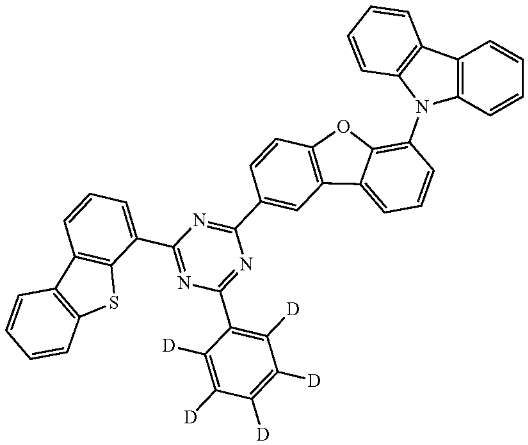
-continued
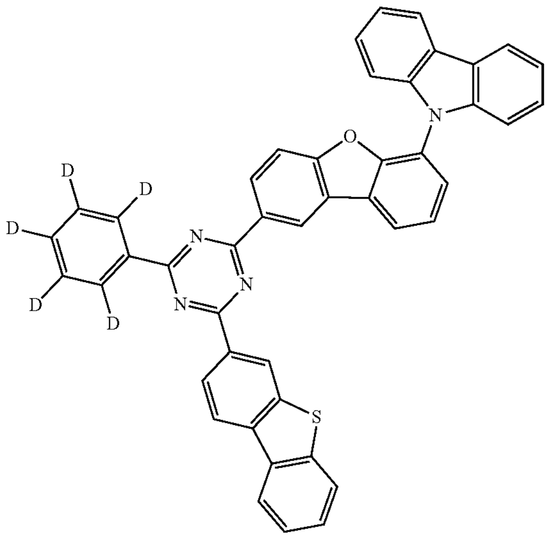
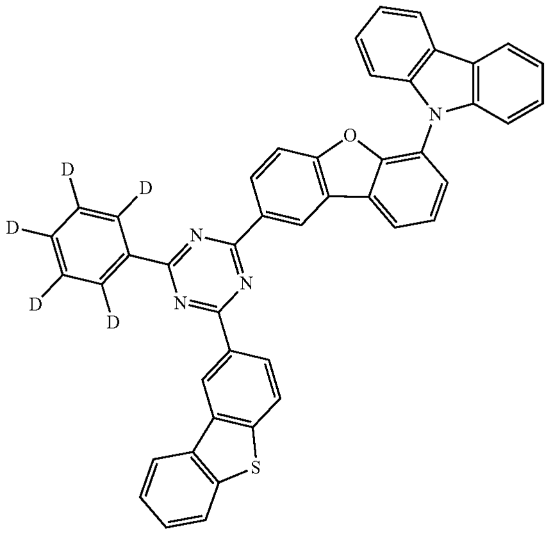
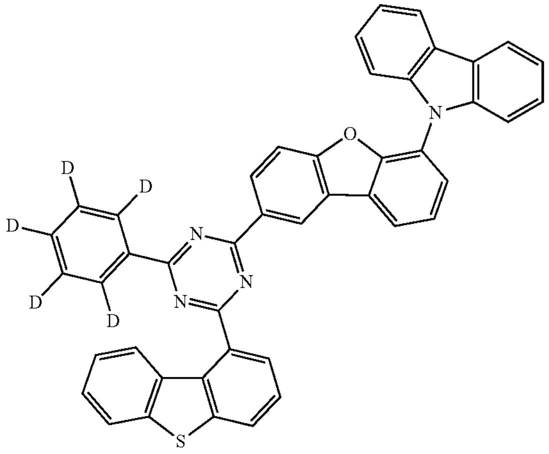

-continued
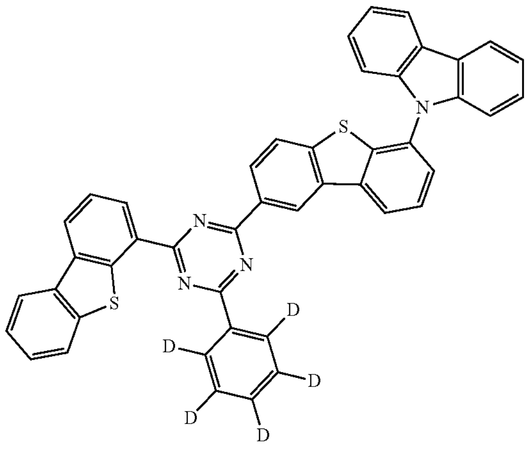
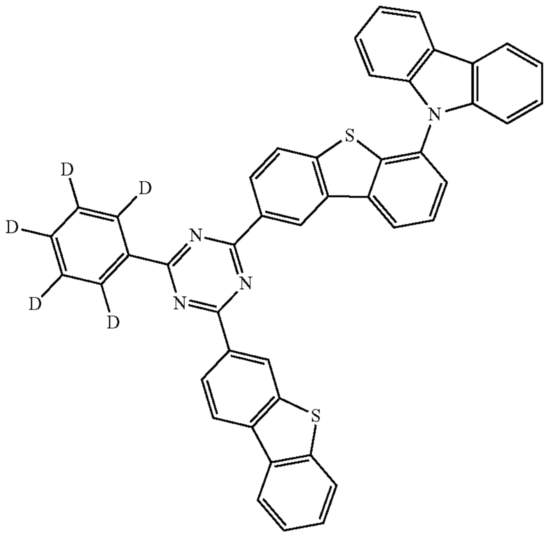
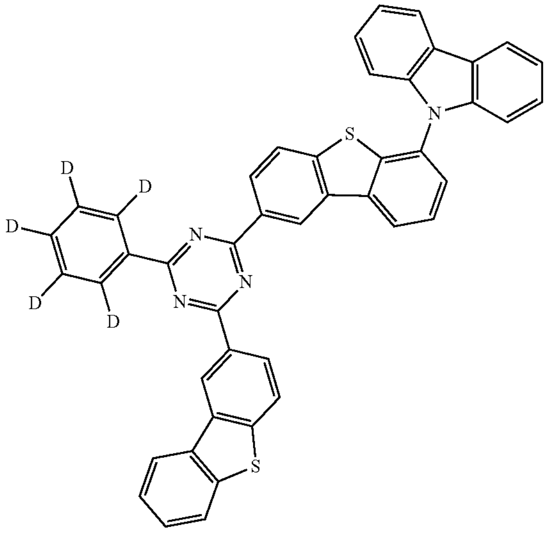
-continued
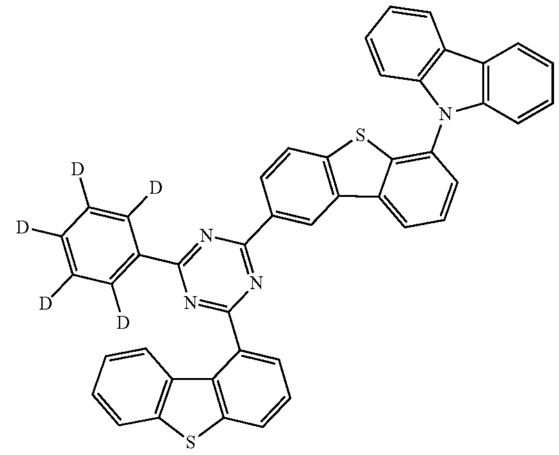
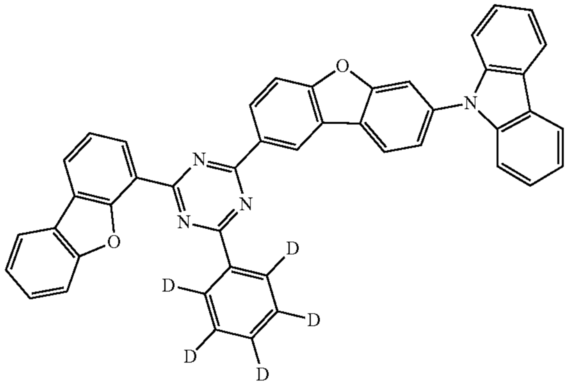
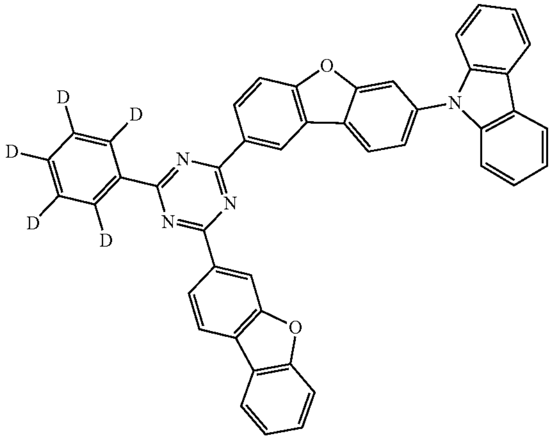
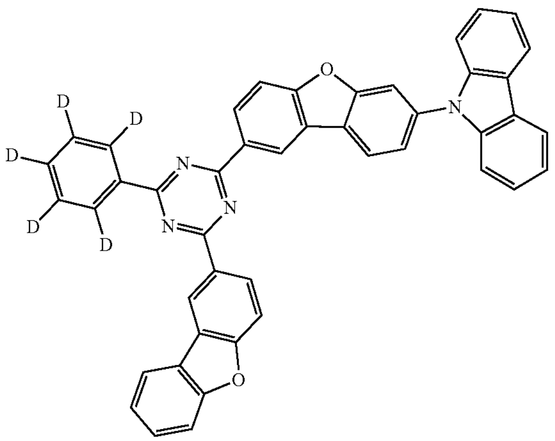

-continued
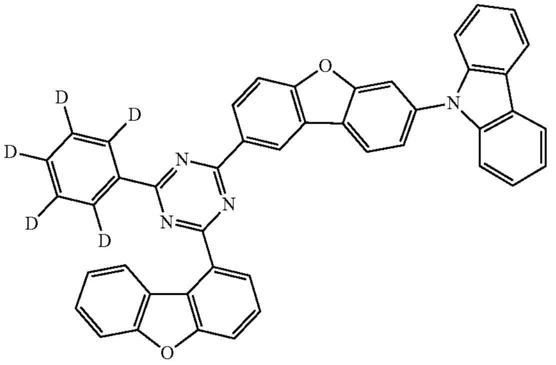
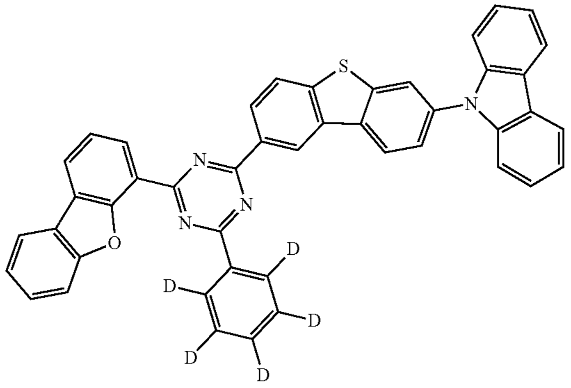
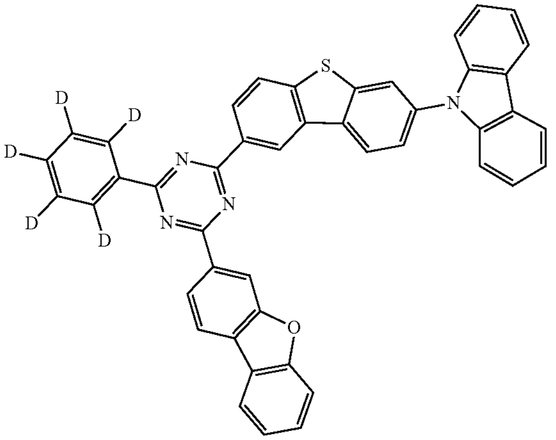
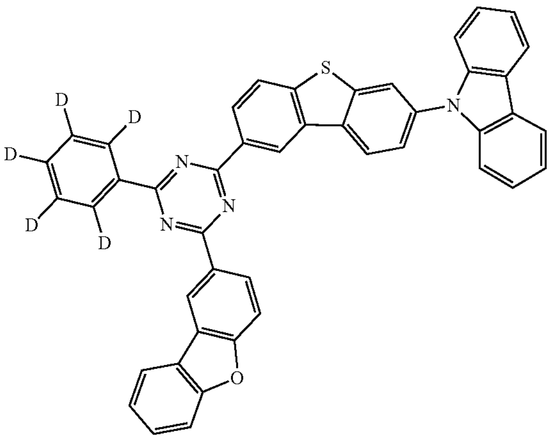
-continued
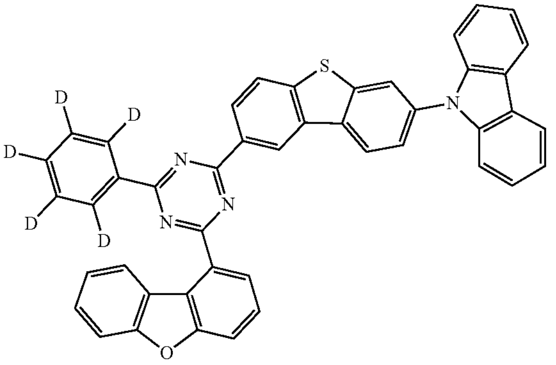
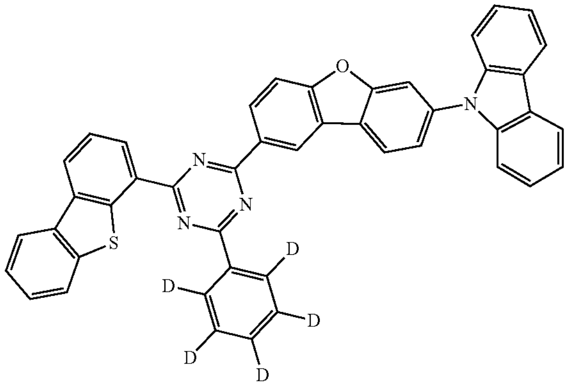
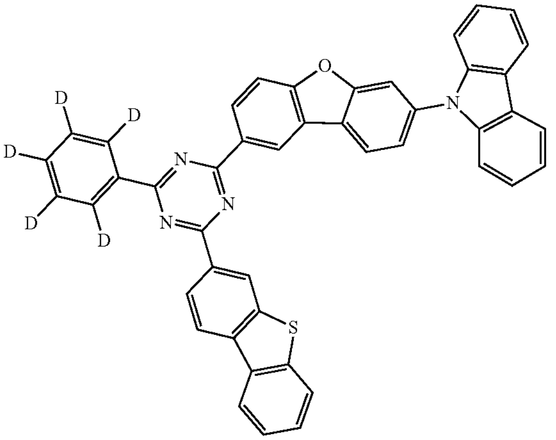
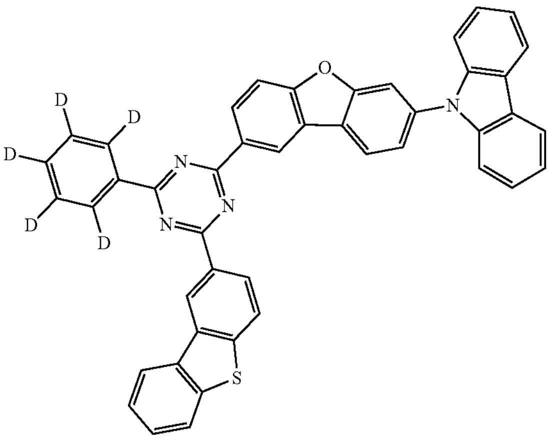

-continued
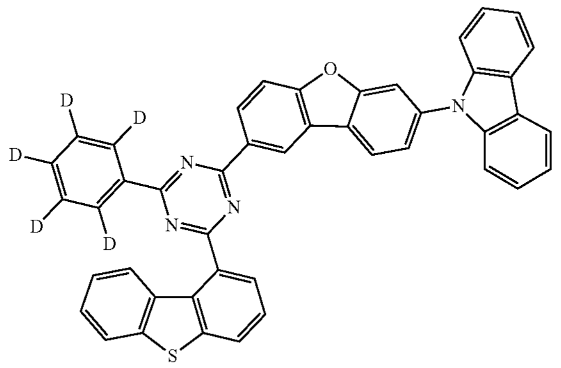
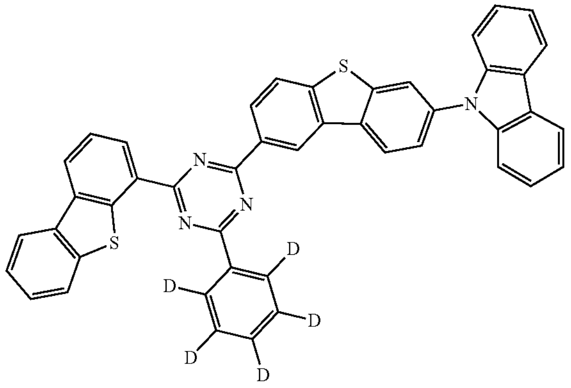
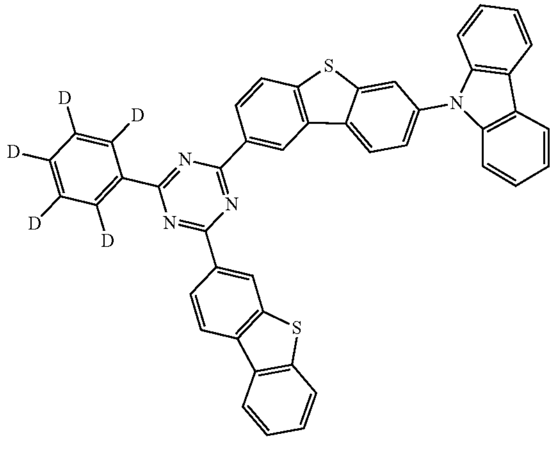
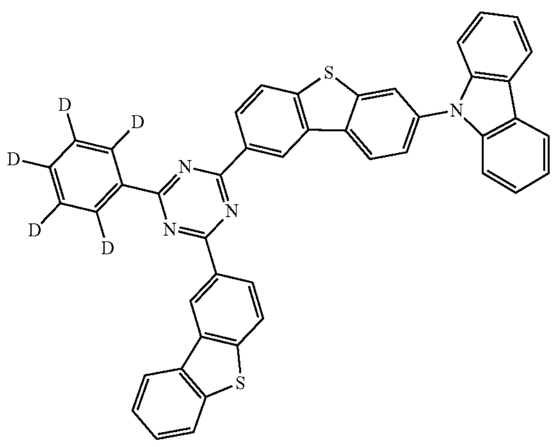
-continued
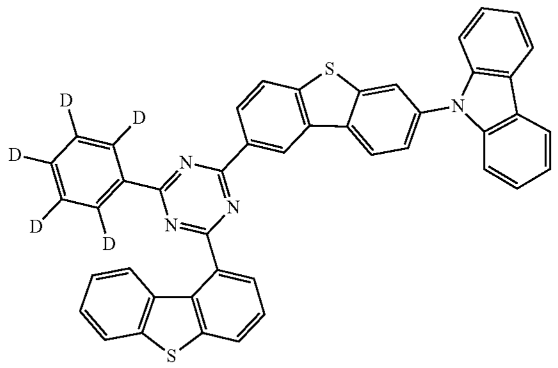
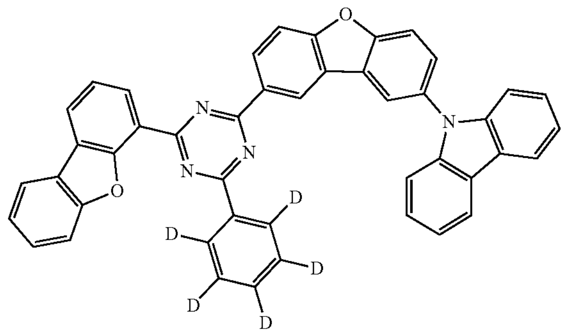
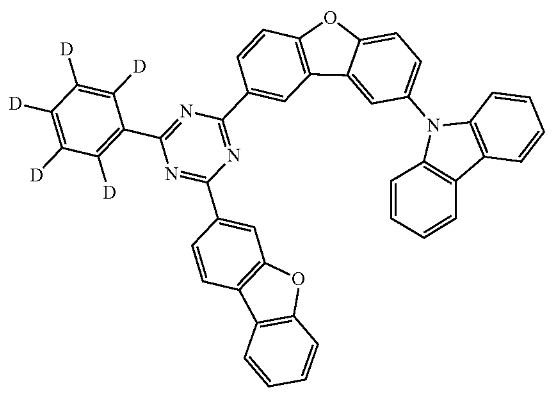
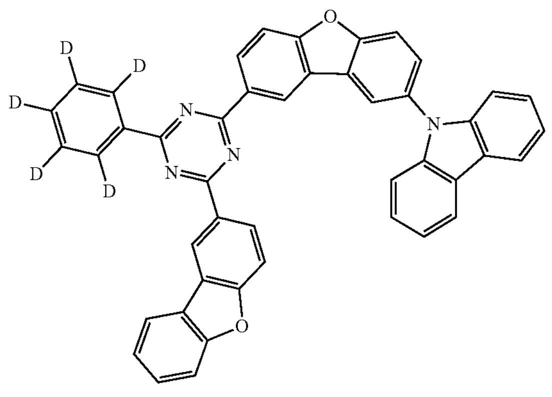

-continued
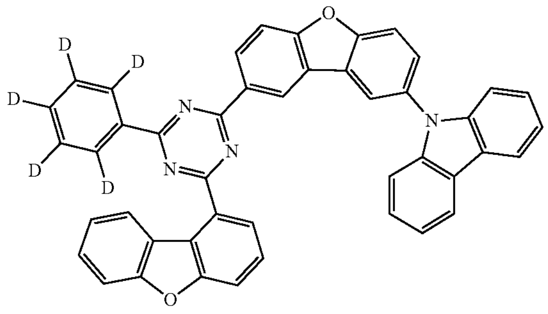
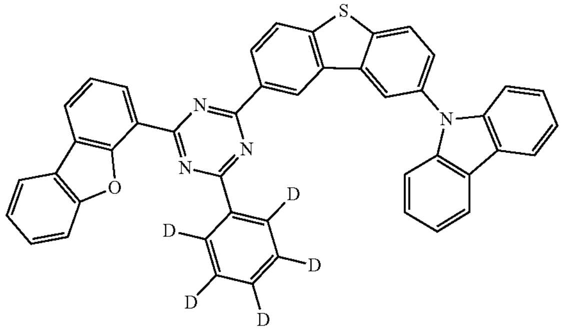
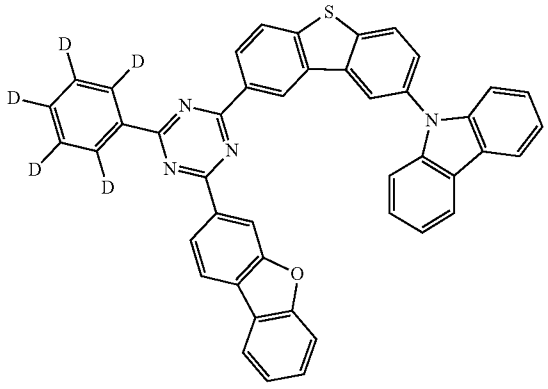
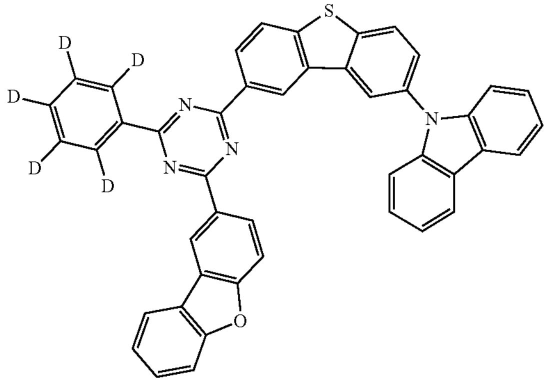
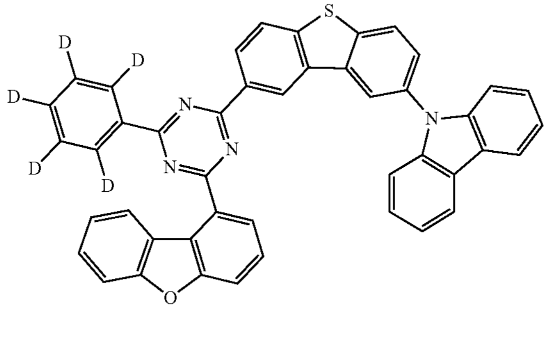
-continued
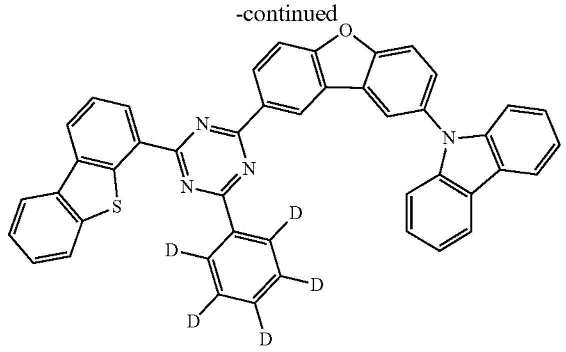
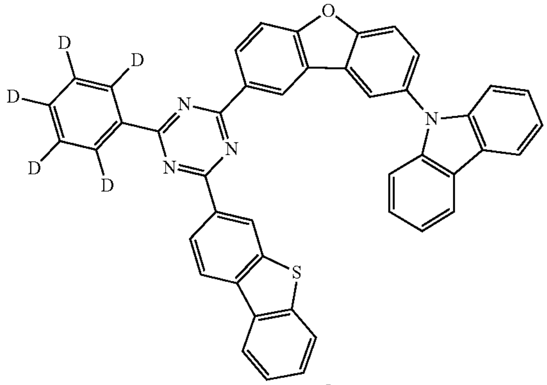
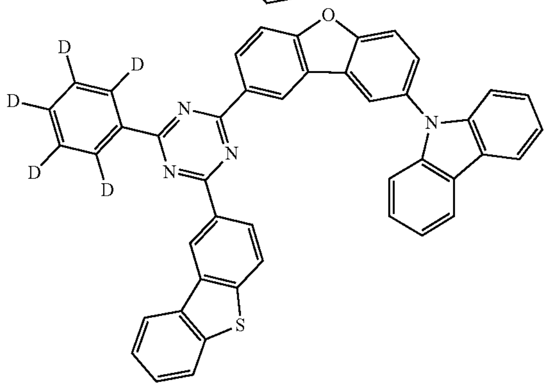
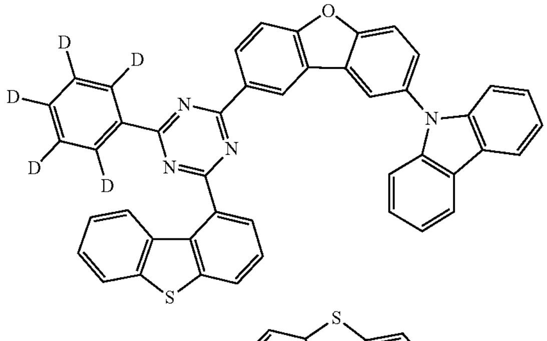
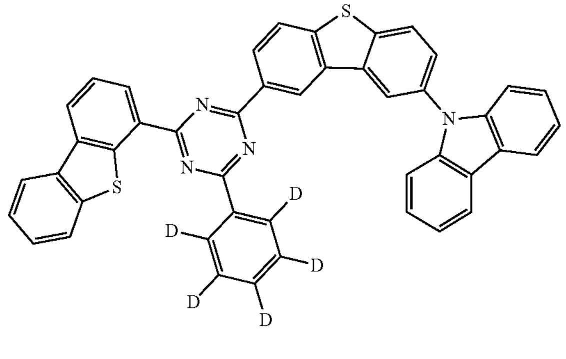

-continued
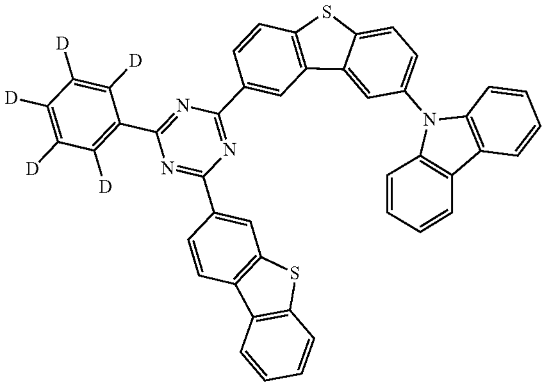
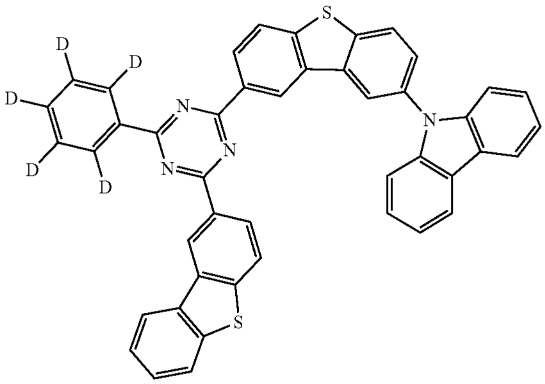
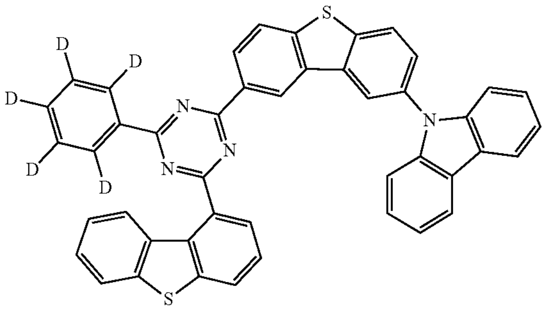
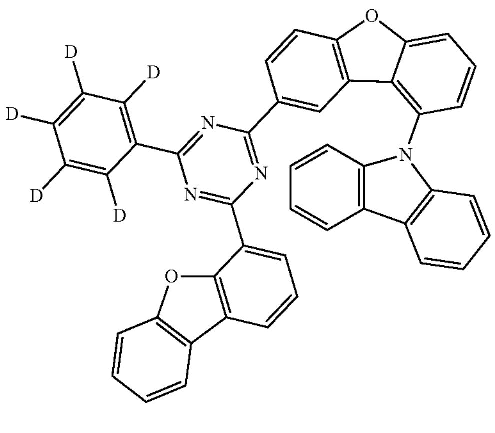
-continued
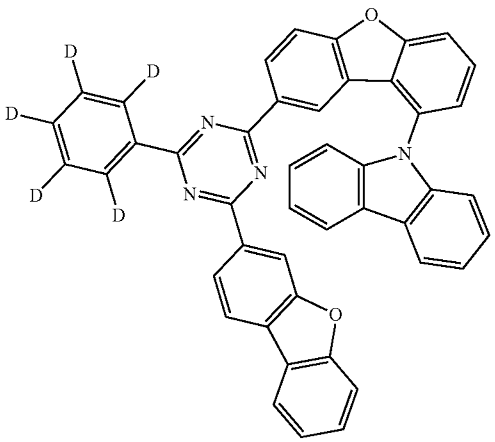
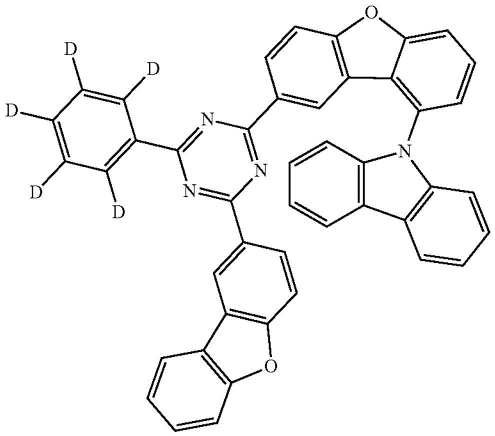
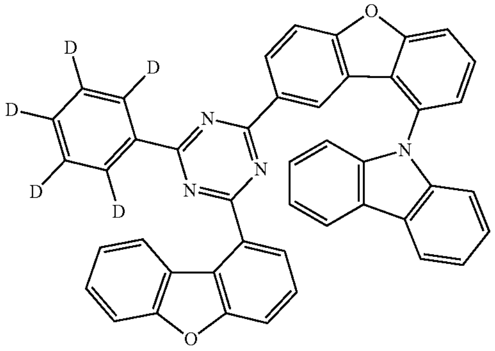
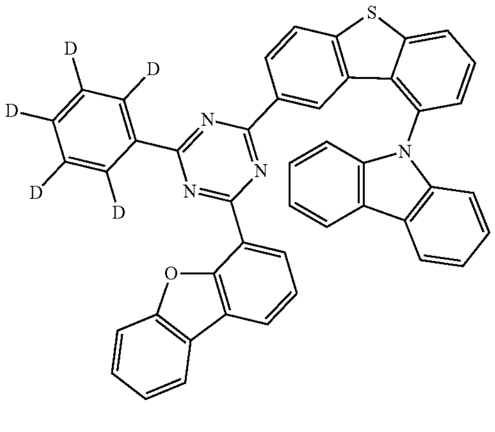

-continued
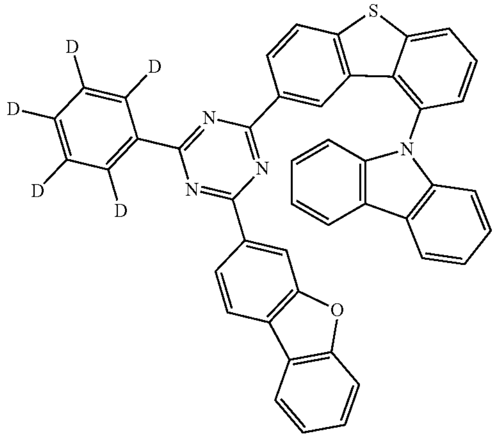
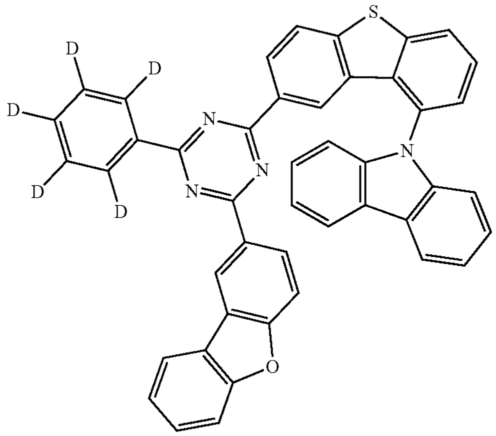
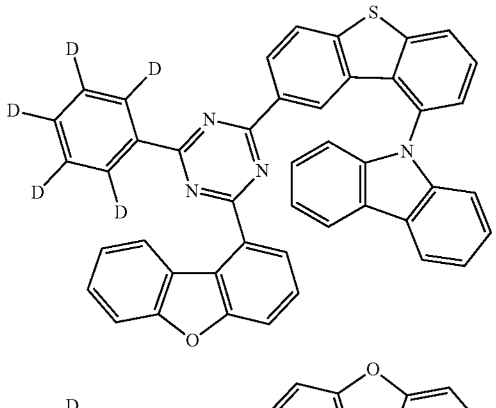
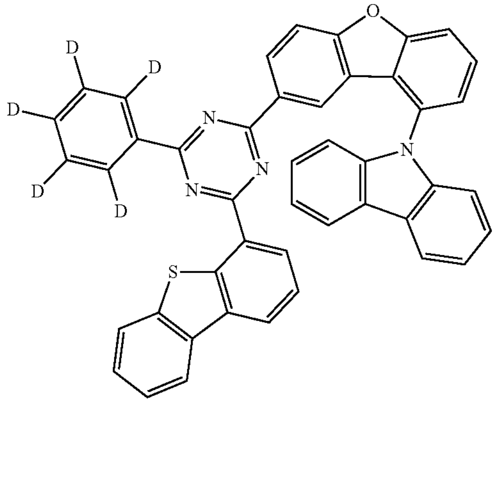
-continued
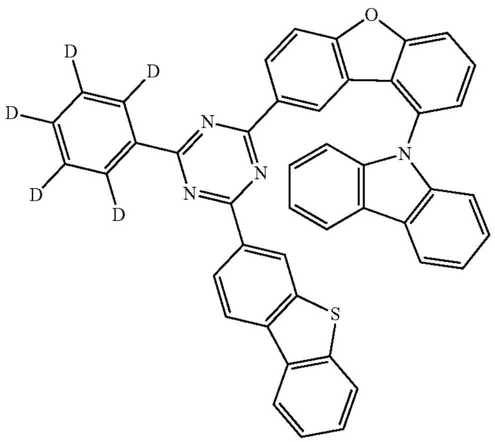
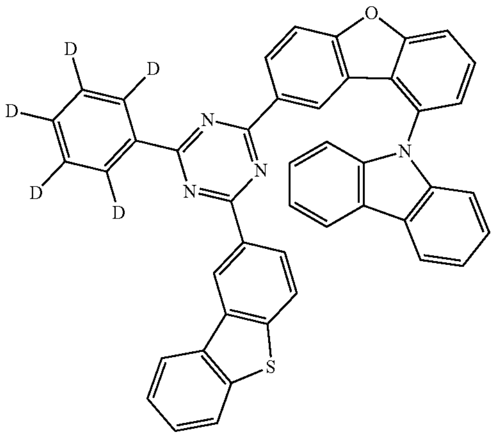
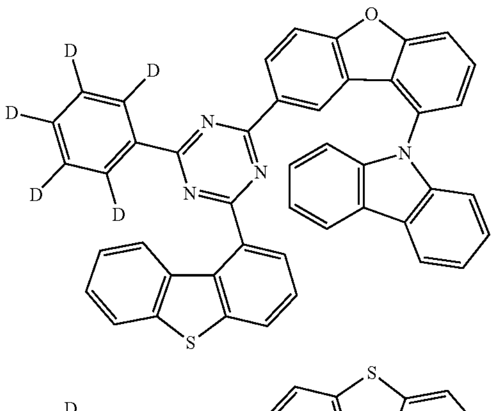
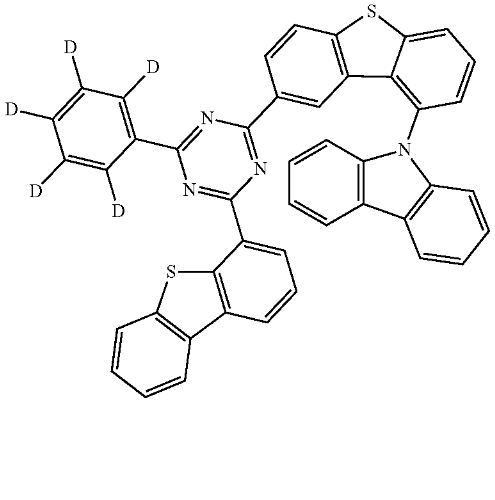

-continued
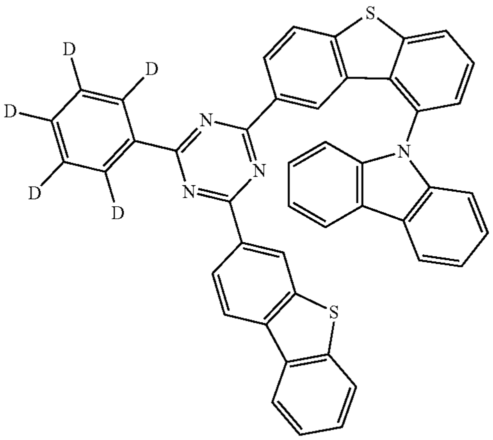
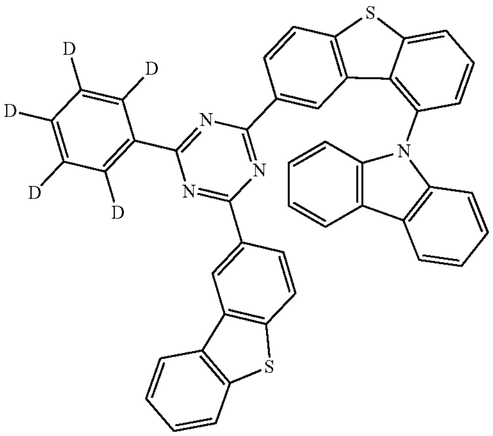
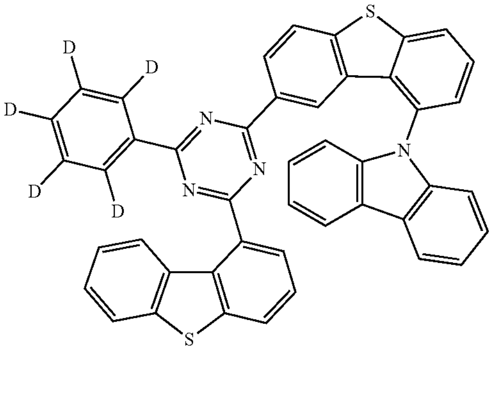
-continued
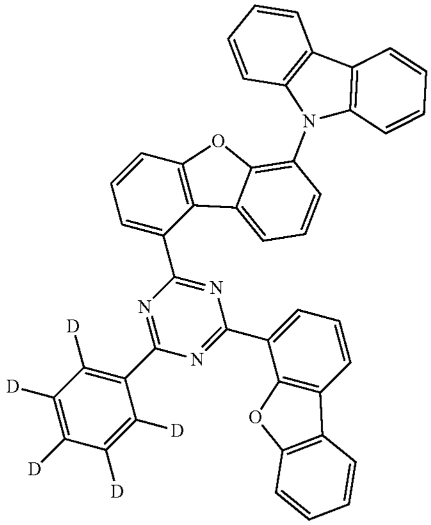
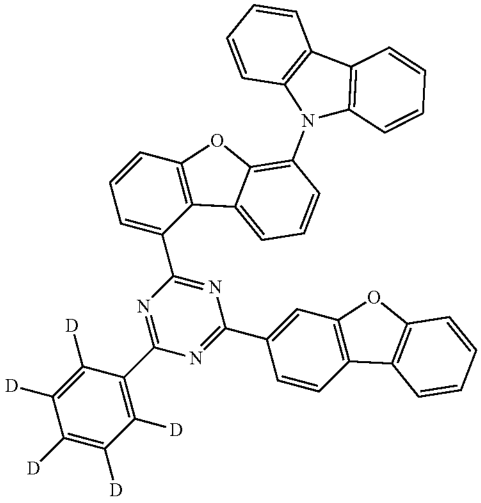
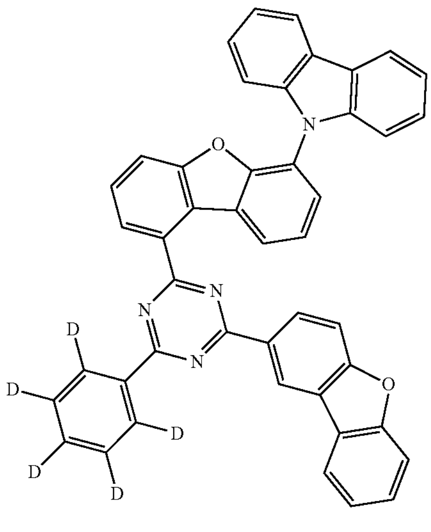

-continued
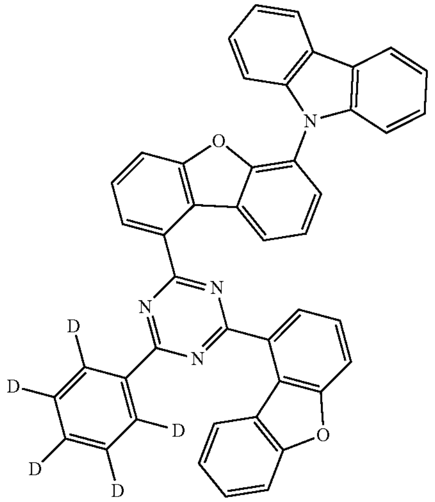
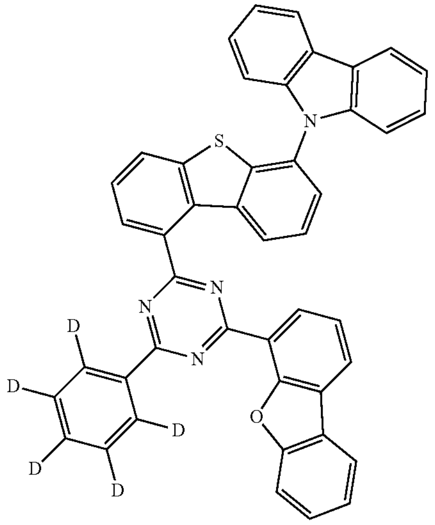
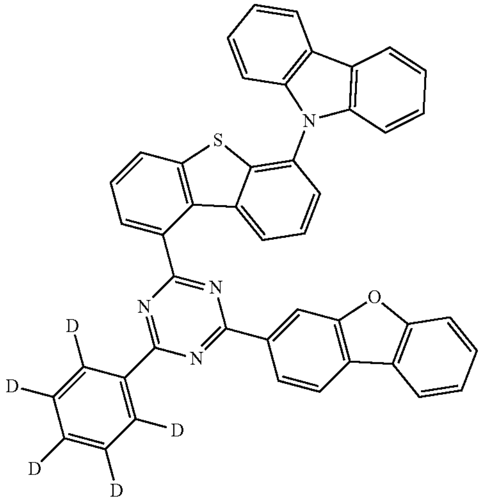
-continued
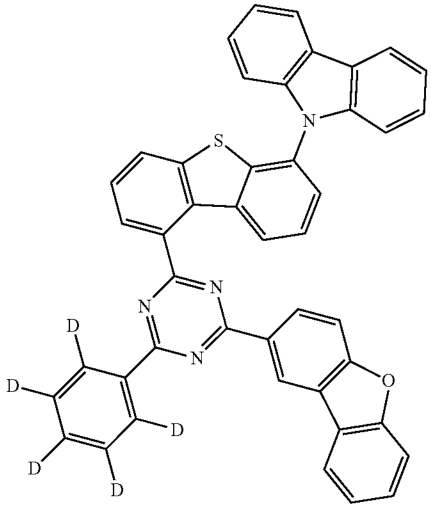
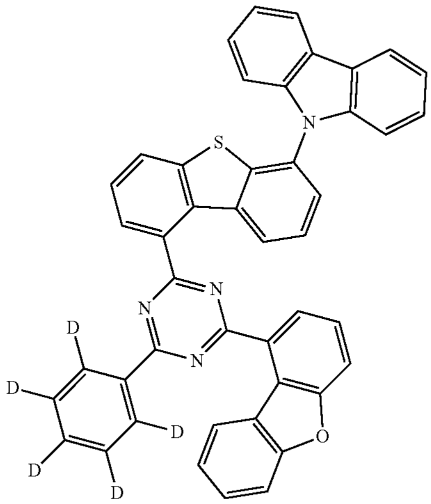
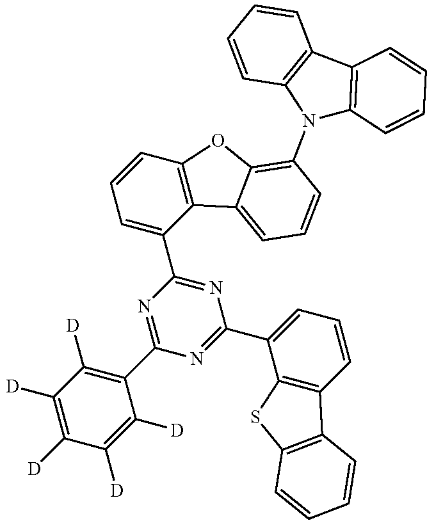

-continued
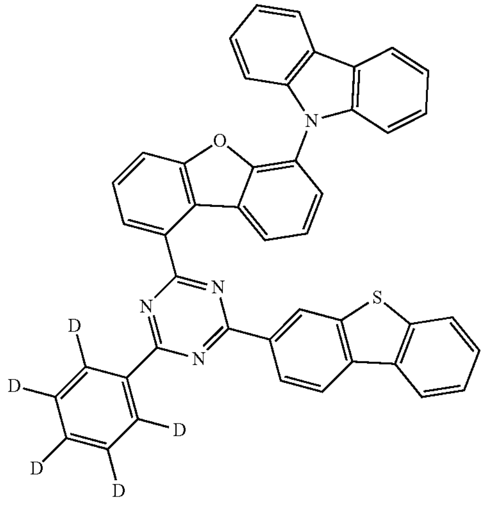
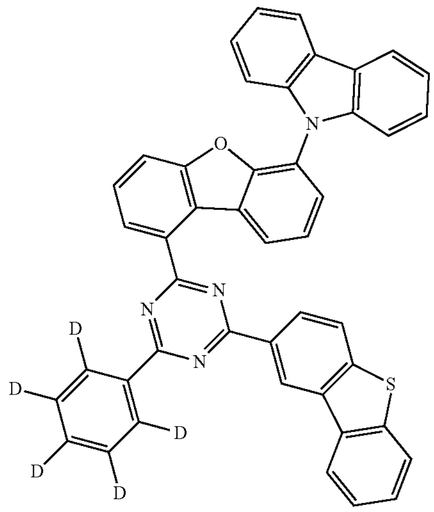
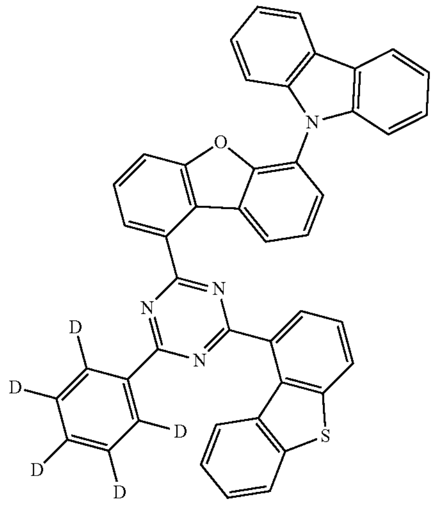
-continued
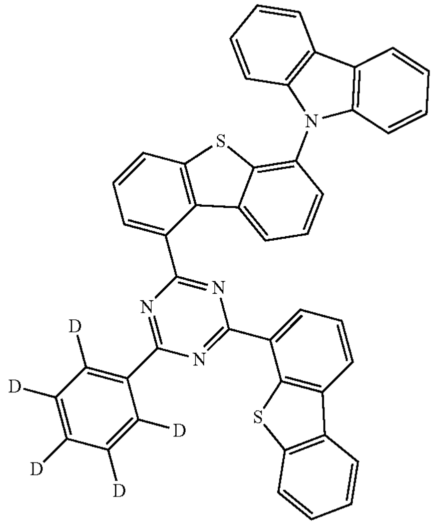
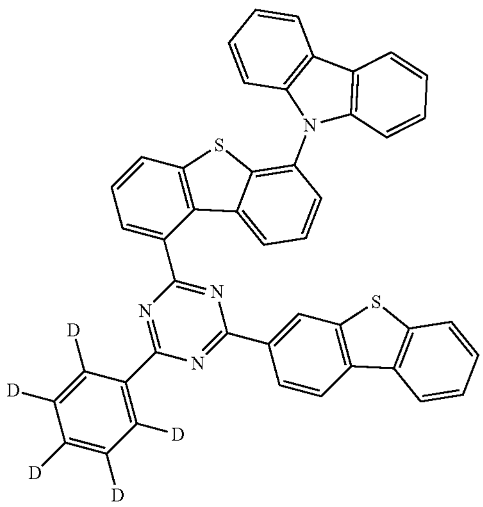
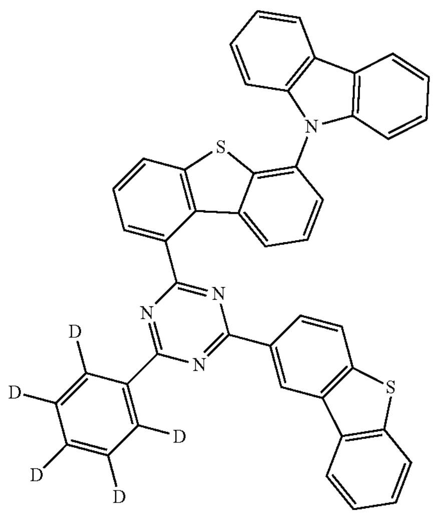

-continued
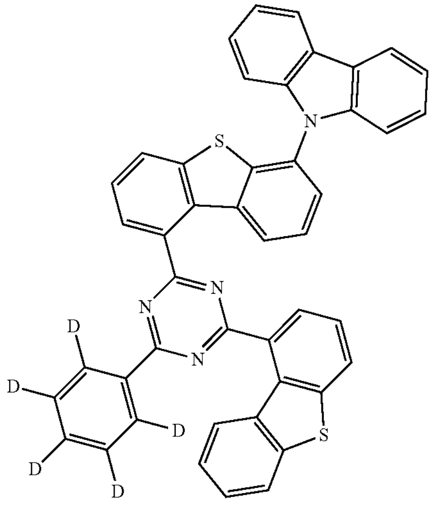
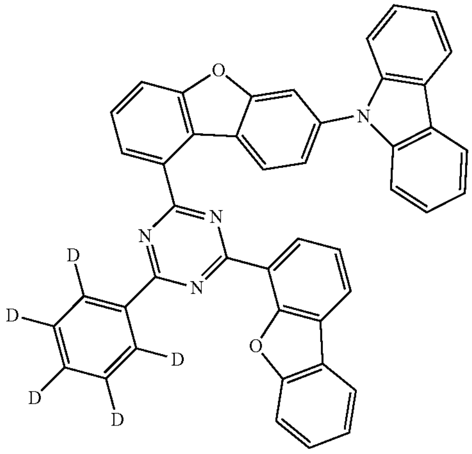
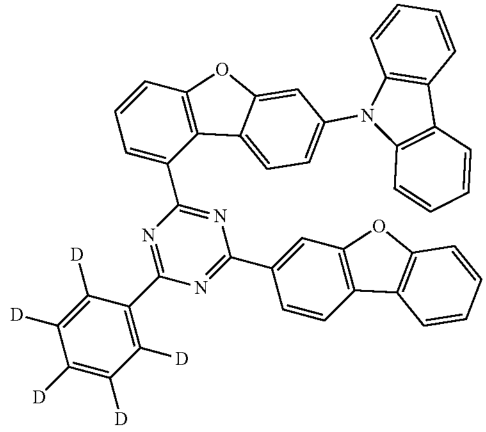
-continued
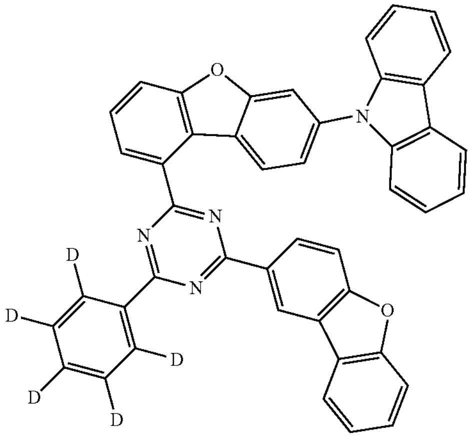
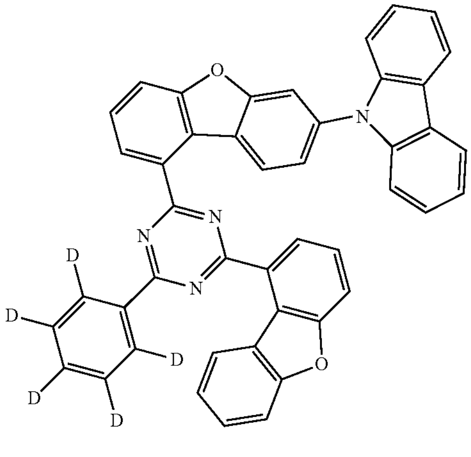
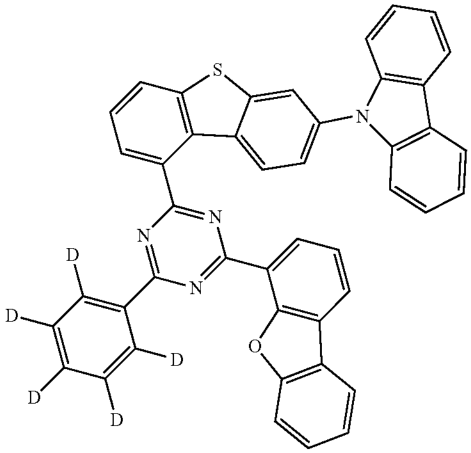

-continued
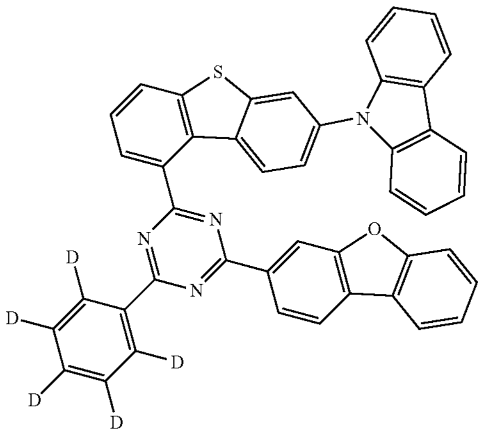
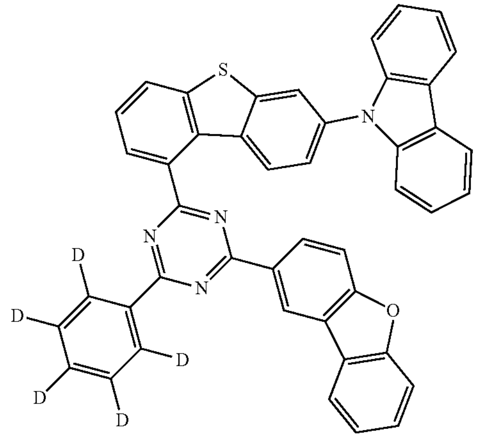
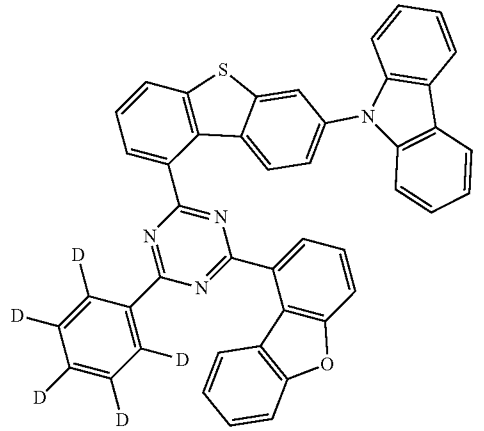
-continued
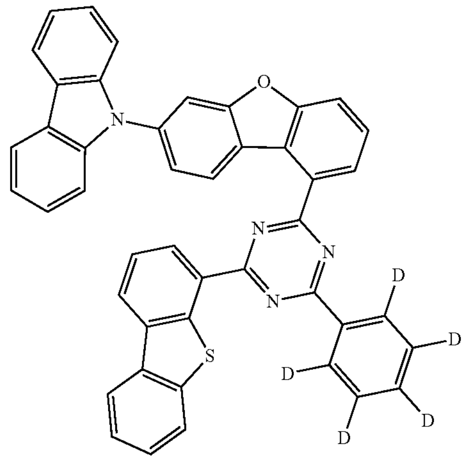
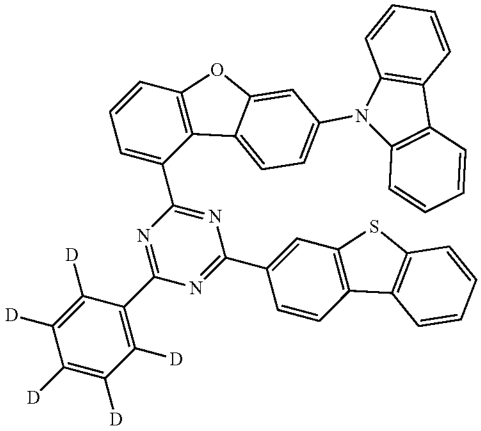
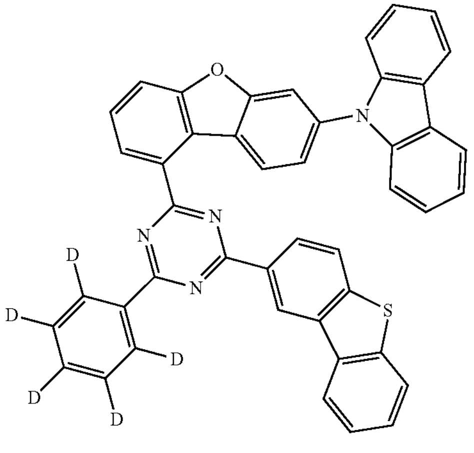

-continued
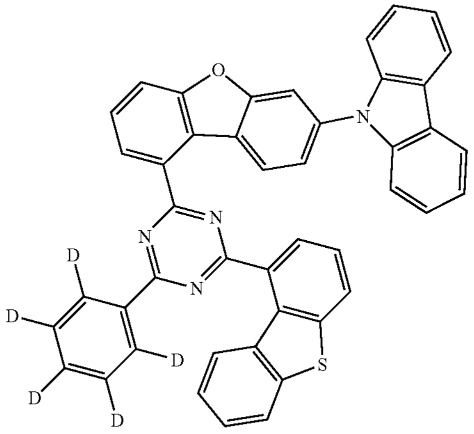
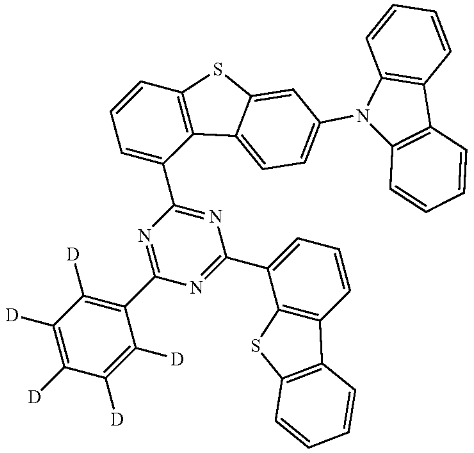
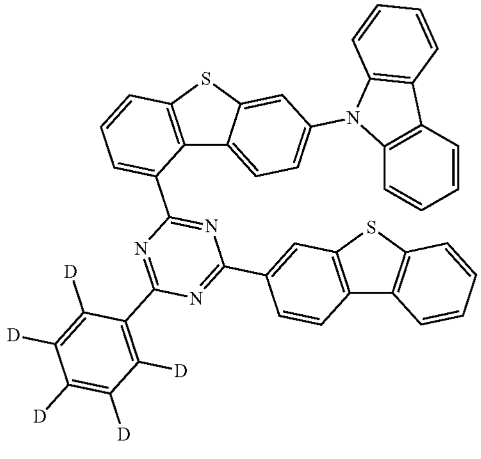
-continued
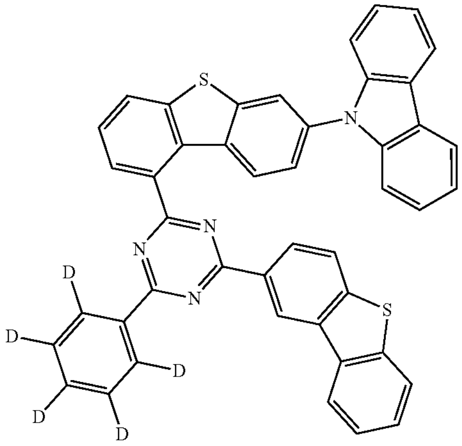
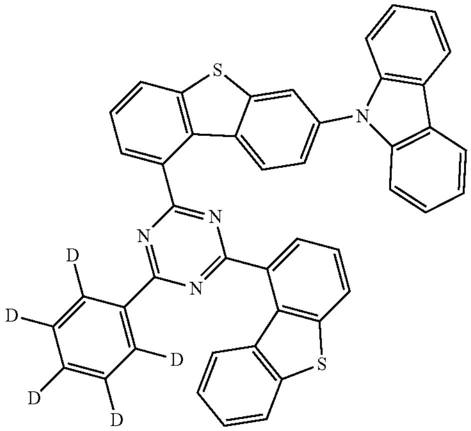
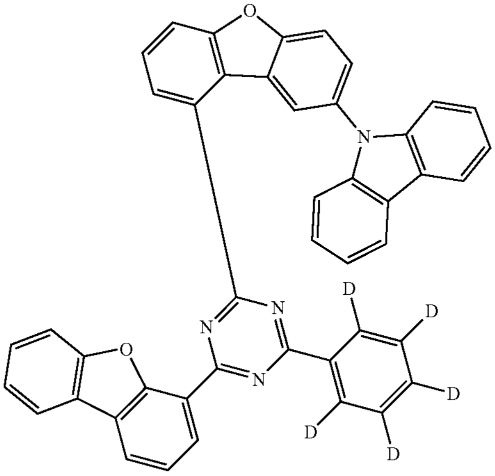

-continued
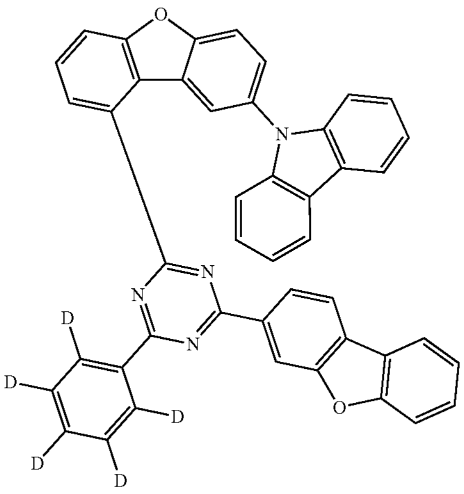
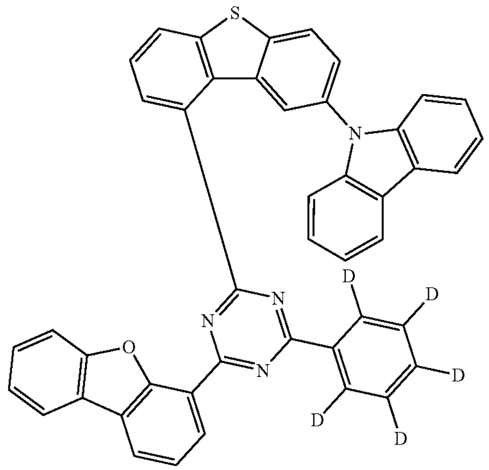
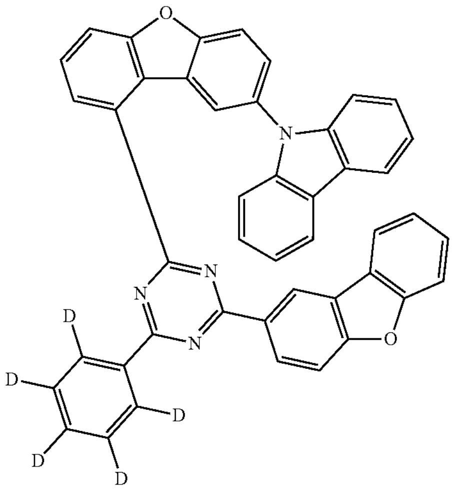
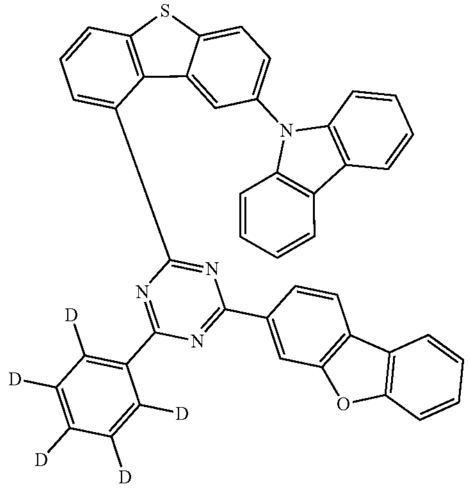
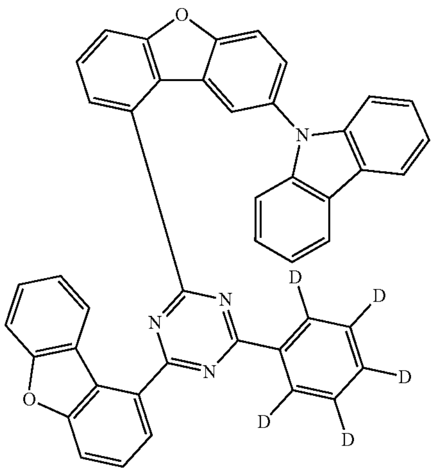
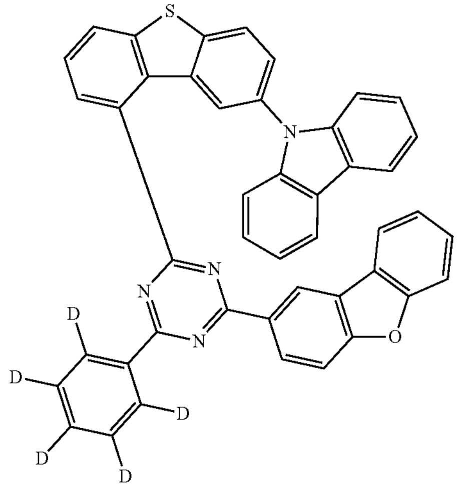

-continued
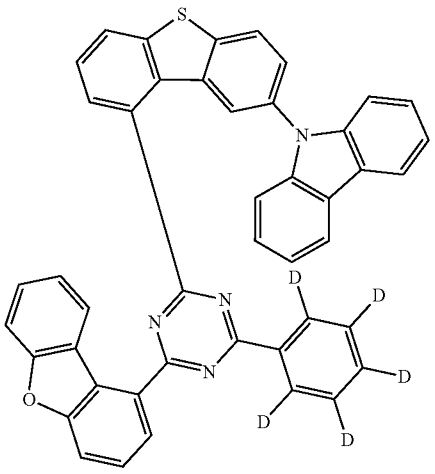
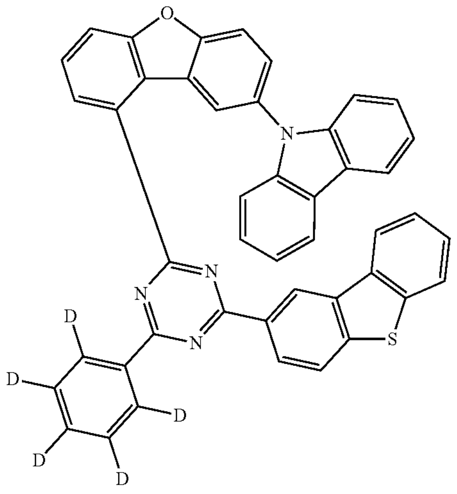
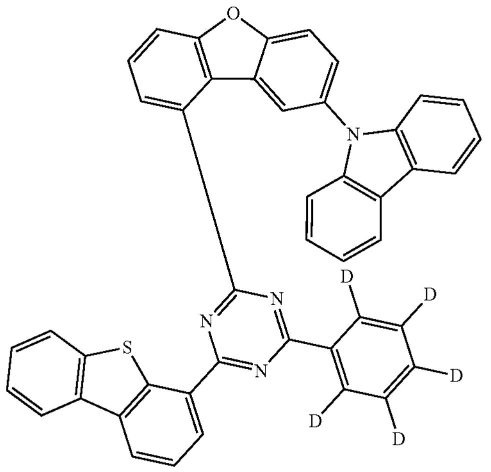
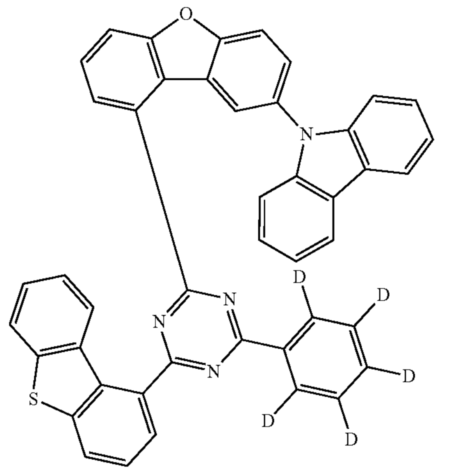
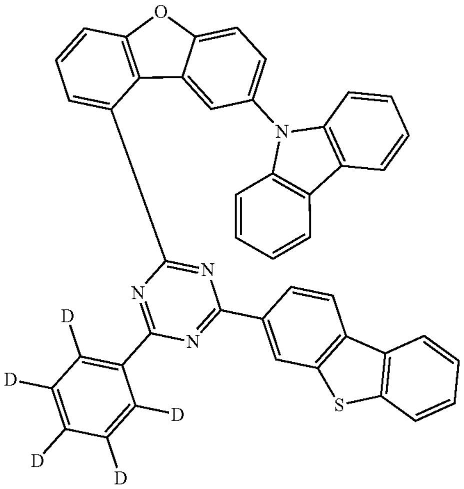
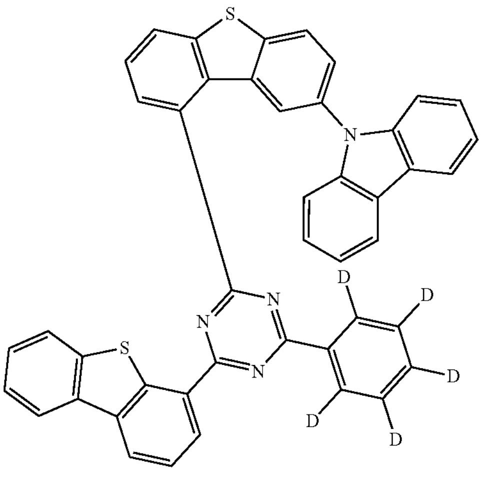

-continued
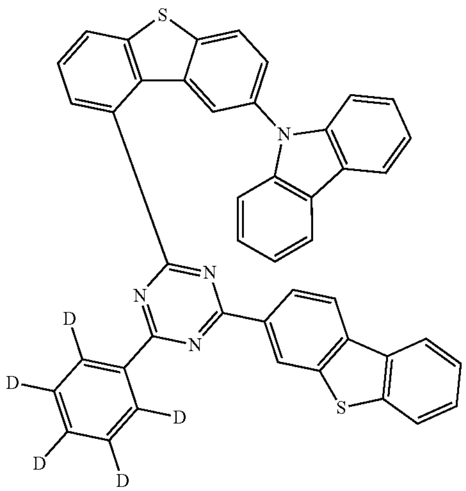
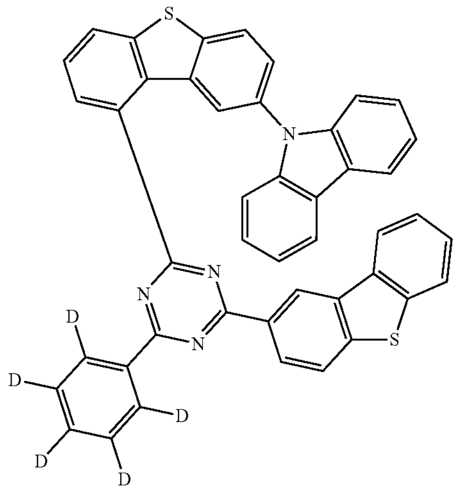
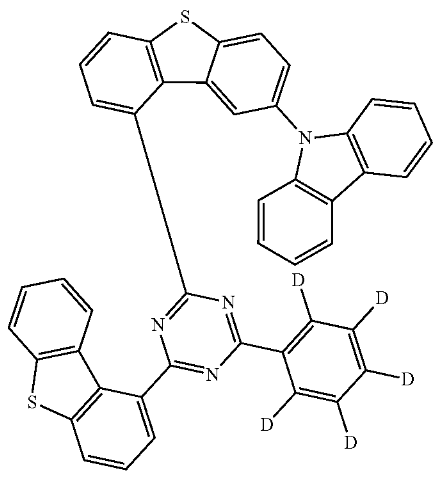
-continued
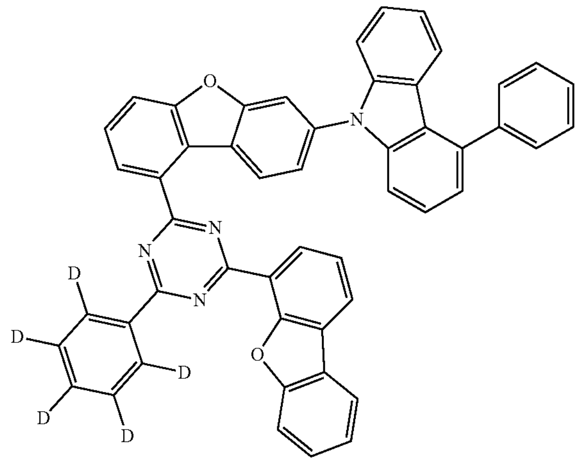
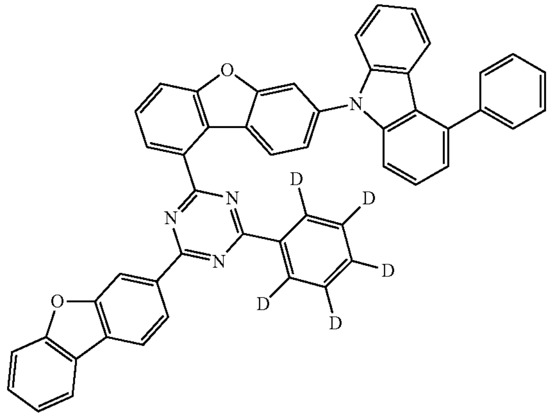
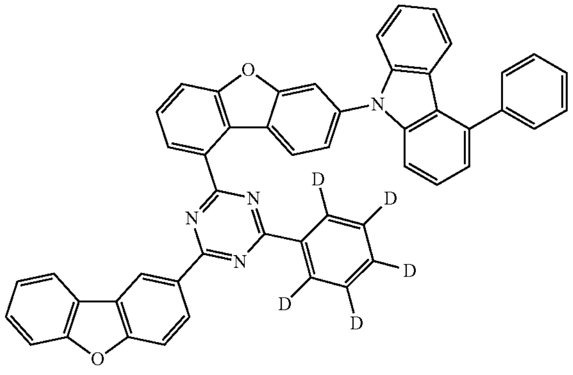
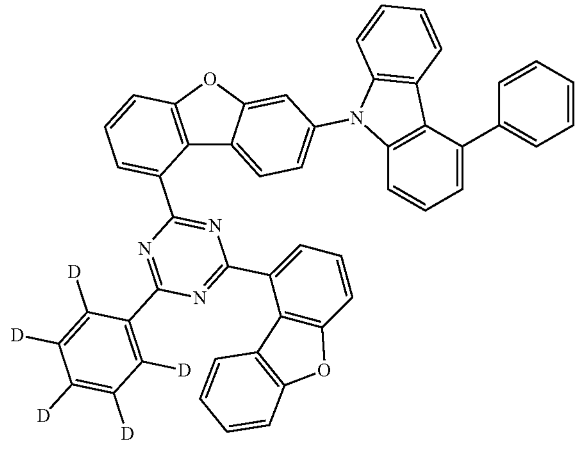

-continued
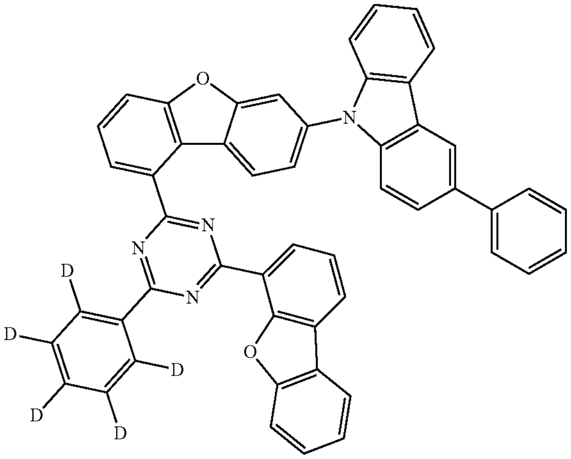
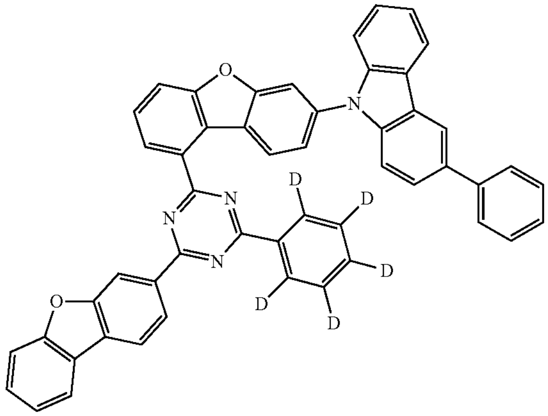
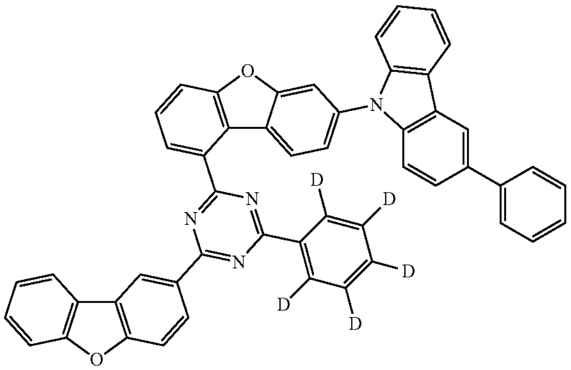
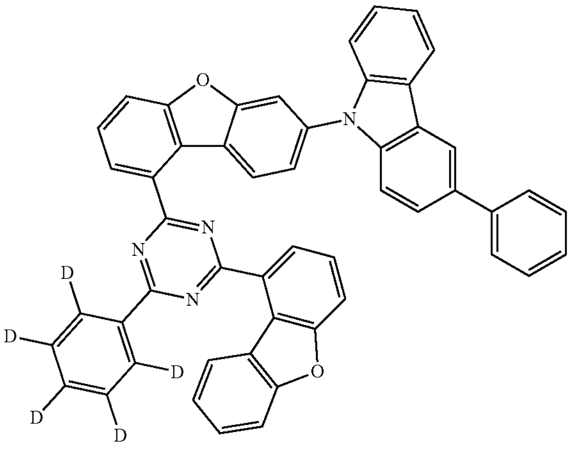
-continued
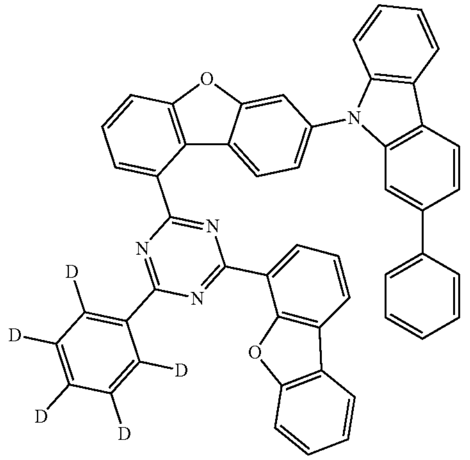
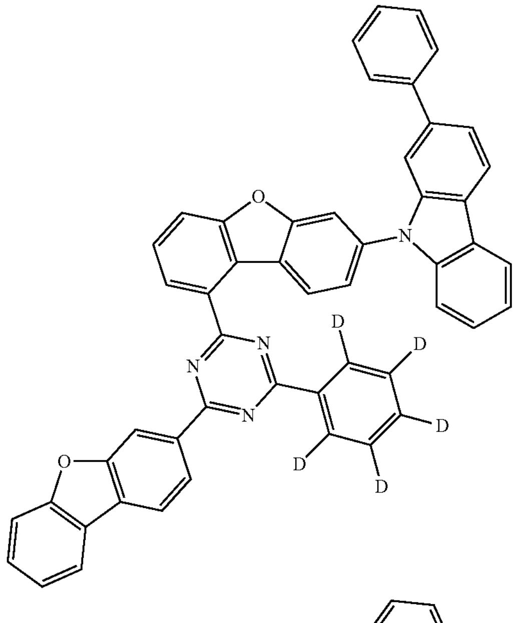
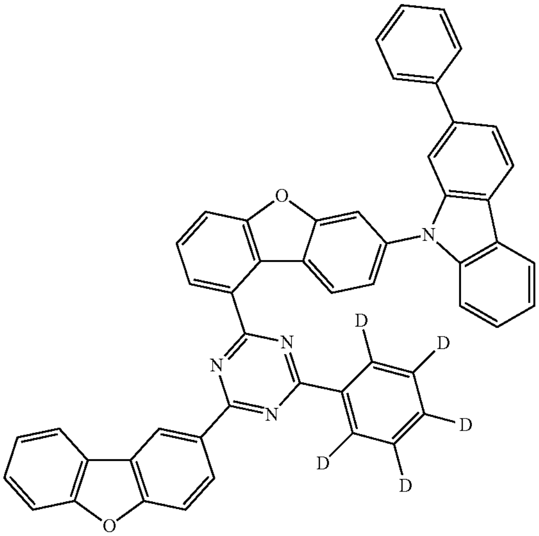

-continued
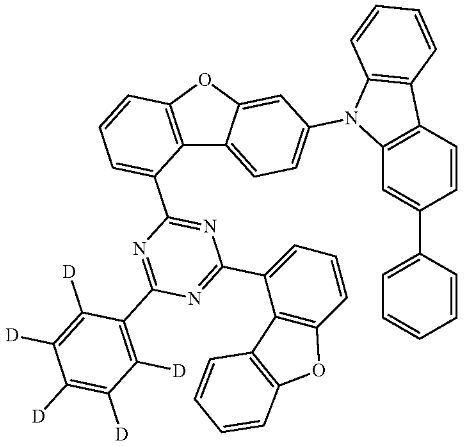
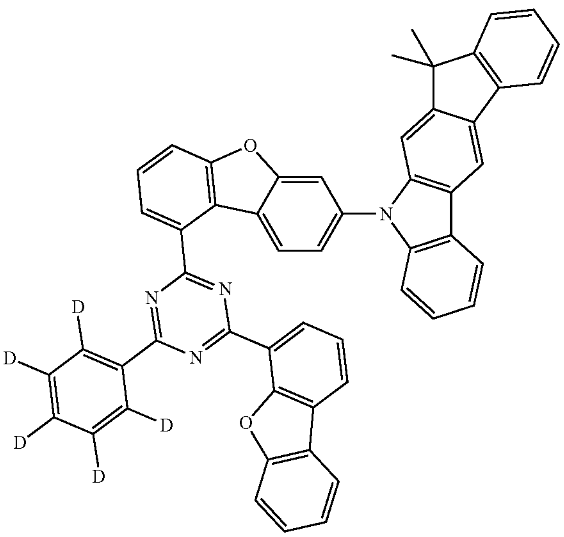
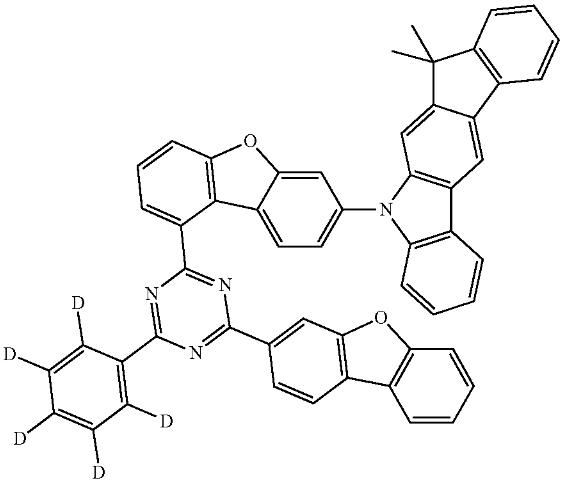
-continued
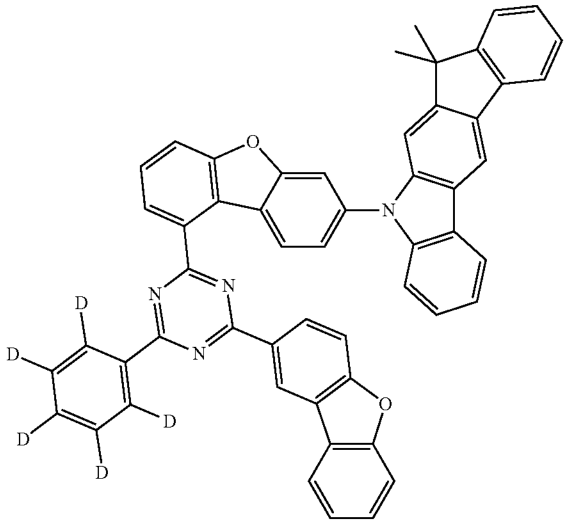
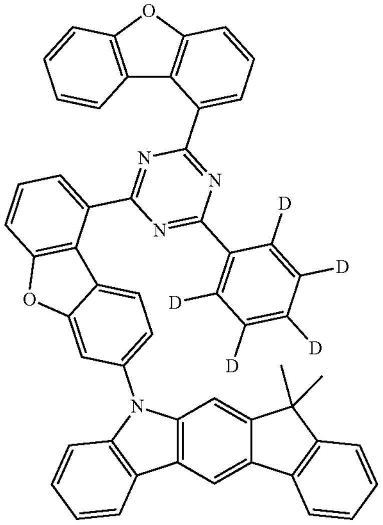
.
The compound of Chemical Formula 1 may be prepared, for example, according to the preparation method as shown in the following Reaction Scheme 1, and the remaining compounds can be prepared in a similar manner.
Reaction Scheme 1
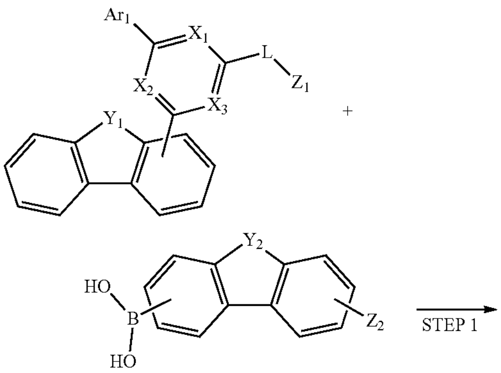

-continued

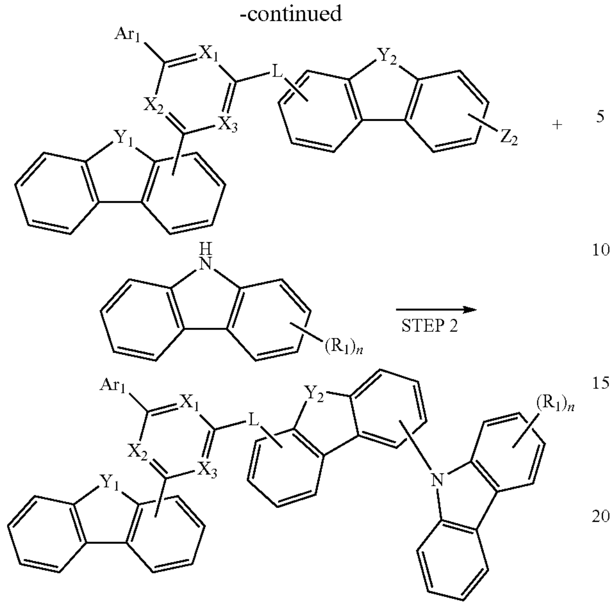

In Reaction Scheme 1 above, $X_1$ to $X_3$, $Y_1$, $Y_2$, L, $Ar_1$, $R_1$, and n are the same as those defined in Chemical Formula 1, $Z_1$ and $Z_2$ are each independently halogen, and preferably, $Z_1$ and $Z_2$ are each independently chloro or bromo.

Step 1 in Reaction Scheme 1 is a Suzuki coupling reaction, which is preferably carried out in the presence of a palladium catalyst and a base, and a reactive group for the Suzuki coupling reaction can be modified as known in the art. In addition, Step 2 in Reaction Scheme 1 is an amine substitution reaction, which is preferably carried out in the presence of a palladium catalyst and a base, and the reactive group for the amine substitution reaction can be modified as known in the art. The above preparation method may be further specified in preparation examples described hereinafter.

In another embodiment of the invention, an organic light emitting device including the compound of Chemical Formula 1 described above is provided. As an example, an organic light emitting device is provided, including: a first electrode; a second electrode provided to face the first electrode; and one or more organic material layers provided between the first electrode and the second electrode, wherein one or more layers of the organic material layers include the compound of Chemical Formula 1.

The organic material layer of the organic light emitting device of the present invention may have a single layer structure, or it may have a multilayered structure in which two or more organic material layers are stacked. For example, the organic light emitting device of the present invention may have a structure including a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a light emitting layer, wherein the light emitting layer includes the compound of Chemical Formula 1. In particular, the compound according to the present invention can be used as a host in a light emitting layer.

The organic material layer may include an electron transport layer or an electron injection layer, wherein the electron transport layer or the electron injection layer may include the compound of Chemical Formula 1.

The electron transport layer, the electron injection layer, or a layer for simultaneously performing the electron transport and electron injection includes the compound of Chemical Formula 1.

The organic material layer may include a light emitting layer and an electron transport layer, wherein the electron transport layer may include the compound of Chemical Formula 1.

The organic light emitting device according to the present invention may be a normal type of organic light emitting device in which an anode, one or more organic material layers, and a cathode are sequentially stacked on a substrate. Further, the organic light emitting device according to the present invention may be an inverted type of organic light emitting device in which a cathode, one or more organic material layers, and an anode are sequentially stacked on a substrate. For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4. In such a structure, the compound of Chemical Formula 1 may be included in the light emitting layer.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound of Chemical Formula 1 may be included in one or more layers of the hole injection layer, the hole transport layer, the electron blocking layer, the light emitting layer, the electron transport layer, and the electron injection layer.

The organic light emitting device according to the present invention may be manufactured by materials and methods known in the art, except that one or more layers of the organic material layers include the compound of Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer, and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

In addition, the compound of Chemical Formula 1 may be formed into an organic layer by a solution coating method as well as a vacuum deposition method at the time of manufacturing an organic light emitting device. Herein, the solution coating method means a spin coating method, a dip coating method, a doctor blading method, an inkjet printing method, a screen printing method, a spray method, a roll coating method, or the like, but is not limited thereto.

In addition to such a method, the organic light emitting device may be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is a layer provided between the hole transport layer and the light emitting layer in order to prevent the electrons injected from the cathode from being transferred to the hole transport layer without being recombined in the light emitting layer, which may also be referred to as an electron inhibition layer or an electron stopping layer. The electron blocking layer is preferably a material having a smaller electron affinity than the electron transport layer.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole, and benzimidazole-based compound; a poly(p-phenylenevinylene)(PPV)-based polymer; a spiro compound; polyfluorene; rubrene; and the like, but are not limited thereto.

The light emitting layer may include a host material and a dopant material. The host material may be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. Preferably, the compound of Chemical Formula 1 may be included as a host material in the light emitting layer.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryl diamine, styryl triamine, styryl tetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has large mobility for electrons. Specific examples thereof include: an Al complex of 8-hydroxyquinoline; a complex including $Alq_3$; an organic radical compound; a hydroxyflavone-metal complex; and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front emission type, a rear emission type, or a double side emission type according to the used material.

The compound of Chemical Formula 1 may be included in an organic solar cell or an organic transistor in addition to an organic light emitting device.

Hereinafter, it will be described in more detail to help understanding of the present invention. However, the following examples are presented for illustrative purposes only, and are not intended to limit the scope of the present invention.

PREPARATION EXAMPLES

Preparation Example 1: Preparation of Compound P-4

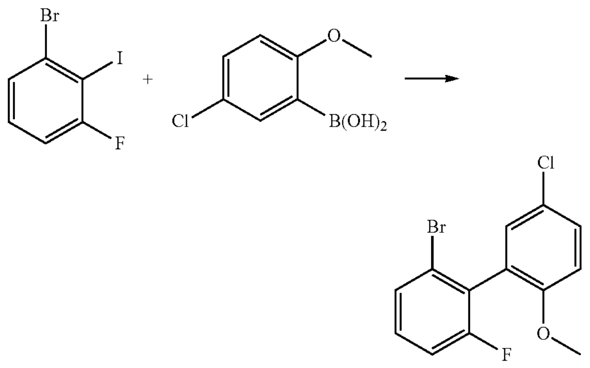

P-1

1-bromo-3-fluoro-2-iodobenzene (100 g, 333.5 mmol) and (5-chloro-2-methoxyphenyl)boronic acid (62.2 g, 333.5 mmol) were dissolved in 800 ml of tetrahydrofuran (THF). A 2M aqueous sodium carbonate ($Na_2CO_3$) solution (500 ml) and tetrakis(triphenylphosphine)palladium(0)[$Pd(PPh_3)_4$] (7.7 g, 6.7 mmol) were added thereto, and the mixture was refluxed for 12 hours. After the reaction was completed, the reaction mixture was cooled to room temperature, and the resulting mixture was extracted three times with water and toluene. The toluene layer was separated, dried over magnesium sulfate, and filtered. The filtrate was distilled under reduced pressure, and the obtained mixture was recrystallized three times with chloroform and ethanol to give Compound P-1 (53.7 g, yield: 51%; MS: $[M+H]^+=314$).

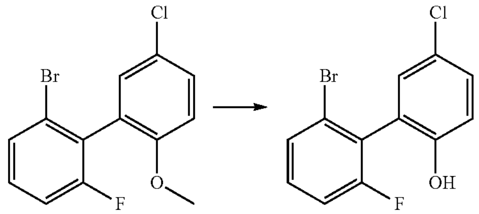

P-1 P-2

Compound P-1 (50.0 g, 158.5 mmol) was dissolved in dichloromethane (600 ml) and then cooled to 0° C. Boron tribromide (15.8 ml, 166.4 mmol) was slowly added dropwise thereto and then stirred for 12 hours. After the reaction was completed, the reaction mixture was washed three times with water, dried over magnesium sulfate, and filtered. The filtrate was distilled under reduced pressure and purified by column chromatography to give Compound P-2 (47.4 g, yield: 99%; MS: $[M+H]^+=300$).

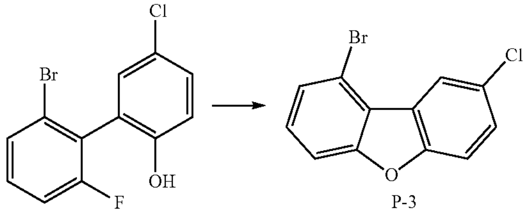

P-2 P-3

Compound P-2 (40.0 g, 132.7 mmol) was dissolved in distilled dimethylformamide (DMF) (400 ml). This was cooled to 0° C. and sodium hydride (3.5 g, 145.9 mmol) was slowly added dropwise thereto. After stirring for 20 minutes, the mixture was stirred at 100° C. for 1 hour. After the reaction was completed, the reaction mixture was cooled to room temperature, and 100 ml of ethanol was slowly added. The above mixture was distilled under reduced pressure, and the obtained mixture was recrystallized with chloroform and ethyl acetate to give Compound P-3 (30.3 g, yield: 81%; MS: $[M+H]^+280$).

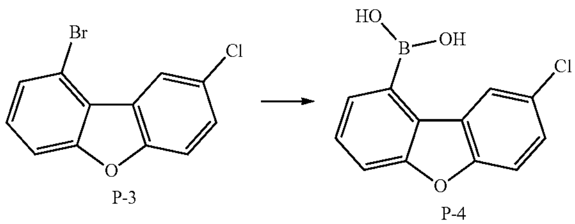

P-3 P-4

After Compound P-3 (30.0 g, 106.6 mmol) was dissolved in tetrahydrofuran (300 ml), the temperature was lowered to −78° C. and 1.7 M tert-butyllithium (t-BuLi) (62.7 ml, 106.6 mmol) was slowly added. After stirring at the same temperature for 1 hour, triisopropylborate ($B(OiPr)_3$) (28.3 ml, 213.1 mmol) was added thereto and then stirred for 3 hours while gradually raising the temperature to room temperature. A 2N aqueous hydrochloric acid solution (200 ml) was added to the reaction mixture, which was stirred at room temperature for 1.5 hours. The produced precipitate was filtered, washed sequentially with water and ethyl ether, and then dried in vacuo. After drying, the result was dispersed in ethyl ether, stirred for 2 hours, filtered, and dried to produce Compound P-4 (24.4 g, yield: 93%; MS: $[M+H]^+$=247).

Preparation Example 2: Preparation of Compound Q-4

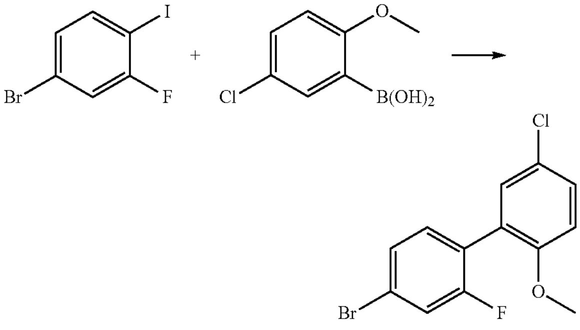

Q-1

1-bromo-3-fluoro-4-iodobenzene (50 g, 166.6 mmol) and (5-chloro-2-methoxyphenyl)boronic acid (31.1 g, 166.6 mmol) were dissolved in 800 ml of tetrahydrofuran (THF). A 2M aqueous sodium carbonate ($Na_2CO_3$) solution (250 ml) and tetrakis(triphenylphosphine)palladium(0) [$Pd(PPh_3)_4$] (3.8 g, 3 mol %) were added thereto, and the mixture was refluxed for 12 hours. After the reaction was completed, the reaction mixture was cooled to room temperature, and the resulting mixture was extracted three times with water and toluene. The toluene layer was separated, dried over magnesium sulfate, and filtered. The filtrate was distilled under reduced pressure, and the obtained mixture was recrystallized three times with chloroform and ethanol to give Compound Q-1 (27.5 g, yield: 51%; MS: $[M+H]^+$=314).

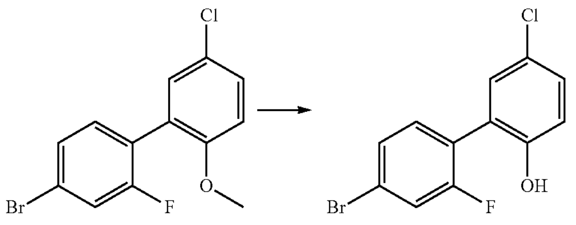

Q-1 Q-2

Compound Q-1 (25.0 g, 150 mmol) was dissolved in dichloromethane (300 ml) and then cooled to 0° C. Boron tribromide (7.9 ml, 83.2 mmol) was slowly added dropwise thereto and then stirred for 12 hours. After the reaction was completed, the reaction mixture was washed three times with water, dried over magnesium sulfate, and filtered. The filtrate was distilled under reduced pressure and purified by column chromatography to give Compound Q-2 (23.7 g, yield: 99%; MS: $[M+H]^+$=300).

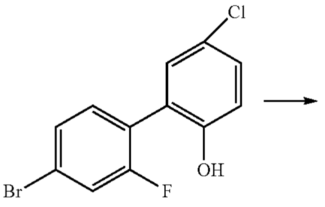

Q-2

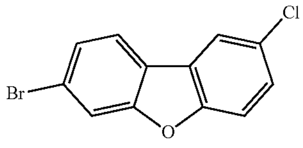

Q-3

Compound Q-2 (20.0 g, 66.4 mmol) was dissolved in distilled dimethylformamide (DMF) (200 ml). This was cooled to 0° C. and sodium hydride (1.8 g, 72.9 mmol) was slowly added dropwise thereto. After stirring for 20 minutes, the mixture was stirred at 100° C. for 1 hour. After the reaction was completed, the reaction mixture was cooled to room temperature, and 100 ml of ethanol was slowly added. The above mixture was distilled under reduced pressure, and the obtained mixture was recrystallized with chloroform and ethyl acetate to give Compound Q-3 (15.2 g, yield: 81%; MS: $[M+H]^+$=280).

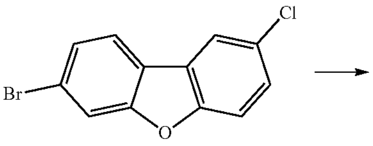

Q-3

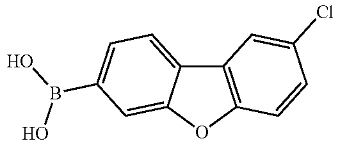

Q-4

After Compound Q-3 (15.0 g, 53.3 mmol) was dissolved in tetrahydrofuran (150 ml), the temperature was lowered to −78° C. and 1.7 M tert-butyllithium (t-BuLi) (31.8 ml, 53.3 mmol) was slowly added thereto. After stirring at the same temperature for 1 hour, triisopropylborate ($B(OiPr)_3$) (14.2 ml 107.0 mmol) was added thereto and then stirred for 3 hours while gradually raising the temperature to room temperature. A 2N aqueous hydrochloric acid solution (100 ml) was added to the reaction mixture, which was stirred at room temperature for 1.5 hours. The produced precipitate was filtered, washed sequentially with water and ethyl ether, and then dried in vacuo. After drying, the result was dispersed in ethyl ether, stirred for 2 hours, filtered, and dried to produce Compound Q-4 (12.2 g, yield: 93%; MS: $[M+H]^+$= 247).

Preparation Example 3: Preparation of Compound R-4

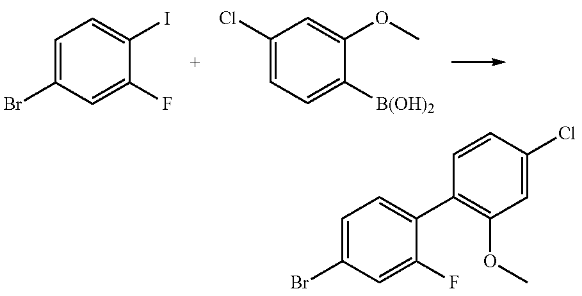

R-1

1-bromo-3-fluoro-4-iodobenzene (50 g, 166.6 mmol) and (4-chloro-2-methoxyphenyl)boronic acid (31.1 g, 166.6 mmol) were dissolved in 800 ml of tetrahydrofuran (THF). A 2M aqueous sodium carbonate ($Na_2CO_3$) solution (250 ml) and tetrakis(triphenylphosphine)palladium(0) [$Pd(PPh_3)_4$] (3.8 g, 3 mol %) were added thereto, and the mixture was refluxed for 12 hours. After the reaction was completed, the reaction mixture was cooled to room temperature, and the resulting mixture was extracted three times with water and toluene. The toluene layer was separated, dried over magnesium sulfate, and filtered. The filtrate was distilled under reduced pressure, and the obtained mixture was recrystallized three times with chloroform and ethanol to give Compound R-1 (27.5 g, yield: 51%; MS: $[M+H]^+=314$).

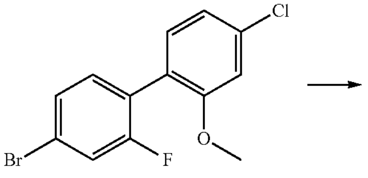

R-1

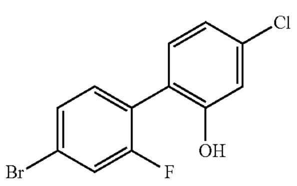

R-2

Compound R-1 (25.0 g, 150 mmol) was dissolved in dichloromethane (300 ml) and then cooled to 0° C. Boron tribromide (7.9 ml, 83.2 mmol) was slowly added dropwise thereto and then stirred for 12 hours. After the reaction was completed, the reaction mixture was washed three times with water, dried over magnesium sulfate, and filtered. The filtrate was distilled under reduced pressure and purified by column chromatography to give Compound R-2 (23.7 g, yield: 99%; MS: $[M+H]^+=300$).

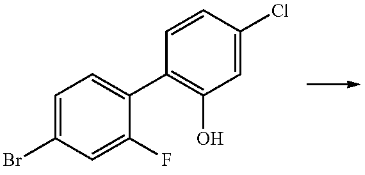

R-2

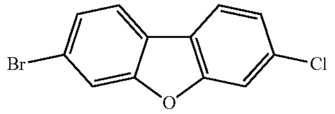

R-3

Compound R-2 (20.0 g, 66.4 mmol) was dissolved in distilled dimethylformamide (DMF) (200 nil). This was cooled to 0° C. and sodium hydride (1.8 g, 72.9 mmol) was slowly added dropwise thereto. After stirring for 20 minutes, the mixture was stirred at 100° C. for 1 hour. After the reaction was completed, the reaction mixture was cooled to room temperature, and 100 ml of ethanol was slowly added. The above mixture was distilled under reduced pressure, and the obtained mixture was recrystallized with chloroform and ethyl acetate to give Compound R-3 (15.2 g, yield: 81%; MS: $[M+H]^+=280$).

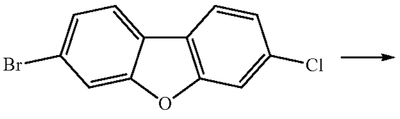

R-3

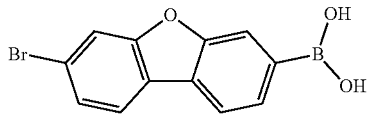

R-4

After Compound R-3 (15.0 g, 53.3 mmol) was dissolved in tetrahydrofuran (150 ml), the temperature was lowered to −78° C. and 1.7 M tert-butyllithium (t-BuLi) (31.8 ml, 53.3 mmol) was slowly added thereto. After stirring at the same temperature for 1 hour, triisopropylborate ($B(OiPr)_3$) (14.2 ml, 107.0 mmol) was added thereto and then stirred for 3 hours while gradually raising the temperature to room temperature. A 2N aqueous hydrochloric acid solution (100 ml) was added to the reaction mixture, which was stirred at room temperature for 1.5 hours. The produced precipitate was filtered, washed sequentially with water and ethyl ether, and then dried in vacuo. After drying, the result was dispersed in ethyl ether, stirred for 2 hours, filtered, and dried to produce Compound R-4 (12.2 g, yield: 93%; MS: $[M+H]^+=247$).

Preparation Example 4: Preparation of Compound T-4

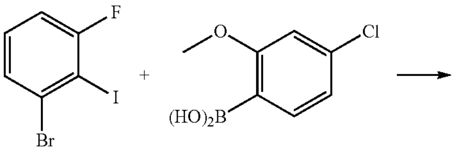

-continued

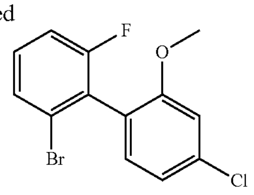

T-1

Compound T-1 (65.3 g, yield: 62%; MS: $[M+H]^+=314$) was prepared in the same manner as in the preparation of P-1 of Preparation Example 1, except that (4-chloro-2-methoxyphenyl)boronic acid)(62.2 g, 333.5 mmol) was used instead of (5-chloro-2-methoxyphenyl)boronic acid)(62.2 g, 333.5 mmol).

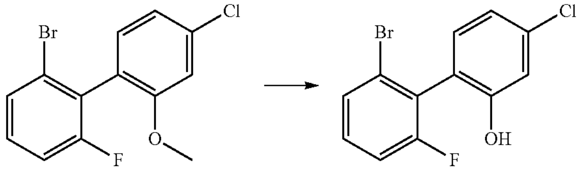

T-1 T-2

Compound T-2 (43.0 g, yield: 90%; MS: $[M+H]^+=300$) was prepared in the same manner as in the preparation of P-2 of Preparation Example 1, except that Compound T-1 (50.0 g, 158.5 mmol) was used instead of Compound P-1 (50.0 g, 158.5 mmol).

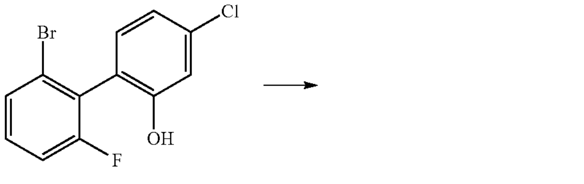

T-2

T-3

Compound T-3 (30.6 g, yield: 82%; MS: $[M+H]^+=280$) was prepared in the same manner as in the preparation of P-3 of Preparation Example 1, except that Compound T-2 (40.0 g, 132.7 mmol) was used instead of Compound P-2 (40.0 g, 132.7 mmol).

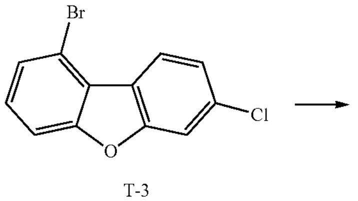

T-3

-continued

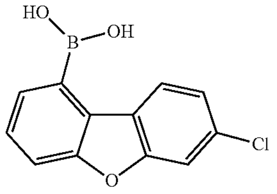

T-4

Compound T-4 (25.0 g, yield: 95%; MS: $[M+H]^+=247$) was prepared in the same manner as in the preparation of P-4 of Preparation Example 1, except that Compound T-3 (30.0 g, 106.6 mmol) was used instead of Compound P-3 (30.0 g, 106.6 mmol).

Preparation Example 5: Preparation of Compounds A1, A2, A4 and A5

1) Preparation of Compound A1

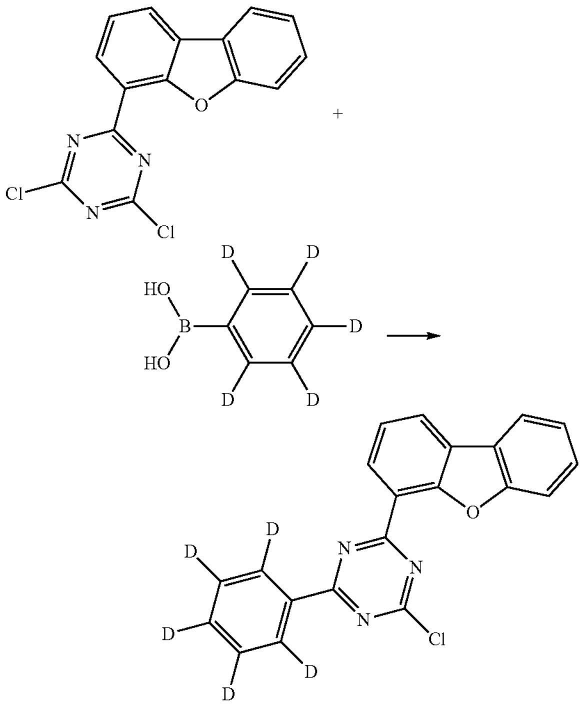

A1

After 2,4-dichloro-6-(dibenzo[b,d]furan-4-yl)-1,3,5-triazine (50.0 g, 158.7 mmol) and (phenyl-d5)boronic acid (20.2 g, 158.7 mmol) were dispersed in tetrahydrofuran (500 ml), a 2M aqueous potassium carbonate solution (aq. $K_2CO_3$) (238 ml, 476.2 mmol) was added and tetrakistriphenylphosphinopalladium $[Pd(PPh_3)_4]$ (5.5 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound A1 (39.1 g, yield: 68%; MS: $[M+H]^+=363$).

2) Preparation of Compound A2

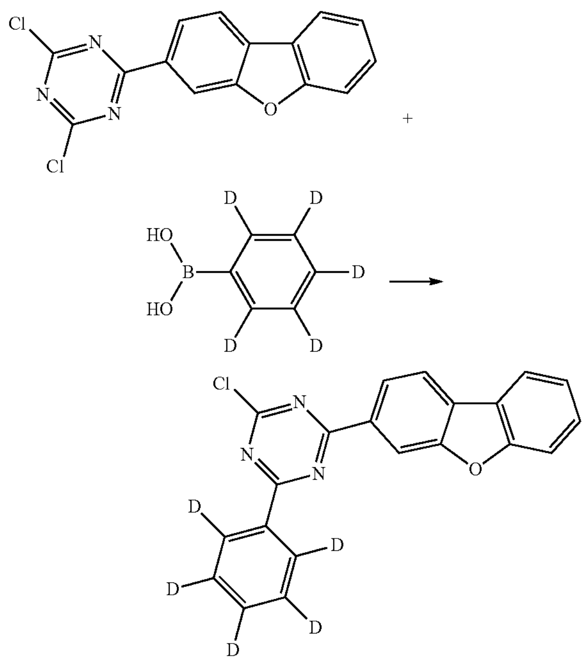

A2

After 2,4-dichloro-6-(dibenzo[b,d]furan-3-yl)-1,3,5-triazine (50.0 g, 158.7 mmol) and (phenyl-d5)boronic acid (20.2 g, 158.7 mmol) were dispersed in tetrahydrofuran (500 ml), a 2M aqueous potassium carbonate solution (aq. $K_2CO_3$) (238 ml, 476.2 mmol) was added and tetrakistriphenylphosphinopalladium [$Pd(PPh_3)_4$] (5.5 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound A2 (42.5 g, yield: 74%; MS: $[M+H]^+=363$).

3) Preparation of Compound A4

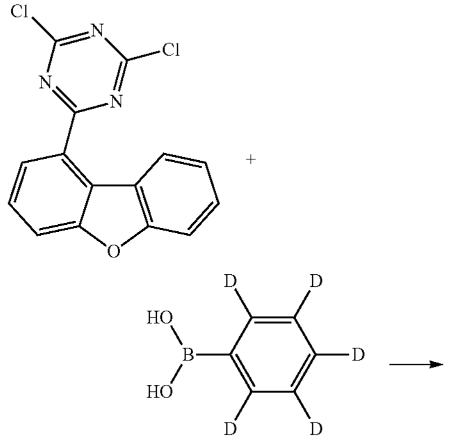

-continued

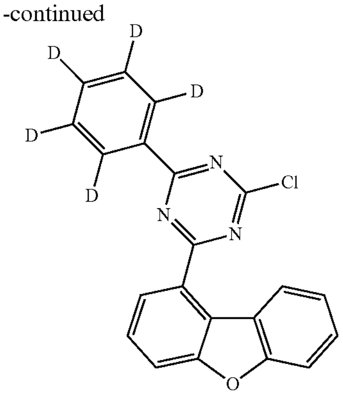

A4

After 2,4-dichloro-6-(dibenzo[b,d]furan-1-yl)-1,3,5-triazine (50.0 g, 158.7 mmol) and (phenyl-d5)boronic acid (20.2 g, 158.7 mmol) were dispersed in tetrahydrofuran (500 ml), a 2M aqueous potassium carbonate solution (aq. $K_2CO_3$) (238 ml, 476.2 mmol) was added and tetrakistriphenylphosphinopalladium [$Pd(PPh_3)_4$] (5.5 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound A4 (33.9 g, yield: 59%; MS: $[M+H]^+=363$).

4) Preparation of Compound A5

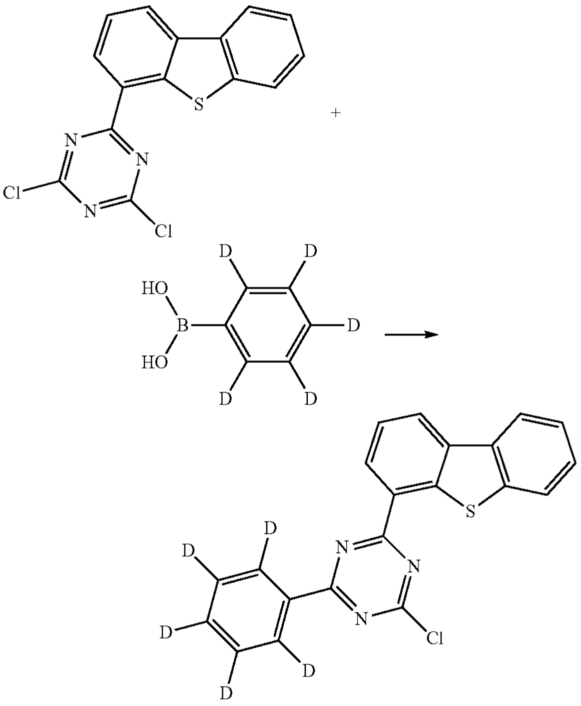

A5

After 2,4-dichloro-6-(dibenzo[b,d]thiophen-4-yl)-1,3,5-triazine (50.0 g, 151.1 mmol) and (phenyl-d5)boronic acid (19.2 g, 151.1 mmol) were dispersed in tetrahydrofuran (500 ml), a 2M aqueous potassium carbonate solution (aq.

$K_2CO_3$) (226 ml, 453.2 mmol) was added and tetrakistriphenylphosphinopalladium [$Pd(PPh_3)_4$] (5.2 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound A5 (42.8 g, yield: 75%; MS: $[M+H]^+$=379).

Preparation Example 6: Preparation of Compounds Sub 1 to Sub 16

1) Preparation of Compound Sub 1

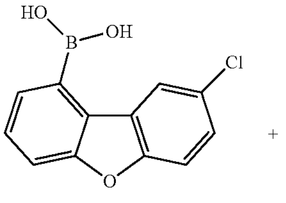

P-4

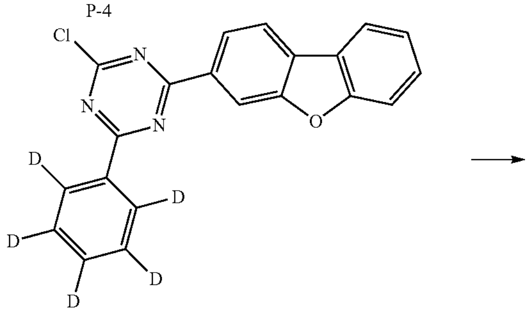

A2

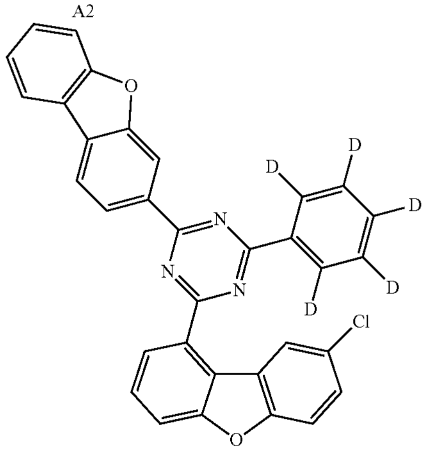

sub 1

After Compound P-4 (20.0 g, 81.3 mmol) and Compound A2 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 1 (21.9 g, yield: 51%; MS: $[M+H]^+$=529).

2) Preparation of Compound Sub 2

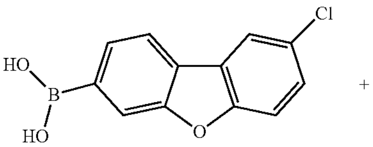

Q-4

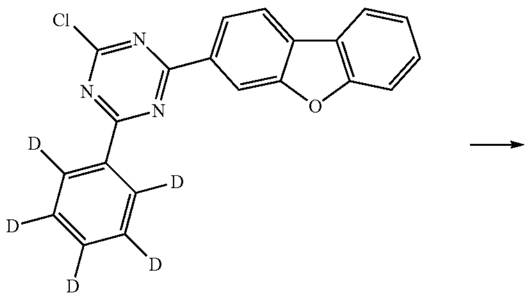

A2

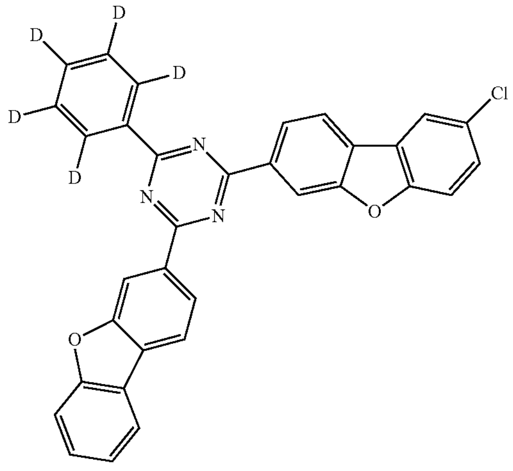

sub 2

After Compound Q-4 (20.0 g, 81.3 mmol) and Compound A2 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 2 (28.3 g, yield: 66%; MS: $[M+H]^+$=529).

3) Preparation of Compound Sub 3

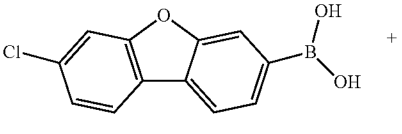

R-4

-continued

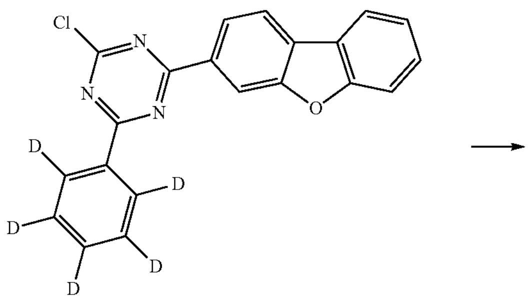

A2

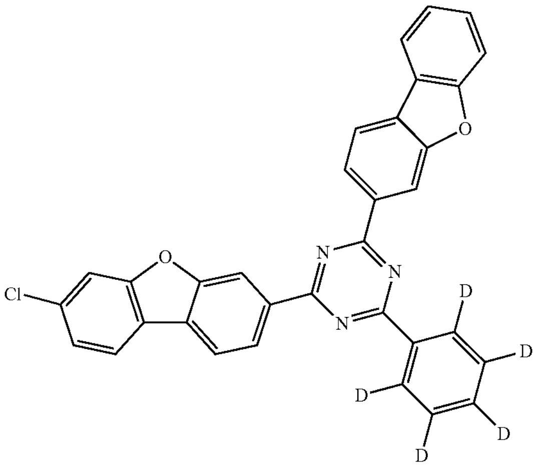

sub 3

After Compound R-4 (20.0 g, 81.3 mmol) and Compound A2 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 3 (28.3 g, yield: 66%; MS: $[M+H]^+$=529).

4) Preparation of Compound Sub 4

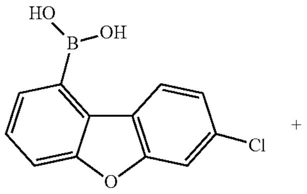

T-4

-continued

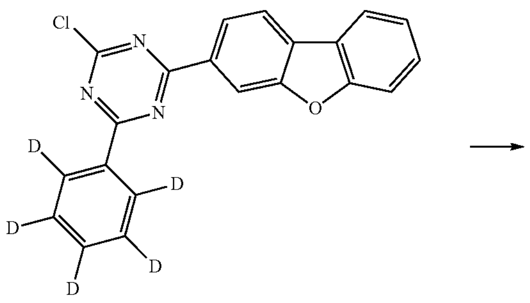

A2

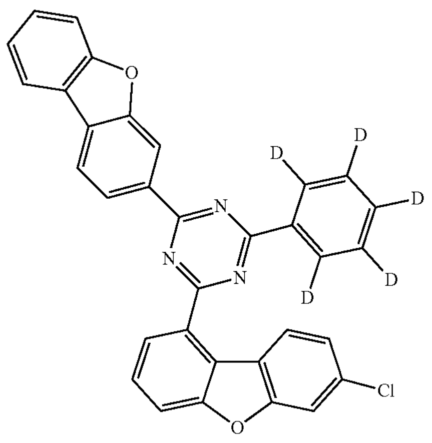

sub 4

After Compound T-4 (20.0 g, 81.3 mmol) and Compound A2 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 4 (21.5 g, yield: 50%; MS: $[M+H]^+$=529).

5) Preparation of Compound Sub 5

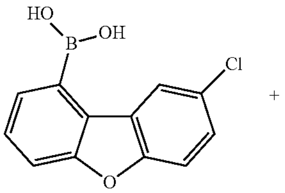

P-4

-continued

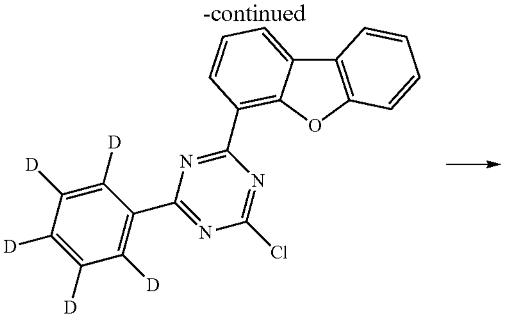

A1

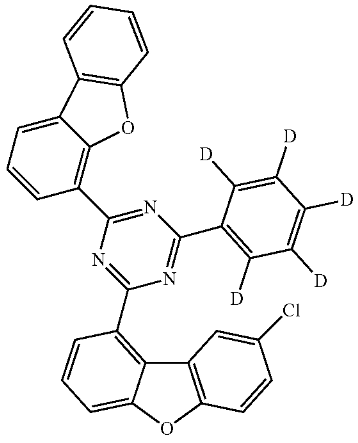

sub 5

After Compound P-4 (20.0 g, 81.3 mmol) and Compound A1 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 5 (25.8 g, yield: 60%; MS: $[M+H]^+$=529).

6) Preparation of Compound Sub 6

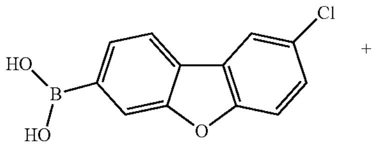

Q-4

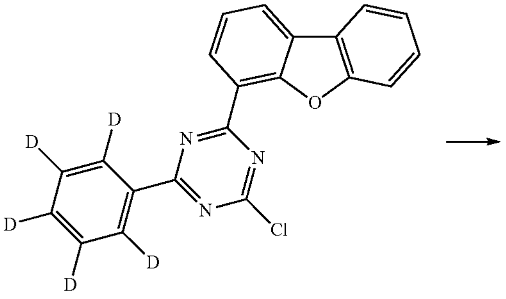

A1

-continued

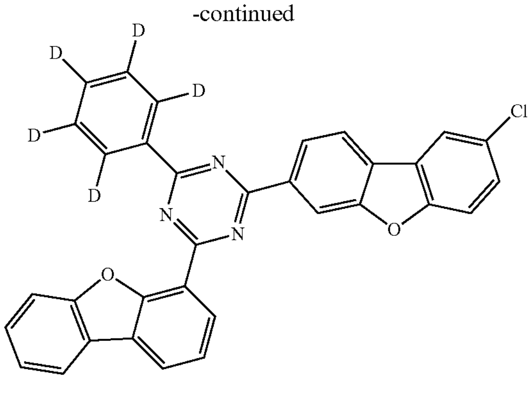

sub 6

After Compound Q-4 (20.0 g, 81.3 mmol) and Compound A1 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 6 (24.5 g, yield: 57%; MS: $[M+H]^+$=529).

7) Preparation of Compound Sub 7

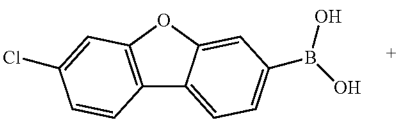

R-4

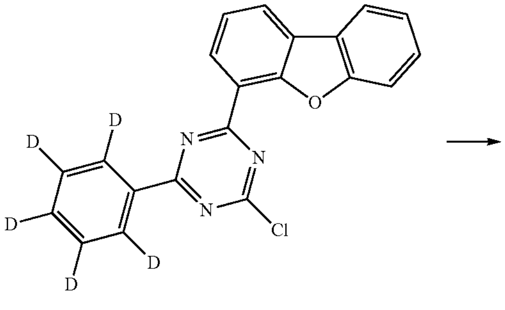

A1

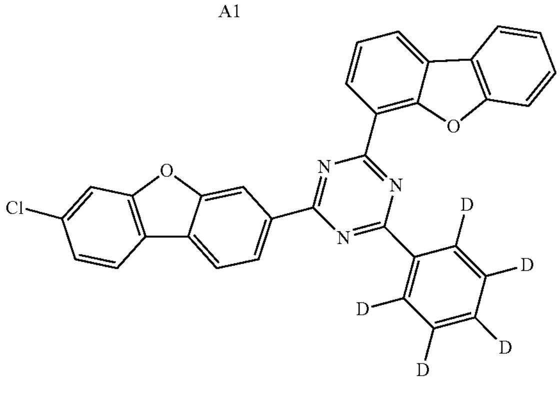

sub 7

After Compound R-4 (20.0 g, 81.3 mmol) and Compound A1 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 7 (32.2 g, yield: 75%; MS: $[M+H]^+$=529).

8) Preparation of Compound Sub 8

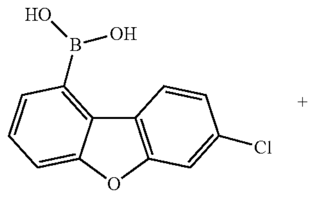

T-4

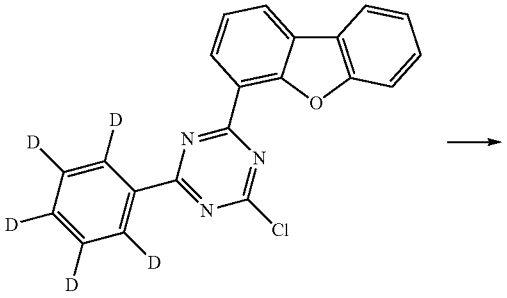

A1

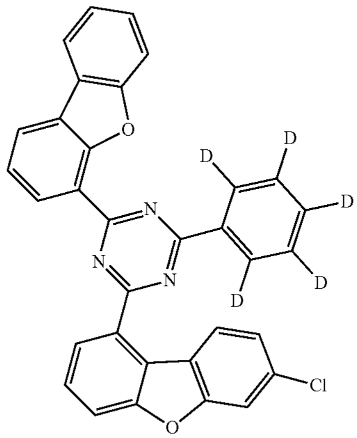

sub 8

After Compound T-4 (20.0 g, 81.3 mmol) and Compound A1 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 8 (27.9 g, yield: 65%; MS: $[M+H]^+$=529).

9) Preparation of Compound Sub 9

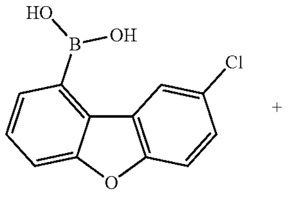

P-4

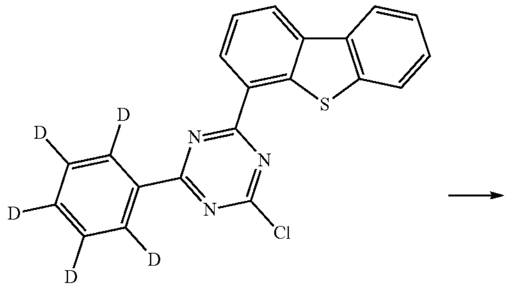

A5

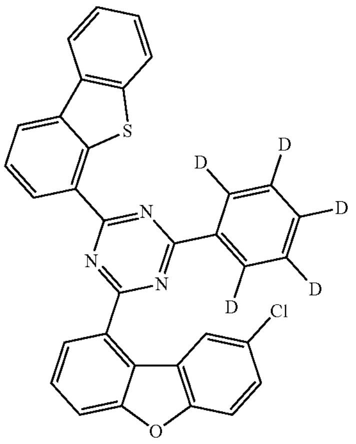

sub 9

After Compound P-4 (20.0 g, 81.3 mmol) and Compound A5 (30.7 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 9 (24.8 g, yield: 56%; MS: $[M+H]^+$=545).

10) Preparation of Compound Sub 10

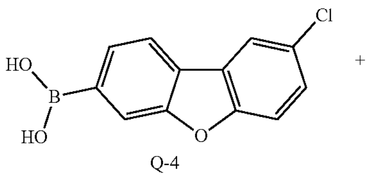

Q-4

-continued

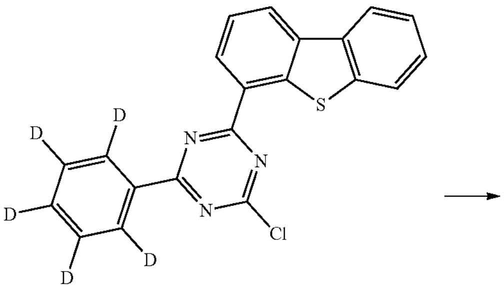

A5

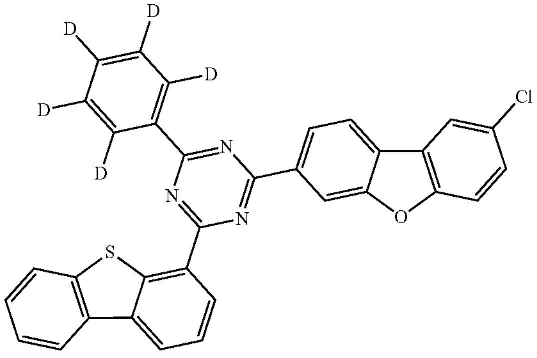

sub 10

After Compound Q-4 (20.0 g, 81.3 mmol) and Compound A5 (30.7 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 10 (26.5 g, yield: 60%; MS: $[M+H]^+$=545).

11) Preparation of Compound Sub 11

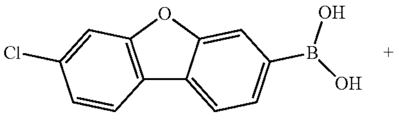

R-4

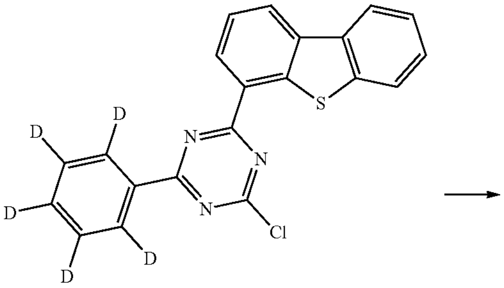

A5

-continued

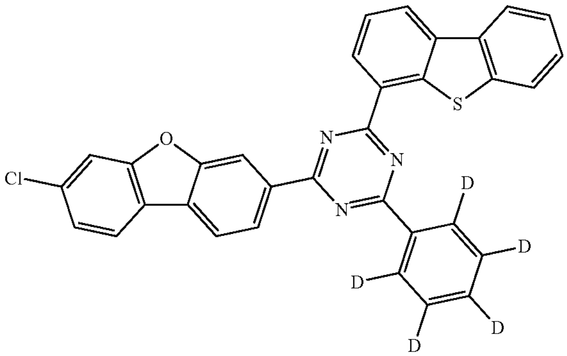

sub 11

After Compound R-4 (20.0 g, 81.3 mmol) and Compound A5 (30.7 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 11 (31.0 g, yield: 70%; MS: $[M+H]^+$=545).

12) Preparation of Compound Sub 12

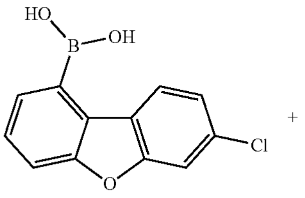

T-4

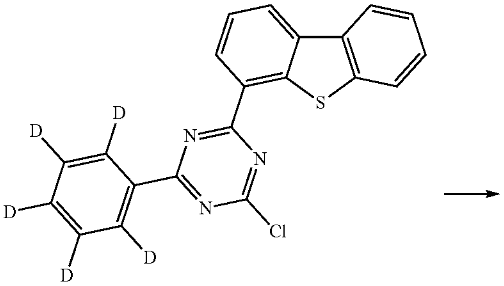

A5

-continued

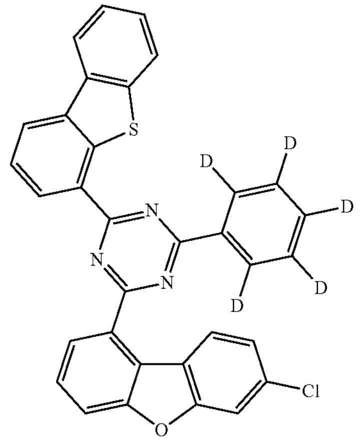

sub 12

After Compound T-4 (20.0 g, 81.3 mmol) and Compound A5 (30.7 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 12 (29.2 g, yield: 66%; MS: $[M+H]^+$=545).

13) Preparation of Compound Sub 13

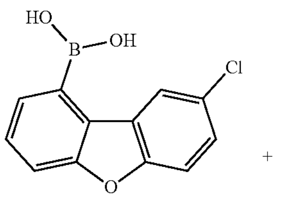

P-4

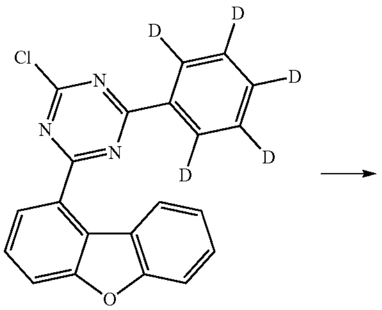

A4

-continued

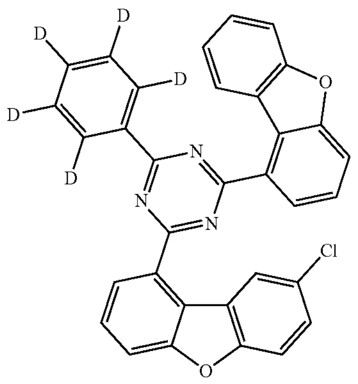

sub 13

After Compound P-4 (20.0 g, 81.3 mmol) and Compound A4 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 13 (27.0 g, yield: 63%; MS: $[M+H]^+$=529).

14) Preparation of Compound Sub 14

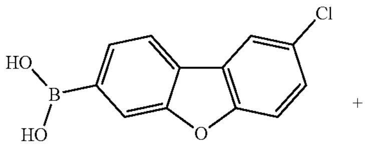

Q-4

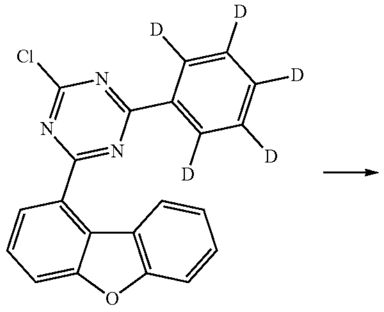

A4

-continued

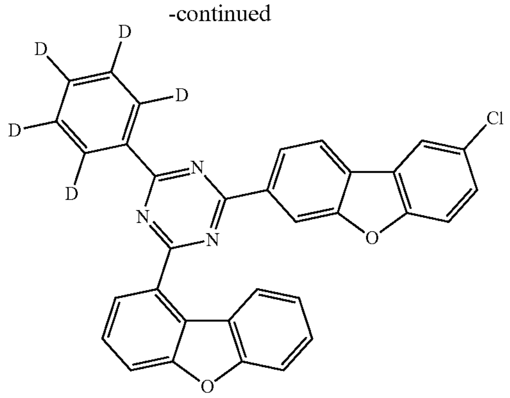

sub 14

After Compound Q-4 (20.0 g, 81.3 mmol) and Compound A4 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 14 (26.6 g, yield: 62%; MS: $[M+H]^+$=529).

15) Preparation of Compound Sub 15

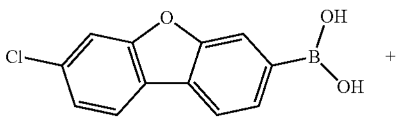

R-4

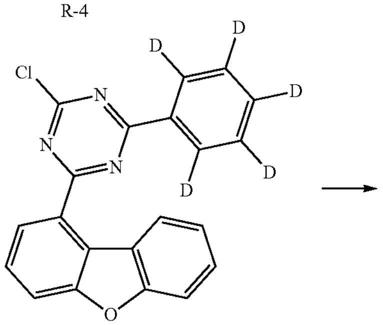

A4

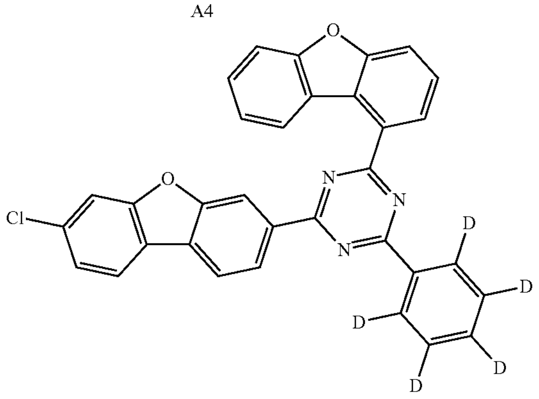

sub 15

After Compound R-4 (20.0 g, 81.3 mmol) and Compound A4 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 15 (30.9 g, yield: 72%; MS: $[M+H]^+$=529).

16) Preparation of Compound Sub 16

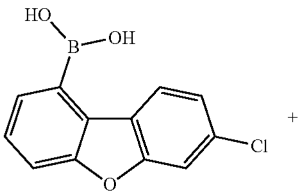

T-4

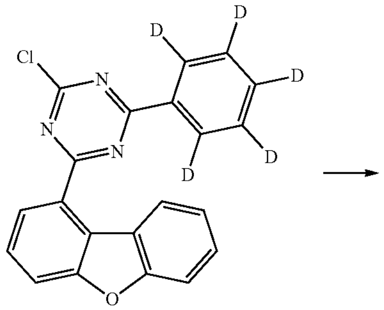

A4

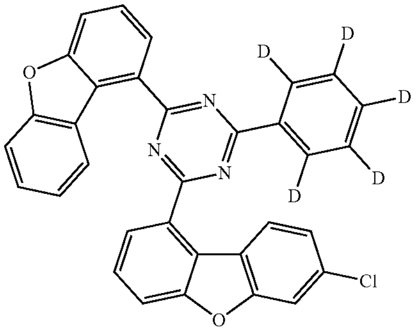

sub 16

After Compound T-4 (20.0 g, 81.3 mmol) and Compound A4 (29.4 g, 81.3 mmol) were dispersed in tetrahydrofuran (200 ml), a 2M aqueous potassium carbonate solution (aq. $K_2CO_3$) (122 ml, 243.9 mmol) was added and tetrakistriphenylphosphinopalladium [$Pd(PPh_3)_4$] (2.8 g, 3 mol %) was added, and then the mixture was stirred and refluxed for 5 hours. The reaction temperature was cooled to room temperature, and the produced solid was filtered. The filtered solid was recrystallized with chloroform and ethyl acetate, filtered, and then dried to give Compound sub 16 (23.2 g, yield: 54%; MS: $[M+H]^+$=529).

Preparation Example 7: Preparation of Compounds 1 to 16

1) Preparation of Compound 1

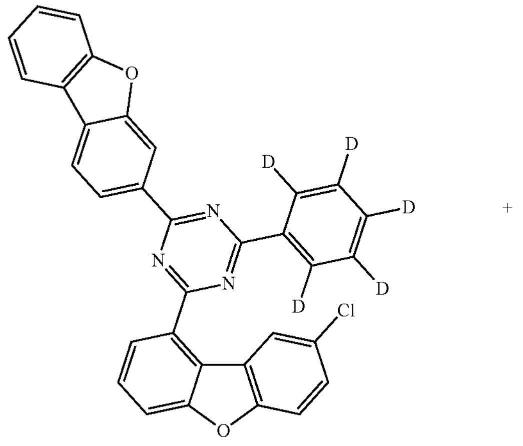

sub 1

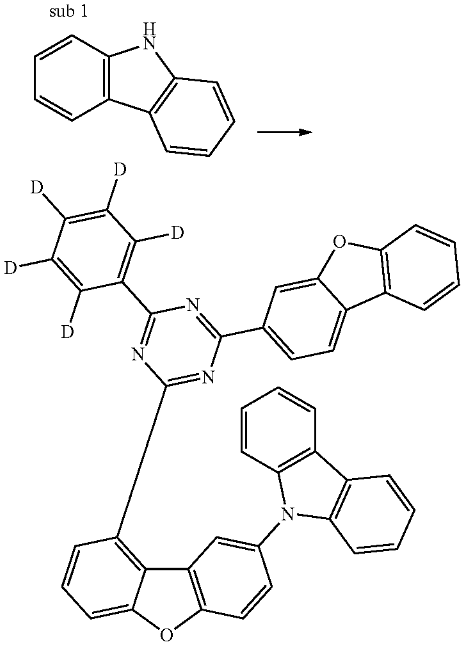

Compound 1

Compound sub 1 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 1 (13.5 g, yield: 54%).

MS: [M+H]+=660

2) Preparation of Compound 2

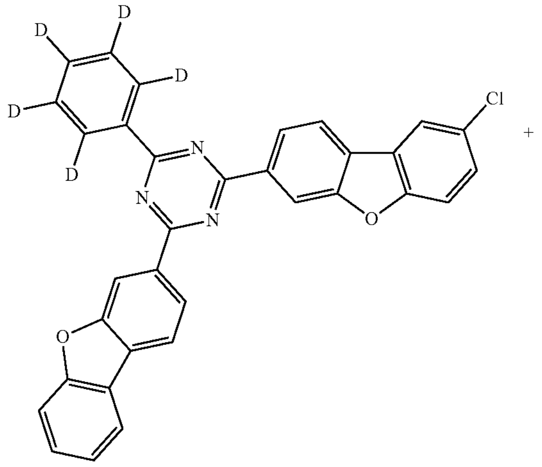

sub 2

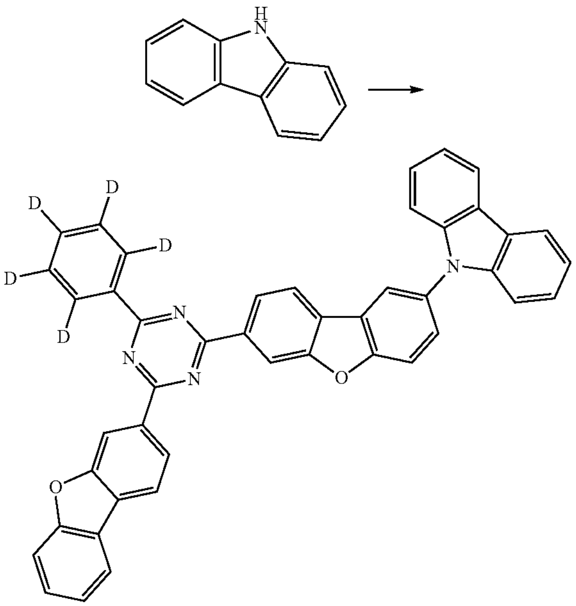

Compound 2

Compound sub 2 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 2 (9.0 g, yield: 36%).

MS: [M+H]+=660

3) Preparation of Compound 3

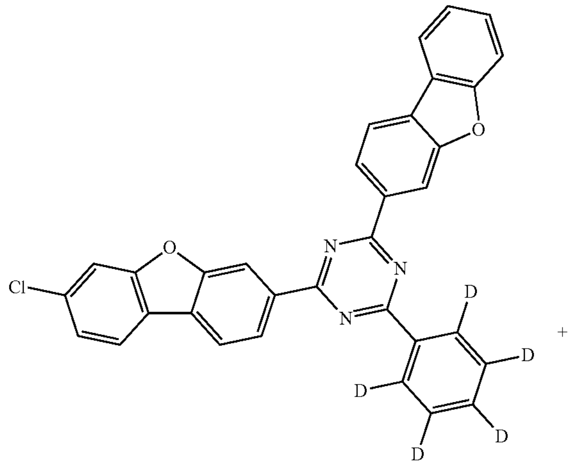

sub 3

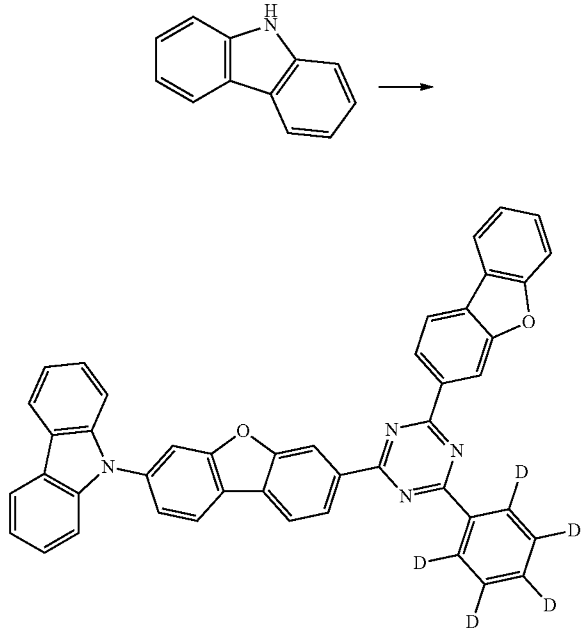

Compound 3

Compound sub 3 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 3 (13.5 g, yield: 54%).

MS: [M+H]+=660

4) Preparation of Compound 4

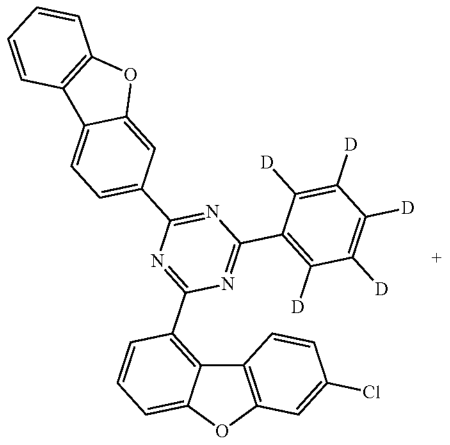

sub 4

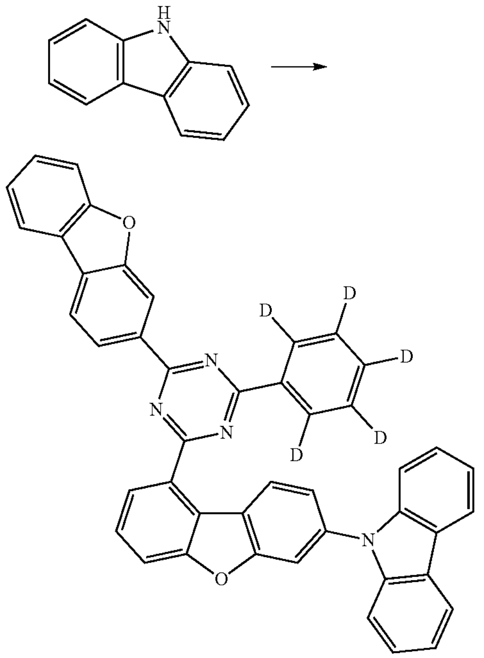

Compound 4

Compound sub 4 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 4 (9.0 g, yield: 36%).

MS: [M+H]+=660

5) Preparation of Compound 5

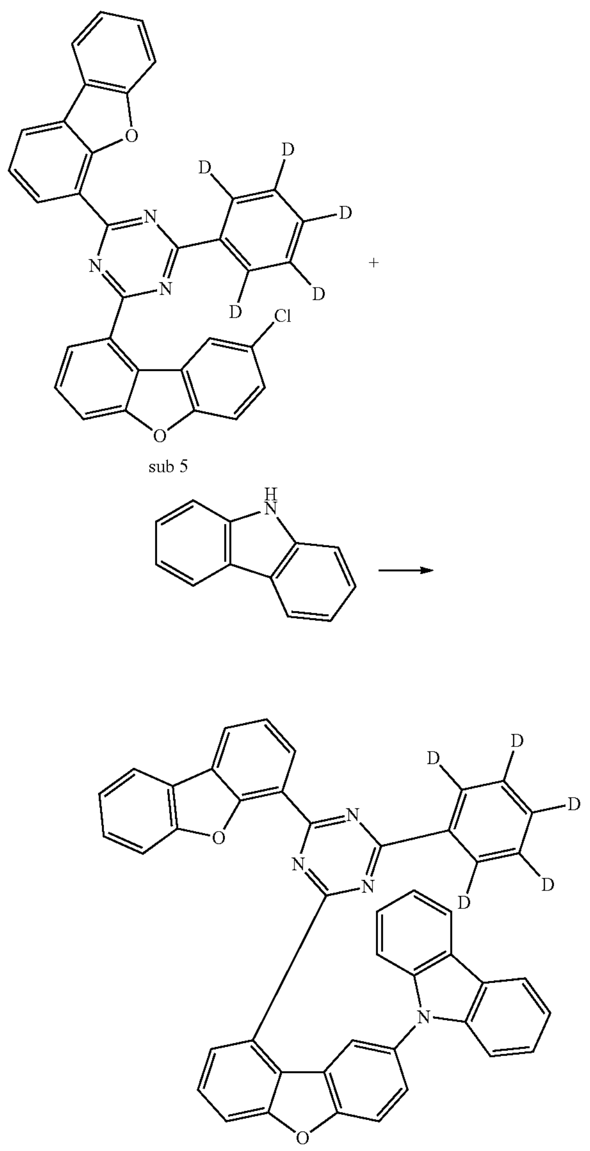

sub 5

Compound 5

Compound sub 5 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 5 (16.7 g, yield: 67%).

MS: [M+H]+=660

6) Preparation of Compound 6

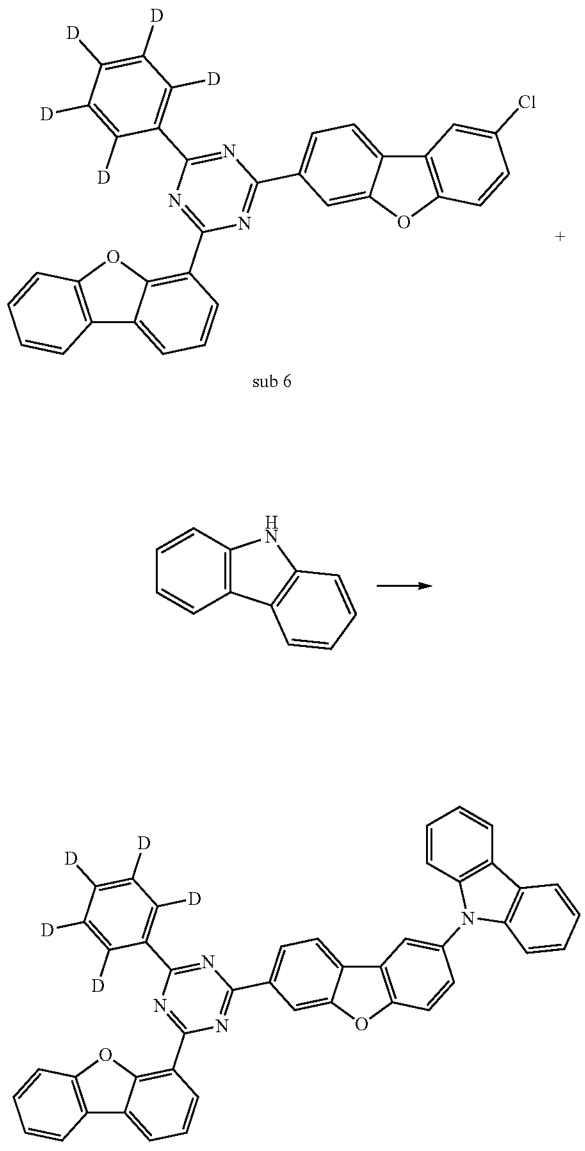

sub 6

Compound 6

Compound sub 6 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 6 (10.0 g, yield: 40%).

MS: [M+H]+=660

7) Preparation of Compound 7

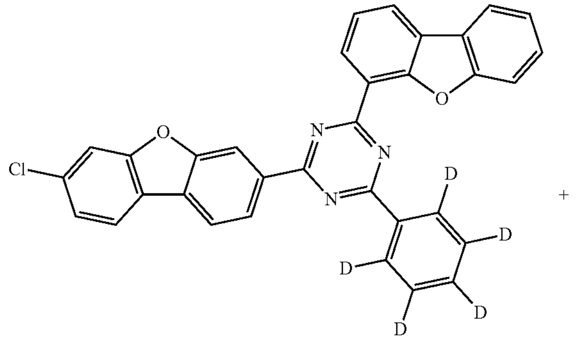

sub 7

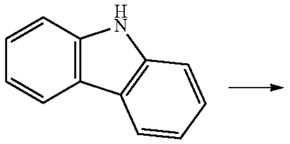

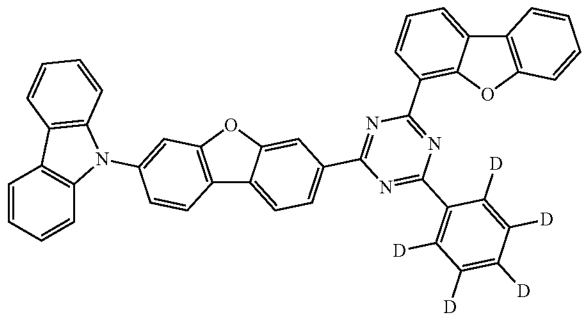

Compound 7

Compound sub 7 (20.0 g, 37.9 mmol) and 9-carbazole (6.3 g, 37.9 mmol) were added to and dissolved in 200 mL of xylene under a nitrogen atmosphere, and sodium Cert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 7 (10.2 g, yield: 41%).

MS: [M+H]+=660

8) Preparation of Compound 8

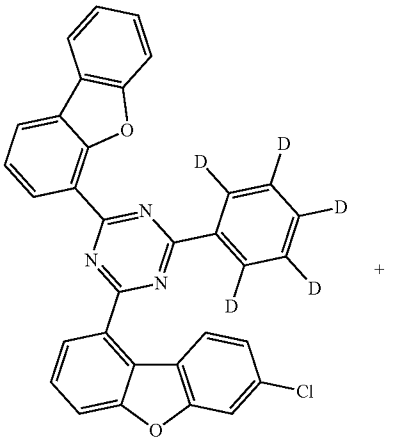

sub 8

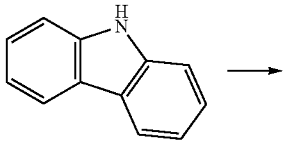

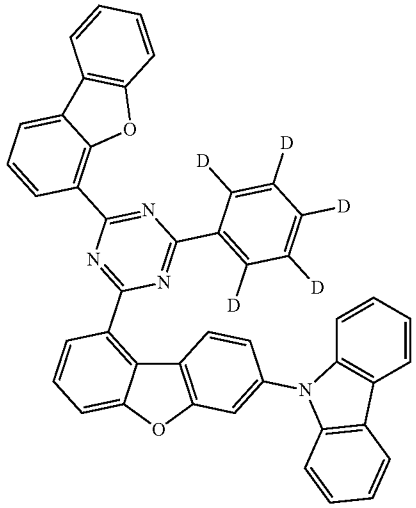

Compound 8

Compound sub 8 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 8 (18.5 g, yield: 74%).

MS: [M+H]+=660

9) Preparation of Compound 9

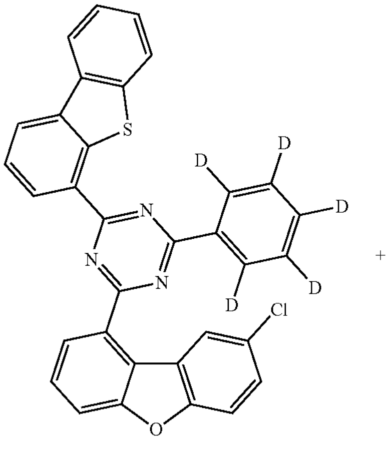

sub 9

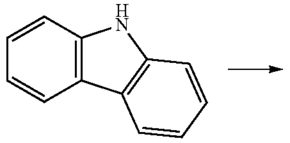

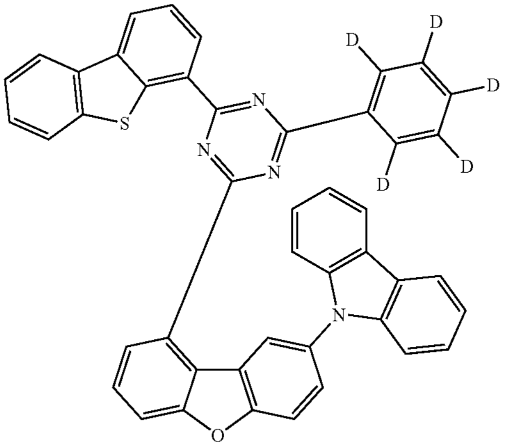

Compound 9

10) Preparation of Compound 10

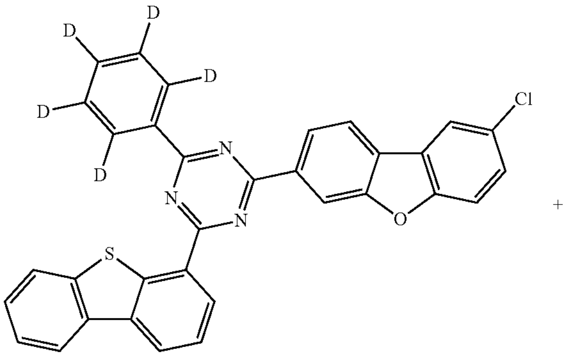

sub 10

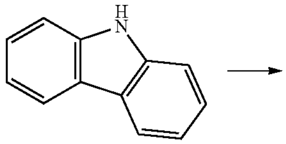

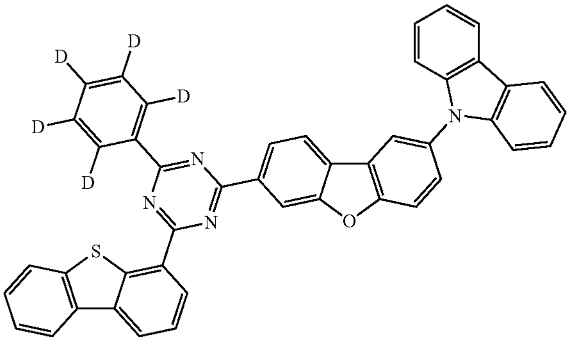

Compound 10

Compound sub 9 (20.0 g, 36.8 mmol) and 9-carbazole (6.1 g, 36.8 mmol) were added to and dissolved in 200 mL of xylene under a nitrogen atmosphere, and sodium tert-butoxide (7.1 g, 73.5 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 9 (9.7 g, yield: 39%).

MS: [M+H]+=676

Compound sub 10 (20.0 g, 36.8 mmol) and 9-carbazole (6.1 g, 36.8 mmol) were added to and dissolved in 200 mL of xylene under a nitrogen atmosphere, and sodium tert-butoxide (7.1 g, 73.5 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 10 (13.9 g, yield: 56%).

MS: [M+H]+=676

11) Preparation of Compound 11

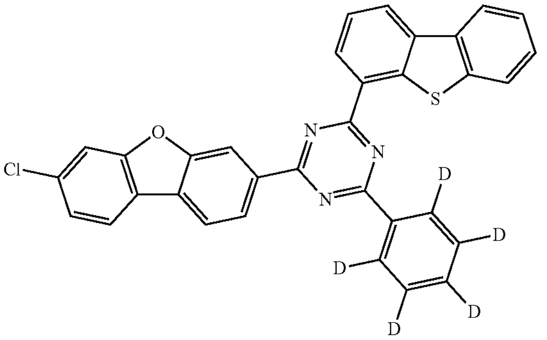

sub 11

+

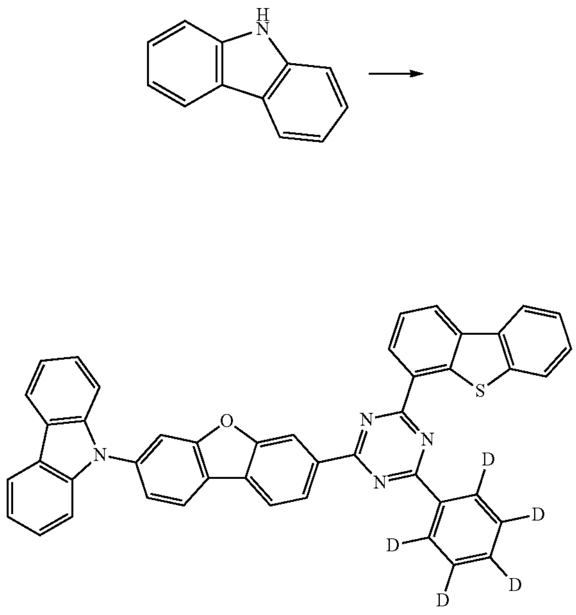

Compound 11

Compound sub 11 (20.0 g, 36.8 mmol) and 9-carbazole (6.1 g, 36.8 mmol) were added to and dissolved in 200 mL of xylene under a nitrogen atmosphere, and sodium tert-butoxide (7.1 g, 73.5 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 11 (14.4 g, yield: 58%).

MS: [M+H]+=676

12) Preparation of Compound 12

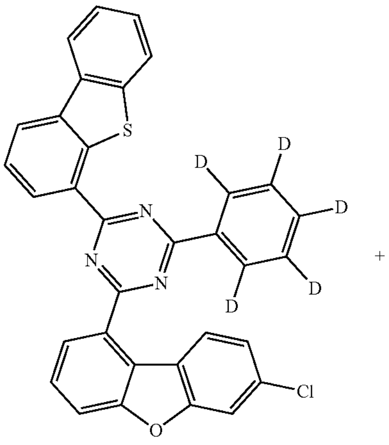

sub 12

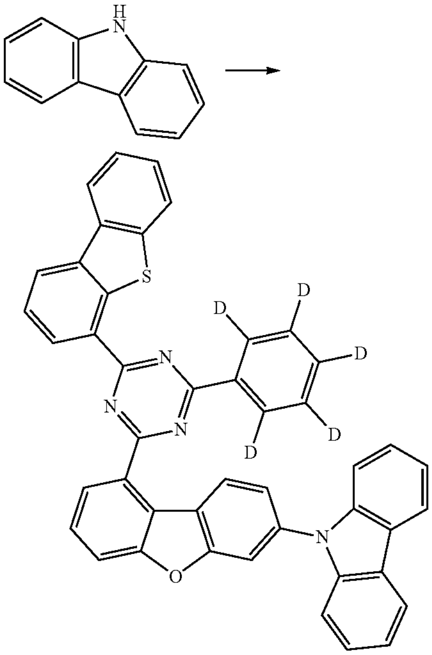

Compound 12

Compound sub 12 (20.0 g, 36.8 mmol) and 9-carbazole (6.1 g, 36.8 mmol) were added to and dissolved in 200 mL of xylene under a nitrogen atmosphere, and sodium tert-butoxide (7.1 g, 73.5 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 12 (11.2 g, yield: 45%).

MS: [M+H]+=676

13) Preparation of Compound 13

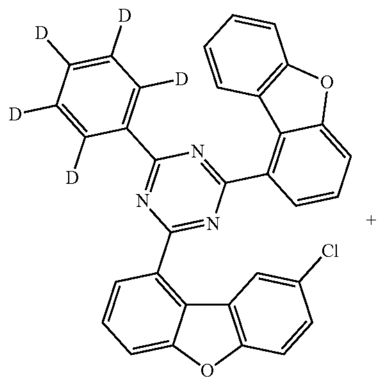

sub 13

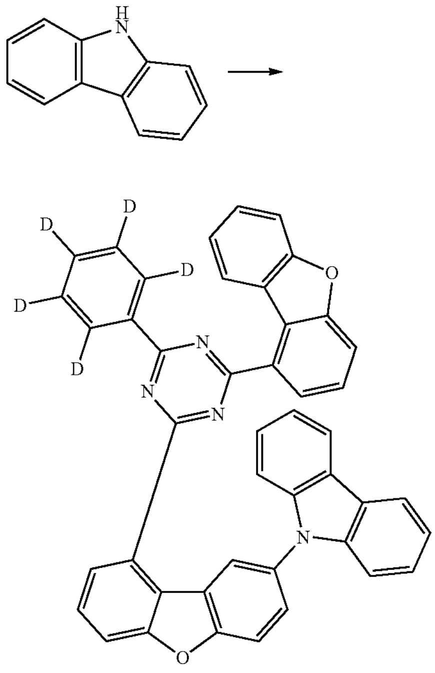

Compound 13

Compound sub 13 (20.0 g, 37.9 mmol) and 9-carbazole (6.3 g, 37.9 mmol) were added to and dissolved in 200 mL of xylene under a nitrogen atmosphere, and sodium Cert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 13 (13.7 g, yield: 55%).

MS: [M+H]+=660

14) Preparation of Compound 14

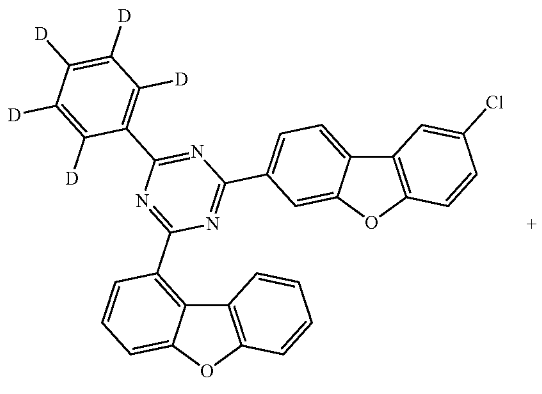

sub 14

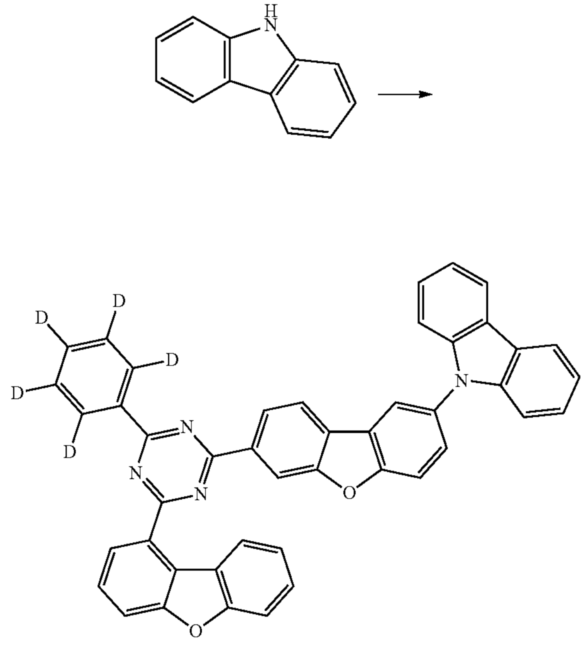

Compound 14

Compound sub 14 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 14 (12.0 g, yield: 48%).

MS: [M+H]+=660

15) Preparation of Compound 15

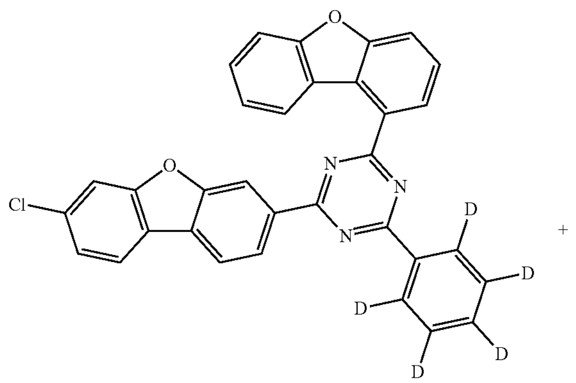

sub 15

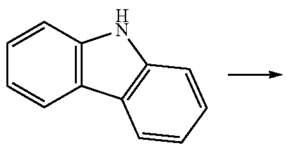

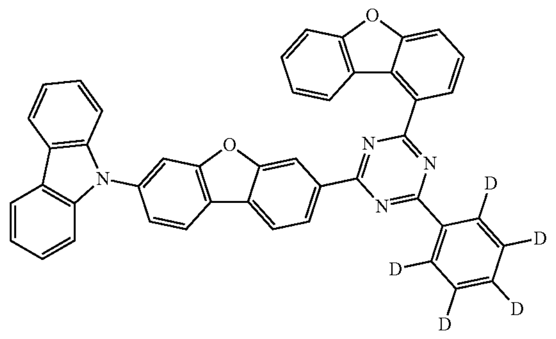

Compound 15

Compound sub 15 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a green solid compound 15 (15.5 g, yield: 62%).

MS: [M+H]+=660

16) Preparation of Compound 16

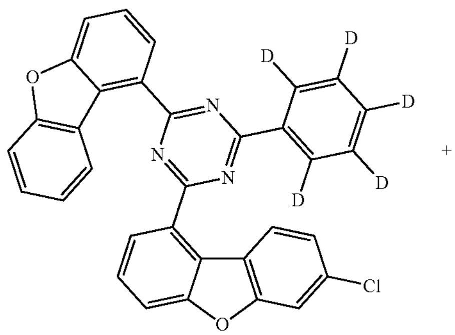

sub 16

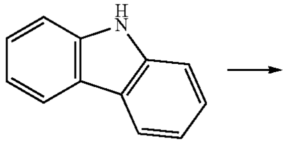

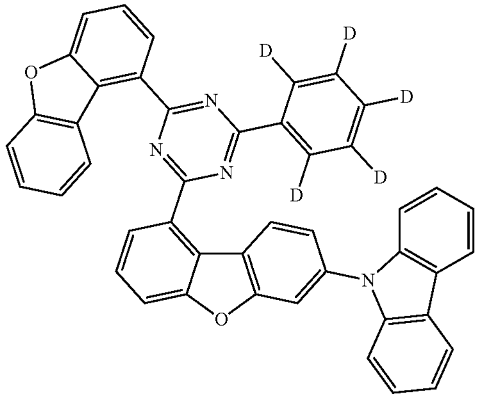

Compound 16

Compound sub 16 (20.0 g, 37.9 mmol) and 9-carbazole (6.3 g, 37.9 mmol) were added to and dissolved in 200 mL of xylene under a nitrogen atmosphere, and sodium tert-butoxide (7.3 g, 75.7 mmol) were added and heated. Bis(tri tert-butylphosphine)palladium (0.6 g, 3 mol %) was added thereto, and the mixture was refluxed and stirred for 12 hours. When the reaction was completed, the reaction temperature was lowered to room temperature, and the produced solid was filtered. The solid was dissolved in 1000 mL of chloroform and washed twice with water. The organic layer was separated, and anhydrous magnesium sulfate was added thereto. The mixture was stirred and filtered, and the filtrate was distilled under reduced pressure. The concentrated compound was purified through a silica column using chloroform and ethyl acetate to produce a yellow solid compound 16 (15.0 g, yield: 60%).

MS: [M+H]+=660

EXAMPLES

Example 1

A glass substrate on which ITO (indium tin oxide) was coated as a thin film to a thickness of 1300 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma, and then transferred to a vacuum depositor.

On the ITO transparent electrode thus prepared, the following compound HI-1 was thermally vacuum deposited to a thickness of 50 Å to form a hole injection layer. The following compound HT-1 was thermally vacuum deposited on the hole injection layer to a thickness of 250 Å to form a hole transport layer, and the following compound HT-2 was vacuum deposited on the HT-1 deposited film to a thickness of 50 Å to form an electron blocking layer. Compound 1 prepared in the previous Preparation Example 7, the following compound YGH-1, and phosphorescent dopant YGD-1 were co-deposited at a weight ratio of 44:44:12 on the HT-2 deposited film to form a light emitting layer with a thickness of 400 Å. The following compound ET-1 was vacuum deposited on the light emitting layer to a thickness of 250 Å to form an electron transport layer, and the following compound ET-2 and Li were vacuum deposited at a weight ratio of 98:2 to form an electron injection layer with a thickness of 100 Å. Aluminum was deposited on the electron injection layer to a thickness of 1000 Å to form a cathode.

HI-1

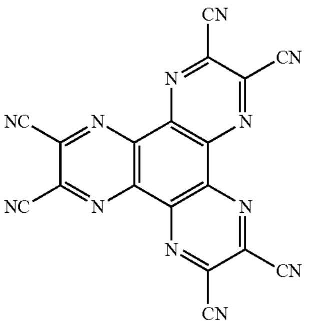

HT-1

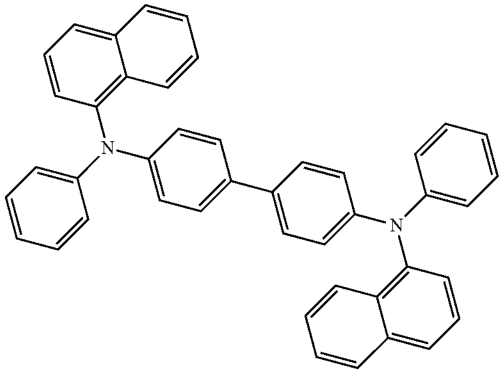

-continued

HT-2

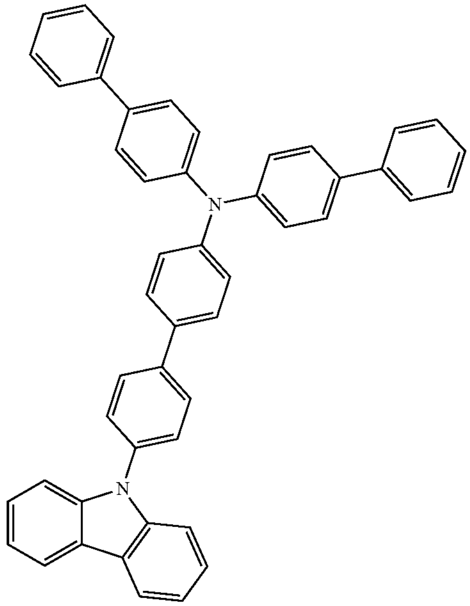

YGH-1

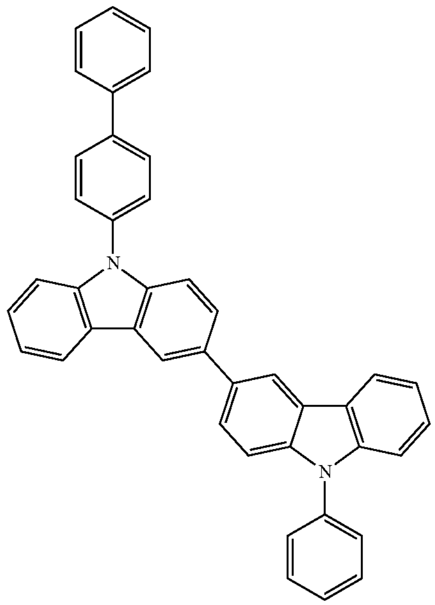

YGD-1

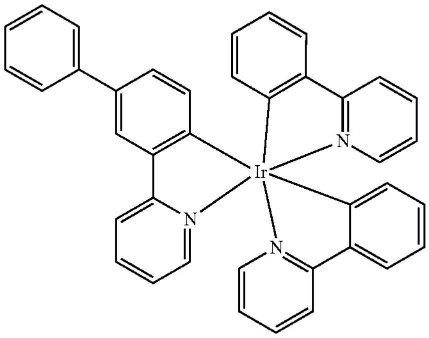

-continued

ET-1

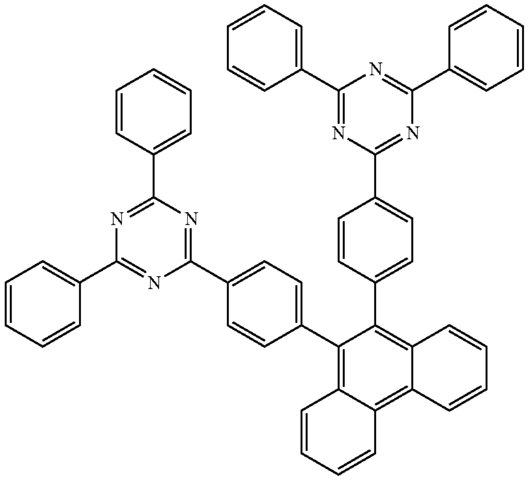

ET-2

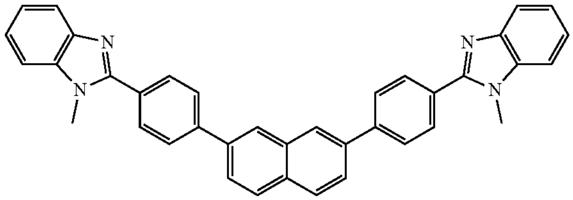

In the above-mentioned process, the vapor deposition rate of the organic material was maintained at 0.4 to 0.7 Ads, the deposition rates of aluminum was maintained at 2 Å/s, and the degree of vacuum during the deposition was maintained at $1\times10^{-7}$ to $5\times10^{-8}$ torr.

Examples 2 to 16

An organic light emitting device was manufactured in the same manner as in Example 1, except that the compounds shown in Table 1 below were used instead of Compound 1 of Preparation Example 7 in Example 1.

Comparative Examples 1 to 4

An organic light emitting device was manufactured in the same manner as in Example 1, except that the compounds shown in Table 1 below were used instead of Compound 1 of Preparation Example 7 in Example 1. The compounds of CE1 to CE4 in Table 1 below are as follows.

CE1

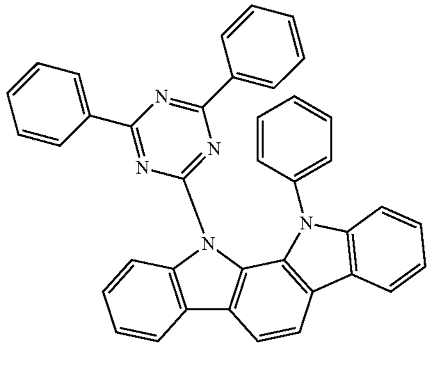

-continued

CE2

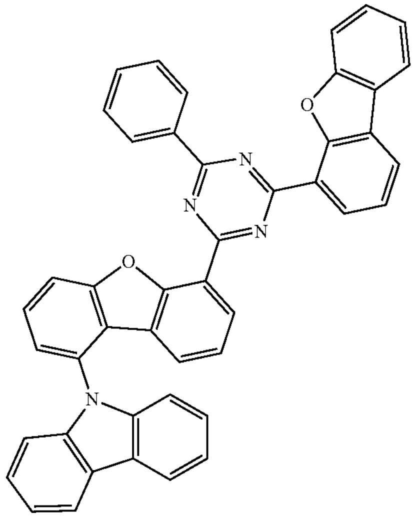

CE3

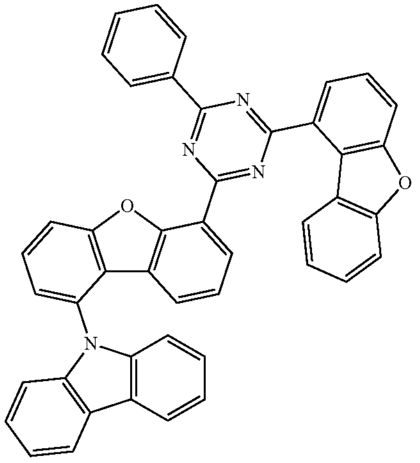

CE4

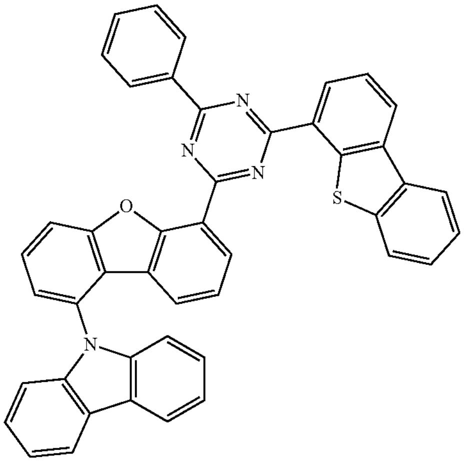

Experimental Example

The voltage and efficiency were measured at a current density of 10 mA/$cm^2$ for the organic light emitting devices manufactured in the examples and comparative examples above, and the lifetime was measured at a current density of 50 $mA/cm^2$. The results are shown in Table 1 below. At this time, $LT_{95}$ means the time required for the luminance to be reduced to 95% of the initial luminance.

TABLE 1

| | Compound | Voltage (V) (@10 $mA/cm^2$) | Efficiency (Cd/A) (@10 $mA/cm^2$) | Color coordinates (x, y) | Lifetime (h) ($LT_{95}$ at 50 $mA/cm^2$) |
|---|---|---|---|---|---|
| Example 1 | Compound 1 | 3.8 | 82 | 0.45, 0.53 | 200 |
| Example 2 | Compound 2 | 3.9 | 84 | 0.46, 0.53 | 185 |
| Example 3 | Compound 3 | 3.8 | 85 | 0.46, 0.54 | 181 |
| Example 4 | Compound 4 | 3.8 | 83 | 0.46, 0.54 | 222 |
| Example 5 | Compound 5 | 3.7 | 84 | 0.46, 0.53 | 165 |
| Example 6 | Compound 6 | 3.8 | 84 | 0.46, 0.54 | 163 |
| Example 7 | Compound 7 | 3.8 | 85 | 0.46, 0.54 | 155 |
| Example 8 | Compound 8 | 3.9 | 81 | 0.46, 0.54 | 194 |
| Example 9 | Compound 9 | 4.0 | 80 | 0.46, 0.53 | 225 |
| Example 10 | Compound 10 | 4.0 | 79 | 0.46, 0.54 | 212 |
| Example 11 | Compound 11 | 4.1 | 82 | 0.46, 0.53 | 201 |
| Example 12 | Compound 12 | 4.1 | 81 | 0.46, 0.54 | 233 |
| Example 13 | Compound 13 | 3.8 | 79 | 0.46, 0.54 | 152 |
| Example 14 | Compound 14 | 3.9 | 78 | 0.46, 0.54 | 142 |
| Example 15 | Compound 15 | 4.0 | 81 | 0.46, 0.53 | 165 |
| Example 16 | Compound 16 | 4.1 | 80 | 0.46, 0.54 | 143 |
| Comparative Example 1 | Compound CE1 | 4.1 | 73 | 0.46, 0.54 | 100 |
| Comparative Example 2 | Compound CE2 | 4.2 | 78 | 0.46, 0.55 | 122 |
| Comparative Example 3 | Compound CE3 | 4.1 | 77 | 0.45, 0.54 | 111 |
| Comparative Example 4 | Compound CE4 | 4.2 | 78 | 0.45, 0.55 | 131 |

As shown in Table 1, it was confirmed that when the compound of the present invention was used as a material of the light emitting layer, it exhibited superior efficiency and lifetime characteristics as compared with the comparative examples. This is considered to be because the electrical stability is increased as a dibenzofuran group or a dibenzothiophene group and a phenyl substituted with deuterium are substituted in the triazine group.

DESCRIPTION OF SYMBOLS

| | |
|---|---|
| 1: substrate | 2: anode |
| 3: light emitting layer | |
| 4: cathode | |
| 5: hole injection layer | |
| 6: hole transport layer | |
| 7: electron blocking layer | |
| 8: electron transport layer | |
| 9: electron injection layer | |

The invention claimed is:

1. A compound of the following Chemical Formula 1:

Chemical Formula 1

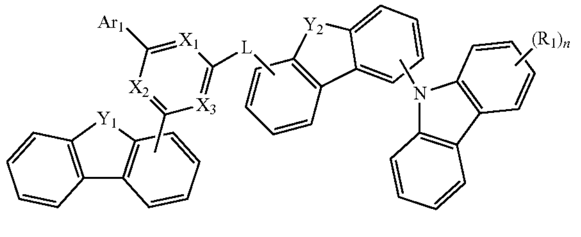

wherein, in Chemical Formula 1, $X_1$ to $X_3$ are each independently CH or N, provided that at least two of $X_1$ to $X_3$ are N, $Y_1$ and $Y_2$ are each independently O or S, L is a single bond, $Ar_1$ is a phenyl substituted with at least one deuterium, each $R_1$ is independently hydrogen; deuterium; a halogen; cyano; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heteroaryl containing any one or more heteroatoms selected from the group consisting of N, O and S, or two adjacent groups of $R_1$ are linked together to form a $C_{6-60}$ aromatic ring or a $C_{2-60}$ heteroaromatic ring containing one or more heteroatoms selected from the group consisting of N, O, and S, and n is an integer of 0 to 4.

2. The compound according to claim 1, wherein Chemical Formula 1 is any one of the following Chemical Formulas 2 to 5:

Chemical Formula 2

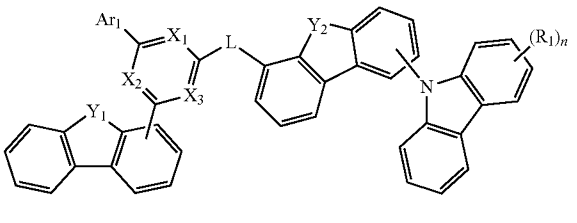

-continued

Chemical Formula 3

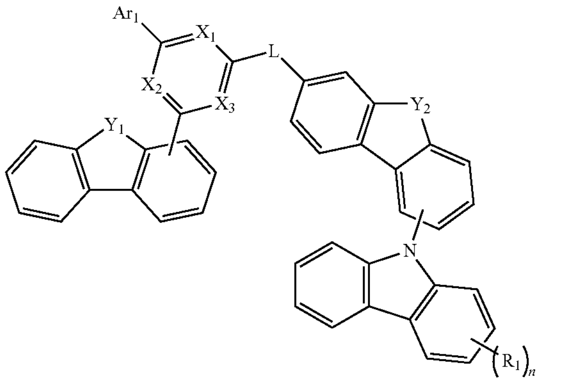

Chemical Formula 4

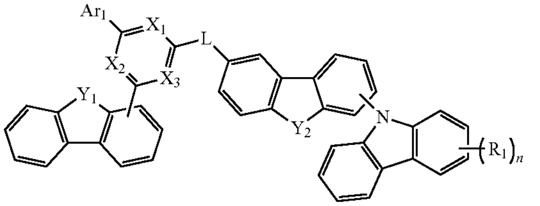

Chemical Formula 5

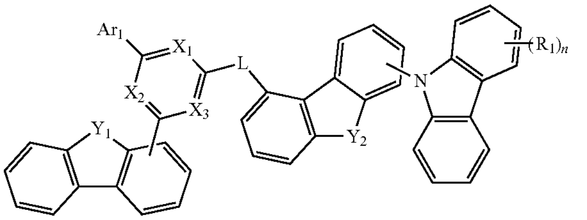

wherein, in Chemical Formulas 2 to 5, $X_1$ to $X_3$, $Y_1$, $Y_2$, L, $Ar_1$, $R_1$, and n are the same as those defined in claim 1.

3. The compound according to claim 1, wherein $X_1$ to $X_3$ all are N.

4. The compound according to claim 1, wherein $Ar_1$ is phenyl substituted with five deuteriums.

5. The compound according to claim 1, wherein each $R_1$ is independently hydrogen or phenyl, or two adjacent groups of $R_1$ are linked together to form

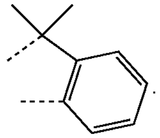

6. The compound according to claim 1, wherein n is an integer of 0 to 2.

7. The compound according to claim 1, wherein Chemical Formula 1 is either one of the following Chemical Formula 1-1 or Chemical Formula 1-2:

Chemical Formula 1-1

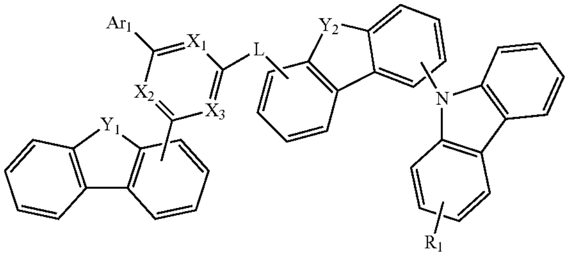

Chemical Formula 1-2

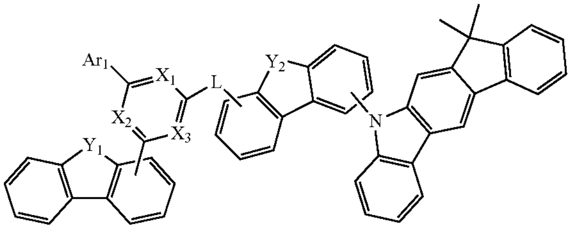

wherein, in Chemical Formula 1-1 or Chemical Formula 1-2, $X_1$ to $X_3$, $Y_1$, $Y_2$, L, $Ar_1$, and $R_1$ are the same as those defined in claim 1.

8. The compound according to claim 1, wherein the compound of Chemical Formula 1 is any one selected from the group consisting of the following:

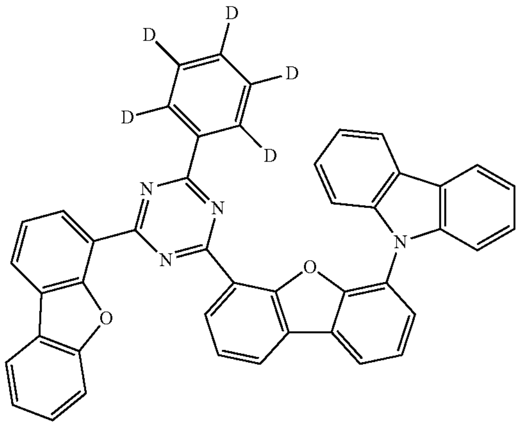

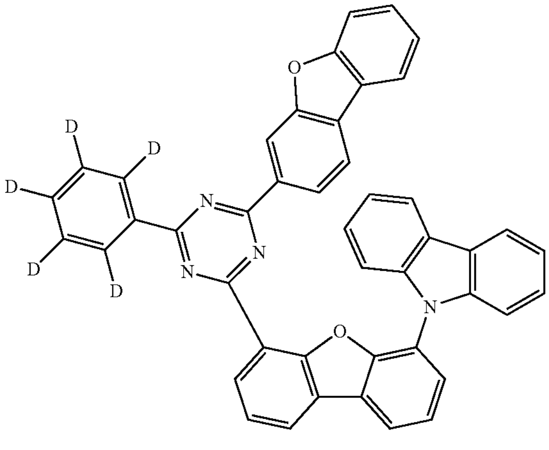

-continued
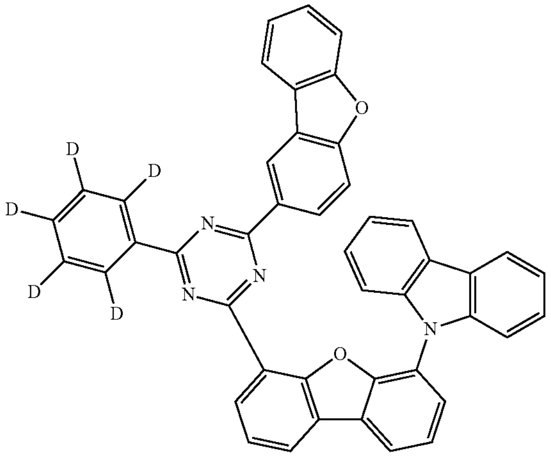
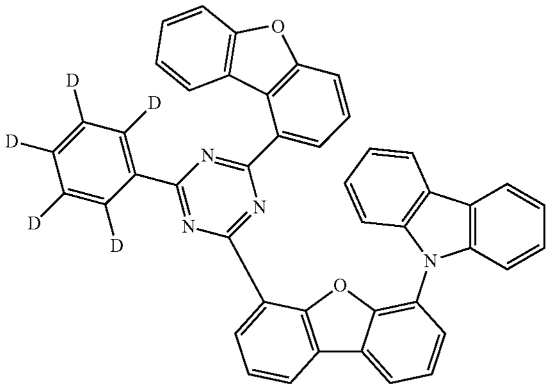
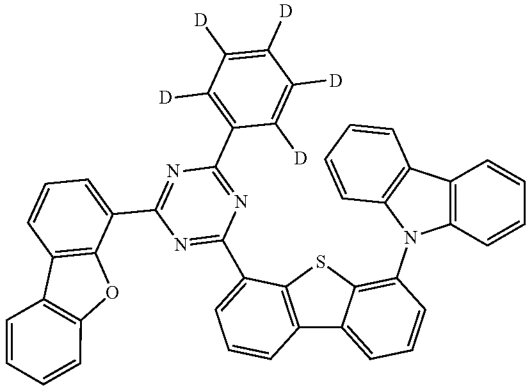
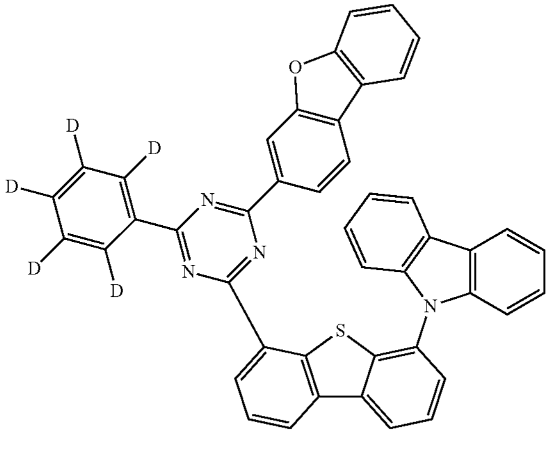
-continued
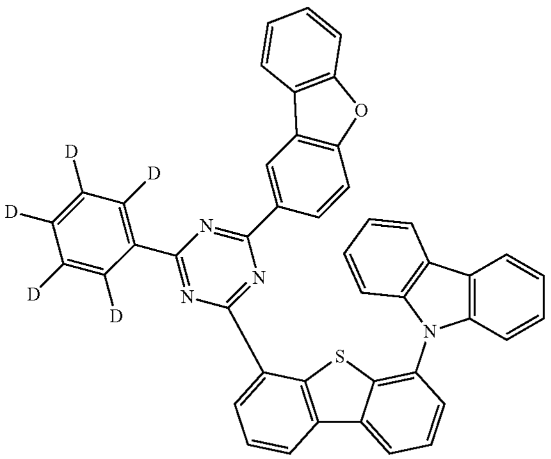
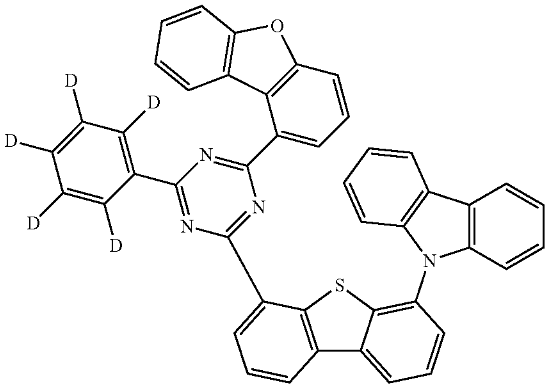
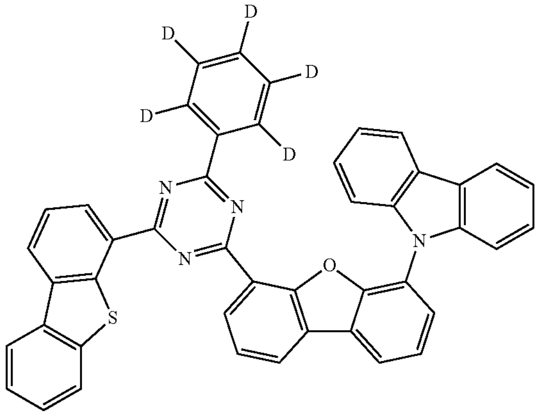
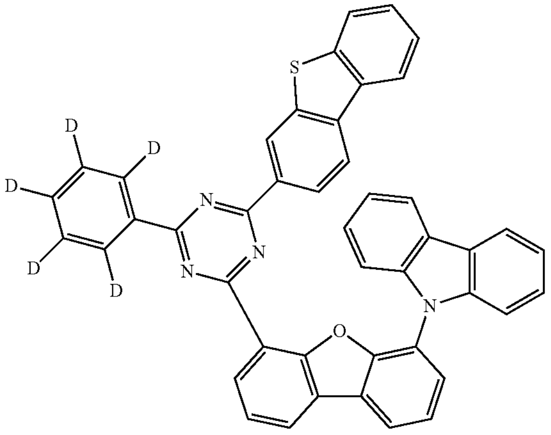

-continued
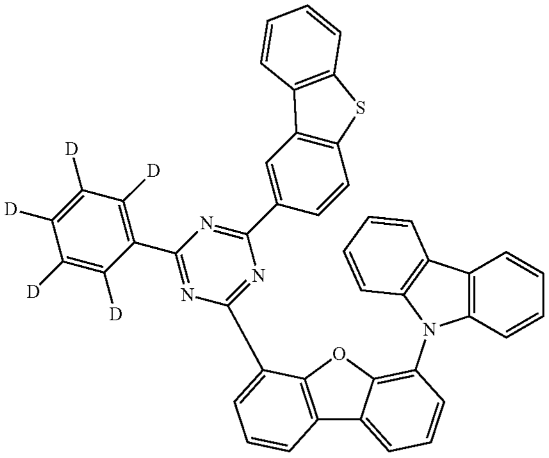
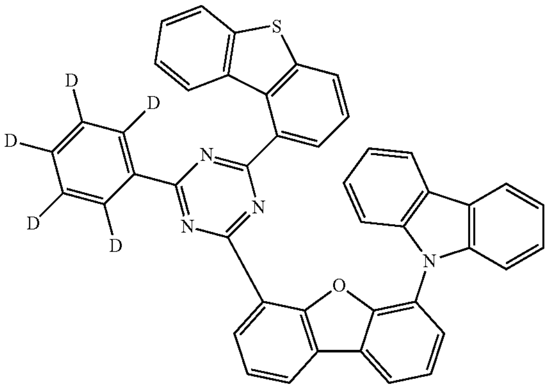
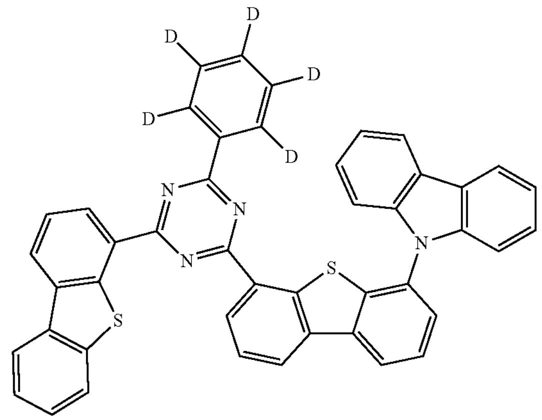
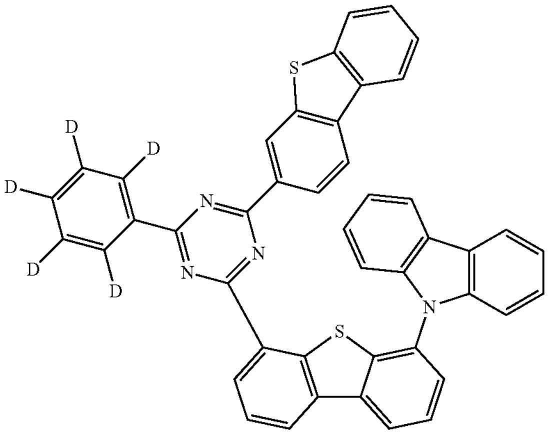
-continued
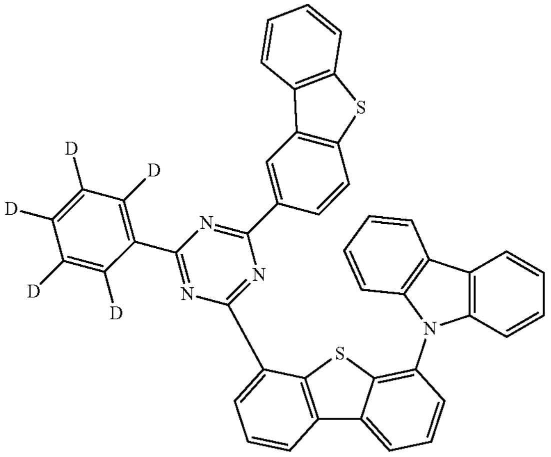
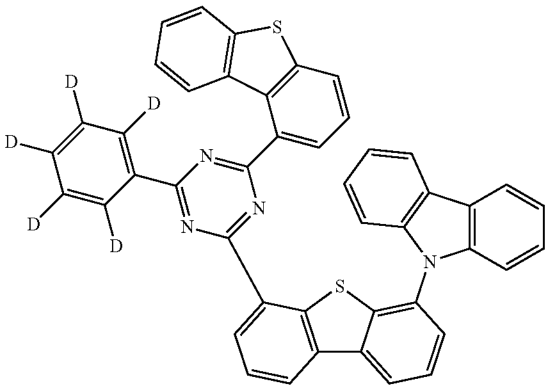
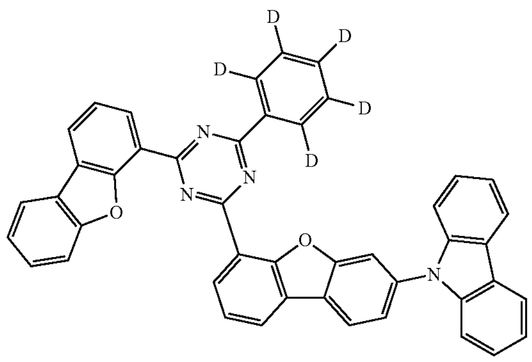
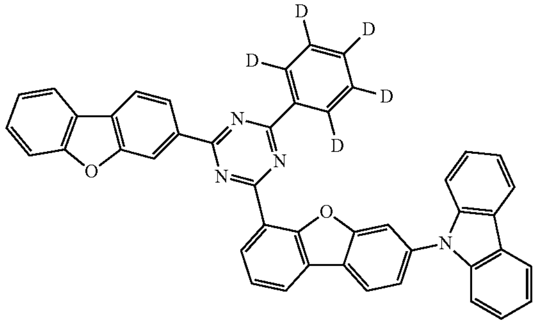

-continued
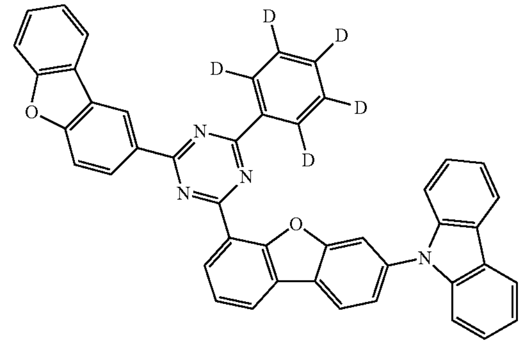
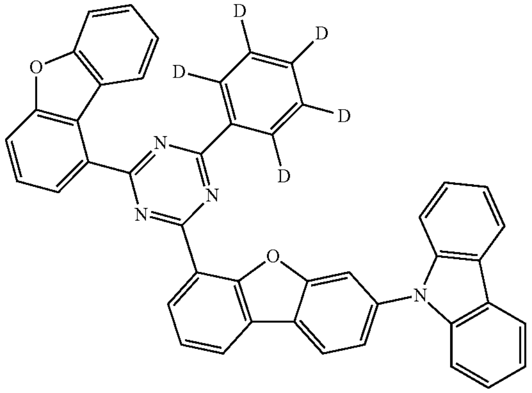
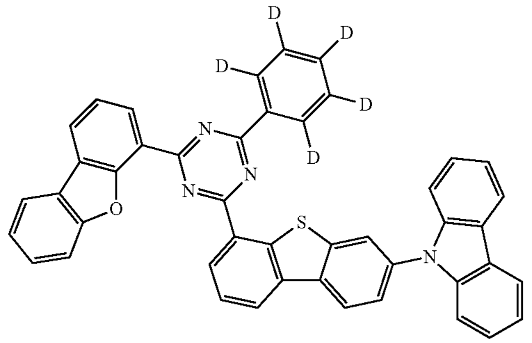
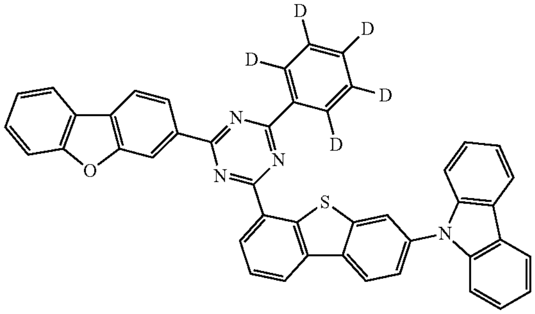
-continued
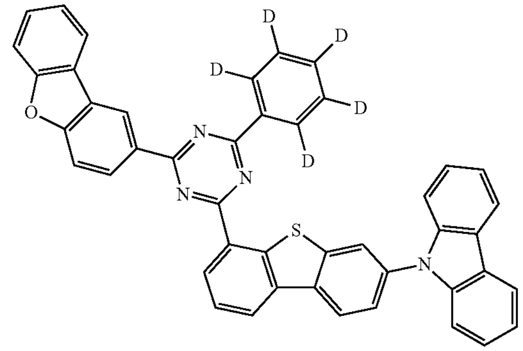
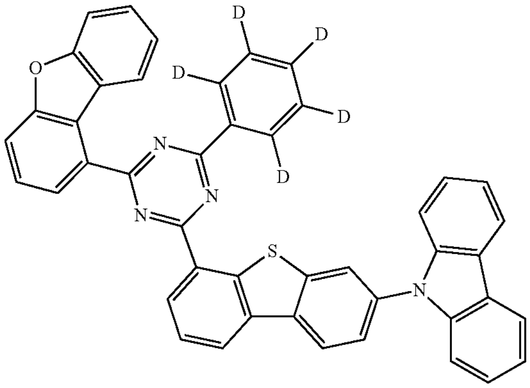
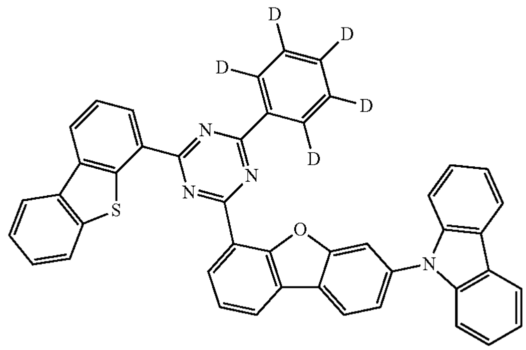
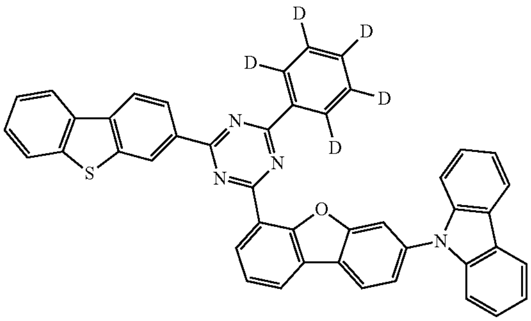

-continued
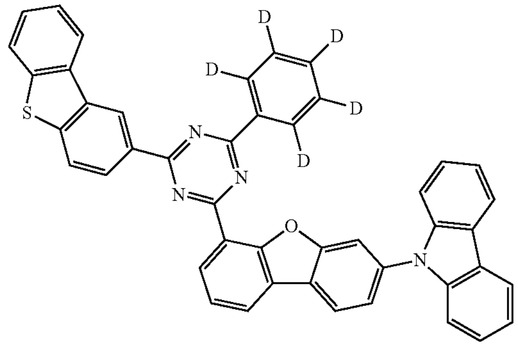
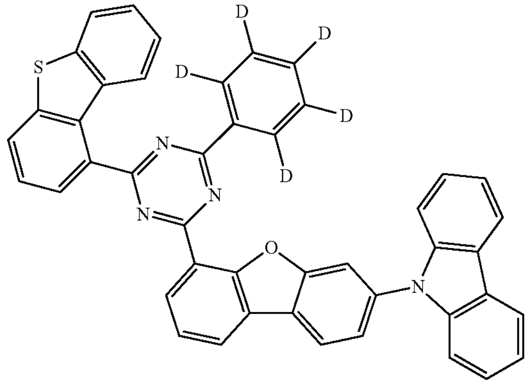
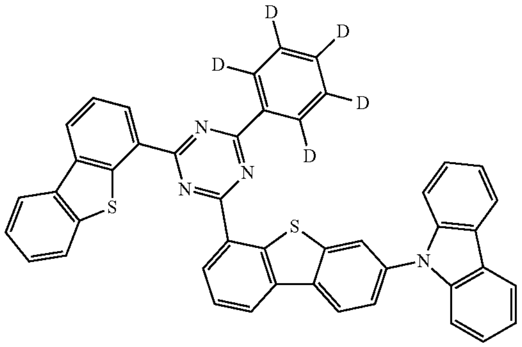
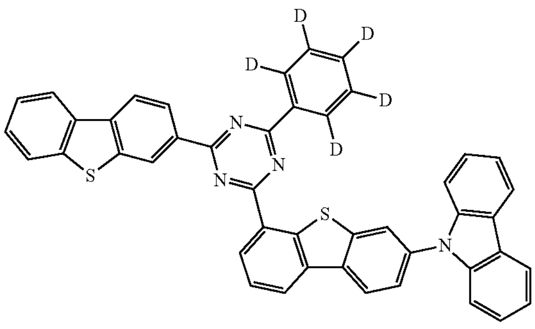
-continued
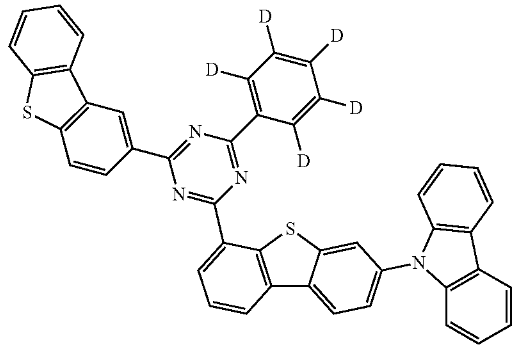
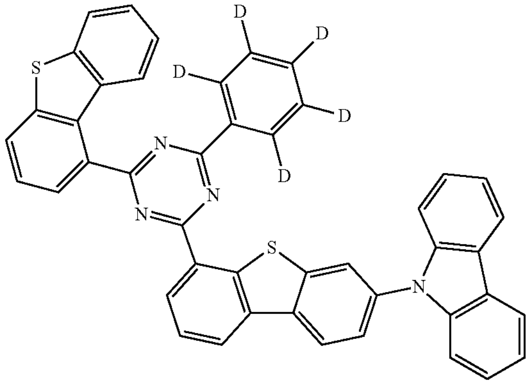
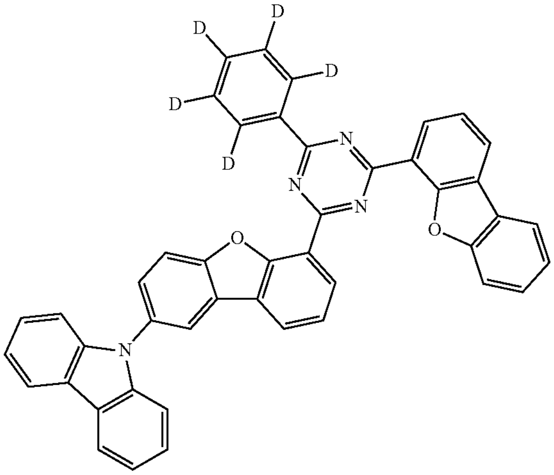
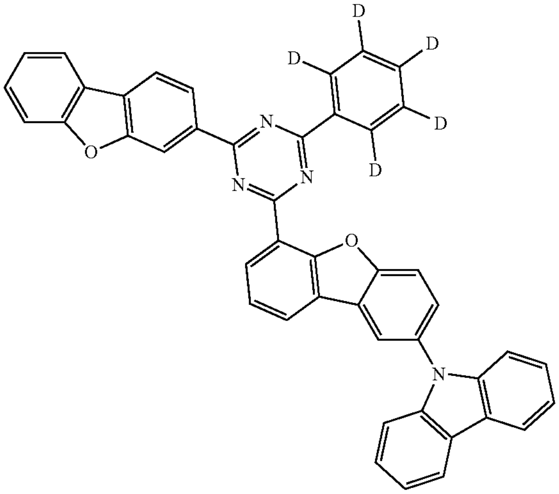

-continued
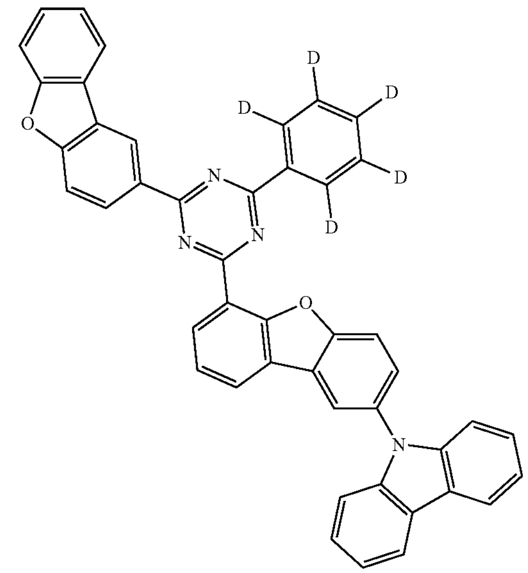
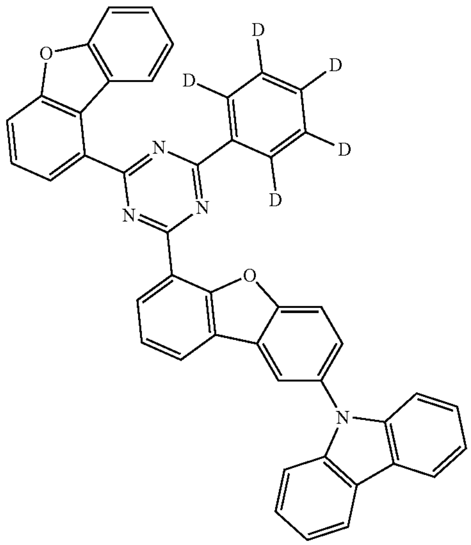
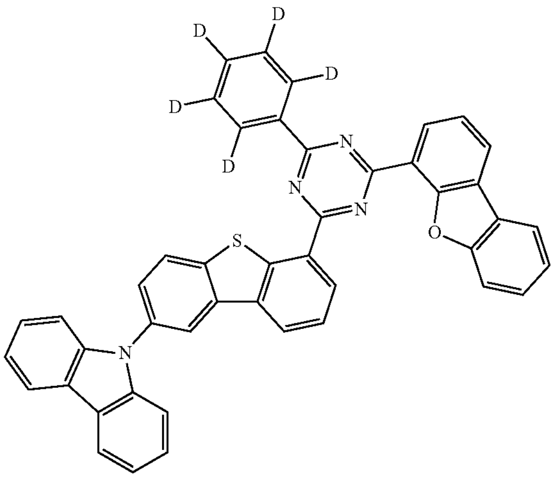
-continued
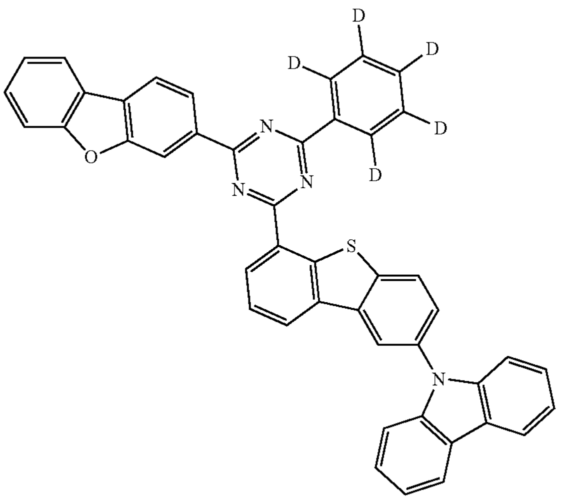
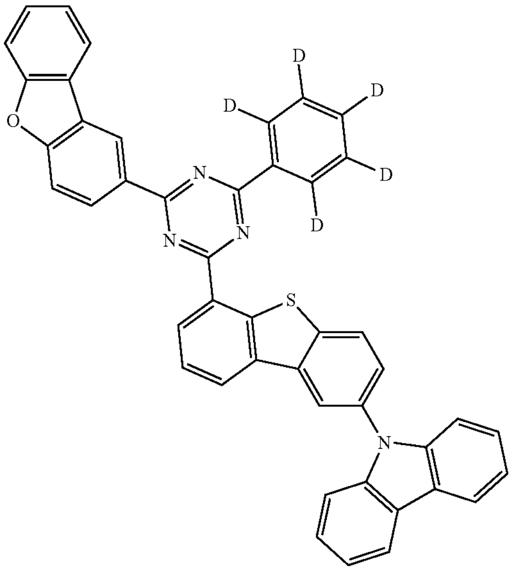
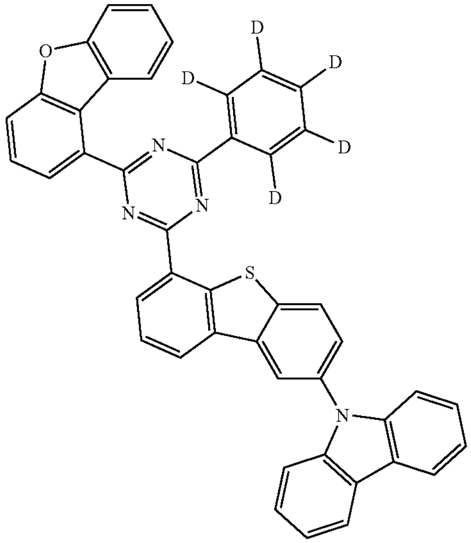

-continued
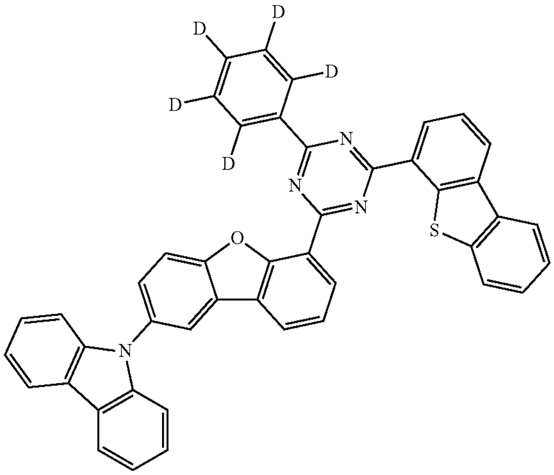
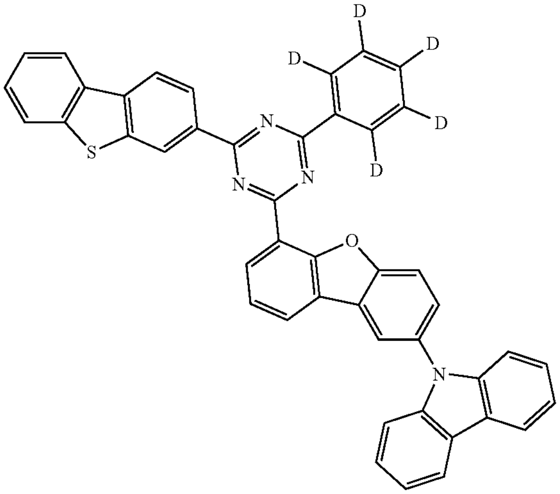
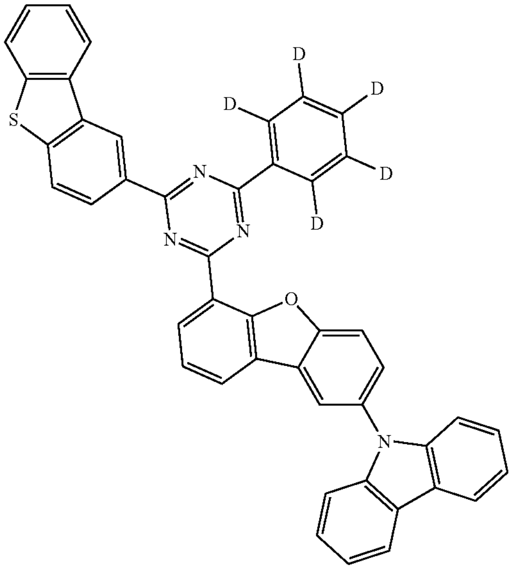
-continued
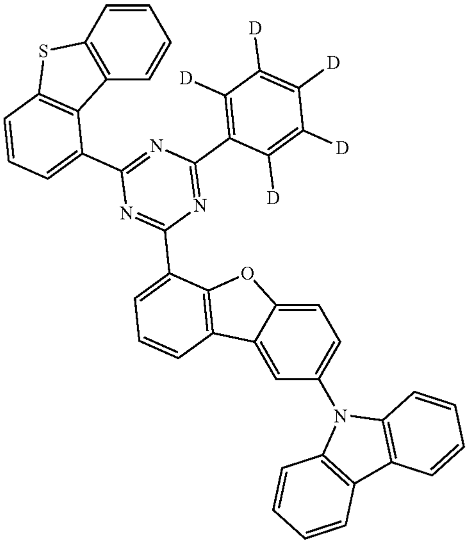
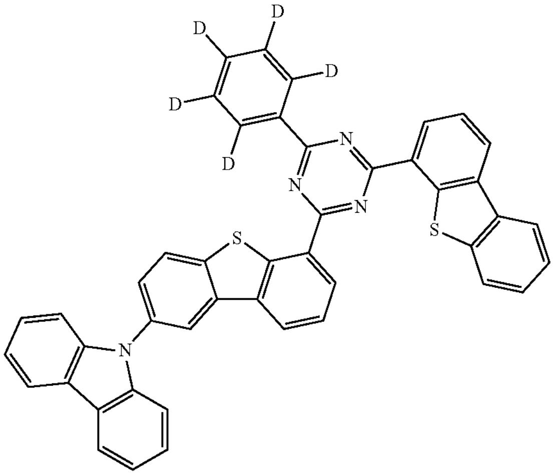
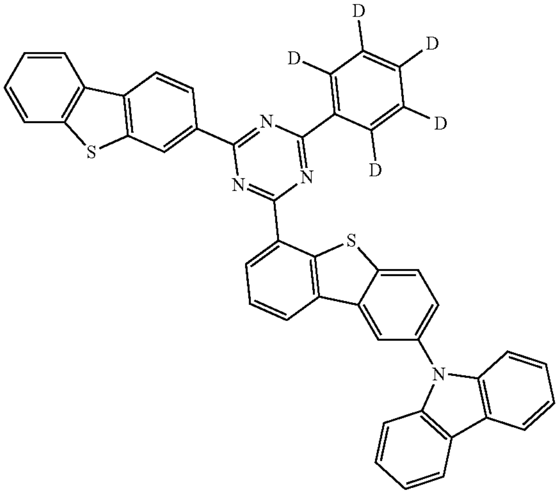

-continued
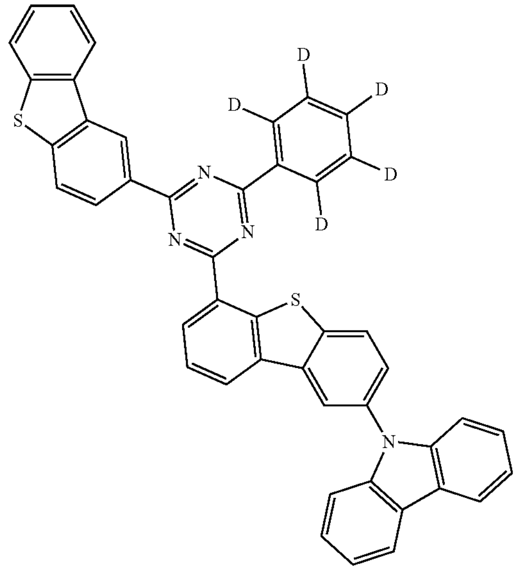
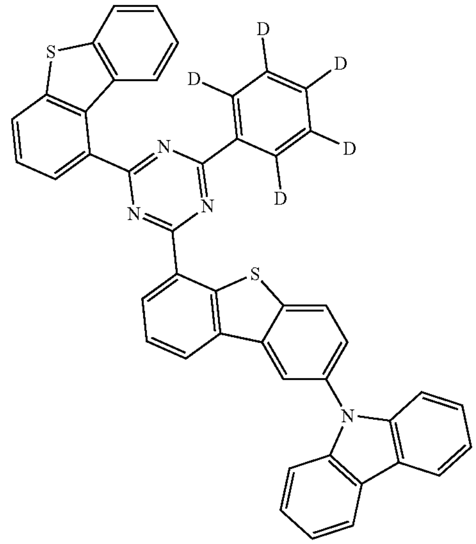
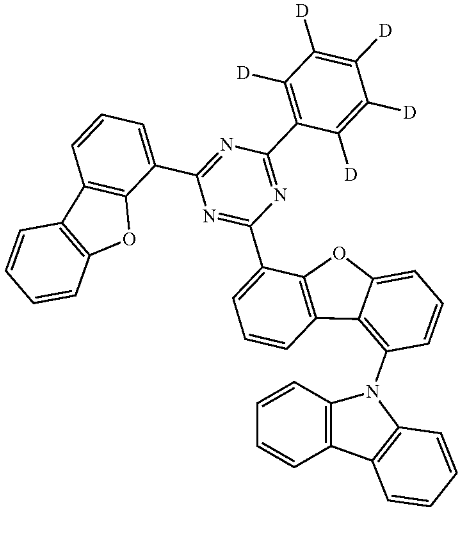
-continued
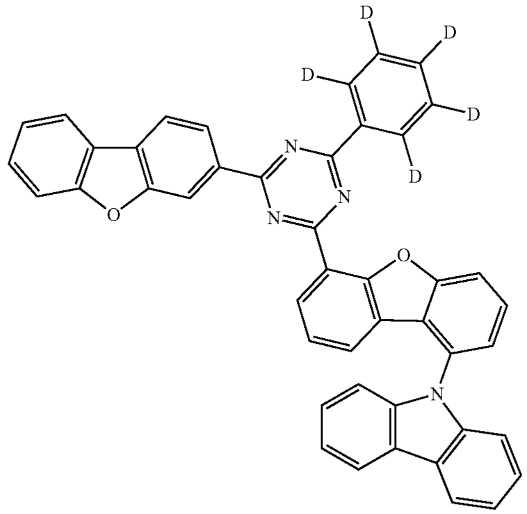
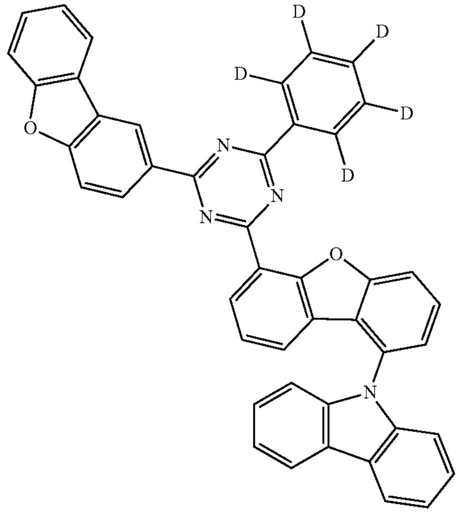
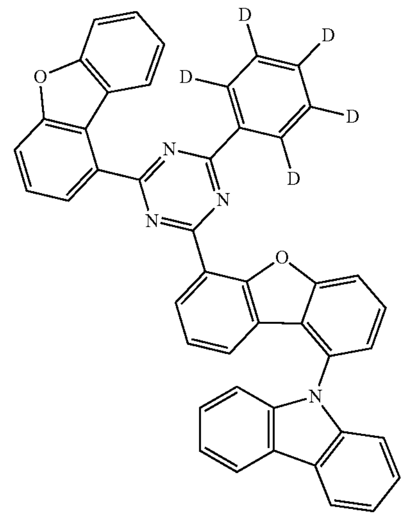

-continued
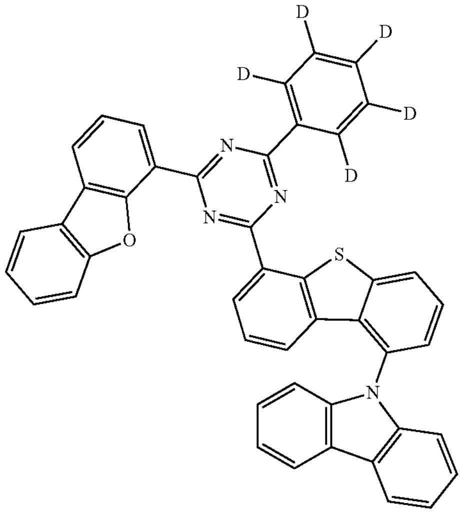
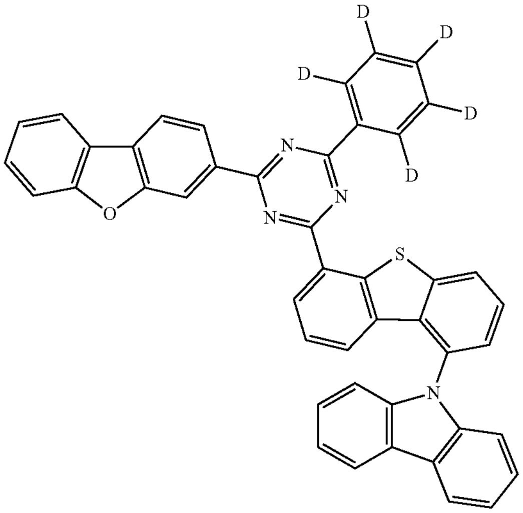
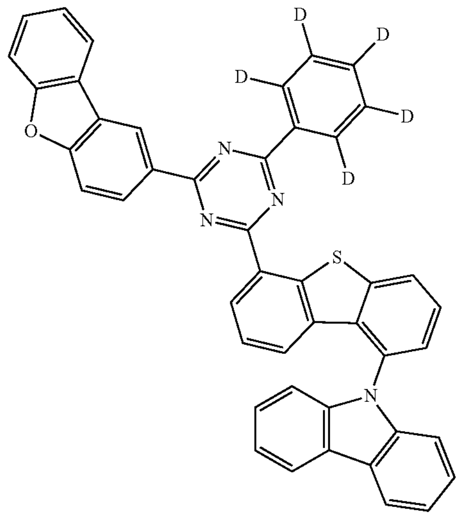
-continued
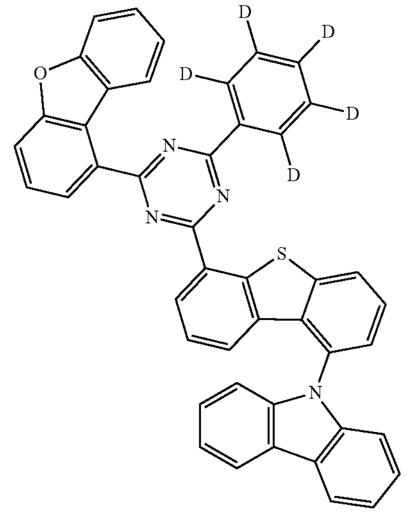
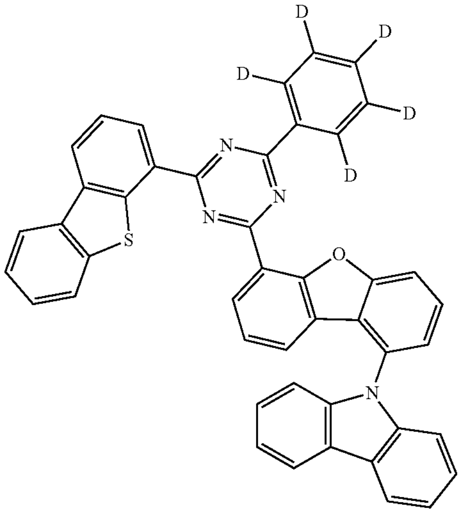
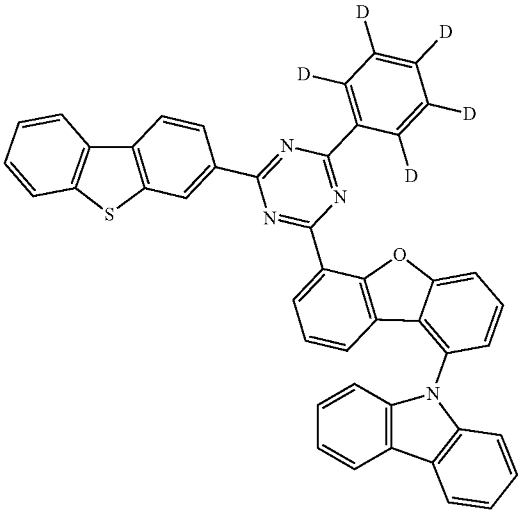

-continued
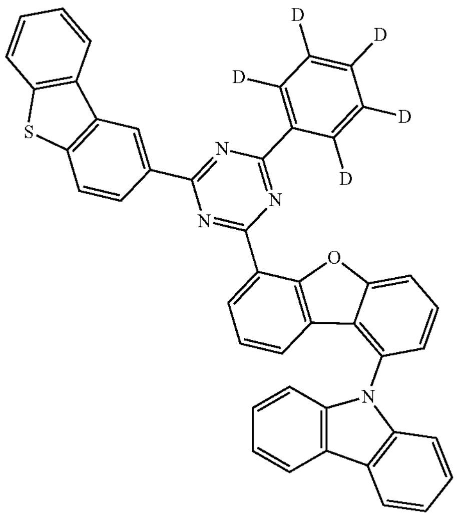
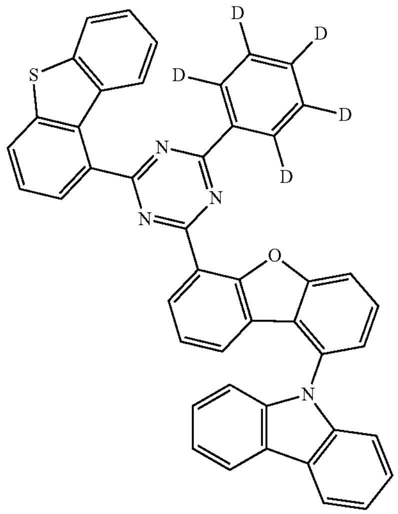
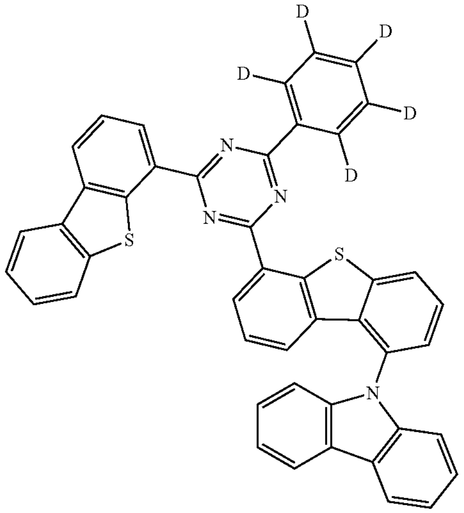
-continued
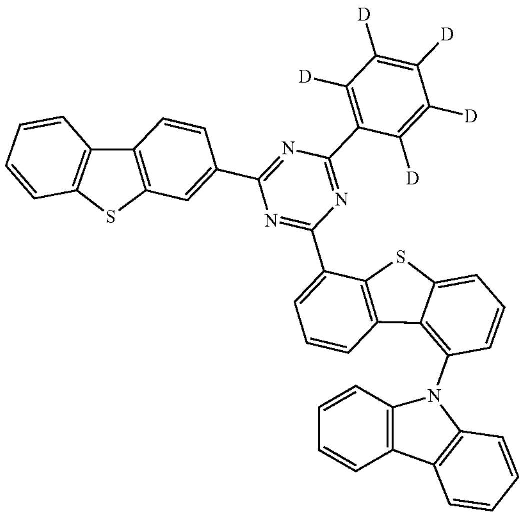
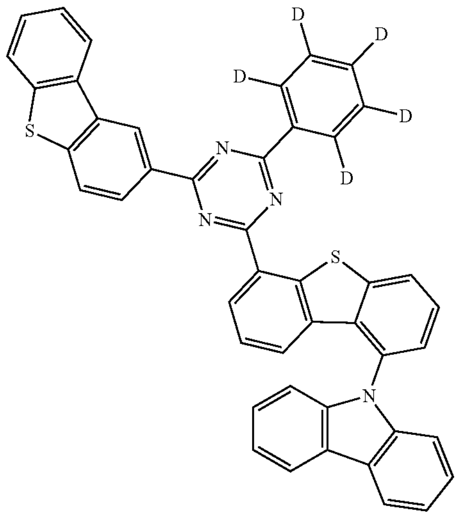
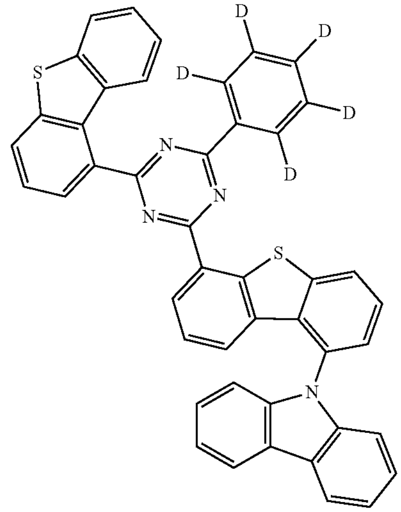

-continued
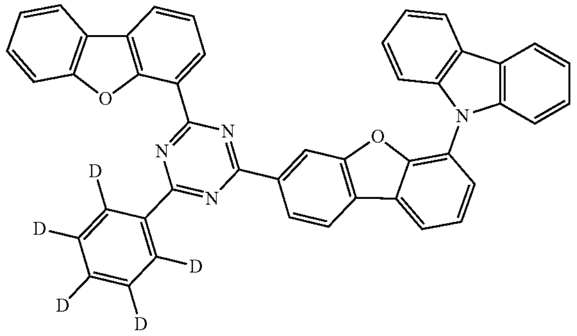
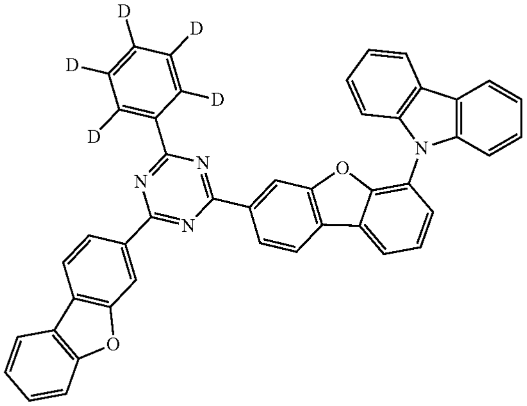
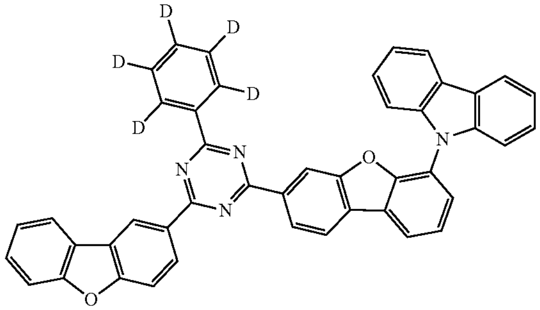
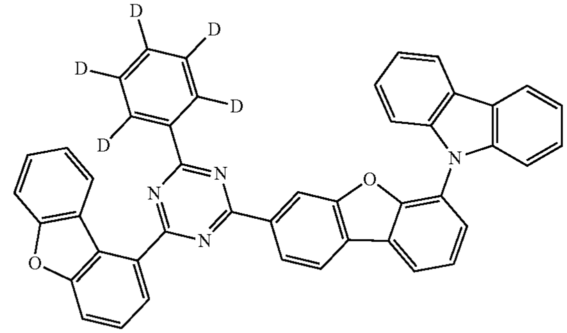
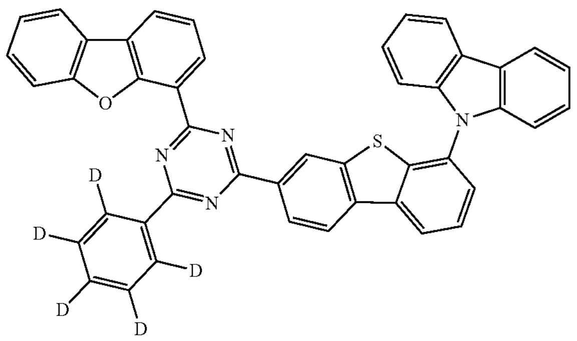
-continued
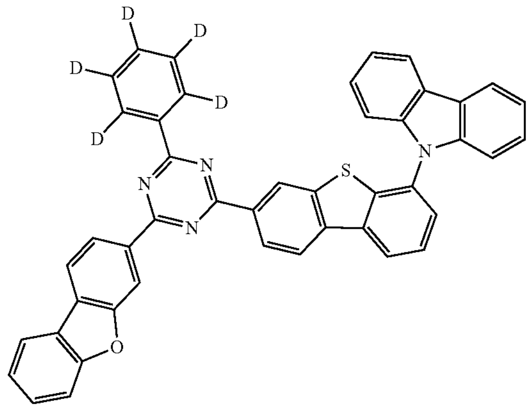
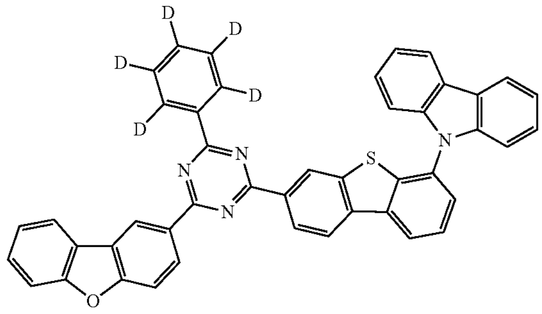
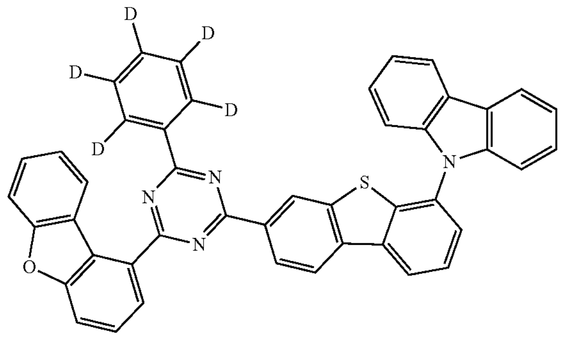
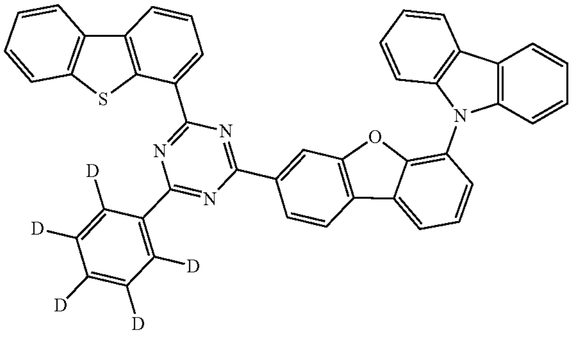

-continued
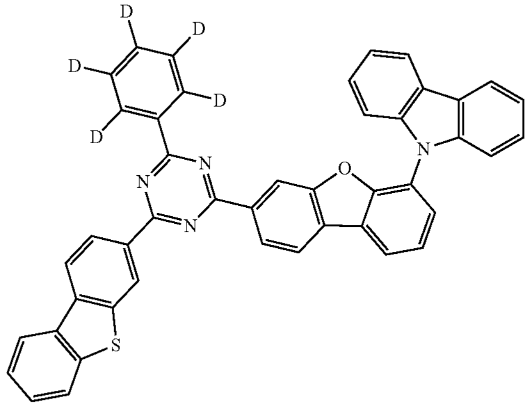
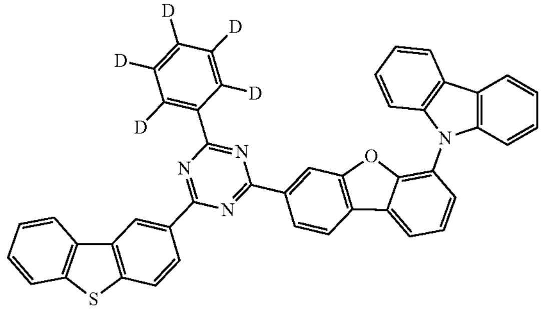
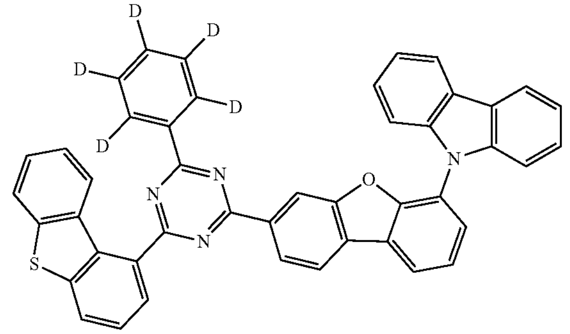
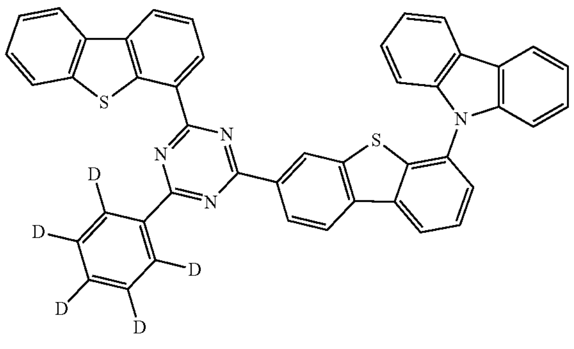
-continued
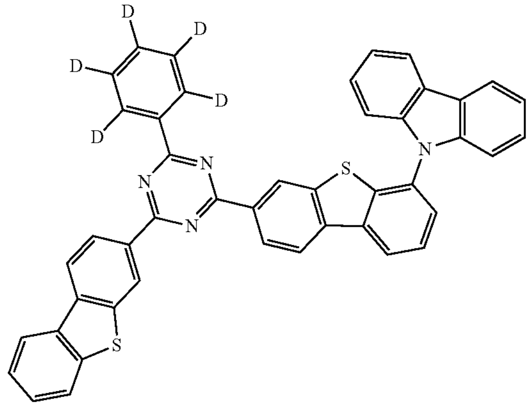
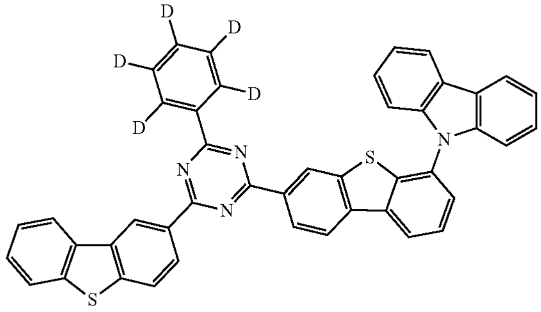
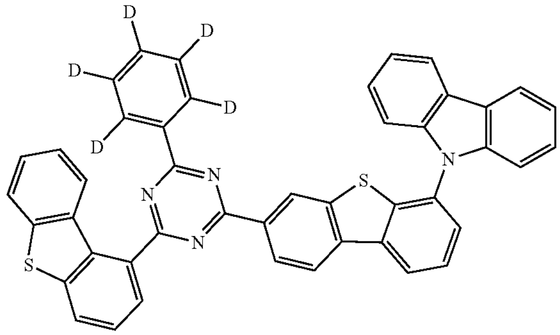
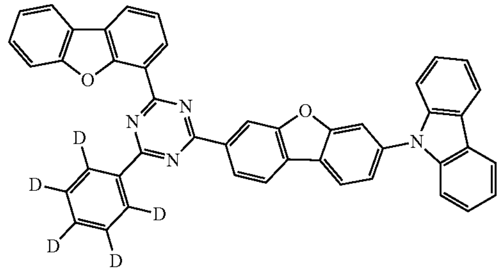
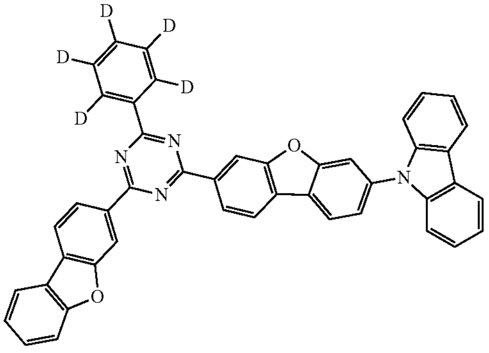

-continued
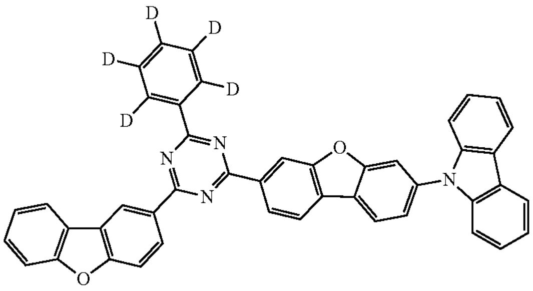
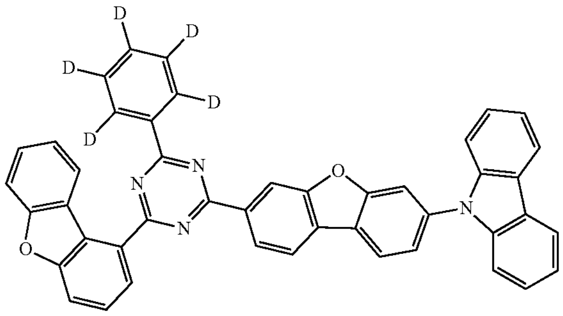
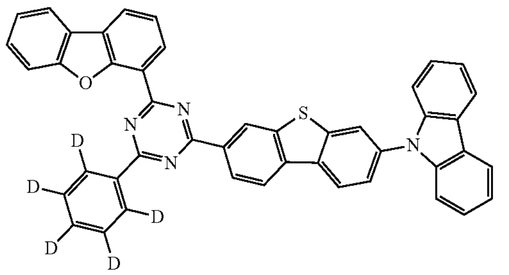
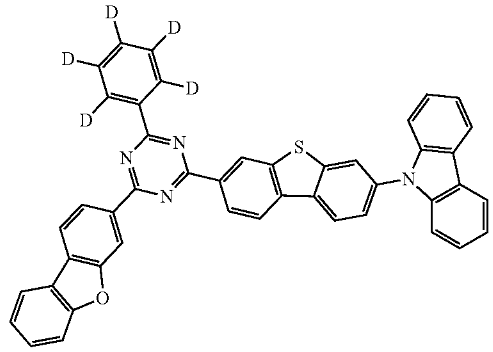
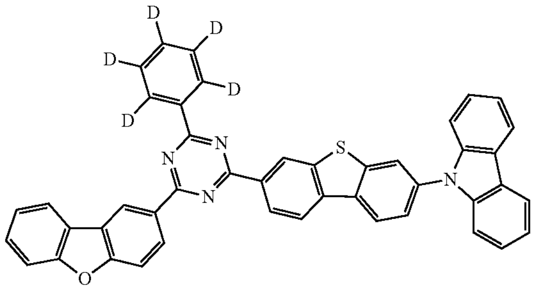
-continued
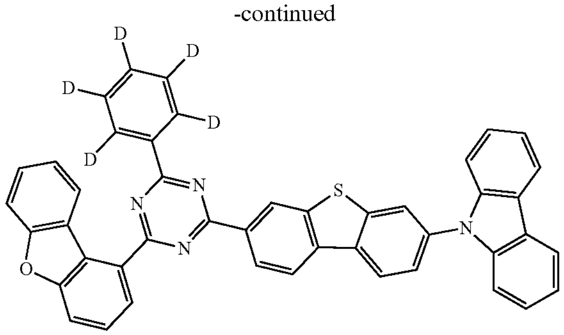
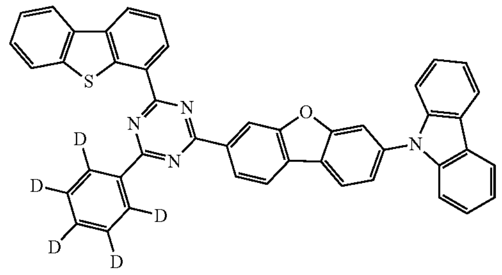
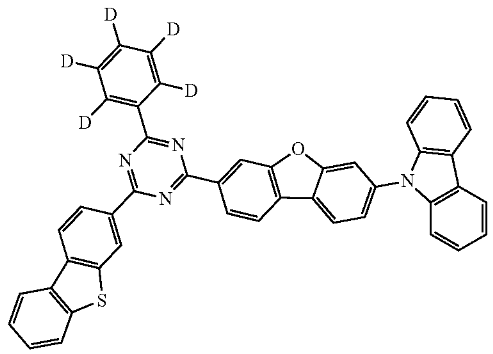
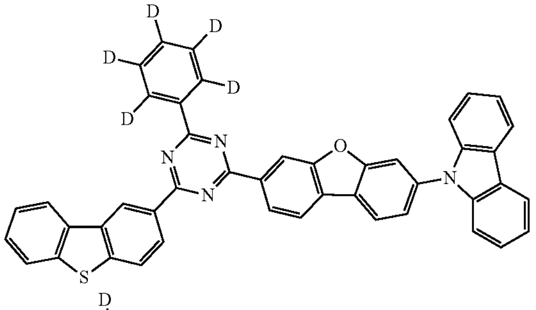
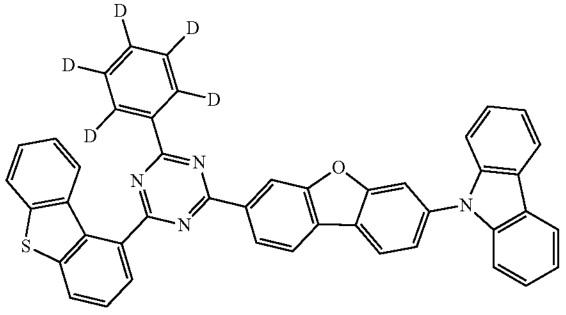

-continued
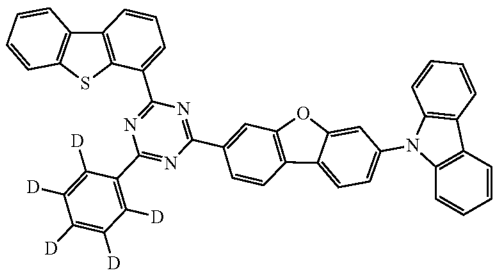
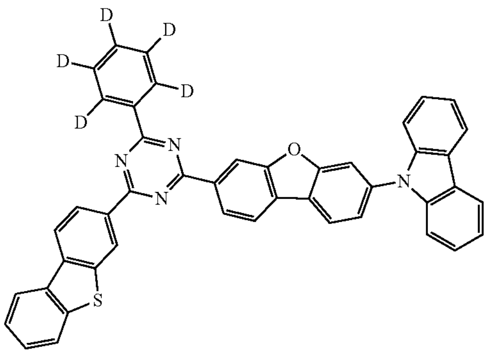
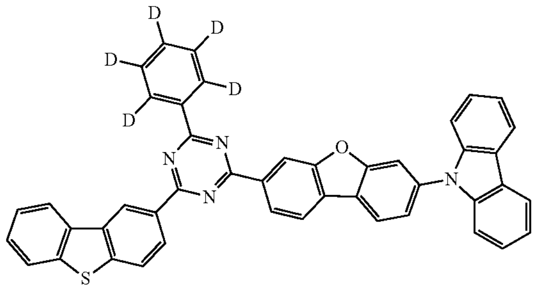
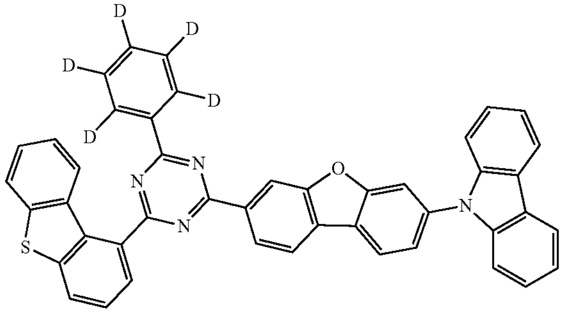
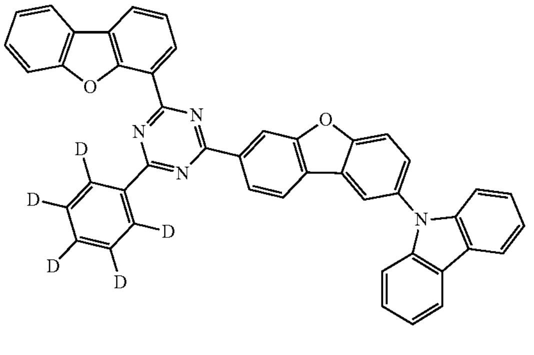
-continued
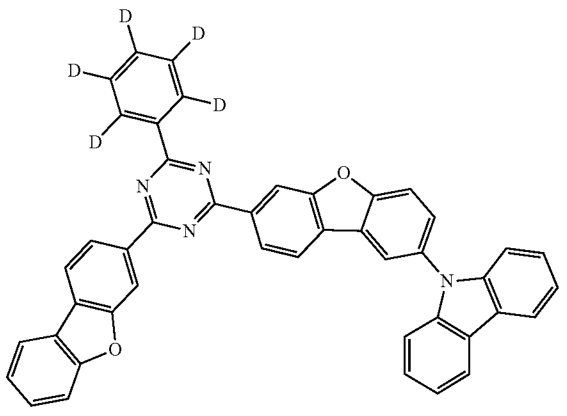
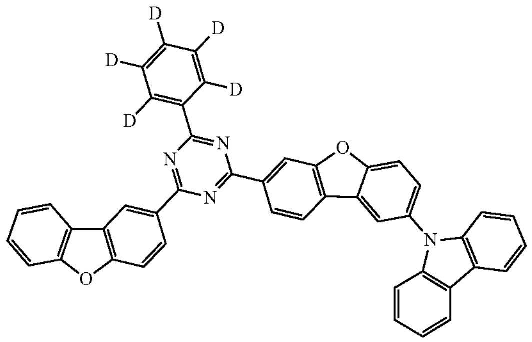
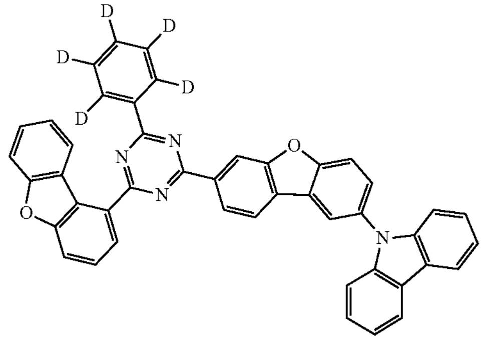
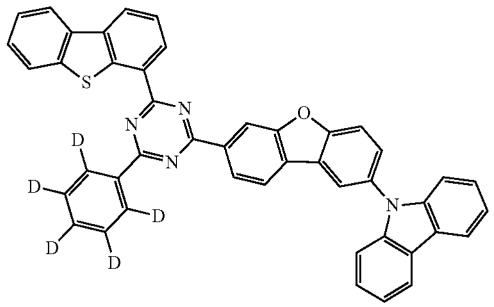

-continued
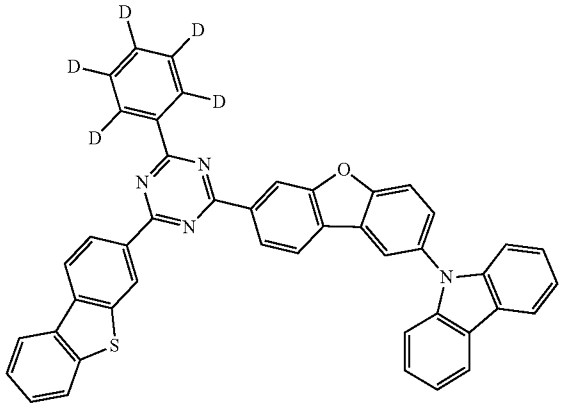
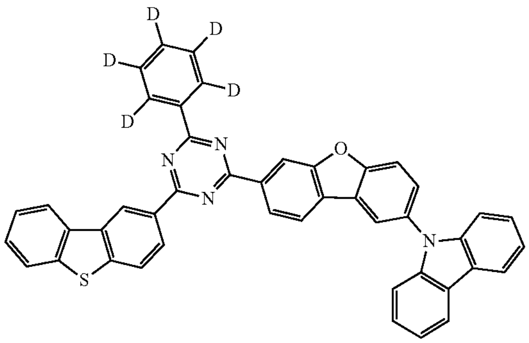
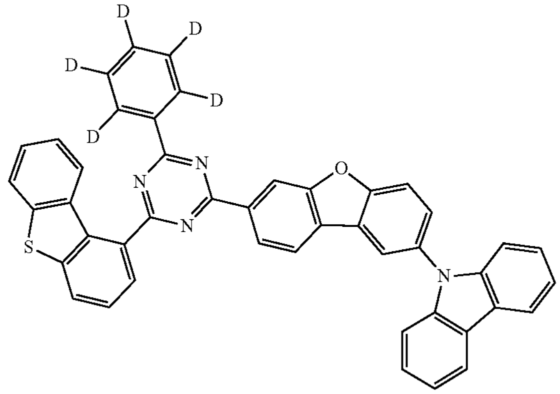
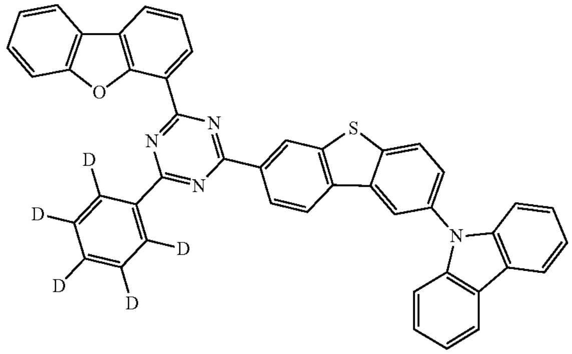
-continued
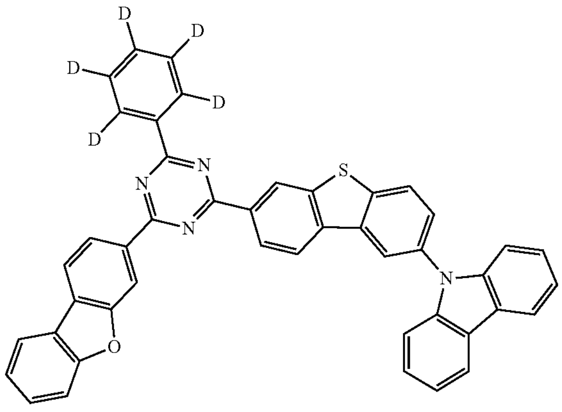
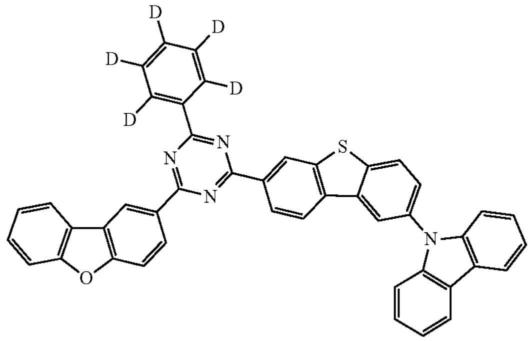
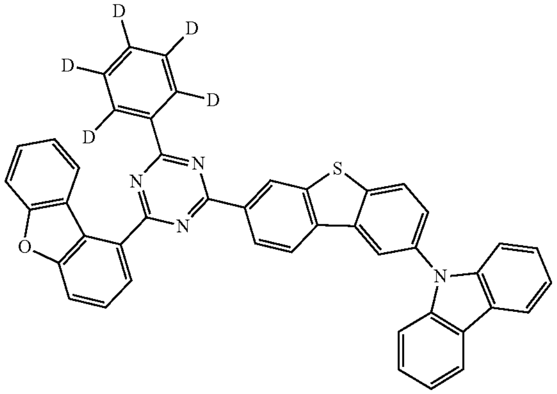
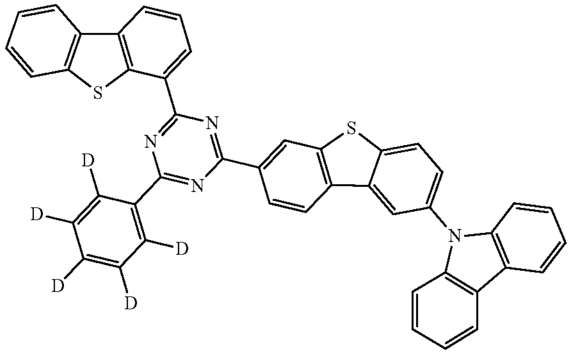

-continued
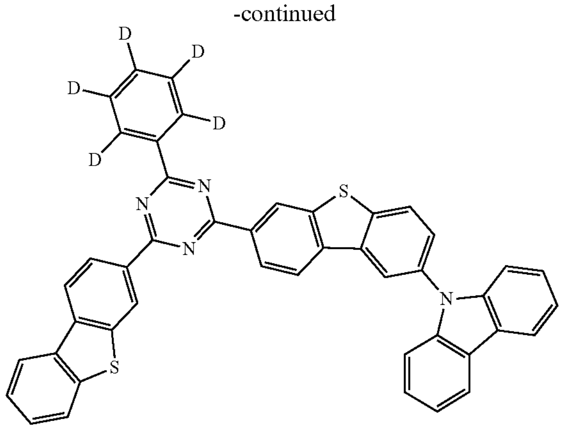
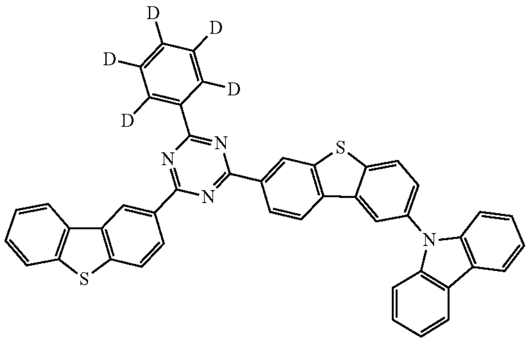
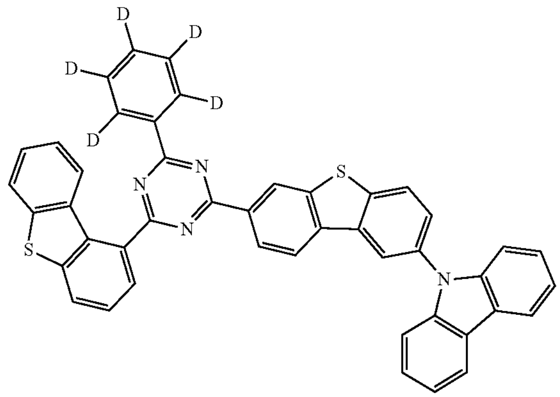
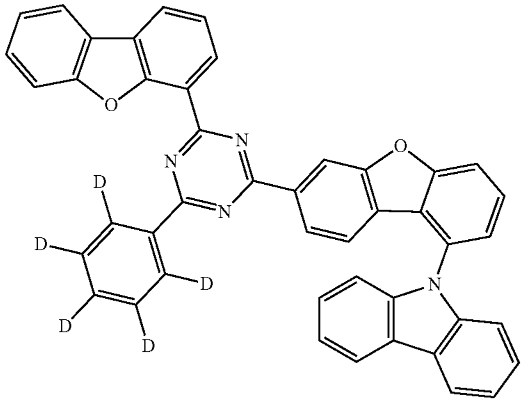 [SMILES: [2H]c1c([2H])c([2H])c(-c2nc(-c3ccc4c(c3)oc3cccc(-n5c6ccccc6c6ccccc65)c34)nc(-c3cccc4c3oc3ccccc34)n2)c([2H])c1[2H]]
-continued
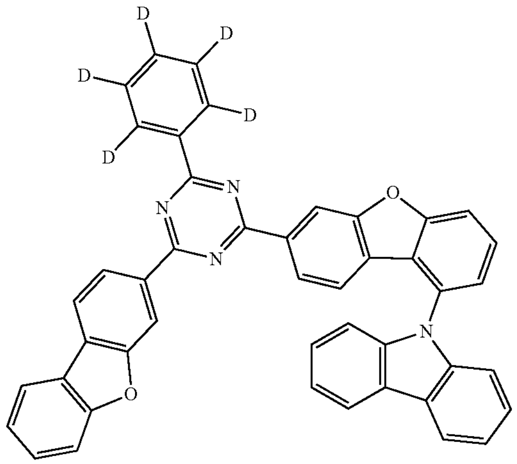
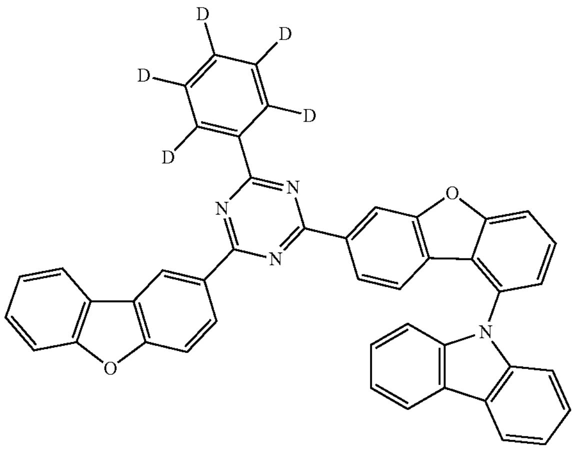
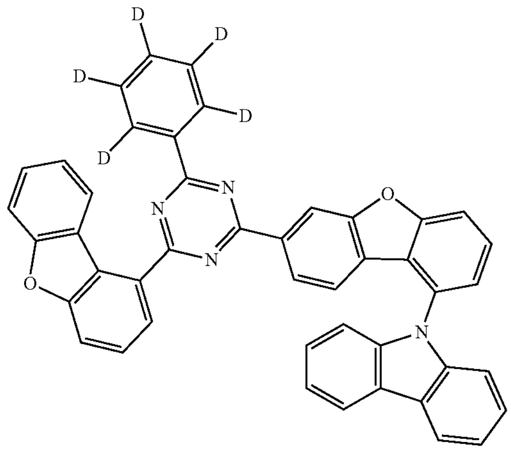

-continued
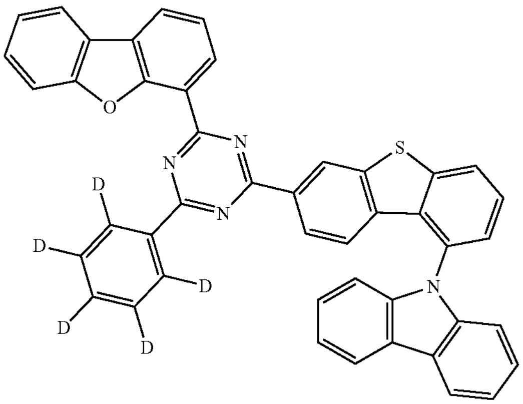
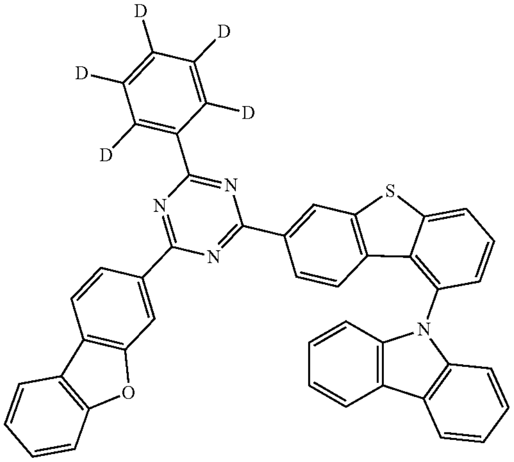
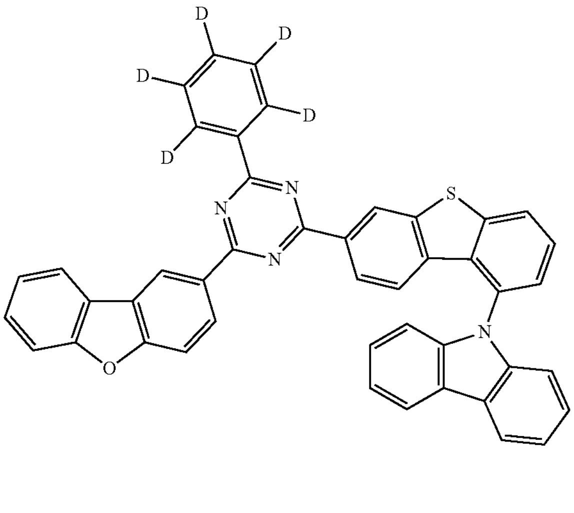
-continued
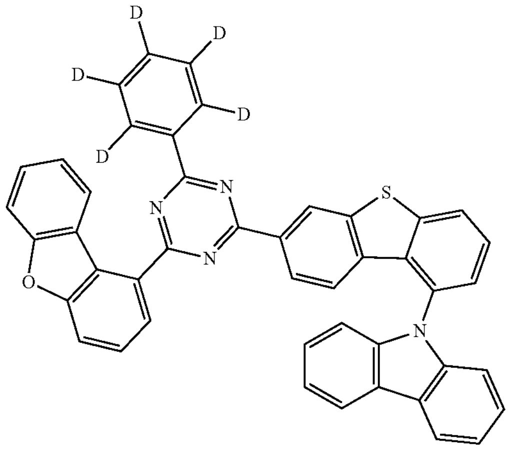
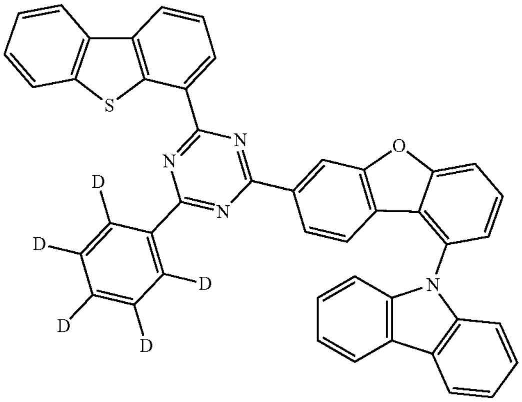
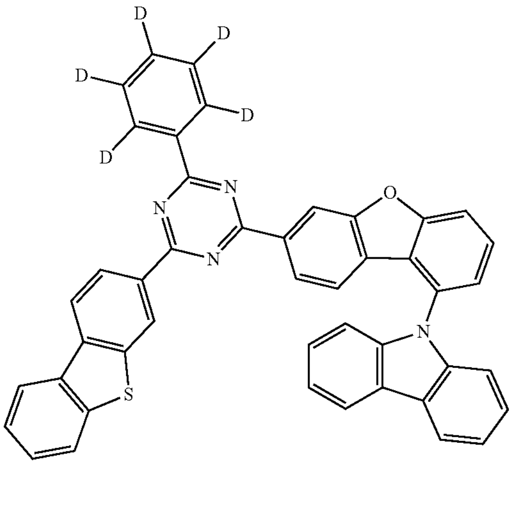

-continued
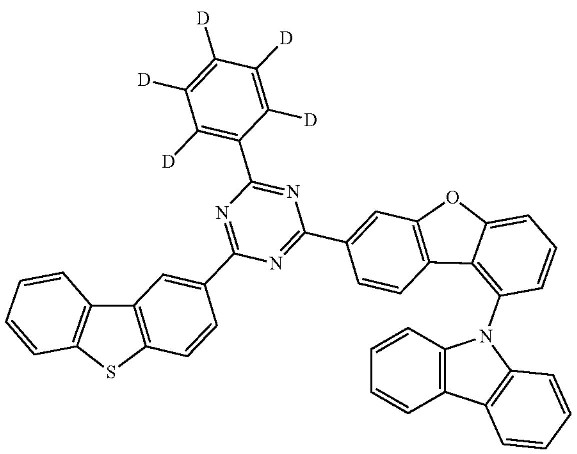
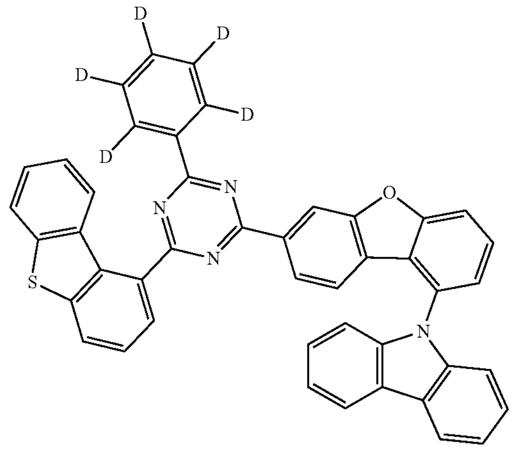
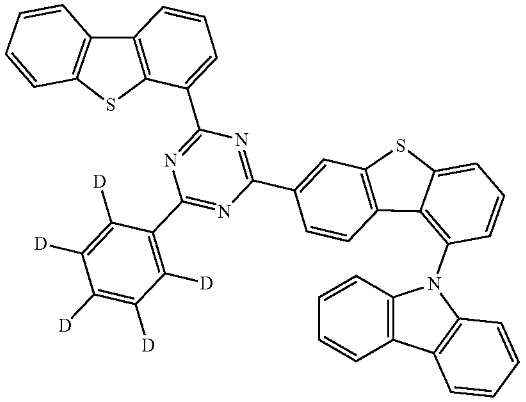
-continued
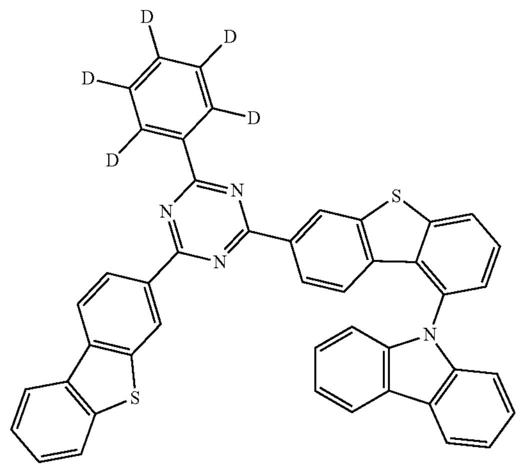
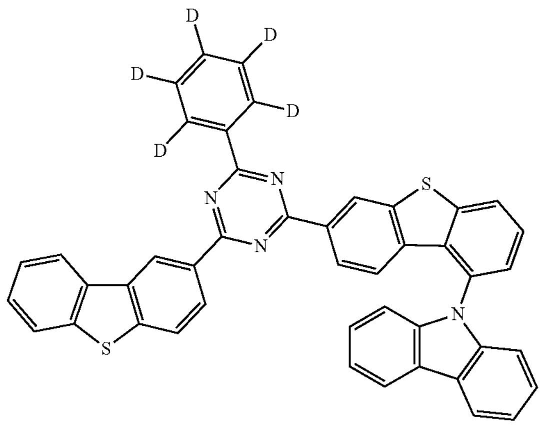
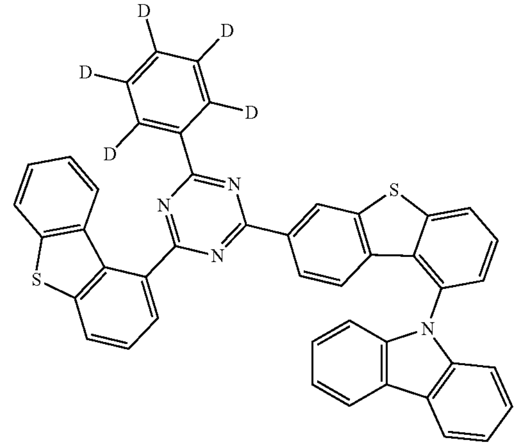

-continued
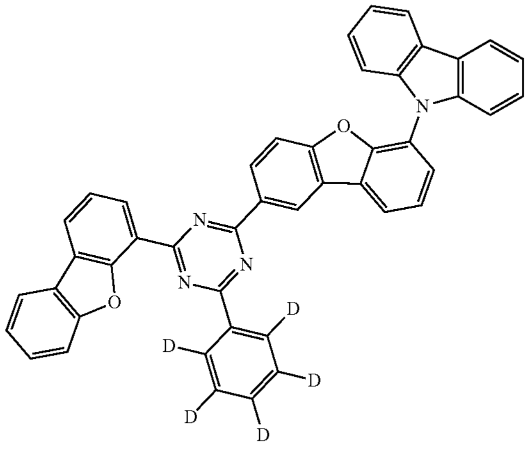
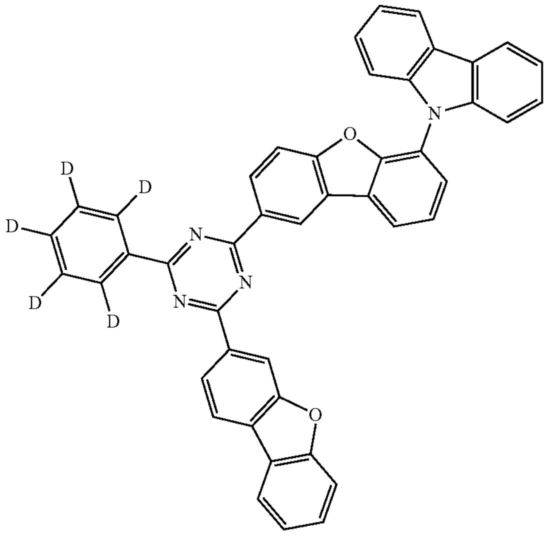
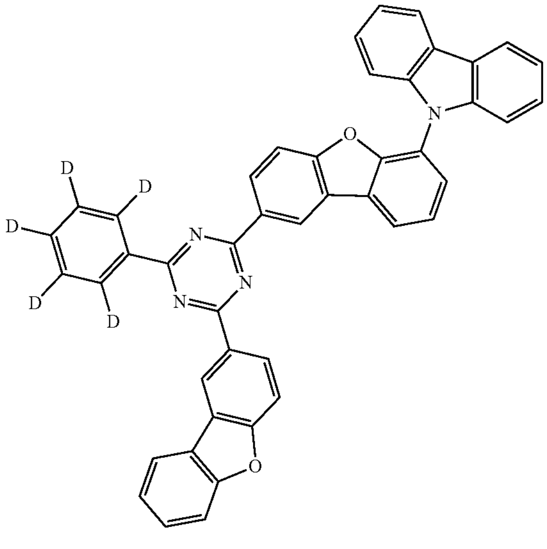
-continued
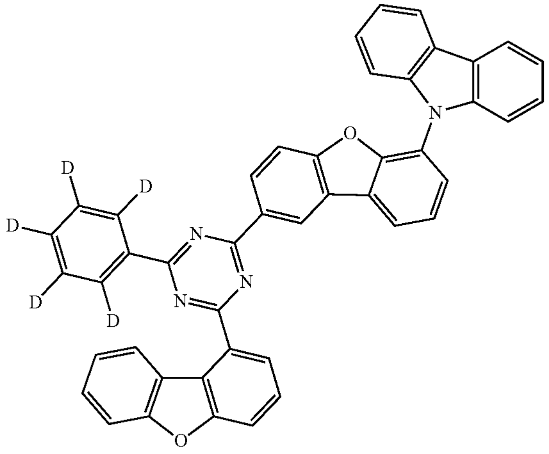
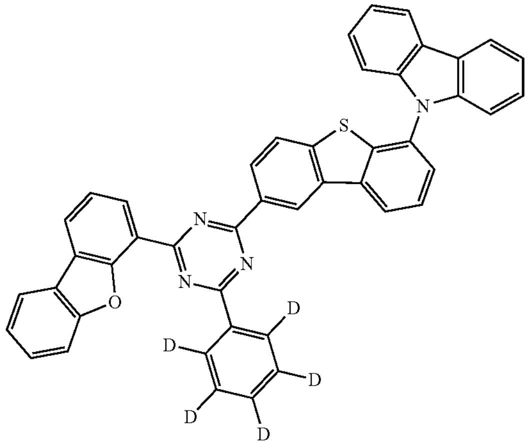
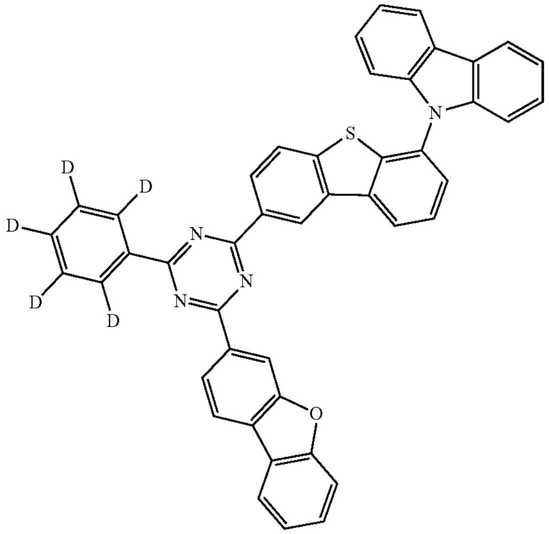

-continued
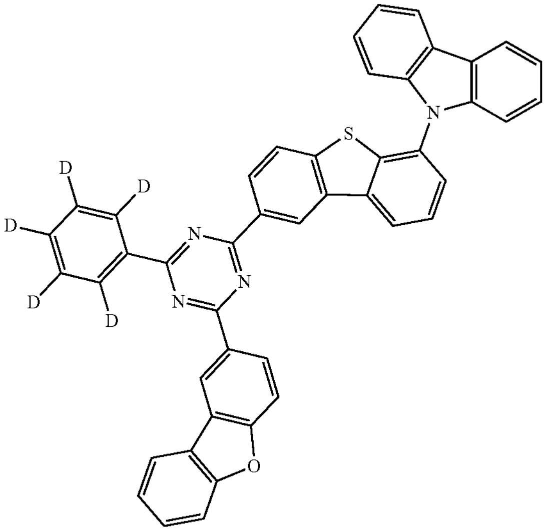
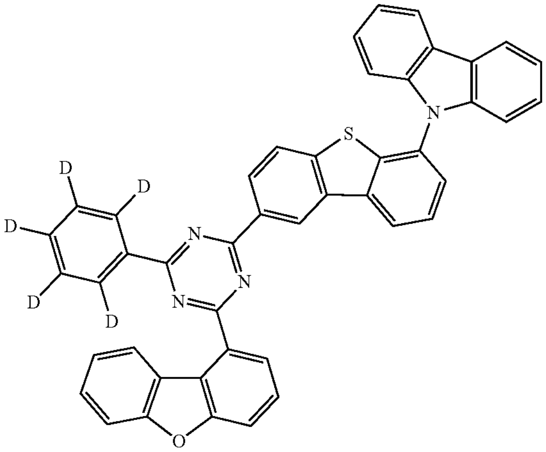
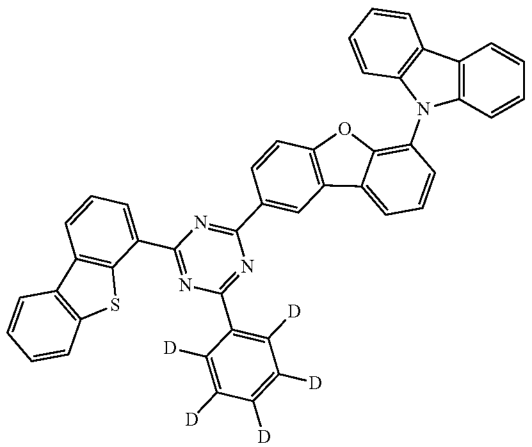
-continued
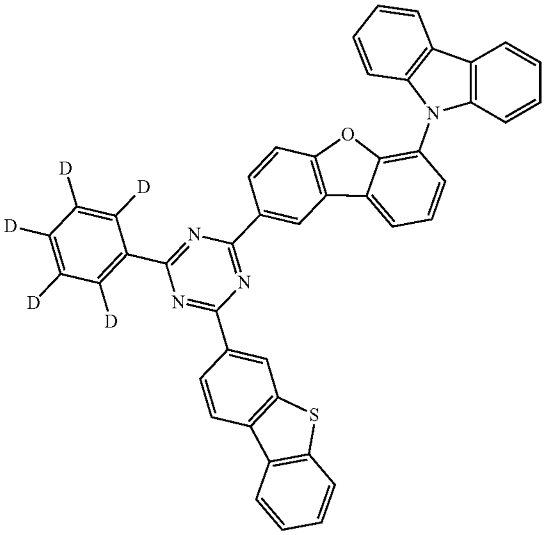
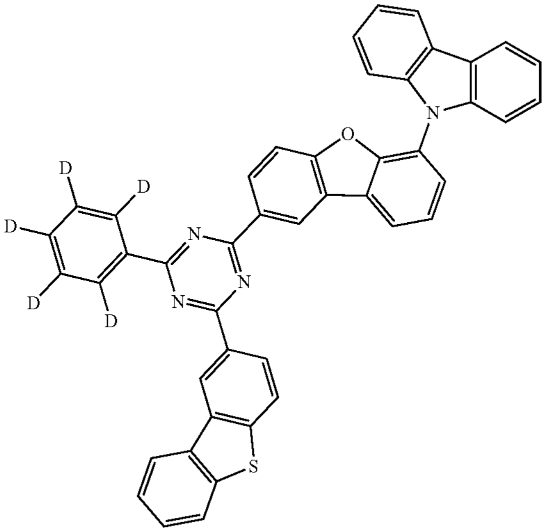
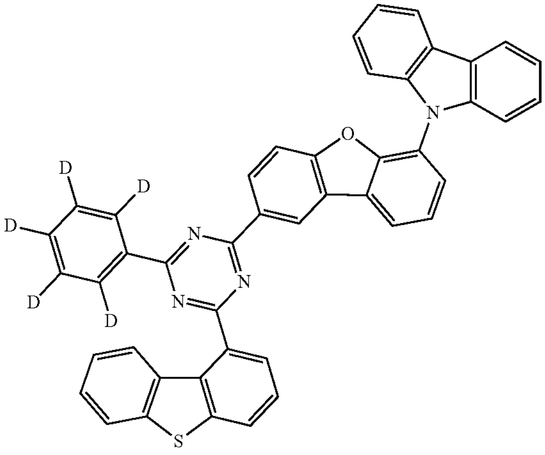

-continued
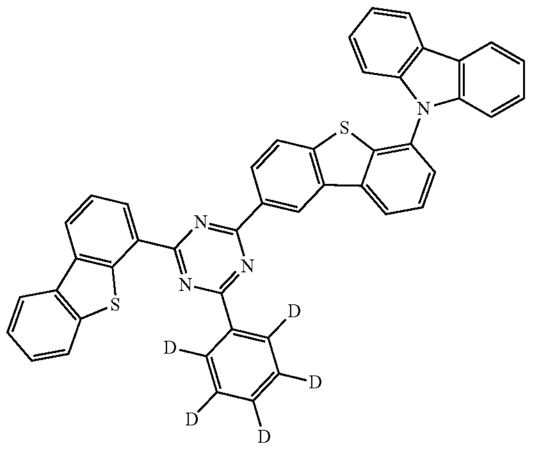
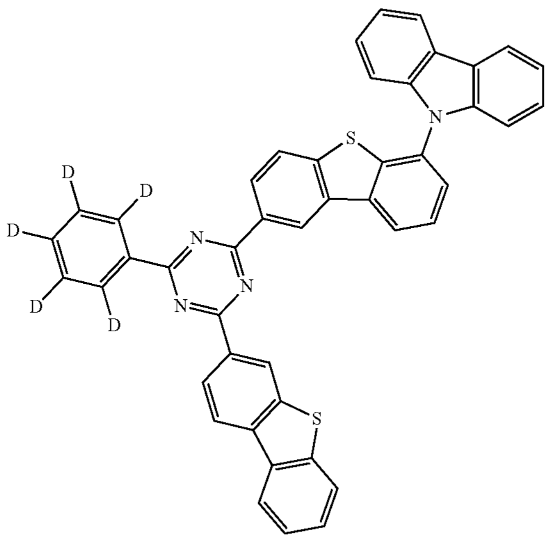
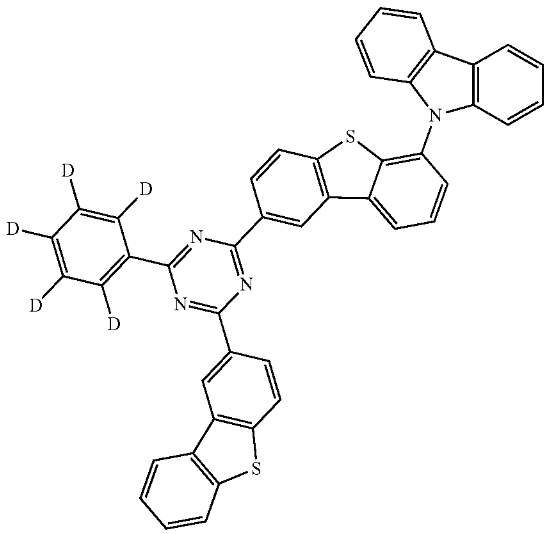
-continued
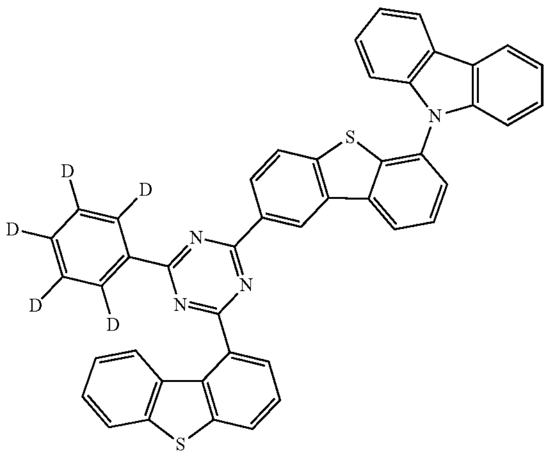
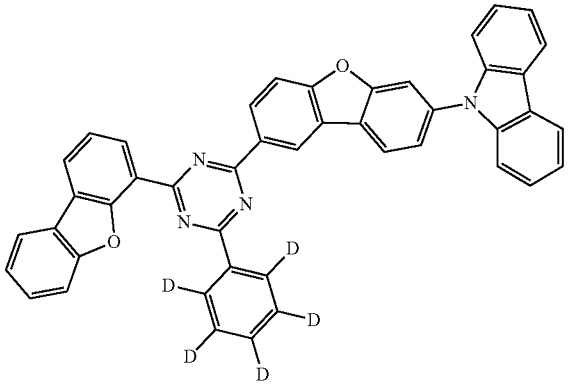
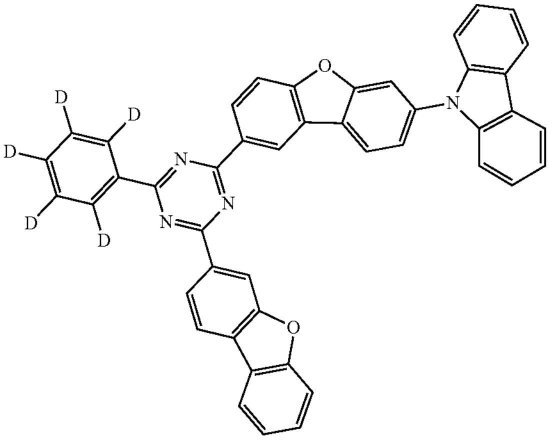
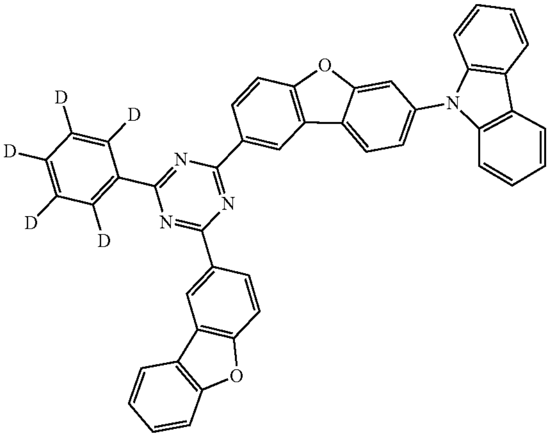

-continued
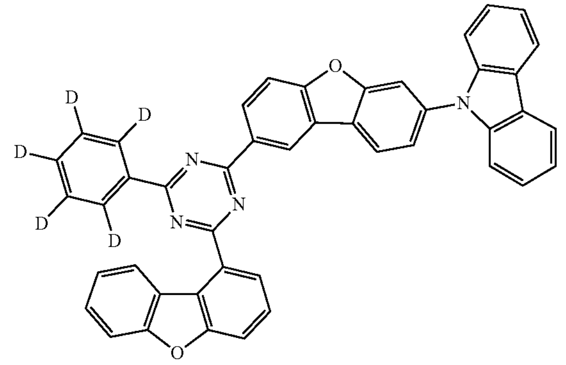
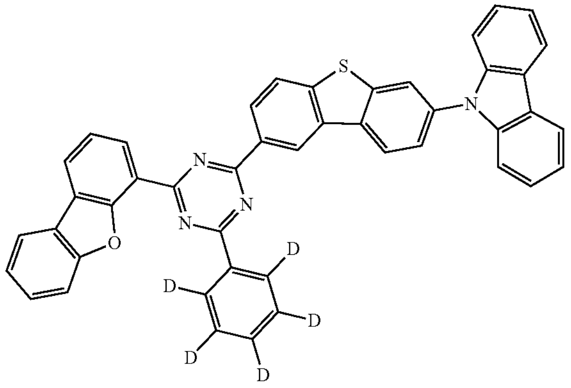
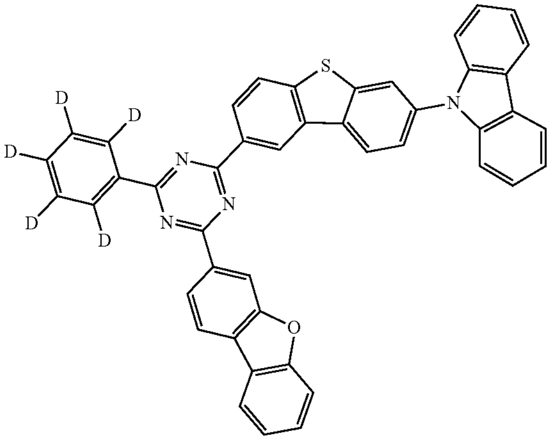
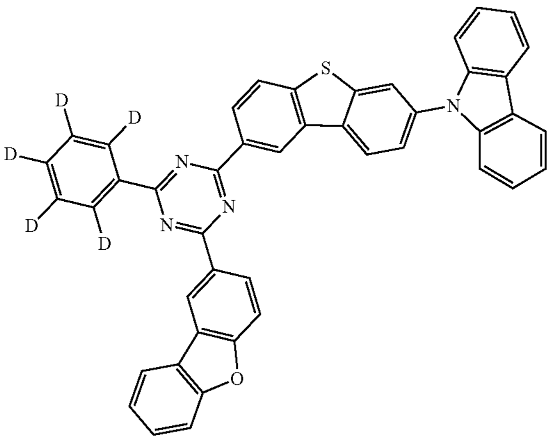
-continued
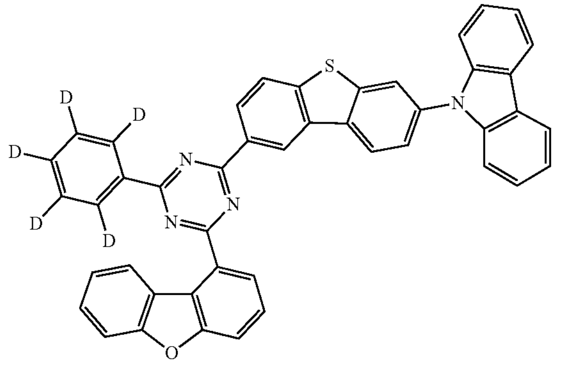
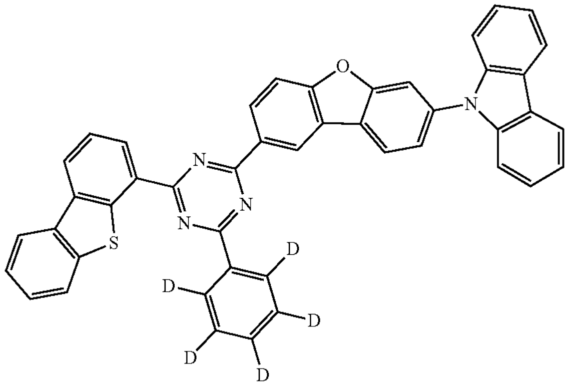
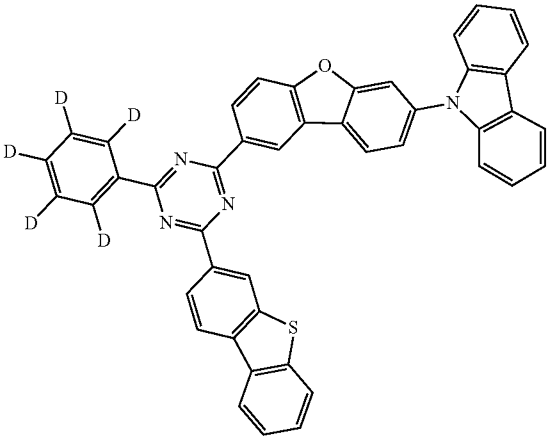
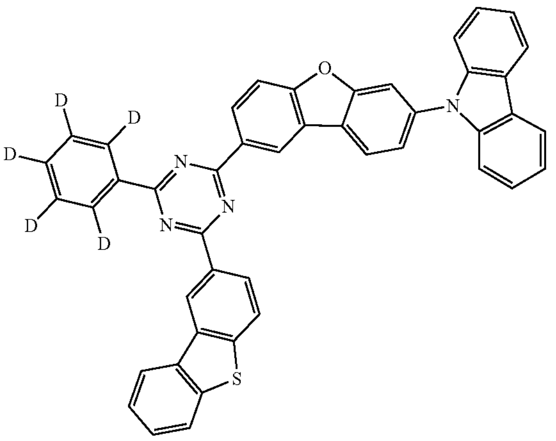

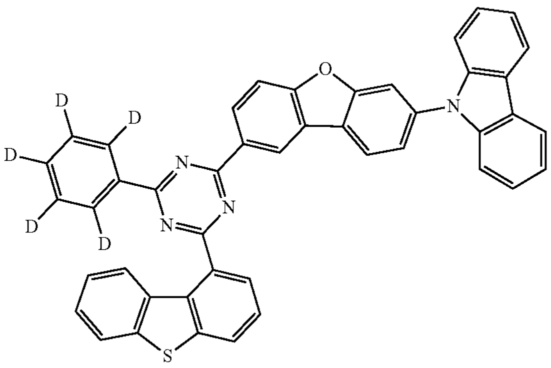
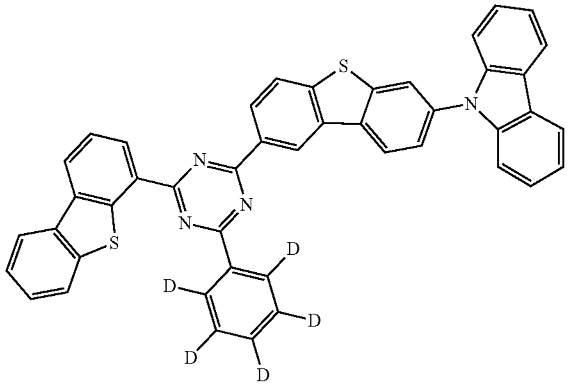
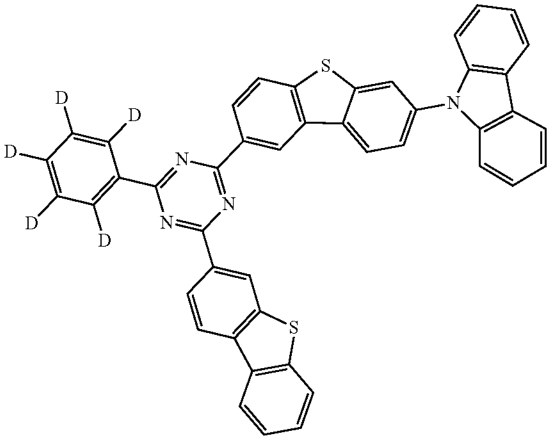
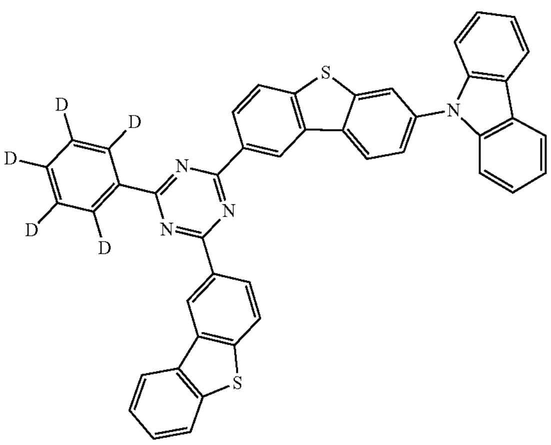
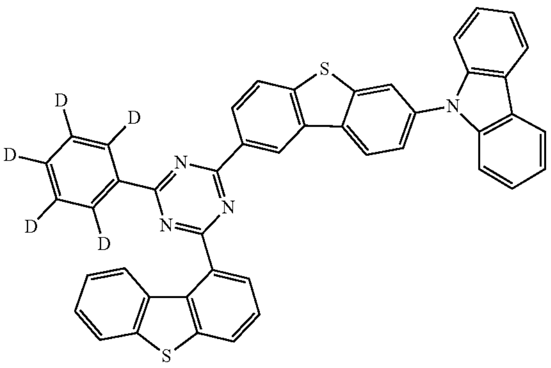
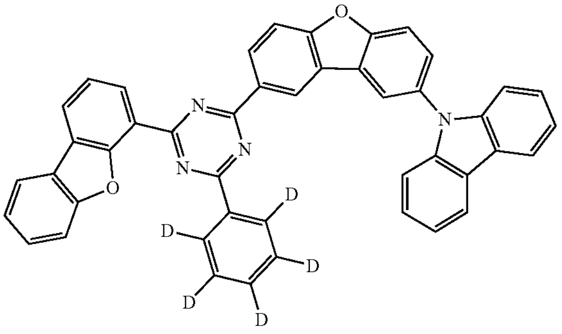
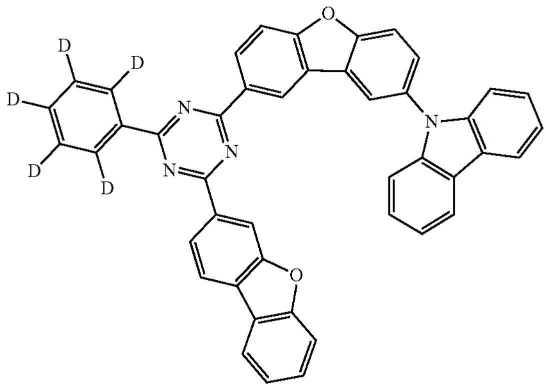
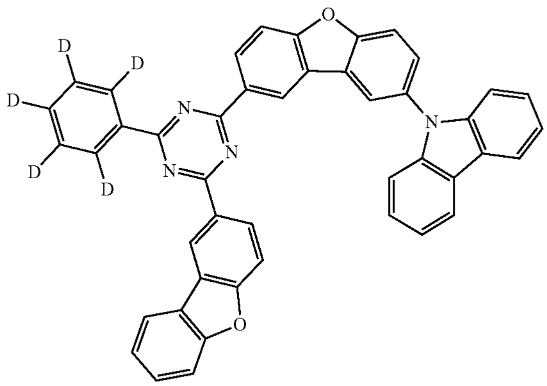

-continued
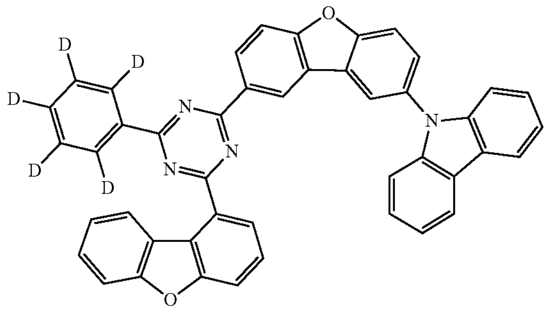
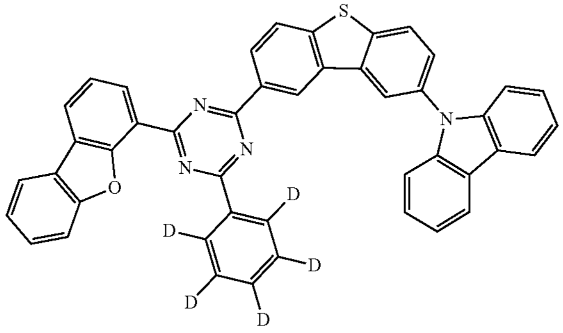
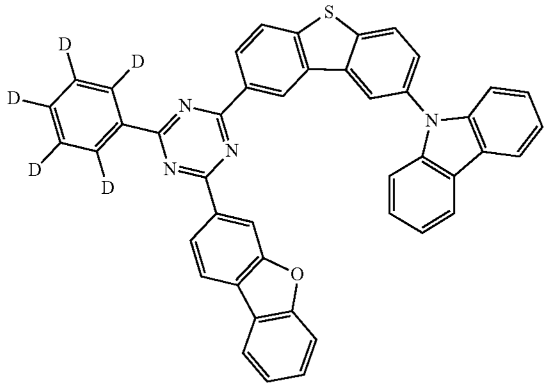
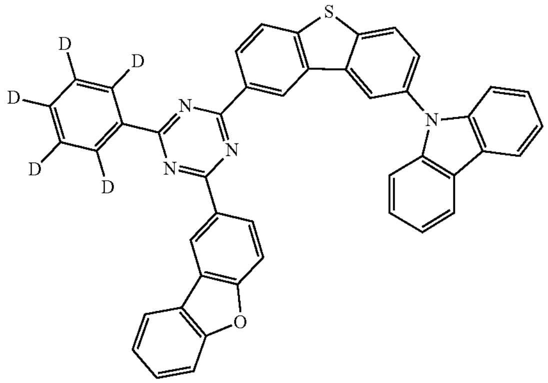
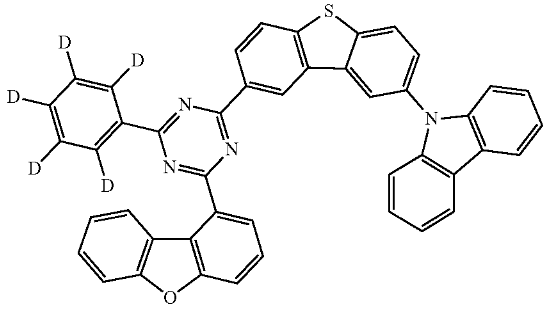
-continued
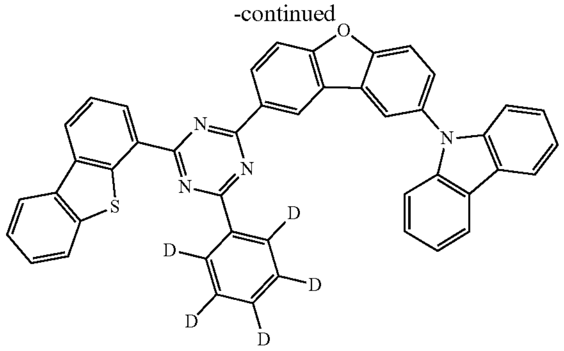
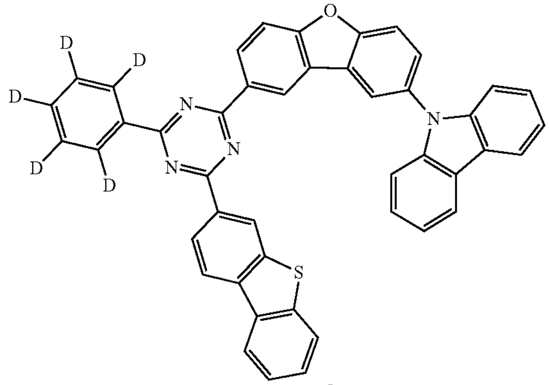
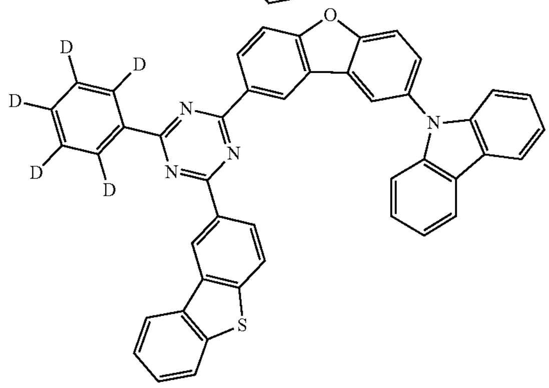
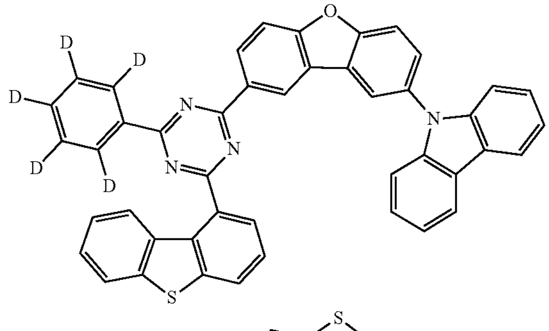
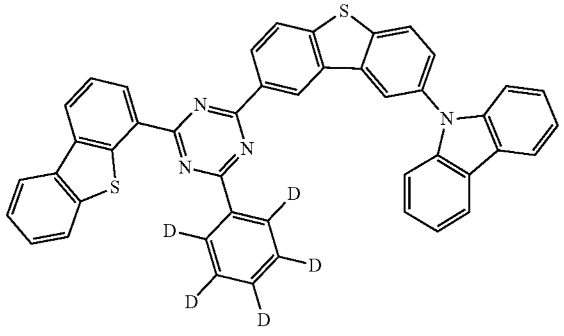

-continued
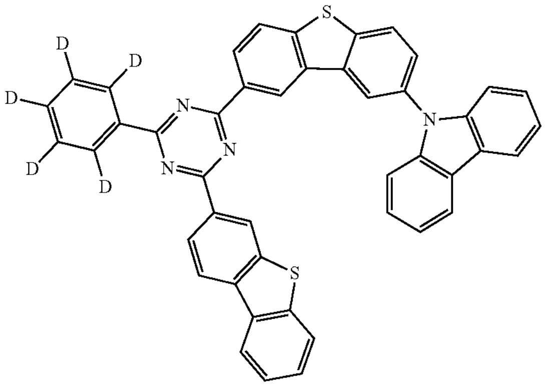
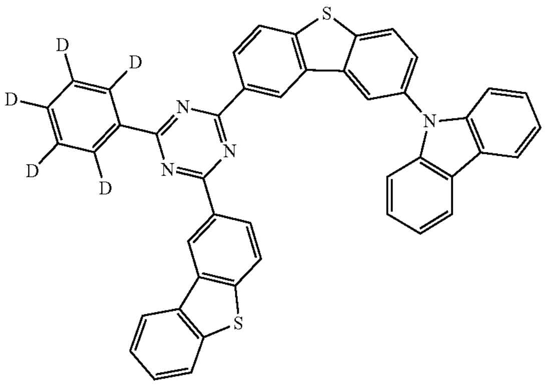
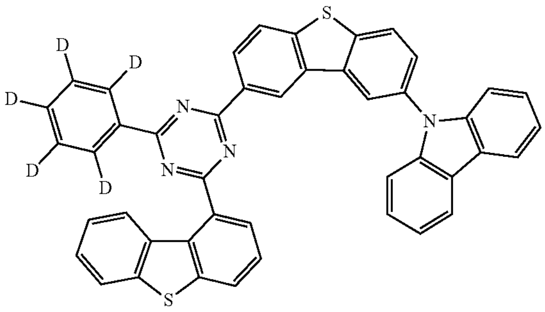
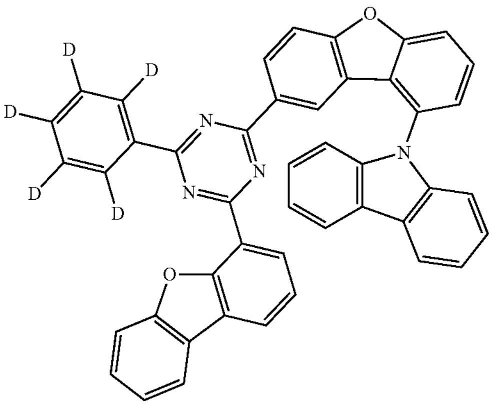
-continued
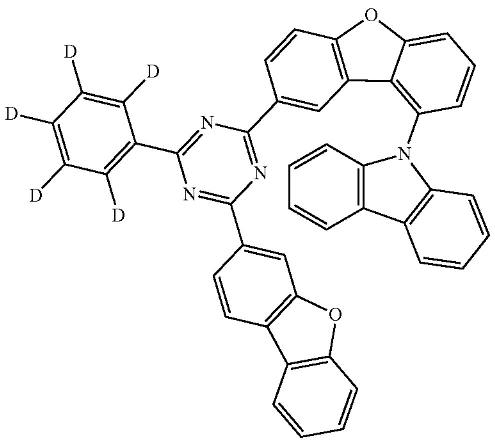
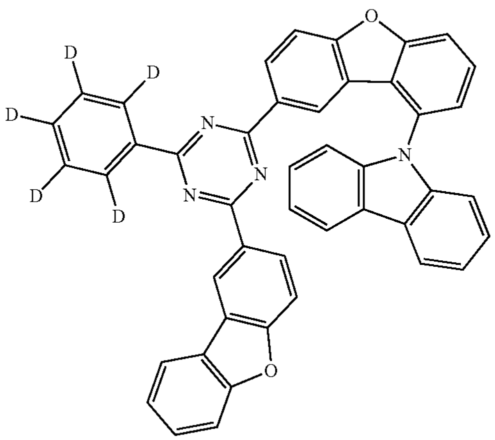
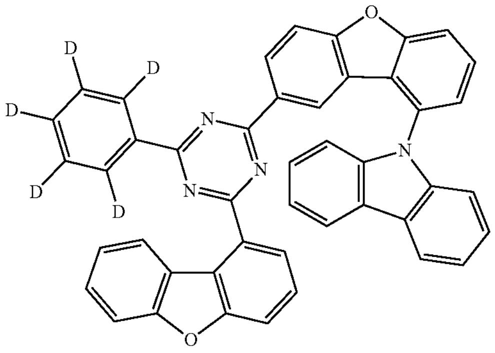
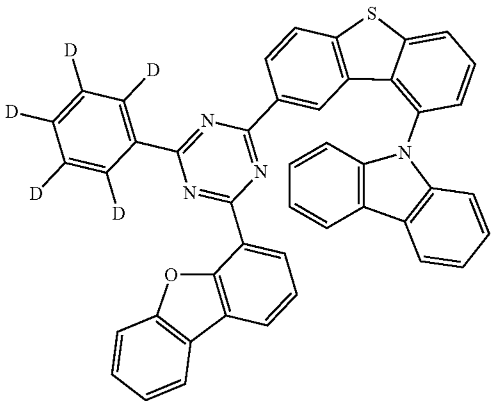

-continued
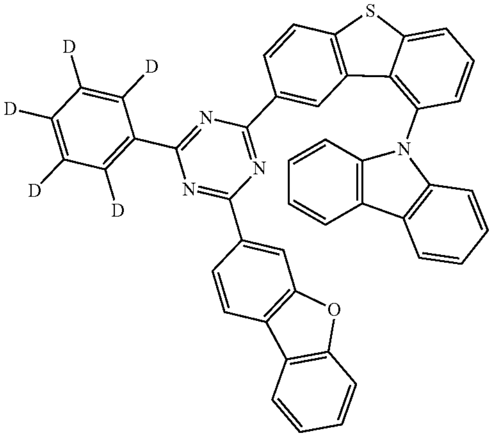
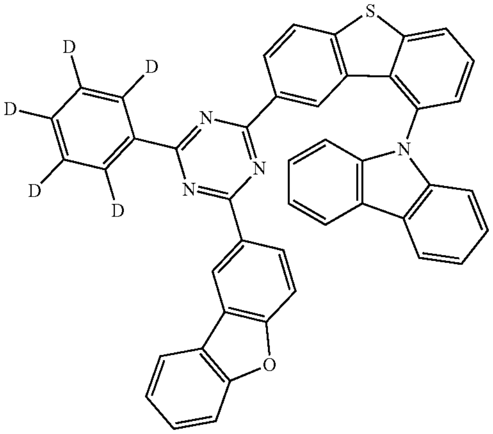
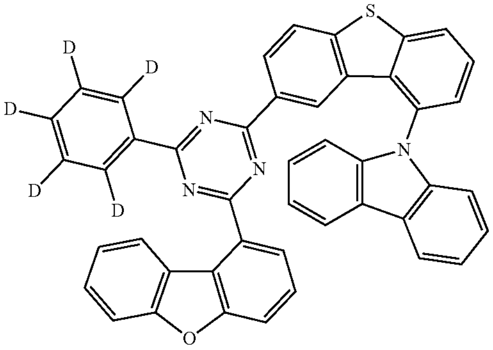
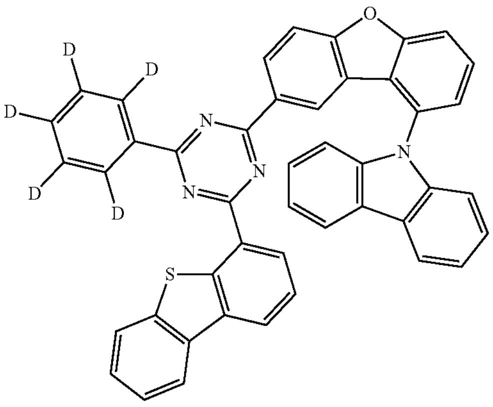
-continued
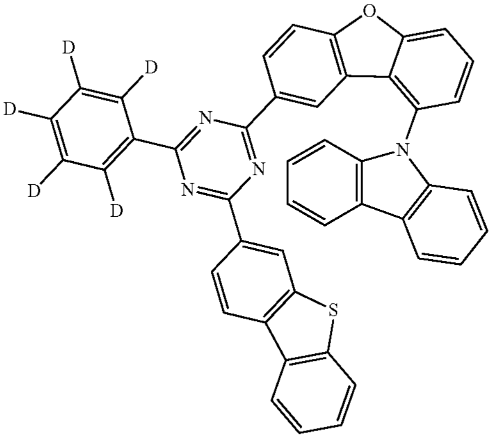
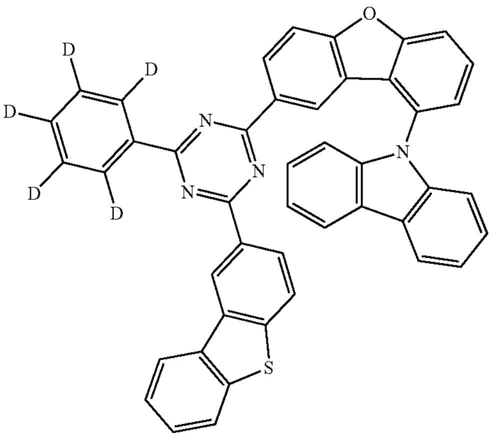
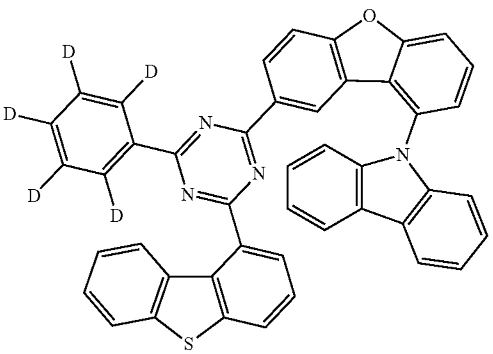
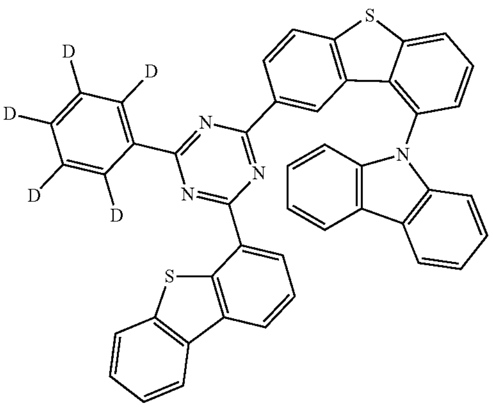

-continued
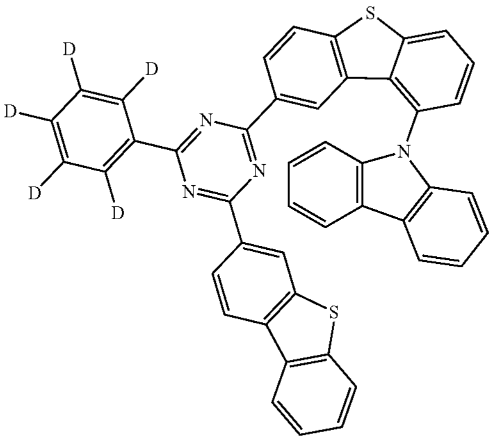
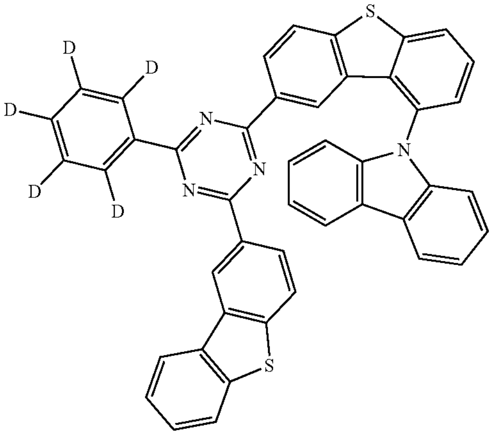
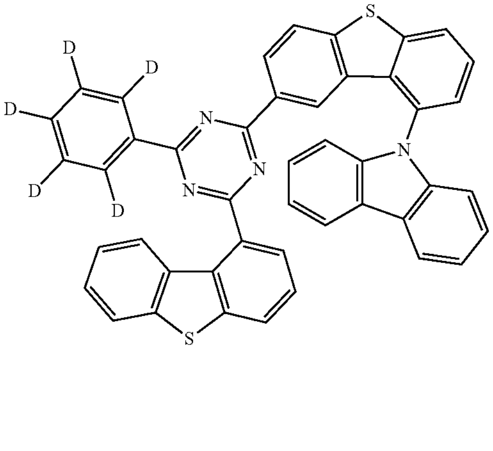
-continued
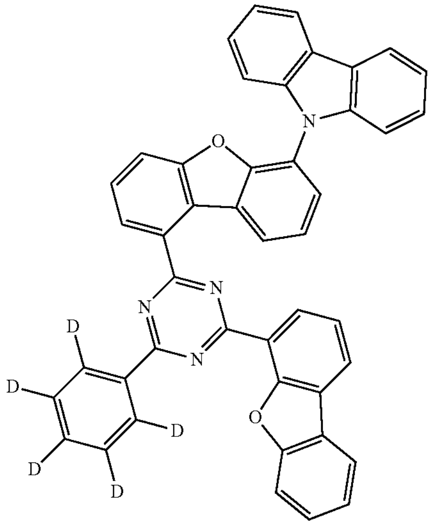
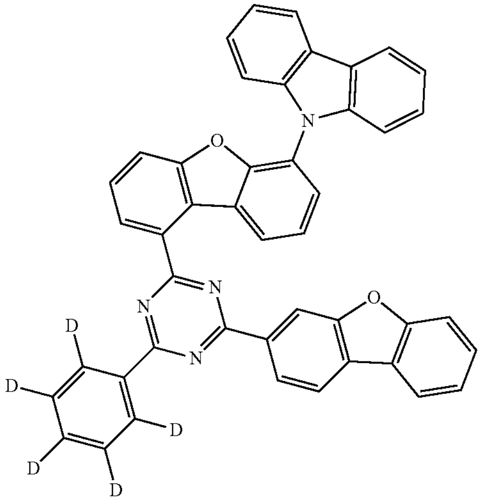
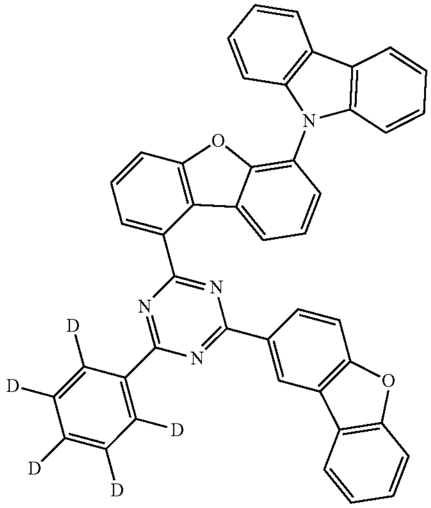

-continued
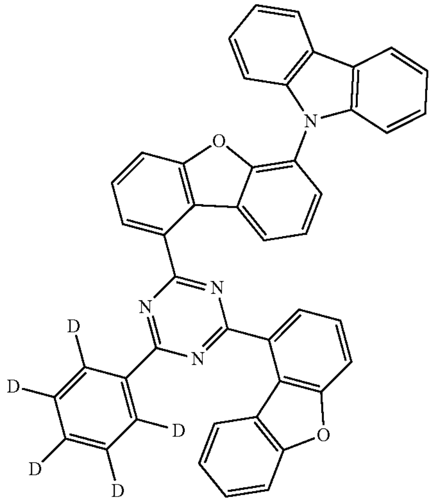
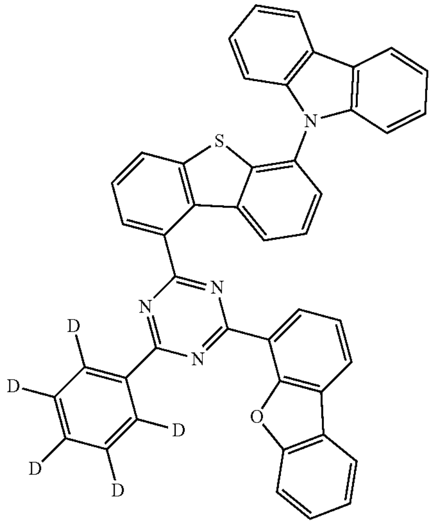
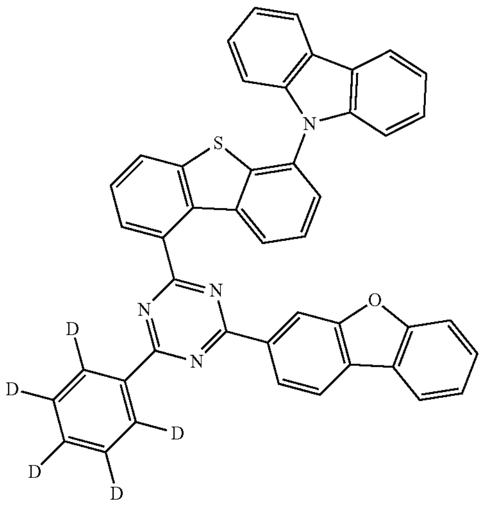
-continued
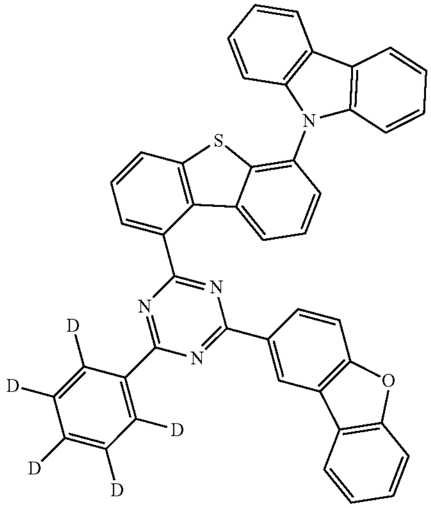
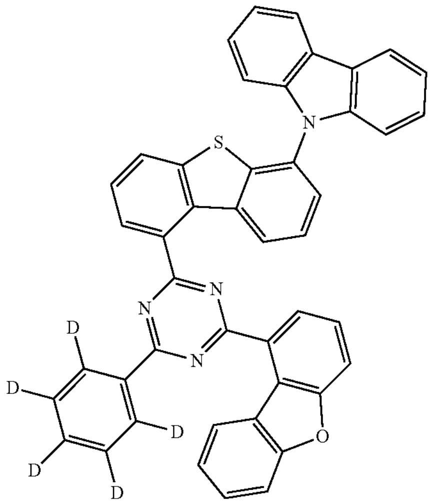
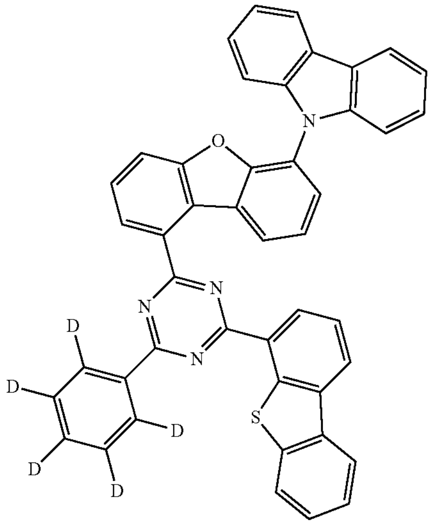

-continued
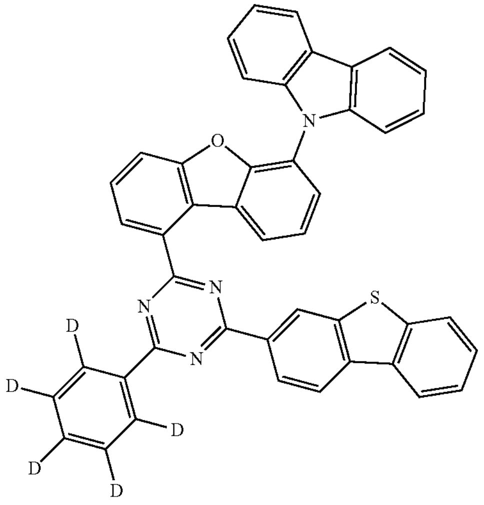
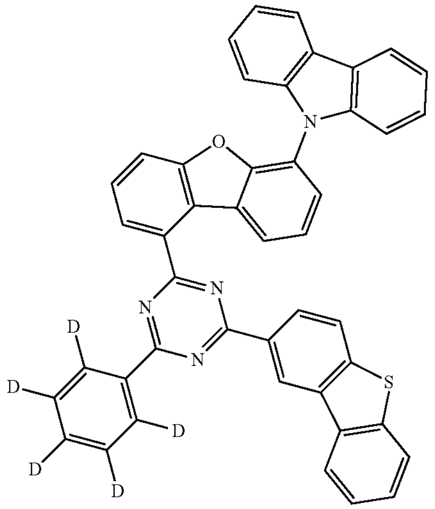
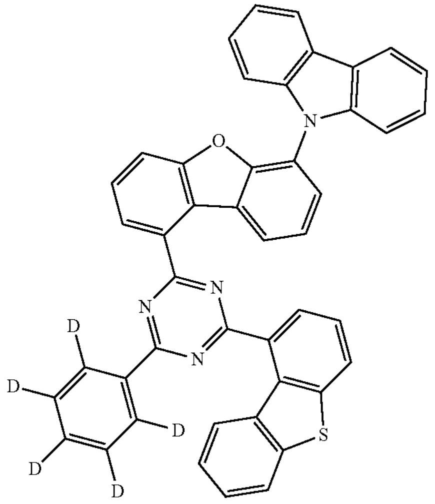
-continued
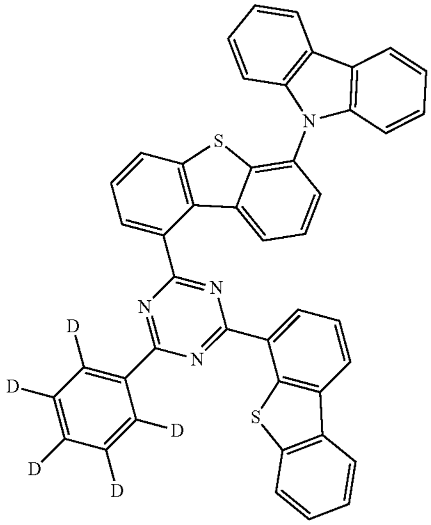
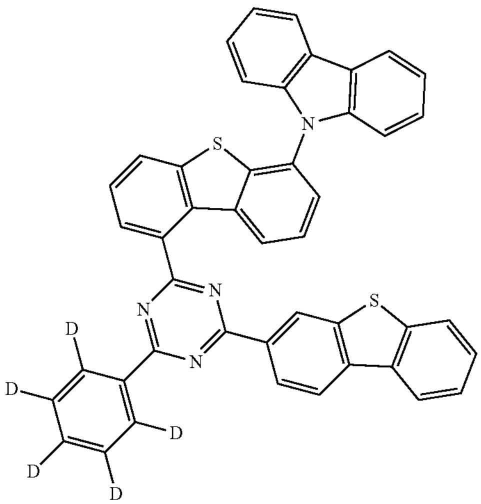
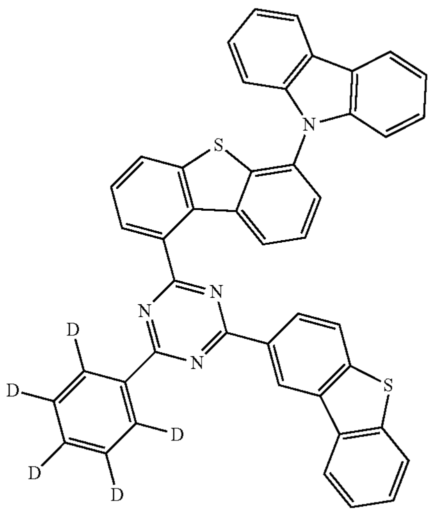

-continued
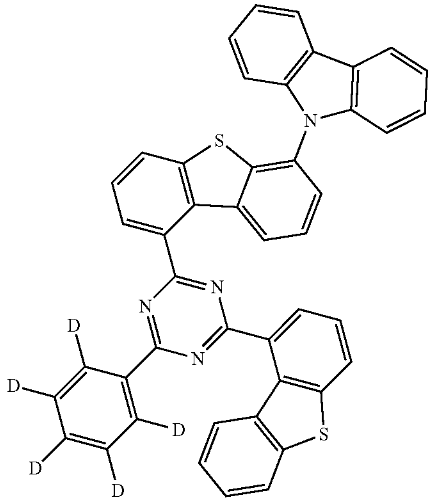
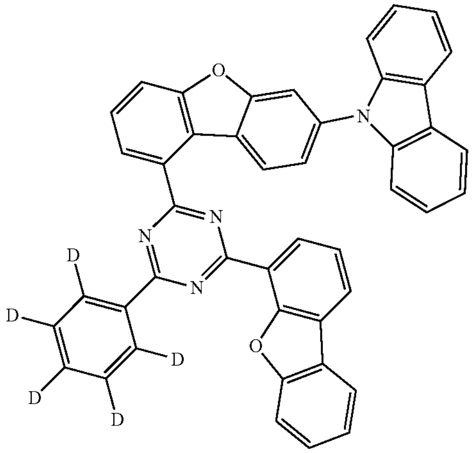
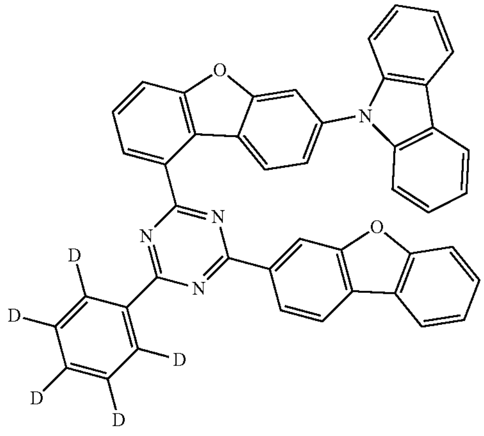
-continued
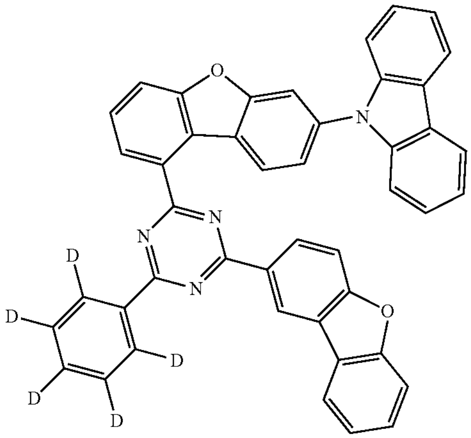
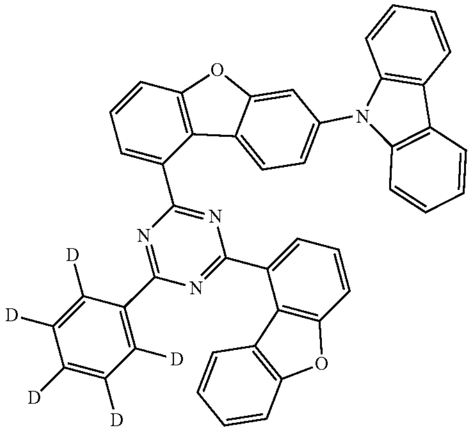
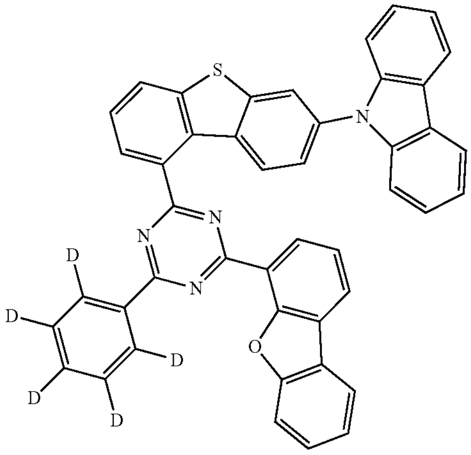

-continued
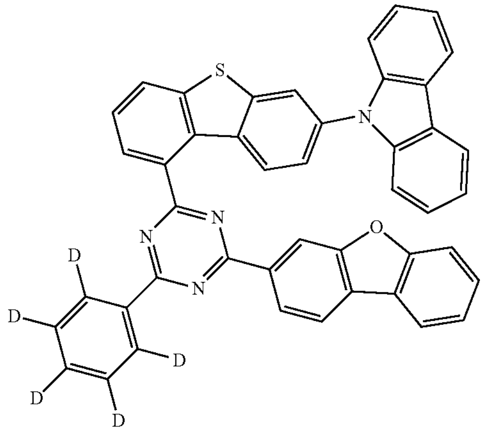
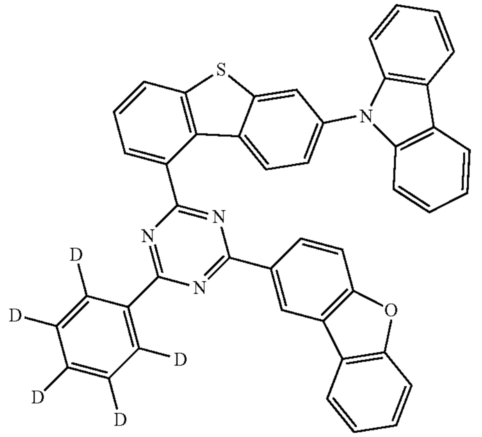
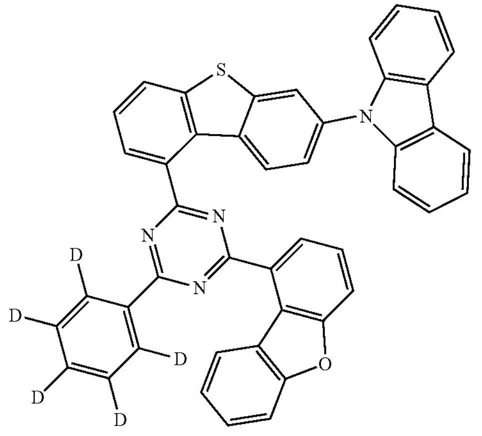
-continued
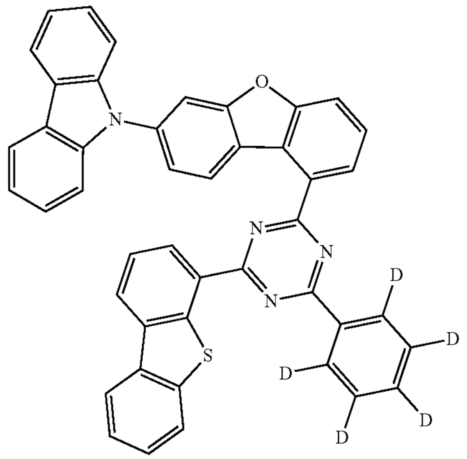
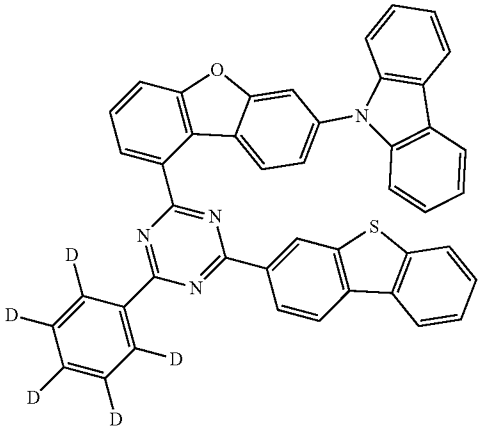
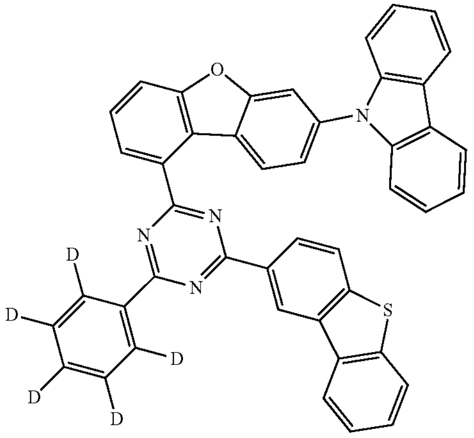

-continued
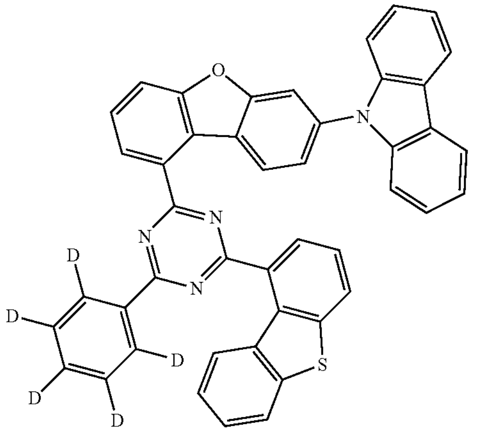
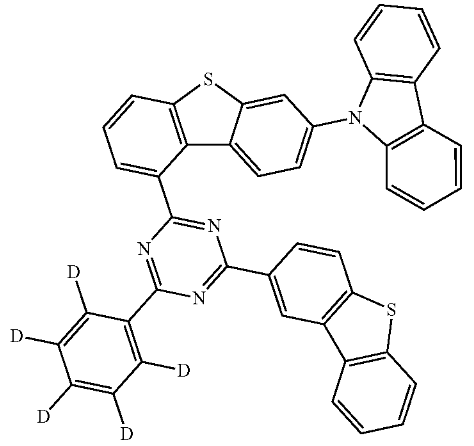
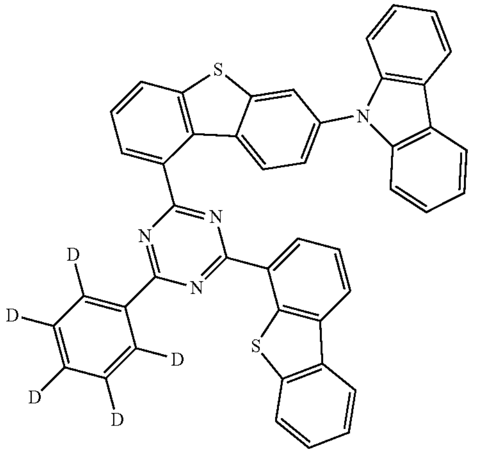
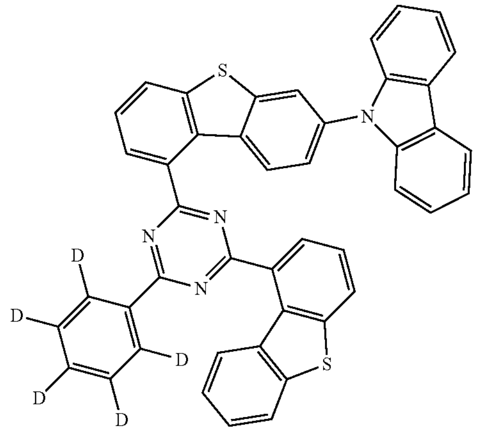
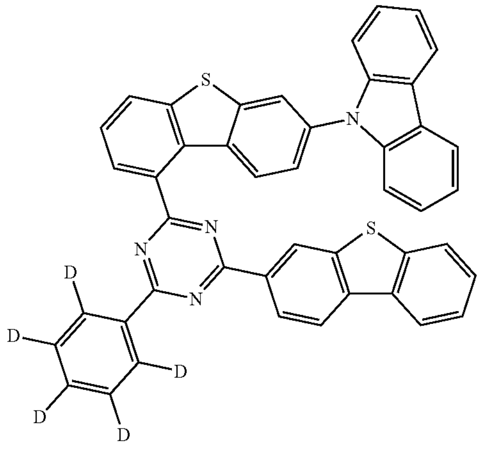
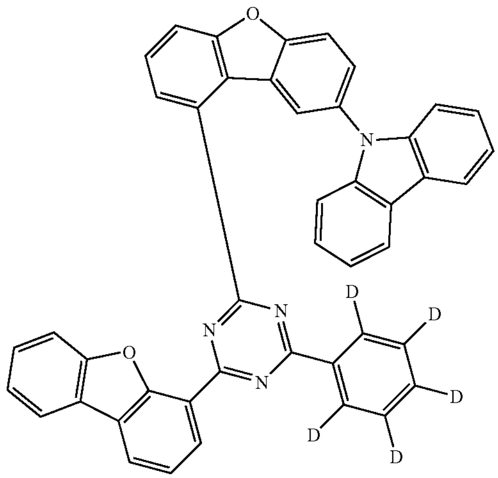
-continued -continued
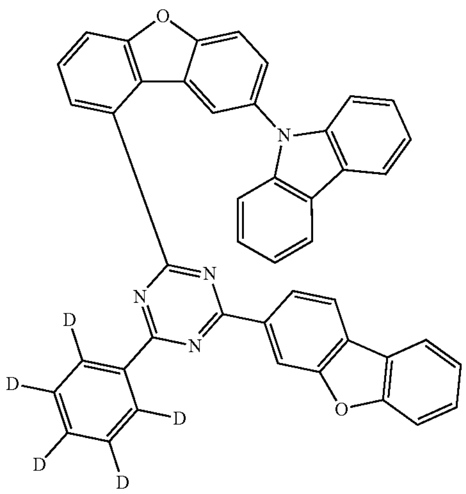
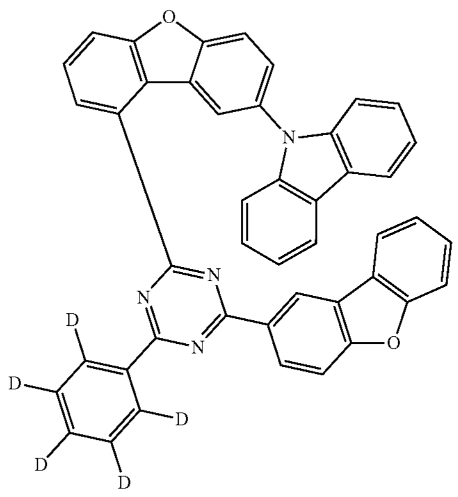
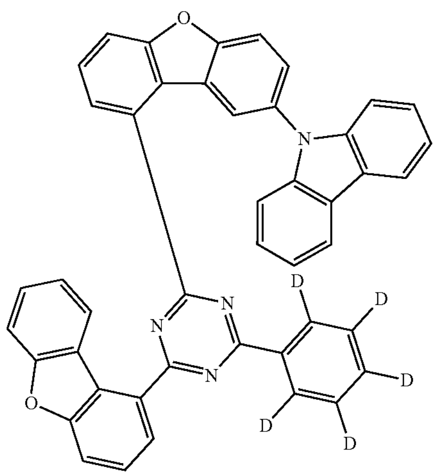
-continued
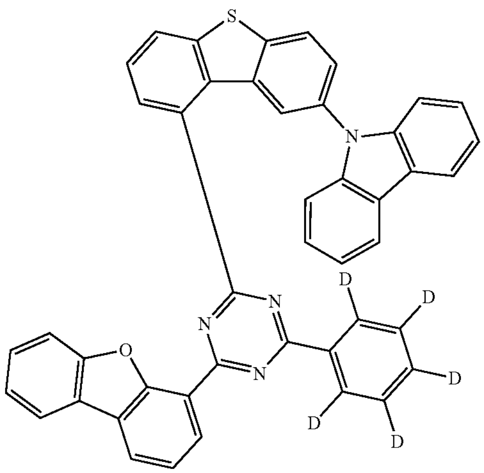
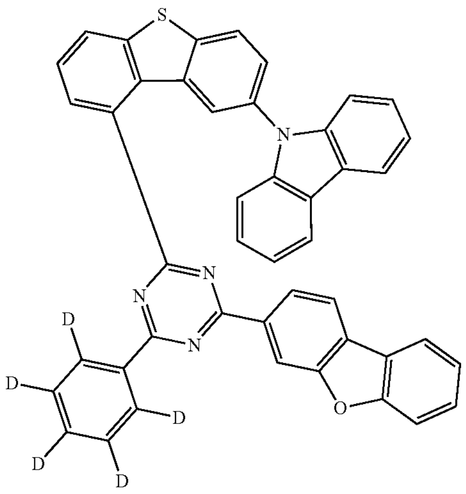
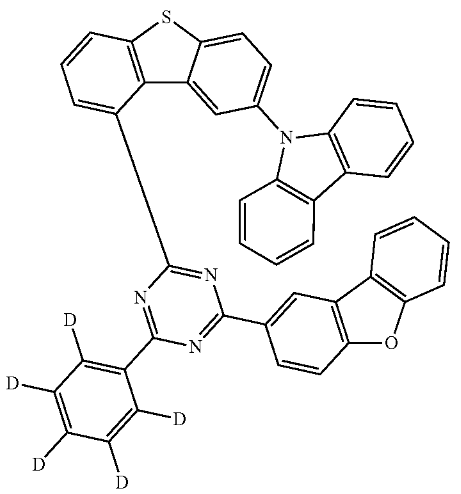

-continued
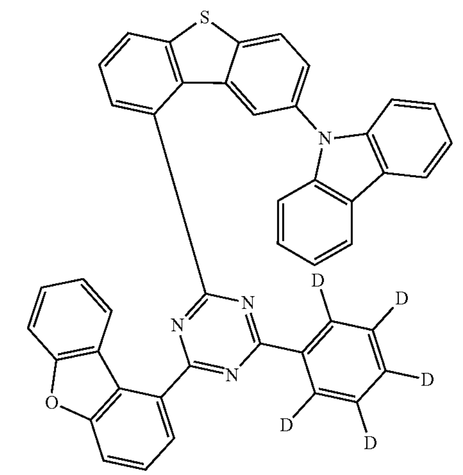
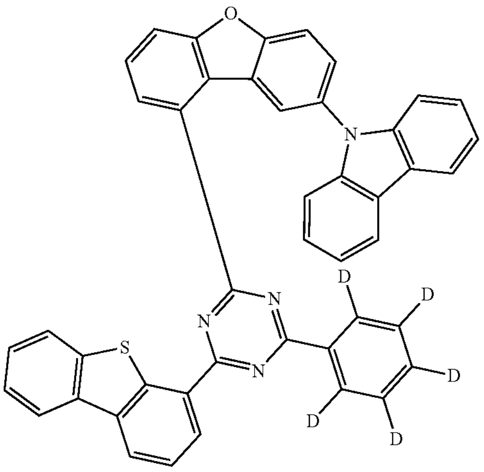
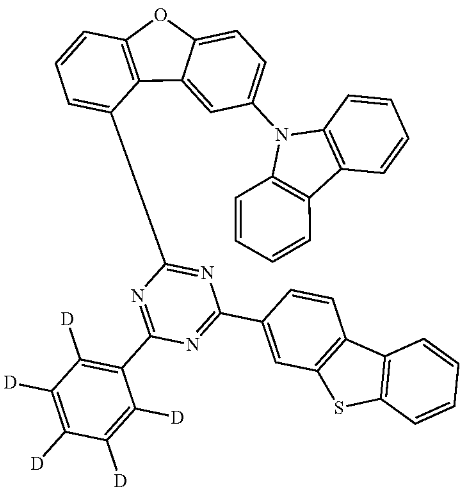
-continued
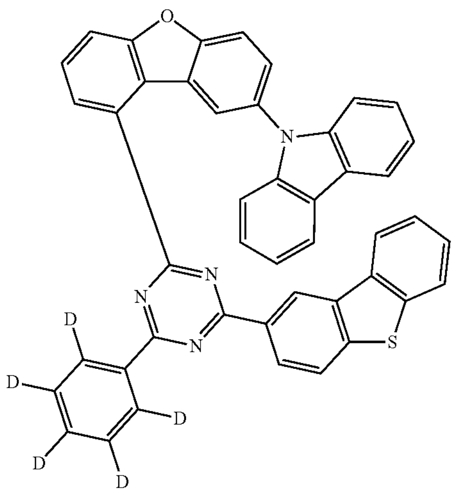
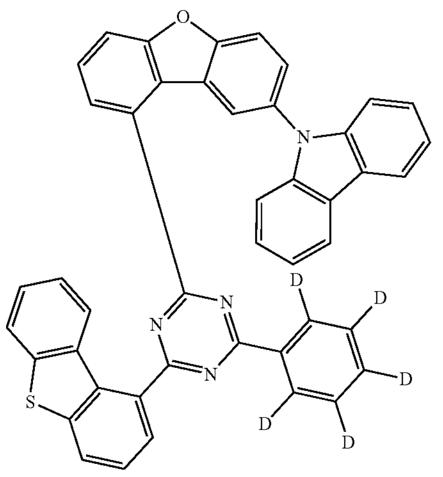
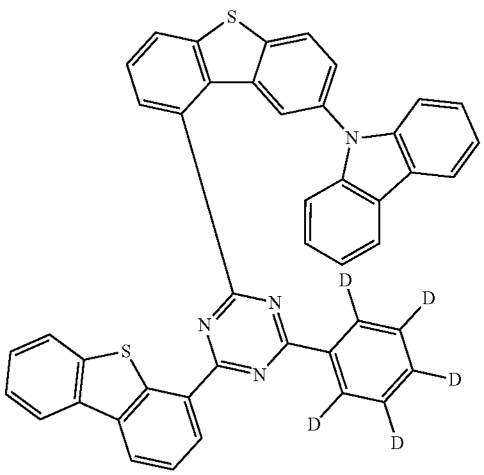

-continued
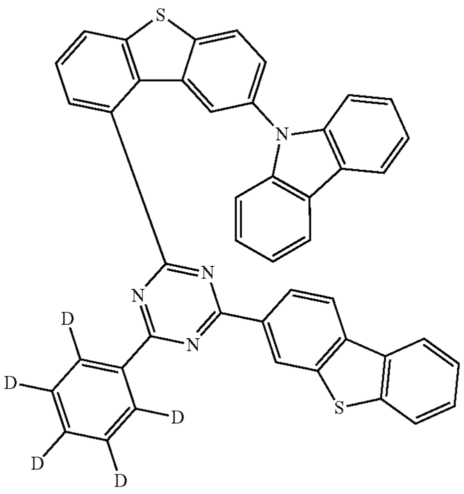
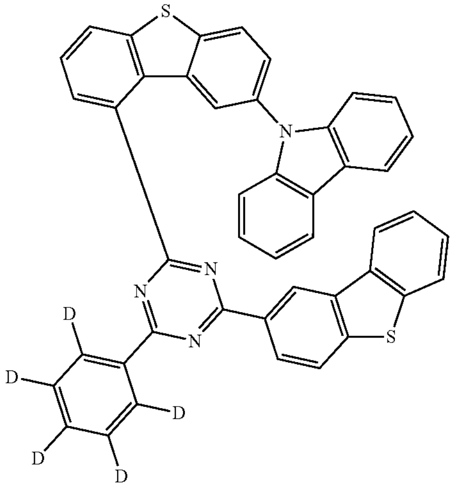
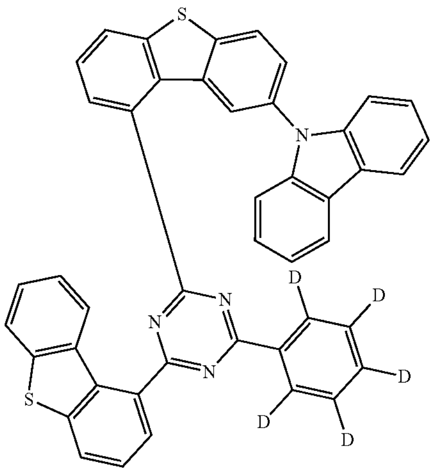
-continued
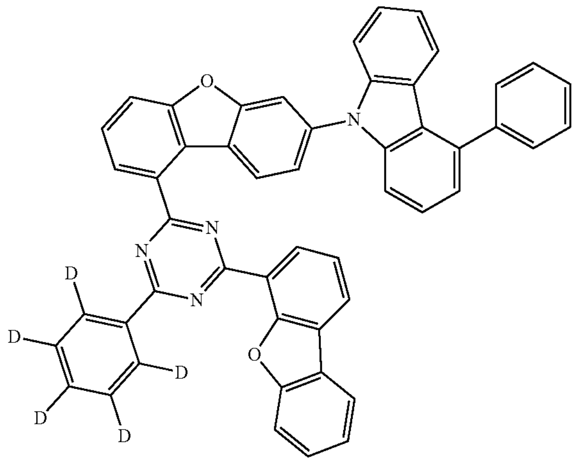
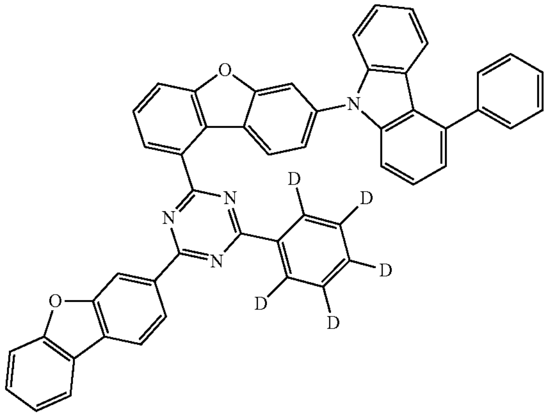
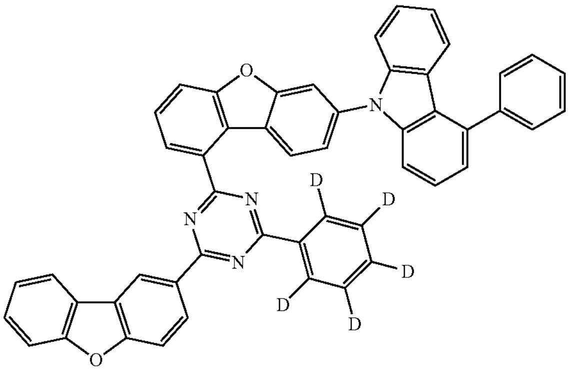
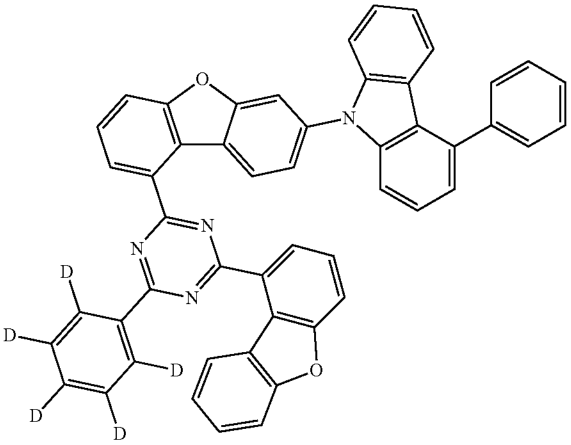

-continued
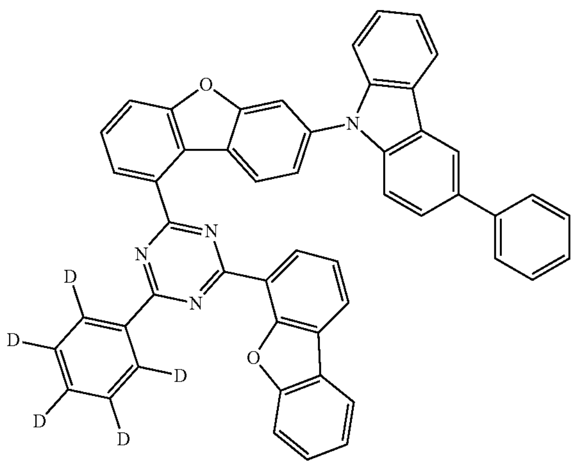
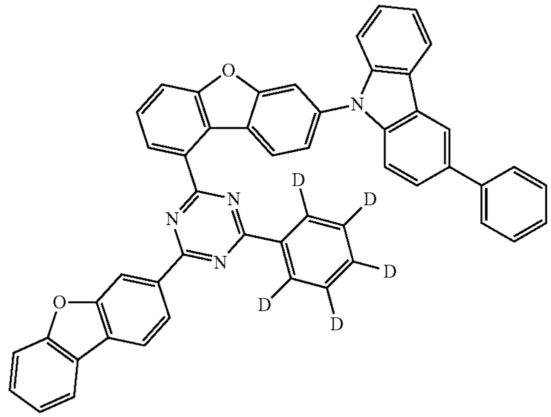
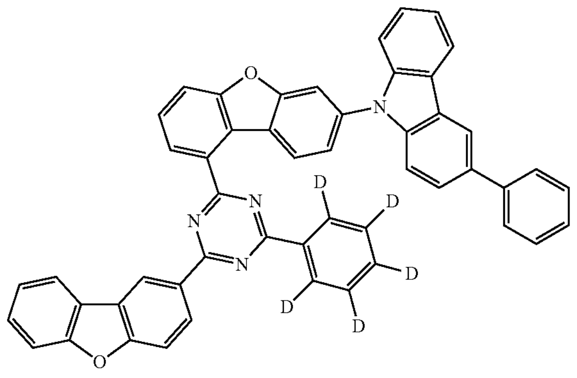
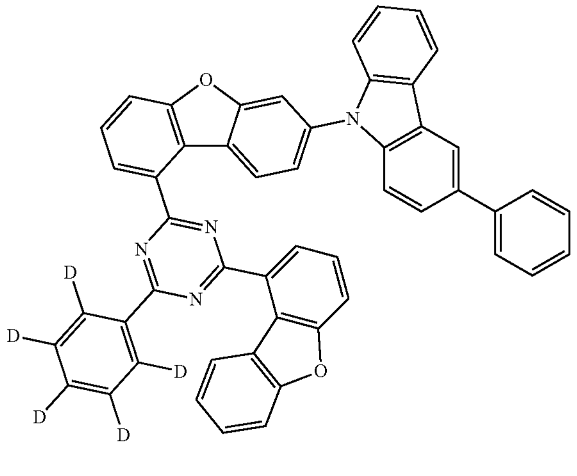
-continued
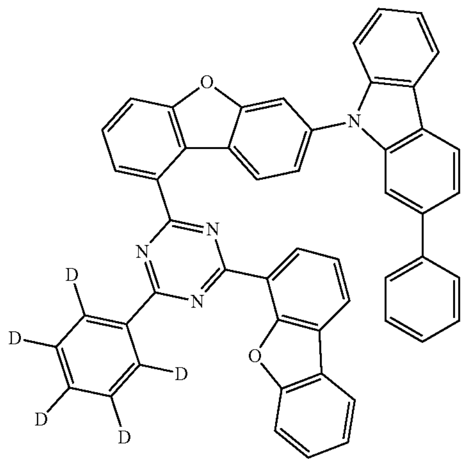
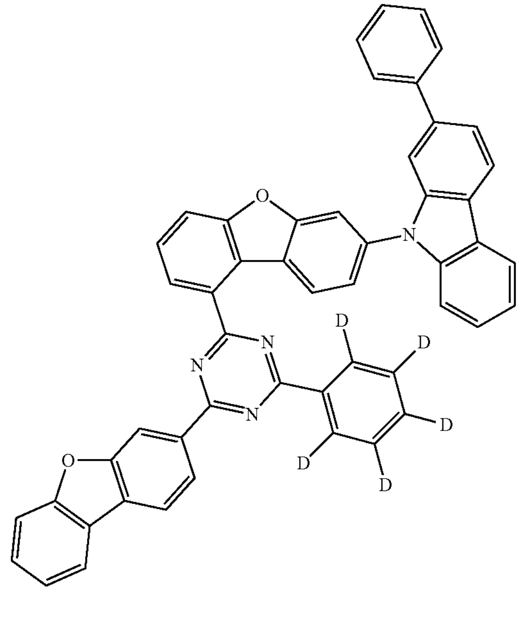
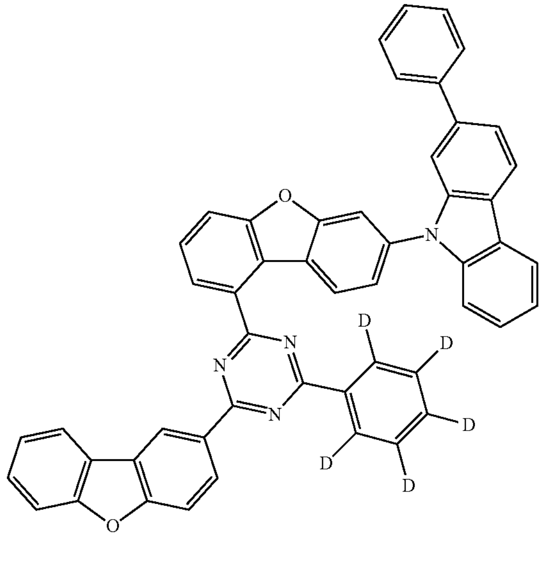

-continued
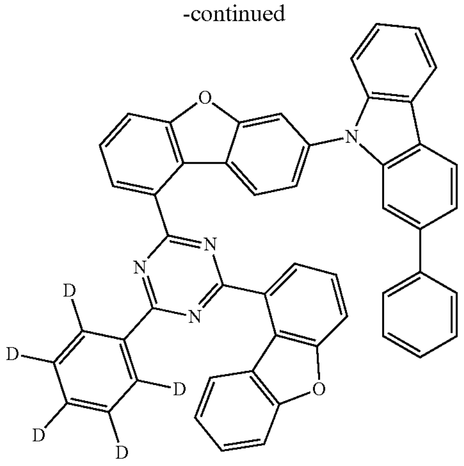
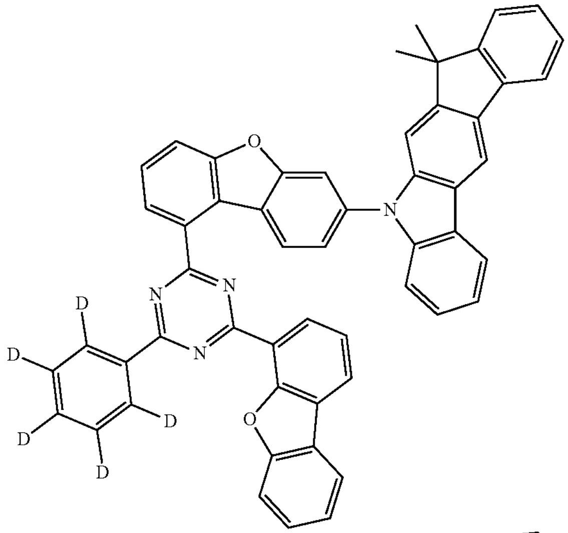
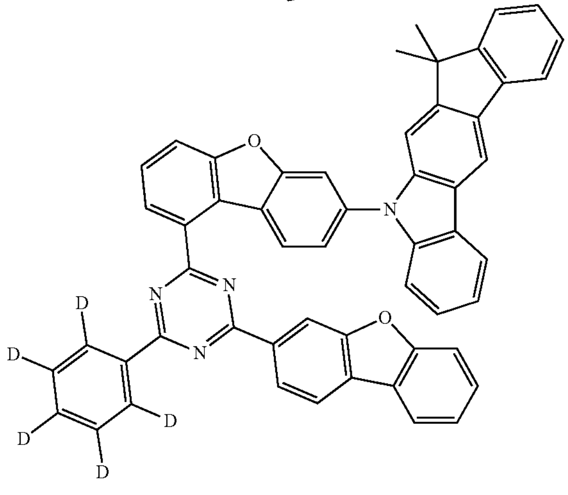
-continued
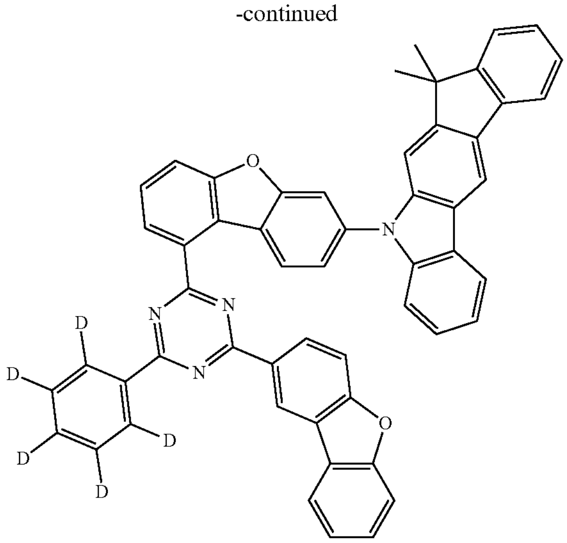
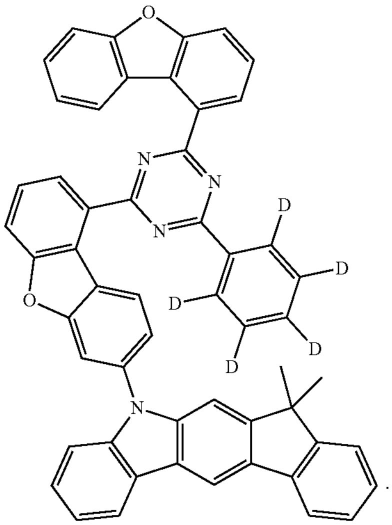 [SMILES: [2H]c1c([2H])c([2H])c(-c2nc(-c3cccc4oc5ccccc5c34)nc(-c3cccc4oc5cc(-n6c7ccccc7c7cc8c(cc76)C(C)(C)c6ccccc6-8)ccc5c34)n2)c([2H])c1[2H]]
9. An organic light emitting device comprising:
a first electrode;
a second electrode provided to face the first electrode; and
one or more organic material layers provided between the first electrode and the second electrode, wherein one or more one layers of the organic material layers comprise the compound according to claim 1.
* * * * *